US012479830B2

(12) United States Patent
Almansa-Rosales et al.

(10) Patent No.: US 12,479,830 B2
(45) Date of Patent: Nov. 25, 2025

(54) HOMOPIPERAZINYL AND HOMOPIPERIDINYL QUINAZOLIN-4(3H)-ONE DERIVATIVES HAVING MULTIMODAL ACTIVITY AGAINST PAIN

(71) Applicant: ESTEVE PHARMACEUTICALS, S.A., Barcelona (ES)

(72) Inventors: Carmen Almansa-Rosales, Barcelona (ES); Ariadna Fernandez-Donis, Barcelona (ES); José-Luís Díaz-Fernández, Barcelona (ES); Monica Garcia-Lopez, Barcelona (ES); Sergi Rodriguez Escrich, Barcelona (ES); Ute Christmann, Viladecans (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 837 days.

(21) Appl. No.: 17/764,257

(22) PCT Filed: Oct. 5, 2020

(86) PCT No.: PCT/EP2020/077770

§ 371 (c)(1),
(2) Date: Mar. 28, 2022

(87) PCT Pub. No.: WO2021/069339

PCT Pub. Date: Apr. 15, 2021

(65) Prior Publication Data

US 2022/0380345 A1 Dec. 1, 2022

(30) Foreign Application Priority Data

Oct. 10, 2019 (EP) .................................... 19382890

(51) Int. Cl.

*C07D 403/06* (2006.01)
*C07D 471/04* (2006.01)
*C07D 471/08* (2006.01)

(52) U.S. Cl.

CPC ......... *C07D 403/06* (2013.01); *C07D 471/04* (2013.01); *C07D 471/08* (2013.01)

(58) Field of Classification Search

CPC ..... A61P 25/04; C07D 401/14; C07D 403/06; C07D 405/14; C07D 471/04; C07D 471/08

See application file for complete search history.

(56) References Cited

U.S. PATENT DOCUMENTS 9,550,798 B2 1/2017 Guckian et al.

FOREIGN PATENT DOCUMENTS

| | | | | |
|---|---|---|---|---|
| WO | WO2004/018058 | | 3/2004 | |
| WO | WO 2004/055008 | | 7/2004 | |
| WO | WO2009/002553 | | 12/2008 | |
| WO | WO-2009002553 | A1 * | 12/2008 | ........... A61K 31/454 |
| WO | WO2017/121645 | | 7/2017 | |

OTHER PUBLICATIONS

International Search Report for 26 PCT/EP2020/027770 dated Jan. 26, 2021.

* cited by examiner

*Primary Examiner* — Jeffrey H Murray
*Assistant Examiner* — Daniel John Burkett
(74) *Attorney, Agent, or Firm* — HUESCHEN AND SAGE

(57) ABSTRACT

The present invention relates to homopiperazinyl and homopiperidinyl quinazolin-4(3H)-one derivatives having dual pharmacological activity towards both the $\alpha_2\delta$ subunit of the voltage-gated calcium channel and the sigma-1 ($\sigma$1) receptor, to processes of preparation of such compounds, to pharmaceutical compositions comprising them, and to their use in therapy, in particular for the treatment of pain.

19 Claims, No Drawings

HOMOPIPERAZINYL AND HOMOPIPERIDINYL QUINAZOLIN-4(3H)-ONE DERIVATIVES HAVING MULTIMODAL ACTIVITY AGAINST PAIN

FIELD OF THE INVENTION

The present invention relates to compounds having dual pharmacological activity towards both the $\alpha_2\delta$ subunit of the voltage-gated calcium channel, and the sigma-1 ($\sigma$1) receptor. More particularly, the present invention relates to homopiperazinyl and homopiperidinyl quinazolin-4(3H)-one derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved (Turk D C, Wilson H D, Cahana A. *Lancet* 2011, 377, 2226-2235). Pain affects a big portion of the population with an estimated prevalence of 20% and its incidence, particularly in the case of chronic pain, is increasing due to the population ageing. Additionally, pain is clearly related to comorbidities, such as depression, anxiety and insomnia, which leads to important productivity losses and socio-economical burden (Goldberg D S, McGee S J. *BMC Public Health,* 2011, 11, 770). Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

Voltage-gated calcium channels (VGCC) are required for many key functions in the body. Different subtypes of voltage-gated calcium channels have been described (Zamponi et al., *Pharmacol. Rev.* 2015, 67, 821-70). The VGCC are assembled through interactions of different subunits, namely $\alpha_1$ ($Ca_v\alpha_1$), $\beta$ ($Ca_v\beta$) $\alpha_2\delta$ ($Ca_v\alpha_2\delta$) and $\gamma$ ($Ca_v\gamma$). The $\alpha_1$ subunits are the key porous forming units of the channel complex, being responsible for the $Ca^{2+}$ conduction and generation of $Ca^{2+}$ influx. The $\alpha_2\delta$, $\beta$, and $\gamma$ subunits are auxiliary, although very important for the regulation of the channel, since they increase the expression of the $\alpha_1$ subunits in the plasma membrane as well as modulate their function, resulting in functional diversity in different cell types. Based on their physiological and pharmacological properties, VGCC can be subdivided into low voltage-activated T-type ($Ca_v3.1$, $Ca_v3.2$, and $Ca_v3.3$), and high voltage-activated L-($Ca_v1.1$ through $Ca_v1.4$), N—($Ca_v2.2$), P/Q-($Ca_v2.1$), and R—($Ca_v2.3$) types, depending on the channel forming $Ca_v\alpha$ subunits. All of these five subclasses are found in the central and peripheral nervous systems. Regulation of intracellular calcium through activation of these VGCC plays obligatory roles in: 1) neurotransmitter release. 2) membrane depolarization and hyperpolarization, 3) enzyme activation and inactivation, and 4) gene regulation (Perret and Luo, Neurotherapeutics 2009, 6, 679-92; Zamponi et al., 2015 supra; Neumaier et al., *Prog. Neurobiol.* 2015, 129, 1-36). A large body of data has clearly indicated that VGCC are implicated in mediating various disease states including pain processing. Drugs interacting with the different calcium channel subtypes and subunits have been developed. Current therapeutic agents include drugs targeting L-type $Ca_v1.2$ calcium channels, particularly 1,4-dihydropyridines, which are widely used in the treatment of hypertension. T-type ($Ca_v3$) channels are the target of ethosuximide, widely used in absence epilepsy. Ziconotide, a peptide blocker of N-type ($Ca_v2.2$) calcium channels, has been approved as a treatment of intractable pain (Perret and Luo, 2009, supra; Vink and Alewood, *Br. J. Pharmacol.* 2012, 167, 970-89).

The $Ca_v1$ and $Ca_v2$ subfamilies contain an auxiliary $\alpha_2\delta$ subunit, which is the therapeutic target of the gabapentinoid drugs of value in certain epilepsies and chronic neuropathic pain. To date, there are four known $\alpha_2\delta$ subunits, each encoded by a unique gene and all possessing splice variants. Each $\alpha_2\delta$ protein is encoded by a single messenger RNA and is posttranslationally cleaved and then linked by disulfide bonds. Four genes encoding $\alpha_2\delta$ subunits have now been cloned. $\alpha_2\delta$-1 was initially cloned from skeletal muscle and shows a fairly ubiquitous distribution. The $\alpha_2\delta$-2 and $\alpha_2\delta$-3 subunits were subsequently cloned from brain. The most recently identified subunit, $\alpha_2\delta$-4, is largely nonneuronal. The human $\alpha_2\delta$-4 protein sequence shares 30, 32 and 61% identity with the human $\alpha_2\delta$-1, $\alpha_2\delta$-2 and $\alpha_2\delta$-3 subunits, respectively. The gene structure of all $\alpha_2\delta$ subunits is similar. All $\alpha_2\delta$ subunits show several splice variants (Davies et al., *Trends Pharmacol. Sci.* 2007, 28, 220-8.: Dolphin A C, *Nat Rev Neurosci.* 2012, 13, 542-55, *Biochim. Biophys. Acta* 2013, 1828, 1541-9).

The $Ca_v\alpha_2\delta$-1 subunit may play an important role in neuropathic pain development (Perret and Luo, 2009, supra; Vink and Alewood, 2012, supra). Biochemical data have indicated a significant $Ca_v\alpha_2\delta$-1, but not $Ca_v\alpha_2\delta$-2, subunit upregulation in the spinal dorsal horn, and DRG (dorsal root ganglia) after nerve injury that correlates with neuropathic pain development. In addition, blocking axonal transport of injury-induced DRG $Ca_v\alpha_2\beta$-1 subunit to the central presynaptic terminals diminishes tactile allodynia in nerve injured animals, suggesting that elevated DRG $Ca_v\alpha_2\delta$-1 subunit contributes to neuropathic allodynia.

The $Ca_v\alpha_2\delta$-1 subunit (and the $Ca_v\alpha_2\delta$-2, but not $Ca_v\alpha_2\delta$-3 and $Ca_v\alpha_2\delta$-4, subunits) is the binding site for gabapentin which has anti-allodynic/hyperalgesic properties in patients and animal models. Because injury-induced $Ca_v\alpha_2\delta$-1 expression correlates with neuropathic pain development and maintenance, and various calcium channels are known to contribute to spinal synaptic neurotransmission and DRG neuron excitability, injury-induced $Ca_v\alpha_2\delta$-1 subunit upregulation may contribute to the initiation and maintenance of neuropathic pain by altering the properties and/or distribution of VGCC in the subpopulation of DRG neurons and their central terminals, therefore modulating excitability and/or synaptic neuroplasticity in the dorsal horn. Intrathecal antisense oligonucleotides against the $Ca_v\alpha_2\delta$-1 subunit can block nerve injury-induced $Ca_v\alpha_2\delta$-1 upregulation and prevent the onset of allodynia and reserve established allodynia.

As mentioned above, the $\alpha_2\delta$ subunits of VGCC form the binding site for gabapentin and pregabalin, which are structural derivatives of the inhibitory neurotransmitter GABA although they do not bind to GABAA, GABAB, or benzodiazepine receptors, or alter GABA regulation in animal brain preparations. The binding of gabapentin and pregabalin to the $Ca_v\alpha_2\delta$ subunit results in a reduction in the calcium-dependent release of multiple neurotransmitters, leading to efficacy and tolerability for neuropathic pain management. Gabapentinoids may also reduce excitability by inhibiting synaptogenesis (Pellet and Luo, 2009, supra; Vink and Alewood, 2012, supra, Zamponi et al., 2015, supra).

The sigma-1 (σ1) receptor was discovered 40 years ago and initially assigned to a new subtype of the opioid family. This receptor is expressed both in the endoplasmic reticulum and in the plasma membrane and plays an important role in the regulation of intracellular calcium concentration. A signaling pathway associated with the activation of the σ1 receptor has not been described, although it is believed that it has an amplification function of activation of intracellular cascades. In this sense, the σ1 receptor regulates and modulates the activity of numerous voltage-dependent ion channels, including Ca2+−, K+−, Na+, Cl−, SK, and NMDA channels and the IP3 receptor.

It is also known that the σ1 receptor is linked to analgesia, since σ1 receptor agonists counteract opioid receptor mediated analgesia, while a1 receptor antagonists, such as haloperidol, potentiated it (Chien C C, Pasternak G W. *Neurosci. Lett.* 1995, 190, 137-9).

Many additional preclinical evidences have indicated a clear role of the σ1 receptor in the treatment of pain (Zamanillo D, Romero L, Merlos M, Vela J M. *Eur. J. Pharmacol.,* 2013, 716, 78-93). The development of the σ1 receptor knockout mice, which show no obvious phenotype and perceive normally sensory stimuli, was a key milestone in this endeavour. In physiological conditions the responses of the σ1 receptor knockout mice to mechanical and thermal stimuli were found to be undistinguishable from WT ones but they were shown to possess a much higher resistance to develop pain behaviours than WT mice when hypersensitivity entered into play. Hence, in the σ1 receptor knockout mice, capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of σ1 receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states (Romero et al. *Br J Pharmacol.* 2012, 166, 2289-306).

Polypharmacology is a phenomenon in which a drug binds multiple rather than a single target with significant affinity. The effect of polypharmacology on therapy can be positive (effective therapy) and/or negative (side effects). Positive and/or negative effects can be caused by binding to the same or different subsets of targets; binding to some targets may have no effect. Multi-component drugs or multi-targeting drugs can overcome toxicity and other side effects associated with high doses of single drugs by countering biological compensation, allowing reduced dosage of each compound or accessing context-specific multitarget mechanisms. Because multitarget mechanisms require their targets to be available for coordinated action, one would expect synergies to occur in a narrower range of cellular phenotypes given differential expression of the drug targets than would the activities of single agents. In fact, it has been experimentally demonstrated that synergistic drug combinations are generally more specific to particular cellular contexts than are single agent activities, such selectivity is achieved through differential expression of the drugs' targets in cell types associated with therapeutic, but not toxic, effects (Lehar et al., *Nat. Biotechnol.* 2009, 27, 659-666).

In the case of chronic pain, which is a multifactorial disease, multi-targeting drugs may produce concerted pharmacological intervention of multiple targets and signaling pathways that drive pain. Because they actually make use of biological complexity, multi-targeting (or multi-component drugs) approaches are among the most promising avenues toward treating multifactorial diseases such as pain (Gilron et al., *Lancet Neurol.* 2013, 12, 1084-95). In fact, positive synergistic interaction for several compounds, including analgesics, has been described (Schrdder et al., *J. Pharmacol. Exp Ther.* 2011, 337, 312-20. Erratum in: *J. Pharmacol. Exp. Ther.* 2012, 342, 232; Zhang et al., *Cell Death Dis.* 2014, 5:e1138; Gilron et al., 2013, supra).

Given the significant differences in pharmacokinetics, metabolisms and bioavailability, reformulation of drug combinations (multi-component drugs) is challenging. Further, two drugs that are generally safe when dosed individually cannot be assumed to be safe in combination. In addition to the possibility of adverse drug-drug interactions, if the theory of network pharmacology indicates that an effect on phenotype may derive from hitting multiple targets, then that combined phenotypic perturbation may be efficacious or deleterious. The major challenge to both drug combination strategies is the regulatory requirement for each individual drug to be shown to be safe as an individual agent and in combination (Hopkins et al, *Nat. Chem. Biol.* 2008, 4, 682-90).

An alternative strategy for multitarget therapy is to design a single compound with selective polypharmacology (multi-targeting drug). It has been shown that many approved drugs act on multiple targets. Dosing with a single compound may have advantages over a drug combination in terms of equitable pharmacokinetics and biodistribution. Indeed, troughs in drug exposure due to incompatible pharmacokinetics between components of a combination therapy may create a low-close window of opportunity where a reduced selection pressure can lead to drug resistance. In terms of drug registration, approval of a single compound acting on multiple targets faces significantly lower regulatory barriers than approval of a combination of new drugs (Hopkins, 2008, supra).

As described above, the σ1 receptor, as well as the α2δ1 subunit, modulate intracellular calcium concentration and the activity of voltage-dependent calcium channels. There is also robust clinical and pre-clinical evidence linking both targets with the treatment of chronic neuropathic pain. Thus, the present application, also relates to the advantages of having dual activity, for the $\sigma_2\delta$-1 subunit of voltage-gated calcium channels and the σ1 receptor, in the same molecule to treat chronic pain.

Pain is multimodal in nature, since in nearly all pain states several mediators, signaling pathways and molecular mechanisms are implicated. Consequently, monomodal therapies can be complemented with a dual mechanism of action to provide complete pain relief. Currently, combining existing therapies is a common clinical practice and many efforts are directed to assess the best combination of available drugs in clinical studies (Mao J, Gold M S, Backonja M. *J. Pain,* 2011, 12, 157-166).

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

The authors of the present invention, have found a series of compounds that show a primary pharmacological activity towards the $\alpha_2\delta$ subunit, in particular the $\alpha_2\delta$-1 subunit, of the voltage-gated calcium channel, or compounds that show dual pharmacological activity towards both the $\alpha_2\delta$; subunit, in particular the $\alpha_2\delta$-1 subunit, of the voltage-gated calcium channel and the σ1 receptor resulting in an innovative, effective, complementary and alternative solution for the treatment of pain.

In view of the existing results of the currently available therapies and clinical practices, the present invention offers a solution by combining in a single compound binding to two different targets relevant for the treatment of pain. This was mainly achieved by providing the compounds according to the invention that bind to both to the σ1 receptor and to the $\alpha_2\delta$ subunit, in particular the $\alpha_2\delta$-1 subunit, of the voltage-gated calcium channel.

SUMMARY OF THE INVENTION

In this invention a family of structurally distinct homopiperazinyl and homopiperidinyl quinazolin-4(3H)-one derivatives, encompassed by formula (I), which have a pharmacological activity towards both the $\alpha_2\delta$ subunit, in particular the $\alpha_2\delta$-1 subunit, of the voltage-gated calcium channel and the σ1 receptor, were identified thus solving the above problem of identifying alternative or improved pain treatments by offering such compounds.

The main object of the invention is directed to a compound having a dual activity binding to the $\alpha_2\delta$ subunit, in particular the $\alpha_2\delta$-1 subunit, of the voltage-gated calcium channel and the σ1 receptor for use in the treatment of pain.

The invention is directed in a main aspect to a compound of general Formula (I), (I)

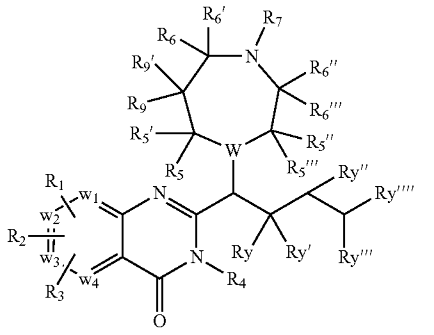

wherein $R_1$, $R_2$, $R_3$, $R_4$, $R_5$, $R_5'$, $R_5''$, $R_5'''$, $R_6$, $R_6'$, $R_6''$, $R_6'''$, $R_7$, $R_9$, $R_9'$, $R_y$, $R_y'$, $R_y'''$, $R_y''''$, W, $w_1$, $w_2$, $w_3$ and $w_4$ are as defined below in the detailed description.

A further object of the invention refers to the processes for preparation of compounds of general formula (I).

A still further object of the invention refers to the use of intermediate compounds for the preparation of a compound of general formula (I).

It is also an object of the invention a pharmaceutical composition comprising a compound of formula (I).

Finally, it is an object of the invention the use of compound as a medicament and more particularly for the treatment of pain and pain related conditions.

DETAILED DESCRIPTION OF THE INVENTION

The invention is directed to a family of structurally distinct homopiperazinyl and homopiperidinyl quinazolin-4(3H)-one derivatives, which have dual pharmacological activity towards both the $\alpha_2\delta$ subunit, in particular the $\alpha_2\delta$-1 subunit, of the voltage-gated calcium channel and the $\sigma_1$ receptor.

The invention is directed to compounds having a dual activity binding to the $\alpha_2\delta$ subunit, in particular the $\alpha_2\delta$-1 subunit, of the voltage-gated calcium channel and the $\sigma_1$ receptor for use in the treatment of pain and related disorders.

As this invention is aimed at providing a compound or a chemically related series of compounds which act as dual ligands of the $\alpha_2\delta$ subunit, in particular the $\alpha_2\delta$-1 subunit, of the voltage-gated calcium channel and the σ1 receptor it is a preferred embodiment if the compound has a binding expressed as $K_i$ responding to the following scales:

$K_s(\sigma_1)$ is preferably <1000 nM, more preferably <500 nM, even more preferably <100 nM.

$K_i(\alpha_2\delta\text{-}1)$ is preferably <10000 nM, more preferably <5000 nM, even more preferably <500 nM or even more preferably <100 nM.

Preferably, when $K_s$ (σ1)>1000 nM, the following scale has been adopted for representing the binding to the σ1-receptor:

$K_i$ $(\sigma_i)$>1000 nM or inhibition ranges between 1% and 50%.

Preferably, when $K_i(\alpha_2\delta\text{-}1)$>5000 nM, the following scale has been adopted for representing the binding to the $\alpha_2\delta$-1 subunit of voltage-gated calcium channels:

$K_i(\alpha_2\delta\text{-}1)$>5000 nM or inhibition ranges between 1% and 50%

The applicant has surprisingly found that the problem of providing a new effective and alternative solution for treating pain and pain related disorders can be solved by using an analgesic approach combining two activities in a single drug (i.e., dual ligands which are bifunctional and bind to σ1 receptor and to $\alpha_2\delta$ subunit, in particular the $\alpha_2\delta$-1 subunit, of the voltage-gated calcium channel).

As described above, the σ1 receptor as well as the α2δ1 subunit, modulate intracellular calcium concentration and the activity of voltage-dependent calcium channels. There is also a robust clinical and pre-clinical evidence linking both targets with the treatment of chronic neuropathic pain. Thus, the present invention, also relates to the advantages of having dual activity, for the $\alpha_2\delta$-1 subunit of voltage-gated calcium channels and the σ1 receptor, in the same molecule to treat pain, i.e. binding to two different targets relevant for the treatment of pain.

A dual compound that possess binding to both the a receptor and to the $\alpha_2\delta$ subunit of the voltage-gated calcium channel shows a highly valuable therapeutic potential by achieving an outstanding analgesia.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies.

It has to be noted, though, that functionalities "antagonism" and "agonism" are also subdivided in their effect into subfunctionalities like partial agonism or inverse agonism.

Accordingly, the functionalities of the compounds should be considered within a relatively broad bandwidth.

An antagonist blocks or dampens agonist-mediated responses. Known subfunctionalities are neutral antagonists or inverse agonists.

An agonist increases the activity of the receptor above its basal level. Known subfunctionalities are full agonists, or partial agonists.

In its broader aspect, the present invention is directed to compounds of general Formula (I):

(I)

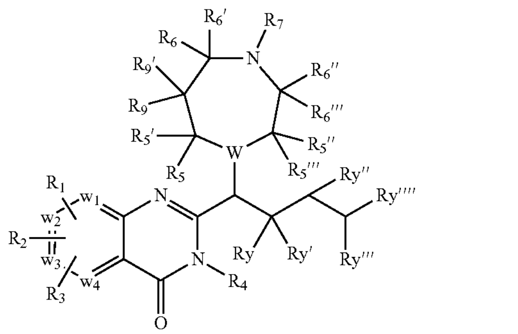

wherein

- $R_y$ and $R_y$ are independently selected from hydrogen, substituted or unsubstituted $C_1$, alkyl, substituted or unsubstituted $C_{2-6}$ alkenyl and substituted or unsubstituted $C_{2-6}$ alkynyl;
  - alternatively, $R_y$ and $R_y'$ form, with the carbon atom to which they are attached, a substituted or unsubstituted cycloalkyl;
- $R_y''$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
- $R_y'''$ and $R_y''''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
  - alternatively, $R_y''$ and $R_y''''$ form, with the carbon atom to which they are attached, a substituted or unsubstituted cycloalkyl;
- W is nitrogen or —$CR_w$— wherein $R_w$ is hydrogen or halogen;
  - alternatively, $R_w$ and one of $R_5$, $R_{5'}$, $R_{5''}$ or $R_5'''$ form a double bond;
- w1, w2, w3 and w4 are independently selected from the group consisting of nitrogen and carbon;
- $R_1$ is selected from the group consisting of hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_8$, —$NR_8R_8'$, —$NR_8C(O)R_8'$, —$NR_8C(O)OR_8'$, —$C(O)NR_8R_{8'}$, —$C(O)OR_8$, —$OCHR_8R_8'$, haloalkyl, haloalkoxy, —CN, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;
- $R_8$ and $R_8'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;
- $R_2$ is selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_{21}$, —$NO_2$, —$NR_{21}R_{21}'$, —$NR_{21}C(O)R_{21}'$, —$NR_{21}S(O)_2R_{21}'$, —$S(S)_2NR_{21}R_{21}'$, —$NR_{21}C(O)NR_{21}R_{21}''$, —$SR_{21}$, —$S(O)R_{21}$, —$S(O)_2R_{21}$, —CN, haloalkyl, haloalkoxy, —$C(O)OR_{21}$, —$C(O)NR_{21}R_{21}'$, —$NR_{21}S(O)_2NR_{21}'R_{21}''$ and —$C(CH_3)_2OR_{21}$;
- wherein $R_{21}$, $R_{21}'$ and $R_{21}''$ are independently selected from hydrogen, substituted or unsubstituted $C_{1-13}$ alkyl, substituted or unsubstituted $C_{2-6}$ alkenyl and substituted or unsubstituted $C_{2-6}$ alkynyl;
- $R_3$ is selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_{31}$, —$NO_3$, —$NR_{31}R_{31}'$, —$NR_{31}C(O)R_{31}'$, $R_{31}S(O)_3R_{31}'$, —$S(O)_3NR_{31}R_{31}'$, —$NR_{31}C(O)NR_{31}'R_{31}''$, —$SR_{31}$—$S(O)R_{31}$, —$S(O)_3R_{31}$, —CN, haloalkyl, haloalkoxy, —$C(O)OR_{31}$, —$C(O)NR_{31}R_{31}'$, —$NR_{31}S(O)_3NR_{31}'R_{31}''$ and —$C(CH_3)_3O\ R_{31}$;
- wherein $R_{31}$, $R_{31}'$ and $R_{31}''$ are independently selected from hydrogen, substituted or unsubstituted $C_{1-6}$ alkyl, substituted or unsubstituted Cas alkenyl and substituted or unsubstituted $C_{3-6}$ alkynyl;
- $R_4$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylheterocyclyl, substituted or unsubstituted alkylaryl and substituted or unsubstituted alkylcycloalkyl;
- $R_4$ and $R_y$ taken together with the nitrogen and carbon atoms to which they are attached, respectively, may form a five or six atom members substituted or unsubstituted heterocyclyl;
- $R_4$ and $R_y'''$ taken together with the nitrogen and carbon atoms to which they are attached, respectively, may form a six atom members substituted or unsubstituted heterocyclyl;
- $R_5$, $R_5'R_5''$ and $R_5''$ are independently selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
  - alternatively, $R_5$ and $R_5'$ and/or $R_5''$ and $R_5'''$ taken together with the carbon atom to which they are attached form a carbonyl group;
- $R_6$, $R_6'$, $R_6''$ and $R_6'''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
- $R_7$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkheterocyclyl and substituted or unsubstituted alkylaryl;
- one of $R_5$ and $R_5'$, taken together with $R_7$ form a —$[CH_2]_n$— bridge; or
- one of $R_5''$ and $R_5'''$, taken together with $R_7$ form a —$[CH_2]$— bridge; or
- one of $R_5$ and $R_5'$, taken together with one of $R_5''$ and $R_5''$ form a —$[CH_2]_n$— bridge; or one of $R_5$ and $R_5'$, taken together with one of $R_5''$ and $R_5'''$ form a —$[CH_2]_n$— bridge; or one of $R_5$ and $R_6'$, taken together with one of $R_6''$ and $R_6'''$ form a —$[CH_2]_n$— bridge; or one of $R_6$ and $R_6'$, taken together with one of $R_6''$ and $R_6'''$ form a —$[CH_2]_n$— bridge; or one of $R_9$ and $R_9'$, taken together with $R_7$ form a —$[CH_2]_n$— bridge; or one of $R_9$ and $R_9'$, taken together with one of $R_6''$ and $R_6'''$ form a —$[CH_2]_n$— bridge; or one of $R_9$ and $R_9'$, taken together with one of $R_5''$ and $R_5'''$ form a —$[CH_2]_n$— bridge; or wherein n is 1, 2 or 3;

$R_9$ and $R_9'$ are independently selected from the group consisting of hydrogen, halogen, —$OR_{91}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

These compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment, these compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

Note that "or a corresponding salt thereof" does also mean "or a corresponding pharmaceutically acceptable salt thereof". This does apply to all below described embodiments and uses of "salt" being thus equivalent to "pharmaceutically acceptable salt".

In a particular embodiment, the following proviso applies:

w1, w2, w3 and w4 are all carbon, or wherein one or two of w1, w2, w3 and w4 are nitrogen while the others are carbon:

In a further embodiment the compound according to the invention is a compound of general Formula (I)

(I)

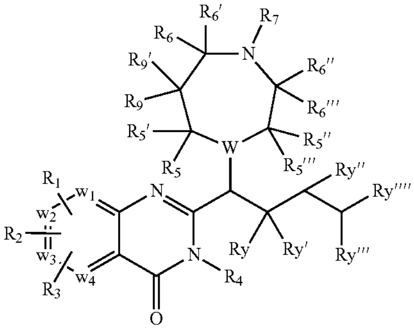

wherein $R_y$ and $R_y'$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_y$ and $R_y'$ form, with the carbon atom to which they are attached, a substituted or unsubstituted cycloalkyl;

$R_y''$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_y'''$ and $R_y''''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_y'''$ and $R_y''''$ form, with the carbon atom to which they are attached, a substituted or unsubstituted cycloalkyl;

W is nitrogen or —$CR_w$—; wherein $R_w$ is hydrogen or halogen;

alternatively, $R_w$ and one of $R_5$, $R_5'$ $R_5''$ or $R_5'''$ form a double bond:

w1, w2, w3 and w4 are independently selected from the group consisting of nitrogen and carbon;

wherein w1, w2, w3 and w4 are all carbon, or wherein one or two of w1, w2, w3 and w4 are nitrogen while the others are carbon;

$R_1$ is selected from the group consisting of hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_8$—$NR_8R_8'$, —$NR_8C(O)R_8'$, —$NR_8C(O)OR_8'$, —$C(O)NR_6R_6$, —$C(O)OR_8$, —$OCHR_8R_8'$, haloalkyl, haloalkoxy, —CN, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

wherein the alkyl, alkenyl or alkynyl defined in $R_1$, if substituted, is substituted with one or more substituent/s selected from —$OR_{11}$, halogen, —CN, haloalkoxy and —$NR_{11}R_{11}'$;

the cycloalkyl, aryl heterocyclyl, defined in $R_1$, also in alkylcycloalkyl, alkylaryl and alkylheterocyclyl, if substituted, is substituted with one or more substituents selected from =O, halogen, —$R_{11}$, —$OR_{11}$, —$NO_2$, μ$NR_{11}R_{11}'$, —$NR_{11}C(O)R_{11}'$, —$NR_{11}S(O)_2R_{11}'$, —$S(O)_2NR_{11}R_{11}'$, —$NR_{11}C(O)NR_{11}'R_{11}''$, —$SR_{11}$, —$S(O)R_{11}$, —$S(O)_2R_{11}$, —CN, haloalkyl, haloalkoxy, —$C(O)OR_{11}R_{11}'$, —$OCH_2CH_2OR_{11}$, —$NR_{11}S(O)_2NR_{11}'R_{11}''$, —$C(CH_3)_2OR_{11}$, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

$R_{11}$, $R_{11}'$ and $R_{11}''$ are independently selected from hydrogen, substituted or unsubstituted $C_{1-6}$ alkyl, substituted or unsubstituted $C_{1-6}$ alkenyl and substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

$R_8$ and $R_8'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

wherein the alkyl, alkenyl or alkynyl defined in $R_8$ or $R_8'$, if substituted, is substituted with one or more substituents selected from —$OR_{81}$, halogen, —CN, haloalkoxy and —$NR_{81}R_{81}'$;

the cycloalkyl heterocyclyl or aryl defined in $R_8$ or $R_8'$, also in alkylcycloalkyl, alkylheterocyclyl and alkylaryl if substituted, is substituted with one or more substituents selected from =O, halogen, —$R_{81}$, —$OR_{81}$, —$NO_2$, —$NR_{81}R_{81}'$, —$NR_{81}C(O)R_{81}'$, —$NR_{81}S(O)_2R_{81}'$, —$S(O)_2NR_{81}R_{81}'$, —$NR_{81}C(O)NR_{81}'R_{81}''$, —$SR_{81}$, —$S(O)R_{81}$, —$S(O)_2R_{81}$, —CN, haloalkyl, haloalkoxy, —$C(O)OR_{81}$, —$C(O)NR_{81}R_{81}'$, —$OCH_2CH_2OR_{81}$, —$NR_{81}S(O)_2NR_{81}'R_{81}''$ and —$C(CH_3)_2OR_{81}$, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

wherein $R_{81}$, $R_{81}'$ and $R_{81}''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_2$ is selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_{21}$, —$NO_2$, —$NR_2R_{21}'$, —$NR_{21}C(O)R_2$, —$NR_{21}S(O)_2R_{21}'$, —$S(O)_2NR_2R_{21}'$, —$NR_{21}C(O)NR_{21}'R_{21}''$, —$SR_{21}$, —$S(O)R_{21}$, —$S(O)_2R_{21}$, —CN, haloalkyl, haloalkoxy, —$C(O)OR_{21}$, —$C(O)NR_{21}R_{21}'$, —$NR_{21}S(O)_2NR_{21}''R_{21}''$ and —$C(CH_3)_2OR_{21}$;

wherein $R_{21}$, $R_{21}'$ and $R_{21}''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_3$ is selected from hydrogen, halogen, substituted or unsubstituted Cis alkyl, substituted or unsubstituted $C_{2-6}$ alkenyl, substituted or unsubstituted $C_{2-6}$ alkynyl, —$OR_{31}$, —$NO_3$, —$NR_{31}R_{31}'$, —$NR_{31}C(O)R_{31}'$, —$NR_{31}S(O)_{31}R_{31}'$, —$S(O)_3NR_{31}R_{31}'$, $NR_{31}C(O)NR_{31}'R_{31}''$, —$SR_{31}$, —$S(O)R_{31}$, —$S(O)_3R_{31}$, —CN, haloalkyl, haloalkoxy, —$C(O)OR_{31}$, —$C(O)NR_3$, $R_{31}'$, —$NR_{31}S(O)_3NR_{31}'R_{31}''$ and —$C(CH_3)_3OR_{31}$:

wherein $R_{31}$, $R_{31}'$ and $R_{31}''$ are independently selected from hydrogen, substituted or unsubstituted $C_{1-6}$ alkyl, substituted or unsubstituted $C_{3-6}$ alkenyl and substituted or unsubstituted $C_{3-6}$ alkynyl;

$R_4$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylheterocyclyl, substituted or unsubstituted alkylaryl and substituted or unsubstituted alkylcycloalkyl;

wherein the alkyl, alkenyl or alkynyl defined in $R_4$, if substituted, is substituted with one or more substituent/s selected from —$OR_{41}$, halogen, —CN, —$C(O)OR_{41}$, haloalkoxy, —$NR_{41}R_{41}'$, substituted or unsubstituted cycloalkyl, substituted or unsubstituted heterocyclyl and substituted or unsubstituted aryl;

the cycloalkyl as defined in $R_4$, also in alkylcycloalkyl, or the heterocyclyl in alkylheterocyclyl, or the aryl in alkylaryl, if substituted and the substitution has not been defined otherwise, it is substituted with one or more substituent/s selected from halogen, —$R_{41}$, —$OR_{41}$, —$NO_2$, —$NR_{41}R_{41}'$, —$NR_{41}C(O)R_{41}'$, —$NR_{41}S(O)_2R_{41}'$, —$S(O)_2NR_{41}R_{41}'$, —$NR_{41}C(O)NR_{41}R_{41}''$, —$SR_{41}$—$S(O)_2R_{41}$, —CN, haloalkyl, haloalkoxy, —$C(O)OR_{41}$, —$C(O)NR_{41}R_{41}'$, —$OCH_2CH_2OR_{41}$, —$NR_0S(O)_2NR_{41}R_{41}''$ and —$C(CH_3)_2OR_{41}$;

wherein $R_{41}$, $R_{41}'$ and $R_{41}''$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

$R_4$ and $R_y$ taken together with the nitrogen and carbon atoms to which they are attached, respectively, may form a five or six atom members substituted or unsubstituted heterocyclyl;

$R_4$ and $R_y'''$ taken together with the nitrogen and carbon atoms to which they are attached, respectively, may form a six atom members substituted or unsubstituted heterocyclyl;

$R_5$, $R_5'$ $R_5''$ and $R_5'''$ are independently selected from hydrogen, halogen, substituted or unsubstituted $C_{1-6}$ alkyl, substituted or unsubstituted $C_{2-6}$ alkenyl and substituted or unsubstituted $C_{2-4}$ alkynyl;

alternatively, $R_5$ and $R_5'$ and/or $R_5''$ and $R_5'''$ taken together with the carbon atom to which they are attached form a carbonyl group;

wherein the alkyl, alkenyl or alkynyl, in $R_5$, $R_5''$, $R_5''$ and $R_5'''$, if substituted, it is substituted with one or more substituents selected from —$OR_{51}$, —$C(O)OR_{51}$ halogen, —CN haloalkoxy and —$NR_{51}R_{51}'$;

wherein $R_{51}$ and $R_{51}'$ are independently selected from hydrogen, unsubstituted $C_{1-5}$ alkyl, unsubstituted $C_{2-5}$ alkenyl, and unsubstituted $C_{2-5}$ alkynyl;

$R_6$, $R_6'$, $R_6''$ and $R_6'''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the alkyl, alkenyl or alkynyl, in $R_5$, $R_5'$, $R_6''$ and $R_6'''$, if substituted, it is substituted with one or more substituent/s selected from —$OR_{61}$, —$C(O)OR_{61}$, halogen, —CN, haloalkoxy and —$NR_{61}R_{61}'$;

wherein $R_{61}$ and $R_{61}'$ are independently selected from hydrogen, unsubstituted $C_{1-6}$ alkyl, unsubstituted $C_{2-6}$ alkenyl, and unsubstituted $C_{2-6}$ alkynyl;

$R_7$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

wherein the alkyl, alkenyl or alkynyl defined in $R_7$, if substituted, is substituted with one or more substituent/s selected from —$OR_{71}$, halogen, —CN, haloalkoxy and —$NR_{71}R_{71}''$;

the cycloalkyl heterocyclyl or aryl defined in $R_7$, also in alkylcycloalkyl, alkylheterocyclyl and alkylaryl if substituted, is substituted with one or more substituent/s selected from =O, halogen, —Rn, —$OR_{71}$, —$NO_2$, —$NR_{71}R_{71}$', $NR_{71}C(O)R_{71}$', —$NR_{71}S(O)_2R_{71}$', —$S(O)_2NR_{71}R_{71}$', —$NR_{71}C(O)NR_{71}$'$R_{11}$", —$SR_{71}$, —$S(O)R_{71}$, —$S(O)_2R_{71}$', —CN, haloalkyl, haloalkoxy, —$C(O)OR_{71}$, —$C(O)NR_{71}R_{71}$', —$OCH_2CH_2OR_{71}$, —$NR_{71}S(O)_2NR_{71}$'$R_{71}$" and —$C(CH_3)_2OR_{71}$, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

wherein $R_{71}$, $R_{71}$' and $R_{71}$" are independently selected from hydrogen, substituted or unsubstituted $C_{1-6}$ alkyl, substituted or unsubstituted $C_{2-6}$ alkenyl and substituted or unsubstituted $C_{2-6}$ alkynyl:

one of $R_5$ and $R_5$', taken together with $R_7$ form a —$[CH_2]_n$— bridge; or one of $R_5$" and $R_5$"', taken together with $R_7$ form a —$[CH_2]_n$— bridge; or one of $R_5$ and $R_5$', taken together with one of $R_5$" and $R_5$"' form a —$[CH_2]_n$— bridge; or one of $R_5$ and $R_5$', taken together with one of $R_6$" and $R_6$"' form a —$[CH_2]_n$— bridge; or one of $R_6$ and $R_6$', taken together with one of $R_6$" and $R_6$"' form a —$[CH_2]_n$— bridge; or one of $R_6$ and $R_6$', taken together with one of $R_5$" and $R_5$"' form a —$[CH_2]_n$— bridge; or one of $R_9$ and $R_9$', taken together with $R_7$ form a —$[CH_2]_n$— bridge; or one of $R_9$ and $R_9$', taken together with one of $R_5$ and $R_5$"' form a —$[CH_2]_n$— bridge; or one of $R_9$ and $R_9$', taken together with one of $R_5$" and $R_5$"' form a —$[CH_2]_n$— bridge; or wherein n is 1, 2 or 3;

$R_9$ and $R_9$' are independently selected from the group consisting of hydrogen, halogen, —$OR_{91}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

wherein the alkyl, alkenyl or alkynyl defined in $R_9$ or $R_9$', if substituted, is substituted with one or more substituents selected from —$OR_{91}$, halogen, —CN, haloalkoxy and —$NR_{91}R_{91}$';

the cycloalkyl heterocycyl or aryl defined in $R_9$ or $R_9$', also in alkylcycloalkyl, alkylheterocyclyl and alkylaryl if substituted, is substituted with one or more substituents selected from =O, halogen, —$R_{91}$, —$OR_{91}$, —$NO_2$, —$NR_{91}R_{91}$', —$NR_{91}C(O)R_{91}$', —$NR_{91}S(O)_2R_{91}$', —$S(O)_2NR_{91}R_{91}$', —$NR_{91}C(O)NR_{91}$'$R_{91}$", —$SR_{91}$—$S(O)R_{91}$, —$S(O)_2R_{91}$, —CN, haloalkyl, haloalkoxy, —$C(O)OR_{91}$, —$C(O)NR_9$, $R_{91}$', —$OCH_2CH_2OR_{91}$, —$NR_{91}S(O)_2NR_{91}$'$R_{91}$" and —$C(CH_3)_2OR_{91}$, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

wherein $R_{91}$, $R_{91}$' and $R_{91}$" are independently selected from hydrogen, substituted or unsubstituted $C_{1-6}$ alkyl, substituted or unsubstituted $C_{2-4}$ alkenyl and substituted or unsubstituted $C_{2-4}$ alkynyl;

the alkyl, alkenyl or alkynyl, if substituted and the substitution has not been defined otherwise, it is substituted with one or more substituent/s selected from —$OR_{13}$, halogen, —CN haloalkoxy and —$NR_{13}R_{13}$';

wherein $R_{13}$ and $R_{13}$' are independently selected from hydrogen, unsubstituted $C_{1-6}$ alkyl, unsubstituted $C_{2-6}$ alkenyl, and unsubstituted $C_{2-6}$ alkynyl;

the aryl, heterocyclyl or cycloalkyl, also in alkylaryl, alkylheterocyclyl or alkylcycloalkyl, if substituted and the substitution has not been defined otherwise, it is substituted with one or more substituent/s selected from halogen, —$R_{14}$, —$OR_{14}$, —$NO_2$, —$NR_{14}R_{14}$', —$NR_{14}C(O)R_{14}$", —$NR_{14}S(O)_2R_{14}$', —$S(O)_2NR_{14}R_{14}$', —$NR_{14}C(O)NR_{14}$'$R_{14}$", —$SR_{14}$, —$S(O)R_{14}$, —$S(O)_2R_{14}$, —CN, haloalkyl, haloalkoxy, —$C(O)OR_{14}$, —$C(O)NR_{14}R_{14}$', $OCH_2CH_2OR_{14}$, —$NR_{14}S(O)_2NR_{14}$'$R_{14}$" and —$C(CH_3)_2OR_{14}$;

wherein $R_{14}$, $R_{14}$' and $R_{14}$" are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula (I)

(I')

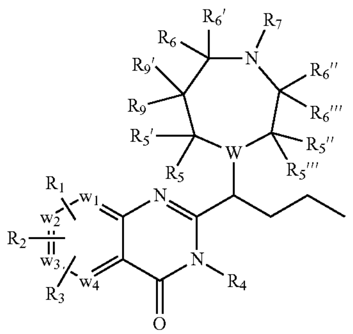

wherein $R_1$, $R_2$, $R_3$, $R_4$, $R_5$, $R_5$', $R_5$", $R_5$"', $R_6$, $R_6$', $R_6$", $R_6$"', $R_7$, $R_9$, $R_9$', W, $w_1$, $w_2$, $w_3$ and $w_4$ are as defined below in the detailed description:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula ($I^{2}$')

$(I^{2\prime})$

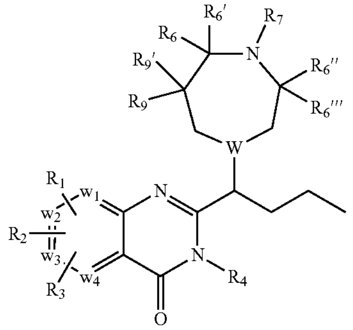

wherein $R_1$, $R_2$, $R_3$, $R_4$, $R_6$, $R_6'$, $R_6''$, $R_6'''$, $R_9$, $R_9'$, W, $w_1$, $w_2$, $w_3$ and $w_4$ are as defined below in the detailed description;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula (P')

$(I^{3\prime})$

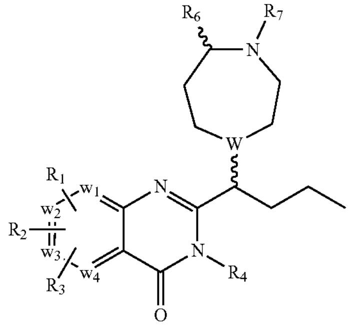

wherein $R_1$, $R_2$, $R_3$, $R_4$, $R_6$, $R_7$, W, $w_1$, $w_2$, $w_3$ and $w_4$ are as defined below in the detailed description;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula $(I^{4\prime})$ $(I^{4\prime})$

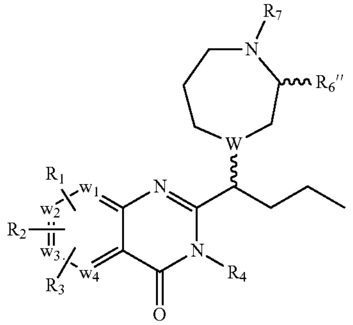

wherein $R_1$, $R_7$, $R_3$, $R_4$, $R_6''$, $R_7$, W, $w_1$, $w_2$, $w_3$ and $w_4$ are as defined below in the detailed description;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula $(I^{5\prime})$ $(I^{5\prime})$

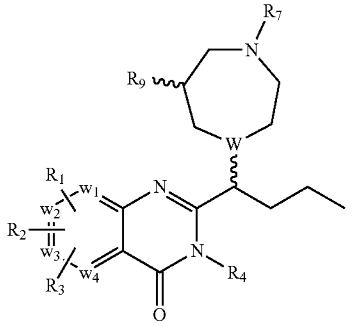

wherein $R_1$, $R_2$, $R_3$, $R_4$, $R_7$, $R_9$, W, $w_1$, $w_2$, $w_3$ and $w_4$ are as defined below in the detailed description;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

For clarity purposes, all groups and definitions described in the present description and referring to compounds of general Formula (I), also apply to compounds of general Markush Formulae (I'), $(I^{2\prime})$, $(I^{3\prime})$, $(I^{4\prime})$ or $(I^{5\prime})$ (where applicable), and to all intermediate of synthesis, when those groups are present in the mentioned general Markush formulae, since compounds of general Markush Formulae (I'), $(I^{2\prime})$, $(I^{3\prime})$, $(I^{4\prime})$ or $(I^{5\prime})$ are included within the scope of the larger definition of general Markush Formula (I).

For clarity purposes, the expression e.g. "the cycle in $R_8$—$R_8'$", means the cycle resulting when $R_8$ and $R_8'$ form a cycle together with the atom(s) to which they are attached. This cycle can then be substituted or not. This definition is also generally applicable and can be also applied as a definition of any other cycle (preferably cycloalkyls, heterocyclyls or aryls) formed from two different functional groups like e.g. "the cycle in $R_i$-$R_i$" means the cycle resulting when $R_i$ and $R_i$' form a cycle together with the atom(s) to which they are attached. This cycle can then be substituted or not.

In the context of this invention, alkyl is understood as meaning saturated, linear or branched hydrocarbons, which may be unsubstituted or substituted once or several times. It encompasses e.g. —$CH_3$ and —$CH_2$—$CH_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C1-6-, C17- or C18-alkyl. The alkyl radicals are preferably methyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-6}$ alkyl like methyl, ethyl, propyl, butyl, pentyl, hexyl, heptyl, or octyl; preferably is $C_{1-6}$ alkyl like methyl, ethyl, propyl, butyl, pentyl, or hexyl; more preferably is $C_{1-4}$ alkyl like methyl, ethyl, propyl or butyl.

Alkenyl is understood as meaning unsaturated, linear or branched hydrocarbons, which may be unsubstituted or substituted once or several times. It encompasses groups like e.g. —CH═CH—$CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylene.

Alkynyl is understood as meaning unsaturated, linear or branched hydrocarbons, which may be unsubstituted or substituted once or several times. It encompasses groups like e.g. —C═C—$CH_3$ (1-propinyl). Preferably alkynyl in the context of this invention is $C_{2-10}$-alkynyl or $C_{2-8}$-alkynyl like ethyne, propyne, butylene, pentyne, hexyne, heptyne, or octyne; or is $C_{2-8}$-alkynyl like ethyne, propyne, butylene, pentyne, or hexyne; or is $C_{2-4}$-alkynyl like ethyne, propyne, butylene, pentyne, or hexyne.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), —$NR_kR_{k'}$, —$SR_k$, —S(O)$R_k$, —S(O)$_2R_k$, —$OR_k$, —C(O)$R_k$, —C(O)O$R_k$, —CN, —C(O)$NR_kR_{k'}$, haloalkyl, haloalkoxy, being $R_k$ represented by $R_{11}$, $R_{13}R_{41}$, $R_{51}$, $R_{61}$, $R_{71}$, $R_{81}$ or $R_{91}$ (being $R_k$ represented by $R_{11}$' $R_{13}$' $R_{41}$' $R_{51}$' $R_{61}$' $R_{71}$' $R_{81}$' or $R_{91}$') wherein $R_1$ to $R_{91}$" are as defined in the description, and wherein when different radicals $R_1$ to $R_{91}$" are present simultaneously in Formula I they may be identical or different.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted with one or more of halogen (F, Cl, Br, I), —$NR_kR_k$, —$OR_k$, —CN, —$SR_k$ haloalkyl, haloalkoxy, being $R_k$ represented by $R_{11}$, $R_{13}$, $R_{41}R_{51}$, $R_{61}R_{71}R_{81}$ or $R_{91}$, (being $R_k$ represented by $R_{11}$' $R_{13}$' $R_{41}$' $R_{51}$' $R_{61}$' $R_{71}$' $R_{81}$' or $R_{91}$') wherein wherein $R_1$ to $R_{91}$" are as defined in the description, and wherein when different radicals $R_1$ to $R_{91}$" are present simultaneously in Formula I they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH═CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2C_1$, —$OCH_2F$, —$OCHCl_2$, —$OCHF_2$, —$OCCl_3$, —$OCF_3$ and $OCH_2$—$CHCl_2$. Preferably haloalkoxy is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-27}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-5}$-cycloalkyl represents C4-, C5-, C6- or C7- or C8-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl. 2-methylcyclopropyl, cyclopropylmethyl, cyclobutyl, cyclopentyl, cyclopentylmethyl, cyclohexyl, cycloheptyl, cyclooctyl, and also adamantyl. Preferably in the context of this invention cycloalkyl is $C_{3-8}$ cycloalkyl like cyclopropyl, cyclobutyl, cyclopentyl, cyclohexyl, cycloheptyl, or cyclooctyl; or is $C_{3-7}$ cycloalkyl like cyclopropyl, cyclobutyl, cyclopentyl, cyclohexyl, or cycloheptyl; or is $C_{3-6}$ cycloalkyl like cyclopropyl, cyclobutyl, cyclopentyl or cyclohexyl, especially cyclopentyl or cyclohexyl.

Aryl is understood as meaning 5 to 18 membered mono or polycyclic ring systems with at least one aromatic ring but without heteroatoms even in only one of the rings. Examples are phenyl, naphthyl, fluoranthenyl, fluorenyl, tetralinyl or indanyl, 9H-fluorenyl or anthracenyl radicals, which can be unsubstituted or once or several times substituted. Most preferably aryl is understood in the context of this invention as phenyl, naphthyl or anthracenyl, preferably is phenyl.

A heterocyclyl radical or group (also called heterocyclyl hereinafter) is understood as meaning 5 to 18 membered mono or polycyclic heterocyclic ring systems, with at least one saturated or unsaturated ring which contains one or more heteroatoms selected from the group consisting of nitrogen, oxygen and/or sulfur in the ring. A heterocyclic group can also be substituted once or several times.

Subgroups inside the heterocyclyls as understood herein include heteroaryls and non-aromatic heterocyclyls.

- the heteroaryl (being equivalent to heteroaromatic radicals or aromatic heterocyclyls) is an aromatic 5 to 18 membered mono or polycyclic heterocyclic ring system of one or more rings of which at least one aromatic ring contains one or more heteroatoms selected from the group consisting of nitrogen, oxygen and/or sulfur in the ring; preferably is a 5 to 18 membered mono or polycyclic aromatic heterocyclic ring system of one or two rings of which at least one aromatic ring contains one or more heteroatoms selected from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;
- the non-aromatic heterocyclyl is a 5 to 18 membered mono or polycyclic heterocyclic ring system of one or more rings of which at least one ring—with this (or these) ring(s) then not being aromatic—contains one or more heteroatoms selected from the group consisting of nitrogen, oxygen and/or sulfur in the ring; preferably is a 5 to 18 membered mono or polycyclic heterocyclic ring system of one or two rings of which one or both rings—with this one or two rings then not being aromatic—contain/s one or more heteroatoms selected from the group consisting of nitrogen, oxygen and/or sulfur in the ring, more preferably is selected from oxazepane, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine and pyrrolidine.

Preferably in the context of this invention heterocyclyl is defined as a 5 to 18 membered mono or polycyclic heterocyclic ring system of one or more saturated or unsaturated rings of which at least one ring contains one or more heteroatoms selected from the group consisting of nitrogen, oxygen and/or sulfur in the ring. Preferably it is a 5 to 18 membered mono or polycyclic heterocyclic ring system of one or two saturated or unsaturated rings of which at least one ring contains one or more heteroatoms selected from the group consisting of nitrogen, oxygen and/or sulfur in the ring.

Preferred examples of heterocyclyls include oxazepane, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, tetrahydroisoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyran, pyrazole, imidazole, piperidine, thiophene, indole, benzimidazole, pyrrolo2,3b]pyridine, benzoxazole, oxopyrrolidine, pyrimidine, oxazepane, azetidine and pyrrolidine.

In the context of this invention oxopyrrolidine is understood as meaning pyrrolidin-2-one.

An N-containing heterocyclyl is a heterocyclic ring system of one or more saturated or unsaturated rings of which at least one ring contains a nitrogen and optionally one or more further heteroatoms selected from the group consisting of nitrogen, oxygen and/or sulfur in the ring; preferably is a heterocyclic ring system of one or two saturated or unsaturated rings of which at least one ring contains a nitrogen and optionally one or more further heteroatoms selected from the group consisting of nitrogen, oxygen and/or sulfur in the ring, more preferably is selected from oxazepane, pyrrolidine, imidazole, oxadiazole, tetrazole, azetidine, pyridine, pyrimidine, piperidine, piperazine, benzimidazole, indazole, benzothiazole, benzodiazole, morpholine, indoline, triazole, isoxazole, pyrazole, pyrrole, pyrazine, pyrrolo[2,3b]pyridine, quinoline, quinolone, isoquinoline, tetrahydrothienopyridine, phthalazine, benzo-1,2,5-thiadiazole, indole, benzotriazole, benzoxazole oxopyrrolidine, carbazole or thiazole.

In the context of this invention, a cyclic amide is defined as a subgroup of a heterocyclyl (as defined above) formed through the cyclization of a carbon sequence, containing at least the sequence

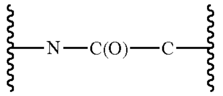

forming part of the cycle. Said cyclic amide may optionally be fused to a ring system. Preferably the cyclic amide is an "indoline-2-one". A cyclic amide may be substituted or unsubstituted as defined for heterocyclyl above.

In the context of this invention, a cyclic urea is defined as a subgroup of a heterocyclyl (as defined above) formed through the cyclization of a carbon sequence containing at least the sequence

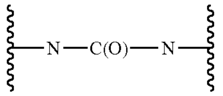

forming part of the cycle. Said cyclic urea may optionally be fused to a ring system. Preferably the cyclic urea is "1H-benzo[d]imidazol-2(3H)-one". A cyclic urea may be substituted or unsubstituted as defined for heterocyclyl above.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkylaryl is understood as meaning an aryl group (see above) being connected to another atom through a $C_{1-6}$-alkyl (see above) which may be branched or linear and is unsubstituted or substituted once or several times.

Preferably alkylaryl is understood as meaning an aryl group (see above) being connected to another atom through 1 to 4 ($-CH_2-$) groups. Most preferably alkylaryl is benzyl (i.e. $-CH_2$-phenyl). More preferably, the "alkyl" in alkylaryl is an unsubstituted alkyl.

In the context of this invention alkylheterocyclyl is understood as meaning an heterocyclyl group being connected to another atom through a Cis-alkyl (see above) which may be branched or linear and is unsubstituted or substituted once or several times. Preferably alkylheterocyclyl is understood as meaning an heterocyclyl group (see above) being connected to another atom through 1 to 4 ($-CH_r$) groups. Most preferably alkylheterocyclyl is $-CH_2$-pyridine. More preferably, the "alkyl" in alkylheterocyclyl is an unsubstituted alkyl.

In the context of this invention alkylcycloalkyl is understood as meaning an cycloalkyl group being connected to another atom through a $C_{1-6}$-alkyl (see above) which may be branched or linear and is unsubstituted or substituted once or several times. Preferably alkylcycloalkyl is understood as meaning a cycloalkyl group (see above) being connected to another atom through 1 to 4 ($-CH_2-$) groups. Most preferably alkylcycloalkyl is $-CH_2$-cyclopropyl. More preferably, the "alkyl" in alkylcycloalkyl is an unsubstituted alkyl.

Preferably, the aryl is a monocyclic aryl. More preferably the aryl is a 5, 6 or 7 membered monocyclic aryl. Even more preferably the aryl is a 5 or 6 membered monocyclic aryl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocytic cycloalkyl.

An heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepane, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, quinolone, isoquinoline, tetrahydrothienopyridine, phthalazine, benzo-1,2,5-thiadiazole, indole, benzotriazole, benzoxazole, oxopyrrolidine, benzodioxolane, benzodioxane, carbazole, oxaspirodecan or thiazole;

In general, such a heterocyclyl may contain between 3 and 32 atoms in the rings (preferably 4 to 20 atoms in the rings, or most preferably 5 to 18 atoms in the rings). Thus, a heterocyclyl may contain between 3 and 12 atoms in the ring (preferably 4 to 10 atoms in the ring, or 5 to 8 atoms in the ring, or 5 to 6 atoms in the ring) in case of a heterocyclyl of one saturated or unsaturated ring. Such a heterocyclyl may also contain between 5 and 22 atoms in both rings together (preferably 6 to 16 atoms in both rings together, or 7 to 12 atoms in both rings together or 8 to 10 atoms in both rings together) in case of a heterocyclyl of two saturated or unsaturated rings. Such a heterocyclyl may also contain between 7 and 32 atoms in the 3 rings together (preferably 10 to 22 atoms in the three rings together, or 12 to 20 atoms in the three rings together or 10 to 18 atoms in the three rings together) in case of a heterocyclyl of three saturated or unsaturated rings.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), $-R_k$, $-OR_k$, $-CN$, $-NO_2$, $-NR_kR_{k'}$, $-C(O)OR_k$, $-NR_kC(O)R_k$, $-C(O)NR_kR_{k'}$, $-NR_kS(O)_2R_{k'}$, $=O$, $-OCH_2CH_2OH$, $-NR_kC(O)NR_k$, $-S(O)_2NR_kR_{k'}$, $-NR_kS(O)_2NR_kR_{k'}-$, haloalkyl, haloalkoxy, $-SR_k$, $-S(O)R_k$, $-S(O)_2R_k$ or $-C(CH_3)OR_k$, or substituted or unsubstituted alkylcycloalkyl, substituted or unsubstituted alkylaryl, substituted or unsubstituted alkylheterocyclyl, with $R_k$, $R_k$ and $R_{k'}$ independently being either H or a saturated or unsaturated, linear or branched, substituted or unsubstituted $C_{1-6}$-alkyl: a saturated or unsaturated, linear or branched, substituted or unsubstituted $C_{1-6}$-alkyl: a saturated or unsaturated, linear or branched, substituted or unsubstituted $-O-C_{1-6}$-alkyl (alkoxy): a saturated or unsaturated, linear or branched, substituted or unsubstituted $S-C_{1-6}$ alkyl; a saturated or unsaturated, linear or branched, substituted or unsubstituted $-C(O)-C_{1-6}$ alkyl-group; a saturated or unsaturated, linear or branched, substituted or unsubstituted $-C(O)-O-C_{1-6}$alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_k$ one of $R_{11}$, $R_{14}$, $R_{41}R_{71}$, $R_{81}$ or $R_{91}$ (being $R_k$' one of $R_{11}$', $R_{14}$', $R_{41}$', $R_{71}$', $R_{81}$' or $R_{91}$' being $R_k$" one of $R_{11}$" $R_{14}$", $R_{41}$" $R_{71}$" $R_{81}$" or $R_{91}$") wherein $R_1$ to $R_{91}$' are as defined in the description, and wherein when different radicals $R_1$ to $R_{91}$" are present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alkylaryl, alkylcycloalkyl or alkylheterocydyl) with one or more of halogen (F, Cl, Br, I), $-R_k$, $-OR_k$, $-CN$, $-NO_2$, $-NR_kR_{k''}-$, $NR_kC(O)R_k$, $-NR_kS(O)_2R_{k'}$, $-S(O)_2NR_kR_{k'}$, $-NR_kC(O)NR_kR_k$", haloalkyl, haloalkoxy, $-SR_k$, $-S(O)R_k$ or $-S(O)_2R_k$, or substituted or unsubstituted alkylcycloalkyl, substituted or unsubstituted alkylaryl, substituted or unsubstituted alkylheterocyclyl, being $R_k$ one of $R_{11}$, $R_{14}$, $R_{41}$, $R_{71}$, $R_{81}$ or $R_{91}$, (being $R_{k'}$ one of $R_{11}$', $R_{14}$', $R_{41}$', $R_{71}$' $R_{81}$' or $R_{91}$' being $R_{k'}$ one of $R_{11}$", $R_{14}$" $R_{41}$" $R_{71}$" $R_{81}$" or $R_{91}$"), wherein $R_1$ to $R_{91}$" are as defined in the description, and wherein when different radicals $R_1$ to $R_{91}$" are present simultaneously in Formula I they may be identical or different.

In connection with cycloalkyl (including alkyl-cycloalkyl), or heterocyclyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl, non-aromatic heterocyclyl or non aromatic alkyl-heterocyclyl with

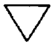 (leading to a Spiro structure) and/or with ═O.

Moreover, in connection with cycloalkyl (including alkyl-cycloalkyl), or heterocyclyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl, non-aromatic heterocyclyl or non aromatic alkyl-heterocyclyl is spirosubstituted or substituted with ═O.

Moreover, in connection with cycloalkyl (including alkyl-cycloalkyl), or heterocyclyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl, non-aromatic heterocyclyl or non aromatic alkyl-heterocyclyl with ═O.

A ring system is an organic system consisting of at least one ring of connected atoms but including also systems in which two or more rings of connected atoms (polycyclic ring system) are joined with "joined" meaning that the respective rings are sharing one (like a spiro structure), two or more atoms being a member or members of both joined rings.

The term "polycyclic ring system" means that the ring system is made of two or more rings joined by sharing at least one atom.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated-especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well-known methods of producing a prodrug of a given acting compound are known to those skilled in the art and can be found e.g. in Krogsgaard-Larsen et al. "Textbook of Drug design and Discovery" Taylor & Francis (April 2002).

Any compound that is an N-oxide of a compound according to the invention like a compound according to general formula I defined above is understood to be also covered by the scope of the invention.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention. This would especially also apply to the provisos described above so that any mentioning of hydrogen or any "H" in a formula would also cover deuterium or tritium.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general Formula (I) is a compound wherein $R_y$ and $R_y$' are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_y$ and $R_y$' are both hydrogen:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_y$" is selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_y$" is hydrogen:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_y$''' and $R_y$'''' are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_y$''' and $R_y$'''' are both hydrogen:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_w$ is hydrogen:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from the group consisting of hydrogen, halogen, substituted or unsubstituted $C_{1-6}$ alkyl, —$OR_8$, —$NR_8R_8$, —$NR_8C(O)R_8$', —$NR_8C(O)OR_8$', —$C(O)NR_8R_8$, —$C(O)OR_8$, —$OCHR_8R_8$', haloalkyl, haloalkoxy, —CN, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from the group consisting of hydrogen, halogen, substituted or unsubstituted $C_{1-6}$ alkyl, —$OR_8$, —$NR_8R_8$', haloalkyl, haloalkoxy, —CN, substituted or unsubstituted aryl and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from hydrogen, halogen, substituted or unsubstituted $C_{1-8}$ alkyl, —$OR_{21}$, —$NO_2$, —$NR_{21}R_{21}$', —$NR_{21}C(O)R_{21}$', —$NR_{21}S(O)_2R_{21}$', —$S(O)_2NR_{21}R_{21}$', —$NR_{21}C(O)NR_{21}$'$R_{21}$", —$SR_{21}$, —$S(O)R_{21}$, —$S(O)_2R_{21}$, —CN, haloalkyl, haloalkoxy, —$C(O)OR_{21}$, —$C(O)NR_{21}R_{21}$', —$NR_{21}S(O)_2NR_{21}$'$R_{21}$" and —$C(CH_3)_2OR_{21}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from hydrogen, halogen, substituted or unsubstituted $C_{1-6}$ alkyl and —$OR_{21}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_3$ is selected from hydrogen, halogen, substituted or unsubstituted $C_{1-6}$ alkyl, —$OR_{31}$, —$NO_3$, —$NR_{31}R_{31}$', —$NR_{31}C(O)R_{31}$', —$NR_{31}S(O)_3R_{31}$', —$S(O)_3NR_{31}R_{31}$', —$NR_{31}C(O)NR_{31}$'$R_{31}$", —$SR_{31}$, —$S(O)R_{31}$, —$S(O)_3R_{31}$, —CN, haloalkyl, haloalkoxy, —$C(O)OR_{31}$, —$C(O)NR_{31}R_{31}$', —$NR_{31}S(O)_3NR_{31}$'$R_{31}$" and —$C(CH_3)_3OR_{31}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_3$ is hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ is selected from hydrogen, substituted or unsubstituted $C_{1-6}$ alkyl, substituted or unsubstituted cycloalkyl, substituted or unsubstituted alkylheterocyclyl, substituted or unsubstituted alkylaryl and substituted or unsubstituted alkylcycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ is selected from hydrogen, substituted or unsubstituted $C_{1-6}$ alkyl, substituted or unsubstituted alkylheterocyclyl and substituted or unsubstituted alkylcycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ and $R_y$ taken together with the nitrogen and carbon atoms to which they are attached, respectively, may form a six atom members substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ and $R_y'''$ taken together with the nitrogen and carbon atoms to which they are attached, respectively, may form a six atom members substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_5$, $R_5'$ $R_5''$ and $R_5'''$ are independently selected from hydrogen, halogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_5$, $R_5'$, $R_5''$ and $R_6'''$ are all hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_6$, $R_6'$, $R_6''$ and $R_6'''$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_7$ is selected from the group consisting of hydrogen, substituted or unsubstituted $C_{1-6}$ alkyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_7$ is selected from the group consisting of hydrogen, substituted or unsubstituted $C_{1-6}$ alkyl and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein one of $R_5$ and $R_5'$, taken together with $R_7$ form a $-[CH_2]_n-$ bridge;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein one of $R_5$" and $R_5$"', taken together with $R_7$ form a —$[CH_2]_n$— bridge;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein one of $R_5$ and $R_5$', taken together with one of $R_5$" and $R_5$"' form a —$[CH_2]_n$— bridge;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein one of $R_5$ and $R_5$', taken together with one of $R_6$" and $R_6$"' form a —$[CH_2]_n$— bridge;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein one of $R_6$ and $R_6$', taken together with one of $R_6$" and $R_6$"' form a —$[CH_2]_n$— bridge:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein one of $R_6$ and $R_6$', taken together with one of $R_5$" and $R_5$"' form a —$[CH_2]_n$— bridge;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein one of $R_9$ and $R_9$', taken together with one of $R_6$" and $R_6$"' form a —$[CH_2]_n$— bridge;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein one of $R_9$ and $R_9$', taken together with one of $R_5$" and $R_5$"' form a —$[CH_2]_n$— bridge;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein n is 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein one of $R_5$ and $R_5$', taken together with $R_7$ form a —$CH_2CH_2$— bridge;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein one of $R_5$" and $R_5$"', taken together with $R_7$ form a —$CH_2CH_2$— bridge:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_8$ and $R_8$' are independently selected from the group consisting of hydrogen, substituted or unsubstituted $C_{1-8}$ alkyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_8$ and $R_8$' are independently selected from the group consisting of hydrogen, substituted or unsubstituted $C_{1-6}$ alkyl and substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_9$ and $R_9$' are independently selected from the group consisting of hydrogen, halogen, —$OR_{91}$, substituted or unsubstituted $C_{1-6}$ alkyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_9$ and $R_9$' are independently selected from the group consisting of hydrogen, halogen, —$OR_{91}$ and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{11}$, $R_{11}$' and $R_{11}$" are independently selected from hydrogen, substituted or unsubstituted $C_{1-6}$ alkyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{11}$, $R_{11}$' and $R_{11}$" are independently selected from hydrogen, substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{13}$ and $R_{13}$' are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{14}$, $R_{14}$' and $R_{14}$" are independently selected from hydrogen, unsubstituted $C_{1-6}$ alkyl, unsubstituted aryl, unsubstituted cycloalkyl and unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{21}$, $R_{21}$' and $R_{21}$" are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{21}$ is substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{31}$, $R_{31}$' and $R_{31}$" are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{41}$, $R_{41}$' and $R_{41}$" are independently selected from hydrogen, substituted or unsubstituted $C_{1-6}$ alkyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{41}$, $R_{41}$' and $R_{41}$" are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{51}$ and $R_{51}$' are independently selected from hydrogen and unsubstituted $C_{1-5}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{61}$ and $R_{61}'$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{71}$, $R_{71}'$ and $R_{71}''$ are independently selected from hydrogen, substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{81}$, $R_{81}'$ and $R_{81}''$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{81}$ is substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{91}$, $R_{91}'$ and $R_{91}''$ are independently selected from hydrogen and substituted or unsubstituted $C_{1-6}$ alkyl:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_y$ and $R_y'$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and/or alternatively, $R_y$ and $R_y'$ form, with the carbon atom to which they are attached, a substituted or unsubstituted cycloalkyl;

and/or $R_y''$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

and/or $R_y'''$ and $R_y''''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and/or alternatively, $R_y'''$ and $R_y''''$ form, with the carbon atom to which they are attached, a substituted or unsubstituted cycloalkyl;

and/or

W is nitrogen or —$CR_w$—;

and/or $R_w$ is hydrogen or halogen;

and/or $R_w$ and one of $R_5$, $R_5'$, $R_5''$ or $R_5'''$ form a double bond;

and/or w1 is selected from the group consisting of nitrogen and carbon;

and/or w2 is selected from the group consisting of nitrogen and carbon:

and/or w3 is selected from the group consisting of nitrogen and carbon;

and/or w4 is selected from the group consisting of nitrogen and carbon;

and/or $R_1$ is selected from the group consisting of hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_6$, —$NR_6R_6'$, —$NR_6C(O)R_8'$, —$NR_8C(O)OR_8'$, —$C(O)NR_8R_8$, —$C(O)OR_8$, —$OCHR_8R_8'$, haloalkyl, haloalkoxy, —CN, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

and/or $R_2$ is selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_{21}$, —$NO_2$, —$NR_{21}R_{21}'$, —$NR_{21}C(O)R_{21}'$, —$NR_{21}S(O)_2R_{21}'$, —$S(O)_2NR_{21}R_{21}'$, —$NR_{21}C(O)NR_{21}'R_{21}''$, —$SR_{21}$—$S(O)R_{21}$, —$S(O)_2R_{21}$, —CN, haloalkyl, haloalkoxy, —$C(O)OR_{21}$, —$C(O)NR_{21}R_{21}$, —$NR_{21}S(O)_2NR_{21}'R_{21}''$ and —$C(CH_3)_2OR_{21}$;

and/or $R_3$ is selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_{31}$, —$NO_3$, —$NR_{31}R_{31}'$, —$NR_{31}C(O)R_{31}'$, —$NR_{31}S(O)_3R_{31}'$, —$S(O)_3NR_{31}R_{31}'$, —$NR_{31}C(O)NR_{31}'R_{31}''$, —$SR_{31}$, —$S(O)R_{31}$, —$S(O)_3R_{31}$, —CN, haloalkyl, haloalkoxy, —$C(O)OR_{31}$, —$C(O)NR_{31}R_{31}'$, —$NR_{31}S(O)_3NR_{31}'R_{31}''$ and —$C(CH_3)_3OR_{31}$;

and/or $R_4$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylheterocyclyl, substituted or unsubstituted alkylaryl and substituted or unsubstituted alkylcycloalkyl;

and/or $R_4$ and $R_y$ taken together with the nitrogen and carbon atoms to which they are attached, respectively, may form a five or six atom members substituted or unsubstituted heterocyclyl;

and/or $R_4$ and $R_y'''$ taken together with the nitrogen and carbon atoms to which they are attached, respectively, may form a six atom members substituted or unsubstituted heterocyclyl;

and/or $R_5$, $R_5'$, $R_5''$ and $R_5'''$ are independently selected from hydrogen, halogen, substituted or unsubstituted $C_{1-6}$ alkyl, substituted or unsubstituted $C_{2-6}$ alkenyl and substituted or unsubstituted $C_{2-4}$ alkynyl;

and/or $R_5$ and $R_5'$ and/or $R_5''$ and $R_5'''$ taken together with the carbon atom to which they are attached form a carbonyl group;

and/or $R_6$, $R_6'$, $R_6''$ and $R_6'''$ are independently selected from hydrogen, substituted or unsubstituted $C_{1-6}$ alkyl, substituted or unsubstituted $C_{2-6}$ alkenyl and substituted or unsubstituted $C_{2-4}$ alkynyl;

and/or $R_7$ is selected from the group consisting of hydrogen, substituted or unsubstituted Cis alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

and/or one of $R_5$ and $R_3$, taken together with $R_7$ form a $—[CH_2]_n—$ bridge:

and/or n is 1, 2 or 3;

and/or $R_8$ and $R_8'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

and/or $R_9$ and $R_9'$ are independently selected from the group consisting of hydrogen, halogen, $—OR_{91}$, substituted or unsubstituted $C_{1-6}$ alkyl, substituted or unsubstituted $C_{2-6}$ alkenyl, substituted or unsubstituted $C_{2-8}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

and/or $R_{11}$, $R_{11}'$ and $R_{11}''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

and/or $R_{13}$ and $R_{13}'$ are independently selected from hydrogen, unsubstituted $C_{1-6}$ alkyl, unsubstituted $C_{2-6}$ alkenyl, and unsubstituted $C_{2-6}$ alkynyl;

and/or $R_{14}$, $R_{14}'$ and $R_{14}''$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and/or $R_{21}$, $R_{21}'$ and $R_{21}''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and/or $R_{31}$, $R_{31}'$ and $R_{31}''$ are independently selected from hydrogen, substituted or unsubstituted $C_{1-6}$ alkyl, substituted or unsubstituted $C_{3-6}$ alkenyl and substituted or unsubstituted $C_{3-6}$ alkynyl;

and/or $R_{41}$, $R_{41}'$ and $R_{41}''$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

and/or $R_{51}$ and $R_{51}'$ are independently selected from hydrogen, unsubstituted $C_{1-5}$ alkyl, unsubstituted $C_{2-5}$ alkenyl, and unsubstituted $C_{2-5}$ alkynyl;

and/or $R_{61}$ and $R_{61}'$ are independently selected from hydrogen, unsubstituted $C_{1-6}$ alkyl, unsubstituted $C_{2-6}$ alkenyl, and unsubstituted $C_{2-6}$ alkynyl;

and/or $R_{71}$, $R_{71}'$ and $R_{71}''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and/or $R_{81}$, $R_{81}'$ and $R_{81}''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and/or $R_{91}$, $R_{91}'$ and $R_{91}''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_y$ and $R_y'$ as defined in any of the embodiments of the present, invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-8}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_y''$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_y'''$ and $R_y''''$ as defined in any of the embodiments of the present invention, the $C_{1-8}$ alkyl is preferably selected from methyl, ethyl, propyl, butyl, pentyl, hexyl, isopropyl, or 2-methylpropyl;

and/or the $C_{2-8}$-alkenyl is preferably selected from ethylene, propylene, butylene, pentylene, hexylene, isopropylene and isobutylene;

and/or the $C_{2-8}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in IR, as defined in any of the embodiments of the present invention, the alkyl in alkylaryl, alkylheterocyclyl, alkylcycloalkyl, haloalkyl or haloalkoxy is $C_{1-8}$ alkyl like methyl, ethyl, propyl, butyl, pentyl, hexyl, isopropyl, or 2-methylpropyl; more preferably the alkyl is methyl;

and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphthyl, or anthracene; preferably is naphthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepane, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline. Isoquinoline, phthalazine, benzo-1,2,5-thiadiazole, indole, benzotriazole, benzoxazole, oxopyrrolidine, pyrimidine, benzodioxolane, benzodioxane, carbazole, octahydro-ethanopyrrolo-pyridine, oxaspirodecane, oxadiazaspiroundecane, indoline-2-one and quinazolines;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_2$ as defined in any of the embodiments of the present invention, the alkyl in haloalkyl or haloalkoxy is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ as defined in any of the embodiments of the present invention, the alkyl in haloalkyl or haloalkoxy is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_4$ as defined in any of the embodiments of the present invention, the alkyl in alkylaryl, alkylheterocyclyl, alkylcycloalkyl, haloalkyl or haloalkoxy is $C_{1-6}$ alkyl like methyl, ethyl, propyl, butyl, pentyl, hexyl, isopropyl, or 2-methylpropyl; more preferably the alkyl is methyl;

and/or the $C_{1-6}$ alkyl is preferably selected from methyl, ethyl, propyl, butyl, pentyl, hexyl, isopropyl, or 2-methylpropyl; more preferably the $C_{1-8}$ alkyl is methyl, ethyl, propyl, isopropyl, butyl, isobutyl or isopentyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl Is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

and/or the aryl is selected from phenyl, naphthyl, or anthracene; preferably is naphthyl and phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepane, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2.3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, octahydro-ethanopyrrolo-pyridine, oxaspirodecane, oxadiazaspiroundecane, indoline-2-one and quinazoline; preferably the heterocyclyl is furan;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$, $R_5'$, $R_5''$ and $R_5'''$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$, $R_6'$ $R_6''$ and $R_6'''$ as defined in any of the embodiments of the present invention, the $C_{1-6}$ alkyl is preferably selected from methyl, ethyl, propyl, butyl, pentyl, hexyl, isopropyl, or 2-methylpropyl; preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_7$ as defined in any of the embodiments of the present invention, the alkyl in alkylaryl, alkylheterocyclyl or alkylcycloalkyl is $C_{1-6}$ alkyl like methyl, ethyl, propyl, butyl, pentyl, hexyl, isopropyl, or 2-methylpropyl; more preferably the alkyl is methyl;

and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl;

and/or the aryl is selected from phenyl, naphthyl, or anthracene; preferably is naphthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepane, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, octahydro-ethanopyrrolo-pyridine, oxaspirodecane, oxadiazaspiroundecane, indoline-2-one and quinazoline;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$ and $R_6'$ as defined in any of the embodiments of the present invention, the alkyl in alkylaryl, alkylheterocyclyl or alkylcycloalkyl is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, or 2-methylpropyl; more preferably the $C_{1-5}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphthyl, or anthracene; preferably is naphthyl and phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepane, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, octahydro-ethanopyrrolo-pyridine, oxaspirodecane, oxadiazaspiroundecane, indoline-2-one and quinazoline; preferably the heterocyclyl is piperidine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_9$ and $R_9$' as defined in any of the embodiments of the present invention, the alkyl in alkylaryl, alkylheterocyclyl, alkylcycloalkyl, haloalkyl or haloalkoxy is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphthyl, or anthracene; preferably is naphthyl and phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more, heteroatoms selected from the group consisting of nitrogen, oxygen and/or sulfur in the ring, more preferably is selected from oxazepane, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, octahydro-ethanopyrrolo-pyridine, oxaspirodecane, oxadiazaspiroundecane, indoline-2-one and quinazoline:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11}$' and $R_{11}$" as defined in any of the embodiments of the present invention, the alkyl in alkylaryl, alkylheterocyclyl or alkylcycloalkyl is $C_{1-8}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-8}$ cycloalkyl like cyclopropyl, cyclobutyl, cyclopentyl or cyclohexyl;

and/or the aryl is selected from phenyl, naphthyl, or anthracene; preferably is naphthyl and phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepane, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, octahydro-ethanopyrrolo-pyridine, oxaspirodecane, oxadiazaspiroundecane, indoline-2-one and quinazoline:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$ and $R_{13}$' as defined in any of the embodiments of the present invention, the $C_{1-5}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14}$, $R_{14}'$ and $R_{14}''$ as defined in any of the embodiments of the present Invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphthyl, or anthracene; preferably is naphthyl and phenyl;

and/or the heterocycyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepane, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, octahydro-ethanopyrrolo-pyridine, oxaspirodecane, oxadiazaspiroundecane, indoline-2-one and quinazoline;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{21}$, $R_{21}'$ and $R_{21}''$ as defined in any of the embodiments of the present invention, the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{31}$, $R_{31}'$ and $R_{31}''$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{41}$, $R_{41}'$ and $R_{41}''$ as defined in any of the embodiments of the present invention, the alkyl in alkylaryl, alkylheterocyclyl or alkylcycloalkyl is $C_{1-6}$ alkyl like methyl, ethyl, propyl, butyl hexyl, isopropyl, or 2-methylpropyl;

and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-8}$ cycloalkyl like cyclopropyl, cyclobutyl, cyclopentyl or cyclohexyl;

and/or the aryl is selected from phenyl, naphthyl, or anthracene; preferably is naphthyl and phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepane, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, octahydro-ethanopyrrolo-pyridine, oxaspirodecane, oxadiazaspiroundecane, indoline-2-one and quinazoline;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{51}$ and $R_{51}$' as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{61}$ and $R_{61}$' as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-4}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{71}$, $R_{71}$' and $R_{71}$" as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{81}$, $R_{81}$' and $R_{81}$" as defined in any of the embodiments of the present invention, the $C_{1-6}$ alkyl is preferably selected from methyl, ethyl, propyl, butyl, pentyl, hexyl, isopropyl, or 2-methylpropyl; more preferably the $C_{1-6}$alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{91}$, $R_{91}$' and $R_{91}$" as defined in any of the embodiments of the present invention, the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein W is nitrogen or —$CR_w$—; wherein $R_w$ is hydrogen or halogen; preferably W is nitrogen or —$CR_w$—; wherein $R_w$ is hydrogen; more preferably W is nitrogen or —CH—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $w_1$ is nitrogen or carbon;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $w_2$ is nitrogen or carbon;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $w_3$ is nitrogen or carbon;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $w_4$ is nitrogen or carbon optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_y$ and $R_y'$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_y$ and $R_y'$ are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_y''$ is selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_y''$ is hydrogen, optionally in form of one of the stereoisomers, preferably enantiomers or diastereomers, a racemate or in form of a mixture of at least two of the stereoisomers.

preferably enantiomers and/or diastereomers, in any mixing ratio, or a corresponding salt thereof, or a corresponding solvate thereof.

In another preferred embodiment of the invention according to general Formula (I) the compound is a compound, wherein $R_y'''$ and $R_y''''$ are independently selected from hydrogen, substituted or unsubstituted $C_{1-6}$ alkyl, substituted or unsubstituted $C_{2-8}$ alkenyl and substituted or unsubstituted $C_{2-6}$ alkynyl; preferably $R_y$ and $R_y'$ are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_1$ is selected from the group consisting of hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_8$, —$NR_8R_8'$, —$NR_8C(O)R_8'$, —$NR_8C(O)OR_8'$, —$C(O)NR_8R_8$, —$C(O)OR_8$, —$OCHR_8R_8'$, haloalkyl, haloalkoxy, —CN, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl; preferably $R_1$ is selected from the group consisting of hydrogen, halogen, substituted or unsubstituted $C_{1-6}$ alkyl, —$OR_8$, —$NR_8R_8'$, haloalkyl, haloalkoxy, —CN, substituted or unsubstituted aryl, and substituted or unsubstituted alkylaryl; more preferably $R_1$ is selected from the group consisting of hydrogen, bromine, chlorine, fluorine, iodine, substituted or unsubstituted methyl, substituted or unsubstituted ethyl, —NH(methylpiperidine), —CN, —$OCH_3$, —OH, —$CF_3$, —$OCF_3$, substituted or unsubstituted phenyl, substituted or unsubstituted benzyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_2$ is selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_{21}$, —$NO_2$, —$NR_{21}R_{21}'$, —$NR_{21}C(O)R_{21}'$, —$NR_{21}S(O)_2R_{21}'$, —$S(O)_2NR_{21}R_{21}'$, —$NR_{21}C(O)NR_{21}'R_{21}''$, —$SR_{21}$, —$S(O)R_{21}$, —$S(O)_2R_{21}$, —CN, haloalkyl, haloalkoxy, —$C(O)OR_{21}$, —$C(O)NR_{21}R_{21}'$, —$NR_{21}S(O)_2NR_{21}'R_{21}''$ and —$C(CH_3)_2OR_{21}$; preferably $R_2$ is selected from hydrogen, halogen, substituted or unsubstituted $C_{1-6}$ alkyl and —$OR_{21}$; more preferably $R_2$ is selected from hydrogen, fluorine, bromine, chlorine, substituted or unsubstituted methyl and —$OCH_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_3$ is selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_{31}$, —$NO_3$, —$NR_{31}R_{31}'$, —$NR_{31}C(O)R_{31}'$, —$NR_{31}S(O)_3R_{31}'$, —$S(O)_3NR_{31}R_{31}'$, —$NR_{31}$, $C(O)NR_{31}'R_{31}''$, —$SR_{31}$, —$S(O)R_{31}$, —$S(O)_3R_{31}$, —CN, haloalkyl, haloalkoxy, —$C(O)OR_{31}$, —$C(O)NR_{31}R_{31}'$, —$NR_{31}S(O)_3NR_{31}R_{31}''$ and —$C(CH_3)_3OR_{31}$; preferably $R_3$ is hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_4$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylheterocyclyl, substituted or unsubstituted alkylaryl and substituted or unsubstituted alkylcycloalkyl; preferably $R_4$ is selected from hydrogen, substituted or unsubstituted alkyl, substituted or unsubstituted alkylheterocyclyl and substituted or unsubstituted alkylcycloalkyl; more preferably at is selected from hydrogen, substituted or unsubstituted methyl, substituted or unsubstituted ethyl, substituted or unsubstituted propyl, substituted or unsubstituted isopropyl, substituted or unsubstituted butyl, substituted or unsubstituted isobutyl, substituted or unsubstituted isopentyl, —$CH_2COOH$, —$CH_2CH_2OCH_3$, substituted or unsubstituted —$CH_2$-cyclopropyl and substituted or unsubstituted —$CH_2$-furan;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_4$ and $R_y$ taken together with the nitrogen and carbon atoms to which they are attached, respectively, may form a five or six atom members substituted or unsubstituted heterocyclyl; preferably, $R_4$ and $R_y$ taken together with the nitrogen and carbon atoms to which they are attached, may form a six atom members substituted or unsubstituted heterocyclyl: more preferably, $R_4$ and $R_y$ taken together with the nitrogen and carbon atoms to which they are attached, may form a substituted or unsubstituted piperidine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_5$, $R_5'$ $R_5''$ and $R_5'''$ are independently selected from hydrogen, halogen, substituted or unsubstituted $C_{1-6}$ alkyl, substituted or unsubstituted $C_{2-4}$ alkenyl and substituted or unsubstituted $C_{2-6}$ alkynyl; preferably $R_5$, $R_5'$, $R_5''$ and $R_5'''$ are all hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_6$, $R_6'$, $R_6''$ and $R_6'''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_6$, $R_6'$ $R_6''$ and $R_6'''$ are independently selected from hydrogen and substituted or unsubstituted $C_{1-6}$ alkyl; more preferably $R_6$, $R_6'$ $R_6''$ and $R_6'''$ are independently selected from hydrogen and substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_7$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl; preferably $R_7$ is selected from the group consisting of hydrogen, substituted or unsubstituted $C_{1-6}$ a alkyl and substituted or unsubstituted alkylaryl; more preferably $R_7$ is selected from the group consisting of hydrogen, substituted or unsubstituted methyl, substituted or unsubstituted ethyl, substituted or unsubstituted benzyl and substituted or unsubstituted phenethyl:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_5$ and $R_5$', taken together with $R_7$ form a —$[CH_2]_n$— bridge; preferably $R_5$ and $R_5$', taken together with $R_7$ form a —$CH_2CH_2$— bridge;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_8$ and $R_8$' are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl; preferably $R_6$ and $R_8$' are independently selected from the group consisting of hydrogen, substituted or unsubstituted $C_{1-6}$ alkyl and substituted or unsubstituted heterocyclyl; more preferably $R_8$ and $R_8$' are independently selected from the group consisting of hydrogen, substituted or unsubstituted methyl and substituted or unsubstituted piperidine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_9$ and $R_9$' are independently selected from the group consisting of hydrogen, halogen, —$OR_{91}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl; preferably $R_9$ and $R_9$' are independently selected from the group consisting of hydrogen, halogen, —$OR_{91}$ and substituted or unsubstituted $C_{1-6}$ alkyl; more preferably $R_9$ and $R_9$' are independently selected from the group consisting of hydrogen, fluorine, —$CH_2OCH_3$, —OH, substituted or unsubstituted methyl and substituted or unsubstituted ethyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{21}$, $R_{21}$' and $R_{21}$" are independently selected from hydrogen, substituted or unsubstituted $C_{1-4}$ alkyl, substituted or unsubstituted $C_{2-6}$ alkenyl and substituted or unsubstituted $C_{2-6}$ alkynyl; preferably, $R_{21}$ is substituted or unsubstituted $C_{1-6}$ alkyl; more preferably, $R_{21}$ is substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{41}$, $R_{41}$' and $R_{41}$" are independently selected from hydrogen and substituted or unsubstituted $C_{1-6}$ alkyl; preferably, $R_{41}$ is selected from hydrogen and substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{61}$ is substituted or unsubstituted $C_{1-6}$ alkyl; preferably, $R_{61}$ is substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{91}$, $R_{91}$' and $R_{91}$" are independently selected from hydrogen and substituted or unsubstituted $C_{1-6}$ alkyl; preferably, $R_{91}$ is selected from hydrogen and substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein W is nitrogen or —$CR_w$—; wherein $R_w$ is hydrogen or halogen;

and/or $w_1$ is nitrogen or carbon;

and/or $w_2$ is nitrogen or carbon;

and/or $w_3$ is nitrogen or carbon;

and/or $w_4$ is nitrogen or carbon and/or $R_y$ and $R_y$" are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_y$, and $R_y$' are both hydrogen;

and/or $R_y$" is selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_y$'' is hydrogen.

and/or $R_y$''' and $R_y$'''' are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_y$ and $R_y$' are both hydrogen;

and/or $R_1$ is selected from the group consisting of hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_8$, —$NR_8R_8$', —$NR_8C(O)R_8$', —$NR_8C(O)OR_8$', —$C(O)NR_8R_8$, —$C(O)OR_8$, —$OCHR_8R_8$', haloalkyl, haloalkoxy. —CN, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl; preferably $R_1$ is selected from the group consisting of hydrogen, halogen, substituted or unsubstituted $C_{1-6}$ alkyl, —$OR_8$, —$NR_8R_8$', haloalkyl, haloalkoxy, —CN, substituted or unsubstituted aryl, and substituted or unsubstituted alkylaryl; more preferably $R_1$ is selected from the group consisting of hydrogen, bromine, chlorine, fluorine, iodine, substituted or unsubstituted methyl, substituted or unsubstituted ethyl, —NH(methylpiperidine), —CN, —$OCH_3$, —OH, —$CF_3$, —$OCF_3$, substituted or unsubstituted phenyl, substituted or unsubstituted benzyl;

and/or $R_2$ is selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_{21}$, —$NO_2$, —$NR_{21}R_{21}$'', —$NR_{21}C(O)R_{21}$', —$NR_{21}S(O)_2R_{21}$', —$S(O)_2NR_{21}R_{21}$', —$NR_{21}C(O)NR_{21}$'$R_{21}$'', —$SR_{21}$, —$S(O)R_{21}$, —$S(O)_2R_{21}$, —CN, haloalkyl, haloalkoxy, —$C(O)OR_{21}$, —$C(O)NR_{21}R_{21}$', —$NR_{21}S(O)_2NR_{21}$''$R_{21}$'' and —$C(CH_3)_2OR_{21}$; preferably $R_2$ is selected from hydrogen, halogen, substituted or unsubstituted $C_{1-6}$ alkyl and —$OR_{21}$; more preferably $R_2$ is selected from hydrogen, fluorine, bromine, chlorine, substituted or unsubstituted methyl and —$OCH_3$:

and/or $R_3$ is selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_{31}$, —$NO_3$, —$NR_{31}R_{31}$', $NR_{31}C(O)R_{31}$', —$NR_{31}S(O)_3R_{31}$', —$S(O)_3NR_{31}R_{31}$', —$NR_{31}C(O)NR_{31}$'$R_{31}$'', —$SR_{31}$—$S(O)R_{31}$, —$S(O)_3R_{31}$, —CN, haloalkyl, haloalkoxy, —$C(O)OR_{31}$, —$C(O)NR_{31}R_{31}$', —$NR_{31}S(O)_3NR_{31}$'$R_{31}$'' and —$C(CH_3)_3OR_{31}$; preferably $R_3$ is hydrogen;

and/or $R_4$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylheterocyclyl, substituted or unsubstituted alkylaryl and substituted or unsubstituted alkylcycloalkyl; preferably $R_4$ is selected from hydrogen, substituted or unsubstituted $C_{1-6}$ alkyl, substituted or unsubstituted alkylheterocyclyl and substituted or unsubstituted alkylcycloalkyl; more preferably $R_4$ is selected from hydrogen, substituted or unsubstituted methyl, substituted or unsubstituted ethyl, substituted or unsubstituted propyl, substituted or unsubstituted isopropyl, substituted or unsubstituted butyl, substituted or unsubstituted isobutyl, substituted or unsubstituted isopentyl, —$CH_2COOH$, —$CH_2CH_2OCH_3$, substituted or unsubstituted —$CH_2$-cyclopropyl and substituted or unsubstituted —$CH_2$-furan;

and/or $R_4$ and $R_y$ taken together with the nitrogen and carbon atoms to which they are attached, respectively, may form a five or six atom members substituted or unsubstituted heterocyclyl; preferably, $R_4$ and $R_y$ taken together with the nitrogen and carbon atoms to which they are attached, may form a six atom members substituted or unsubstituted heterocyclyl; more preferably, $R_4$ and $R_y$ taken together with the nitrogen and carbon atoms to which they are attached, may form a substituted or unsubstituted piperidine;

and/or $R_5$, $R_5$', $R_5$'' and $R_5$''' are independently selected from hydrogen, halogen, substituted or unsubstituted $C_{1-6}$ alkyl, substituted or unsubstituted $C_{2-6}$ alkenyl and substituted or unsubstituted $C_{2-6}$ alkynyl; preferably $R_5$, $R_5$', $R_5$'' and $R_6$''' are all hydrogen;

and/or $R_6$, $R_6$', $R_6$'' and $R_6$''' are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_6$, $R_6$', $R_6$'' and $R_6$''' are independently selected from hydrogen and substituted or unsubstituted $C_{1-6}$ alkyl; more preferably $R_6$, $R_6$' $R_6$'' and $R_6$''' are independently selected from hydrogen and substituted or unsubstituted methyl:

and/or $R_7$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl; preferably $R_7$ is selected from the group consisting of hydrogen, substituted or unsubstituted $C_{1-6}$ alkyl and substituted or unsubstituted alkylaryl; more preferably $R_7$ is selected from the group consisting of hydrogen, substituted or unsubstituted methyl, substituted or unsubstituted ethyl, substituted or unsubstituted benzyl and substituted or unsubstituted phenethyl;

and/or one of $R_5$, $R_5$' $R_5$'' and $R_5$''', taken together with $R_7$ form a —$CH_2CH_2$— bridge; preferably one of $R_5$ and $R_5$', taken together with $R_7$ form a —$CH_2CH_2$— bridge and/or one of $R_5$'' and $R_5$''', taken together with $R_7$ form a —$CH_2CH_2$— bridge; more preferably one of $R_5$ and $R_5$', taken together with $R_7$ form a —$CH_2CH_2$— bridge;

and/or $R_9$ and $R_8$' are independently selected from the group consisting of hydrogen, substituted or unsubstituted $C_{1-6}$ alkyl, substituted or unsubstituted $C_{2-8}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl; preferably $R_8$ and $R_8$' are independently selected from the group consisting of hydrogen, substituted or unsubstituted $C_{1-6}$ alkyl and substituted or unsubstituted heterocyclyl; more preferably $R_8$ and $R_9$' are independently selected from the group consisting of hydrogen, substituted or unsubstituted methyl and substituted or unsubstituted piperidine;

and/or $R_9$ and $R_9$' are independently selected from the group consisting of hydrogen, halogen, —$OR_{91}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl; preferably $R_9$ and $R_9$' are independently selected from the group consisting of hydrogen, halogen, —$OR_{91}$ and substituted or unsubstituted $C_{1-6}$ alkyl; more preferably $R_9$ and $R_9$' are independently selected from the group consisting of hydrogen, fluorine, —$CH_2OCH_3$, —OH, substituted or unsubstituted methyl and substituted or unsubstituted ethyl;

and/or $R_{21}$, $R_{21}$' and $R_{21}$" are independently selected from hydrogen, substituted or unsubstituted $C_{1-4}$ alkyl, substituted or unsubstituted $C_{2-6}$ alkenyl and substituted or unsubstituted $C_{2-6}$ alkynyl; preferably, $R_2$, is substituted or unsubstituted $C_{1-6}$ alkyl; more preferably, $R_{21}$ is substituted or unsubstituted methyl;

and/or $R_{41}$, $R_{41}$' and $R_{41}$" are independently selected from hydrogen and substituted or unsubstituted $C_{1-6}$ alkyl; preferably, $R_{41}$ is selected from hydrogen and substituted or unsubstituted methyl;

and/or $R_{51}$ is substituted or unsubstituted $C_{1-6}$ alkyl; preferably, $R_{51}$ is substituted or unsubstituted methyl:

and/or $R_{91}$, $R_{91}$' and $R_{91}$" are independently selected from hydrogen and substituted or unsubstituted $C_{1-6}$ alkyl; preferably, $R_{91}$ is selected from hydrogen and substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment

W is nitrogen or —$CR_w$—.

In a preferred embodiment $R_w$ is hydrogen.

In a preferred embodiment $w_1$ is nitrogen or carbon.

In a preferred embodiment $w_2$ is nitrogen or carbon.

In a preferred embodiment $w_3$ is nitrogen or carbon.

In a preferred embodiment $w_4$ is nitrogen or carbon.

In a preferred embodiment $w_1$, $w_2$, $w_3$ and $w_4$ are all carbon.

In a preferred embodiment $w_1$ is nitrogen, while $w_2$, $w_3$ and $w_4$ are all carbon.

In a preferred embodiment $w_2$ is nitrogen, while $w_1$, $w_3$ and $w_4$ are all carbon.

In a preferred embodiment $w_3$ is nitrogen, while $w_2$, $w_1$ and $w_4$ are all carbon.

In a preferred embodiment $w_4$ is nitrogen, while $w_2$, $w_3$ and $w_1$ are all carbon.

In a preferred embodiment $R_y$ and $R_y$' are both hydrogen.

In a preferred embodiment $R_y$" is hydrogen.

In a preferred embodiment $R_y$ and $R_y$' are both hydrogen.

In a preferred embodiment $R_1$ is selected from the group consisting of hydrogen, bromine, chlorine, fluorine, iodine, substituted or unsubstituted methyl, substituted or unsubstituted ethyl, —NH (methylpiperidine), —CN, —$OCH_3$, —OH, —$CF_3$, —$OCF_3$, substituted or unsubstituted phenyl, substituted or unsubstituted benzyl.

In a preferred embodiment $R_2$ is selected from hydrogen, fluorine, bromine, chlorine, substituted or unsubstituted methyl and —$OCH_3$.

In a preferred embodiment $R_3$ is hydrogen.

In a preferred embodiment $R_4$ is selected from hydrogen, substituted or unsubstituted methyl, substituted or unsubstituted ethyl, substituted or unsubstituted propyl, substituted or unsubstituted isopropyl, substituted or unsubstituted butyl, substituted or unsubstituted isobutyl, substituted or unsubstituted isopentyl, —$CH_2COOH$, —$CH_2CH_2OCH_3$, substituted or unsubstituted —$CH_2$-cyclopropyl and substituted or unsubstituted —$CH_2$-furan.

In a preferred embodiment $R_4$ and $R_y$ taken together with the nitrogen and carbon atoms to which they are attached, may form a substituted or unsubstituted piperidine.

In a preferred embodiment $R_5$, $R_5$' $R_5$" and $R_5$'" are all hydrogen.

In a preferred embodiment $R_6$, $R_6$' $R_6$" and $R_6$'" are independently selected from hydrogen and substituted or unsubstituted methyl.

In a preferred embodiment $R_6$ is selected from hydrogen and substituted or unsubstituted methyl.

In a preferred embodiment $R_6$' is selected from hydrogen.

In a preferred embodiment $R_6$" is selected from hydrogen and substituted or unsubstituted methyl.

In a preferred embodiment $R_6$'" is selected from hydrogen and substituted or unsubstituted methyl.

In a preferred embodiment $R_6$ is selected from hydrogen and substituted or unsubstituted methyl, while $R_6$' is hydrogen.

In a preferred embodiment $R_6$ is substituted or unsubstituted methyl, while $R_6$' is hydrogen.

In a preferred embodiment $R_6$ and $R_6$' are both hydrogen.

In a preferred embodiment $R_6$" is selected from hydrogen and substituted or unsubstituted methyl, while $R_6$'" is selected from hydrogen and substituted or unsubstituted methyl.

In a preferred embodiment $R_6$'' is selected from hydrogen, while $R_6$''' is selected from hydrogen and substituted or unsubstituted methyl.

In a preferred embodiment $R_6$'' is substituted or unsubstituted methyl, while $R_6$''' is selected from hydrogen and substituted or unsubstituted methyl.

In a preferred embodiment $R_6$'' and $R_6$''' are both hydrogen.

In a preferred embodiment $R_6$'' and $R_6$''' are both substituted or unsubstituted methyl.

In a preferred embodiment $R_7$ is selected from the group consisting of hydrogen, substituted or unsubstituted methyl, substituted or unsubstituted ethyl, substituted or unsubstituted benzyl and substituted or unsubstituted phenethyl.

In a preferred embodiment one of $R_5$ and $R_5$', taken together with $R_7$ form a $—CH_2CH_2—$ bridge.

In a preferred embodiment $R_8$ and $R_8$' are independently selected from the group consisting of hydrogen, substituted or unsubstituted methyl and substituted or unsubstituted piperidine.

In a preferred embodiment $R_8$ is selected from the group consisting of hydrogen and substituted or unsubstituted methyl.

In a preferred embodiment $R_8$' is substituted or unsubstituted piperidine.

In a preferred embodiment $R_8$ is selected from the group consisting of hydrogen and substituted or unsubstituted methyl, while $R_8$' is substituted or unsubstituted piperidine.

In a preferred embodiment $R_8$ is hydrogen, while $R_8$' is substituted or unsubstituted piperidine.

In a preferred embodiment $R_9$ and $R_9$' are independently selected from the group consisting of hydrogen, fluorine, $—CH_2OCH_3$, —OH, substituted or unsubstituted methyl and substituted or unsubstituted ethyl.

In a preferred embodiment $R_9$ is selected from the group consisting of hydrogen, fluorine, $—CH_2OCH_3$, —OH, substituted or unsubstituted methyl and substituted or unsubstituted ethyl, while $R_9$' is selected from the group consisting of hydrogen and substituted or unsubstituted methyl.

In a preferred embodiment $R_9$ is substituted or unsubstituted methyl, while $R_9$' is selected from the group consisting of hydrogen and substituted or unsubstituted methyl.

In a preferred embodiment $R_9$ is substituted or unsubstituted methyl, while $R_9$' is hydrogen.

In a preferred embodiment $R_9$ and $R_9$' are both substituted or unsubstituted methyl.

In a preferred embodiment $R_9$ is substituted or unsubstituted ethyl, while $R_9$' is hydrogen.

In a preferred embodiment $R_9$ is —OH, while $R_9$' is hydrogen.

In a preferred embodiment $R_9$ and $R_9$' are both hydrogen.

In a preferred embodiment $R_9$ and $R_9$' are both fluorine.

In a preferred embodiment $R_{21}$ is substituted or unsubstituted methyl.

In a preferred embodiment $R_{41}$ is selected from hydrogen and substituted or unsubstituted methyl.

In a preferred embodiment $R_{61}$ is substituted or unsubstituted methyl.

In a preferred embodiment $R_{91}$ is selected from hydrogen and substituted or unsubstituted methyl.

In a preferred embodiment the haloalkyl is $—CF_3$.

In a preferred embodiment the haloalkoxy is $—OCF_3$.

In a preferred embodiment the alkyl, alkenyl or alkynyl defined in $R_1$, if substituted, is substituted with one or more substituent/s selected from $—OR_{11}$, halogen, —CN, haloalkoxy and $—NR_{11}R_{11}$';

In a preferred embodiment the alkyl, alkenyl or alkynyl defined in $R_1$, if substituted, is substituted with one or more halogen;

In a preferred embodiment the alkyl defined in $R_1$, if substituted, is substituted with one or more halogen:

In a preferred embodiment the cycloalkyl, aryl heterocyclyl, defined in $R_1$, also in alkylcycloalkyl, alkylaryl and alkylheterocyclyl, if substituted, is substituted with one or more substituent/s selected from =O, halogen, $—R_{11}$, $—OR_{11}$, $—NO_2$, $—NR_{11}R_{11}$', $—NR_{11}C(O)R_{11}$', $—S(O)_2NR_{11}R_{11}$', $—NR_{11}C(O)NR_{11}$'$R_{11}$'', $—S_{11}$, $—S(O)R_{11}$, $—S(O)_2R_{11}$, —CN, haloalkyl, haloalkoxy, $—C(O)OR_{11}$, $—C(O)NR_{11}R_{11}$', $—OCH_2CH_2OR_{11}S(O)_2NR_{11}$'$R_{11}$'', $—C(CH_3)_2OR_{11}$, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

In a preferred embodiment the alkyl, alkenyl or alkynyl defined in $R_8$ or $R_8$', if substituted, is substituted with one or more substituent/s selected from $—OR_{81}$, halogen, —CN, haloalkoxy and $—NR_{81}R_{81}$';

In a preferred embodiment the alkyl defined in $R_8$ or $R_8$', if substituted, is substituted with one or more substituents selected from $—OR_{51}$, halogen, —CN, haloalkoxy and $—NR_{61}R_{61}$';

In a preferred embodiment the cycloalkyl heterocyclyl or aryl defined in $R_8$ or $R_8$', also in alkylcycloalkyl, alkylheterocyclyl and alkylaryl if substituted, is substituted with one or more substituent/s selected from =O, halogen, $—R_{81}$, $—OR_{81}$, $—NO_2$, $—NR_{81}R_{81}$', $—NR_{81}C(O)R_{81}$', $—NR_{81}S(O)_2R_{81}$', $—S(O)_2NR_{81}R_{81}$', $—NR_{81}C(O)NR_{81}$'$R_{81}$'', $—SR_{51}$, $—S(O)R_{81}$, $—S(O)_2R_{81}$, —CN, haloalkyl, haloalkoxy, $—C(O)OR_{81}$, $—C(O)NR_{81}R_{81}$', $—OCH_7CH_2OR_{51}$, $—NR_{51}S(O)_2NR_{51}$'$R_{51}$'' and $—C(CH_3)_2OR_{51}$, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

In a preferred embodiment the cycloalkyl heterocyclyl or aryl defined in $R_8$ or $R_8$', also in alkylcycloalkyl, alkylheterocyclyl and alkylaryl if substituted, is substituted with one or more $—R_{81}$;

In a preferred embodiment the alkyl, alkenyl or alkynyl defined in $R_4$, if substituted, is substituted with one or more substituents selected from —$OR_{41}$, halogen, —CN, —C(O)$OR_{41}$, haloalkoxy, —$NR_{41}R_{41}$', substituted or unsubstituted cycloalkyl, substituted or unsubstituted heterocyclyl and substituted or unsubstituted aryl;

In a preferred embodiment the alkyl, alkenyl or alkynyl defined in $R_4$, if substituted, is substituted with one or more substituent/s selected from —$OR_{41}$ and —C(O)$OR_{41}$;

In a preferred embodiment the alkyl defined in $R_4$, if substituted, is substituted with one or more substituent/s selected from —$OR_4$, and —C(O)$OR_{41}$:

In a preferred embodiment the cycloalkyl as defined in $R_4$, also in alkylcycloalkyl, or the heterocyclyl in alkylheterocyclyl, or the aryl in alkylaryl, if substituted and the substitution has not been defined otherwise, it is substituted with one or more substituent/s selected from halogen, —$R_{41}$, —$OR_{41}$, —$NO_2$, —$NR_{41}R_{41}$', —$NR_{41}$C(O)$R_{41}$', —$NR_{41}S(O)_2R_{41}$', —$S(O)_2NR_{41}R_{41}$', —$NR_{41}$C(O) $NR_{41}$'$R_{41}$", —$SR_{41}$—S(O)$R_{41}$, —$S(O)_2R_{41}$, —CN, haloalkyl, haloalkoxy, —C(O)$OR_{41}$, —C(O)$NR_{41}R_{41}$', —$OCH_2CH_2OR_{41}$, —$NR_{41}S(O)_2NR_{41}$'$R_{41}$" and —$C(CH_3)_2OR_{41}$;

In a preferred embodiment the alkyl, alkenyl or alkynyl, in $R_5$, $R_5$' $R_5$" and $R_5$'", if substituted, it is substituted with one or more substituent/s selected from —$OR_{51}$, —C(O)$OR_{51}$ halogen, —CN haloalkoxy and —$NR_{61}R_{51}$';

In a preferred embodiment the alkyl in $R_5$, $R_5$', $R_6$" and $R_6$", if substituted, it is substituted with one or more substituent/s selected from —$OR_{61}$, —C(O)$OR_6$, halogen, —CN haloalkoxy and —$NR_{51}R_{51}$';

In a preferred embodiment the alkyl, alkenyl or alkynyl, in $R_8$, $R_6$' $R_6$" and $R_6$'", if substituted, it is substituted with one or more substituent/s selected from —$OR_{61}$, —C(O)$OR_{61}$, halogen, —CN, haloalkoxy and —$NR_{61}R_{61}$';

In a preferred embodiment the alkyl in $R_6$, $R_6$', $R_6$" and $R_6$'", if substituted, it is substituted with one or more substituent/s selected from —$OR_{61}$, —C(O)$OR_{61}$ halogen, —CN, haloalkoxy and —$NR_{61}R_{61}$':

In a preferred embodiment the alkyl, alkenyl or alkynyl defined in $R_7$, if substituted, is substituted with one or more substituent/s selected from —$OR_{71}$, halogen, —CN, haloalkoxy and —$NR_{71}R_{71}$';

In a preferred embodiment the alkyl defined in $R_7$, if substituted, is substituted with one or more substituent/s selected from —$OR_{71}$, halogen, —CN, haloalkoxy and —$NR_{71}R_{71}$';

In a preferred embodiment the cycloalkyl heterocyclyl or aryl defined in $R_7$, also in alkylcycloalkyl, alkylheterocyclyl and alkylaryl if substituted, is substituted with one or more substituents selected from =O, halogen, —$R_{71}$, —$OR_{71}$, —$NO_2$, —$NR_{71}R_{71}$', —$NR_{71}$C(O)$R_{71}$', —$NR_{71}S(O)_2R_{71}$', —$S(O)_2NR_{71}R_{71}$', $NR_{71}$C(O)$NR_{71}$'$R_{71}$", —$SR_{71}$', —S(O)$R_{71}$, —$S(O)_2R_{71}$, —CN, haloalkyl, haloalkoxy, —C(O)$OR_{71}$, —C(O)$NR_{71}R_{71}$', —$OCH_2CH_2OR_{71}$, —$NR_{71}S(O)_2NR_{71}R_{71}$" and —$C(CH_3)_2OR_{71}$, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

In a preferred embodiment the alkyl, alkenyl or alkynyl defined in $R_9$ or $R_9$', if substituted, is substituted with one or more substituent/s selected from —$OR_{91}$, halogen, —CN, haloalkoxy and —$NR_{91}R_{91}$';

In a preferred embodiment the alkyl defined in $R_9$ or $R_9$', if substituted, is substituted with one or more substituents selected from —$OR_{91}$, halogen. —CN, haloalkoxy and —$NR_{91}R_{91}$';

In a preferred embodiment the alkyl, alkenyl or alkynyl defined in $R_9$ or $R_9$', if substituted, is substituted with one or more —$OR_{91}$;

In a preferred embodiment the alkyl defined in $R_9$ or $R_9$', if substituted, is substituted with one or more —$OR_{91}$;

In a preferred embodiment the cycloalkyl heterocyclyl or aryl defined in $R_9$ or $R_9$', also in alkylcycloalkyl, alkylheterocyclyl and alkylaryl if substituted, is substituted with one or more substituents selected from =O, halogen, —$R_{91}$, —$OR_{91}$, —$NO_2$, —$NR_{91}R_{91}$', —$NR_{91}$C(O)$R_{91}$'.

—$NR_{91}S(O)_2R_{91}$', —$S(O)_2NR_{91}R_{91}$', $NR_{91}$C(O) $NR_{91}$'$R_{91}$", —$SR_9$, —S(O)$R_{91}$, —$S(O)_2R_{91}$, —CN, haloalkyl, haloalkoxy, —C(O)$OR_{91}$, —C(O)$NR_{91}R_{91}$', —$OCH_2CH_2OR_{91}$, —$NR_{91}S(O)_2NR_{91}$'$R_{91}$" and —$C(CH_3)_2OR_{91}$, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

In a preferred embodiment the alkyl, alkenyl or alkynyl, if substituted and the substitution has not been defined otherwise, it is substituted with one or more substituents selected from —$OR_{13}$, halogen, —CN, haloalkoxy and —$NR_{13}R_{13}$';

In a preferred embodiment the alkyl if substituted and the substitution has not been defined otherwise, it is substituted with one or more substituent/s selected from —$OR_{13}$, halogen, —CN, haloalkoxy and —$NR_{13}R_{13}$':

In a preferred embodiment the aryl, heterocyclyl or cycloalkyl, also in alkylaryl, alkylheterocyclyl or alkylcycloalkyl, if substituted and the substitution has not been defined otherwise, it is substituted with one or more substituents selected from halogen, —$R_{14}$, —$OR_{14}$, —$NO_2$, —$NR_{14}R_{14}$', —$NR_{14}$C(O)$R_{14}$, —$NR_{14}S(O)_2R_{14}$', —$S(O)_2$ $NR_{14}R_{14}$', —$NR_{14}$C(O)$NR_{14}R_{14}$", —S(O)$R_{14}$, —$S(O)_2R_{14}$, —CN, haloalkyl, haloalkoxy, —C(O)$O_{14}$, —C(O)$NR_{14}R_{14}$', —$OCH_2CH_2OR_{14}$, —$NR_{14}S(O)_2NR_{14}$'$R_{14}$" and —$C(CH_3)_2OR_{14}$;

In a preferred embodiment, the compounds are selected which act as dual ligands of the α2δ subunit, particularly the α2δ-1 subunit, of the voltage-gated calcium channel and the σ1 receptor:

| EX | CHEMICAL NAME |
|---|---|
| 1 | 6-bromo-3-ethyl-2-(1-(4-methyl-1,4-diazepan-1-yl)butyl)quinazolin-4(3H)-one |
| 2 | 2-(1-(1,4-diazepan-1-yl)butyl)-6-bromo-3-ethylquinazolin-4(3H)-one |
| 3 | 7-bromo-3-ethyl-2-(1-(4-methyl-1,4-diazepan-1-yl)butyl)quinazolin-4(3H)-one |
| 4 | 2-(1-(1,4-diazepan-1-yl)butyl)-7-bromo-3-ethylquinazolin-4(3H)-one |
| 5 | 6-bromo-3-ethyl-2-(1-(4-phenethyl-1,4-diazepan-1-yl)butyl)quinazolin-4(3H)-one |
| 6 | 2-(1-(4-benzyl-1,4-diazepan-1-yl)butyl)-6-bromo-3-ethylquinazolin-4(3H)-one |
| 7 | 6-bromo-3-ethyl-2-(1-(4-ethyl-1,4-diazepan-1-yl)butyl)quinazolin-4(3H)-one |
| 8 | 3-ethyl-6-methyl-2-(1-(4-methyl-1,4-diazepan-1-yl)butyl)quinazolin-4(3H)-one |
| 9 | 3-ethyl-2-(1-(4-methyl-1,4-diazepan-1-yl)butyl)-4-oxo-3,4-dihydroquinazoline-7-carbonitrile |
| 10 | 3-ethyl-2-(1-(4-methyl-1,4-diazepan-1-yl)butyl)-4-oxo-3,4-dihydroquinazoline-6-carbonitrile |
| 11 | 3-ethyl-7-methyl-2-(1-(4-methyl-1,4-diazepan-1-yl)butyl)quinazolin-4(3H)-one |
| 12 | 3-ethyl-6-iodo-2-(1-(4-methyl-1,4-diazepan-1-yl)butyl)quinazolin-4(3H)-one |
| 13 | 6-bromo-3-ethyl-7-fluoro-2-(1-(4-methyl-1,4-diazepan-1-yl)butyl)quinazolin-4(3H)-one |
| 14 | 6-bromo-3-(2-methoxyethyl)-2-(1-(4-methyl-1,4-diazepan-1-yl)butyl)quinazolin-4(3H)-one |
| 15 | (R)-3-ethyl-6-methoxy-2-(1-(4-methyl-1,4-diazepan-1-yl)butyl)quinazolin-4(3H)-one |
| 16 | (S)-3-ethyl-6-methoxy-2-(1-(4-methyl-1,4-diazepan-1-yl)butyl)quinazolin-4(3H)-one |
| 17 | 3-ethyl-2-(1-(4-methyl-1,4-diazepan-1-yl)butyl)pyrido[3,4-d]pyrimidin-4(3H)-one |
| 18 | 6-bromo-2-(1-(4-methyl-1,4-diazepan-1-yl)butyl)-3-propylquinazolin-4(3H)-one |
| 19 | 6-chloro-3-ethyl-2-(1-(4-methyl-1,4-diazepan-1-yl)butyl)quinazolin-4(3H)-one |
| 20 | 6-bromo-2-(1-(4-ethyl-1,4-diazepan-1-yl)butyl)-3-propylquinazolin-4(3H)-one |
| 21 | 3-ethyl-6-fluoro-2-(1-(4-methyl-1,4-diazepan-1-yl)butyl)quinazolin-4(3H)-one |
| 22 | 2-(1-(1,4-diazepan-1-yl)butyl)-6-chloro-3-ethylquinazolin-4(3H)-one |
| 23 | 6-chloro-2-(1-(4-methyl-1,4-diazepan-1-yl)butyl)-3-propylquinazolin-4(3H)-one |
| 24 | 6-bromo-3-ethyl-5-methyl-2-(1-(4-methyl-1,4-diazepan-1-yl)butyl)quinazolin-4(3H)-one |
| 25 | 6-bromo-3-ethyl-8-methyl-2-(1-(4-methyl-1,4-diazepan-1-yl)butyl)quinazolin-4(3H)-one |
| 26 | 6-bromo-7-fluoro-2-(1-(4-methyl-1,4-diazepan-1-yl)butyl)-3-propylquinazolin-4(3H)-one |
| 27 | 2-(1-(1,4-diazepan-1-yl)butyl)-6-bromo-3-ethyl-7-fluoroquinazolin-4(3H)-one |
| 28 | 6-bromo-2-(1-(6,6-dimethyl-1,4-diazepan-1-yl)butyl)-3-ethylquinazolin-4(3H)-one |
| 29 | 3-ethyl-6,7-difluoro-2-(1-(4-methyl-1,4-diazepan-1-yl)butyl)quinazolin-4(3H)-one |
| 30 | 6-bromo-3-ethyl-2-(1-(4,6,6-trimethyl-1,4-diazepan-1-yl)butyl)quinazolin-4(3H)-one |
| 31 | 7-bromo-6-fluoro-2-(1-(4-methyl-1,4-diazepan-1-yl)butyl)-3-propylquinazolin-4(3H)-one |
| 32 | 2-(1-(1,4-diazepan-1-yl)butyl)-7-bromo-3-ethyl-6-fluoroquinazolin-4(3H)-one |
| 33 | 7-bromo-3-ethyl-6-fluoro-2-(1-(4-methyl-1,4-diazepan-1-yl)butyl)quinazolin-4(3H)-one |
| 34 | 2-(1-(1,4-diazepan-1-yl)butyl)-6-bromo-7-fluoro-3-propylquinazolin-4(3H)-one |
| 35 | 6-bromo-2-((R)-1-((R)-4,6-dimethyl-1,4-diazepan-1-yl)butyl)-3-ethylquinazolin-4(3H)-one |
| 36 | 6-bromo-2-((R)-1-((S)-4,6-dimethyl-1,4-diazepan-1-yl)butyl)-3-ethylquinazolin-4(3H)-one |
| 37 | 6-bromo-2-((S)-1-((S)-4,6-dimethyl-1,4-diazepan-1-yl)butyl)-3-ethylquinazolin-4(3H)-one |
| 38 | 6-bromo-2-((S)-1-((R)-4,6-dimethyl-1,4-diazepan-1-yl)butyl)-3-ethylquinazolin-4(3H)-one |
| 39 | 6-bromo-3-ethyl-7-methyl-2-(1-(4-methyl-1,4-diazepan-1-yl)butyl)quinazolin-4(3H)-one |
| 40 | 6-bromo-3-ethyl-8-fluoro-2-(1-(4-methyl-1,4-diazepan-1-yl)butyl)quinazolin-4(3H)-one |
| 41 | 2-(1-(1,4-diazepan-1-yl)butyl)-6-bromo-3-ethyl-5-methylquinazolin-4(3H)-one |
| 42 | 6-bromo-2-(1-(6,6-difluoro-4-methyl-1,4-diazepan-1-yl)butyl)-3-ethylquinazolin-4(3H)-one |
| 43 | 6-fluoro-3-isobutyl-2-(1-(4-methyl-1,4-diazepan-1-yl)butyl)quinazolin-4(3H)-one |
| 44 | 2-(1-(1,4-diazepan-1-yl)butyl)-6-bromo-3-ethyl-7-methylquinazolin-4(3H)-one |
| 45 | 2-(1-(1,4-diazepan-1-yl)butyl)-3-ethyl-6,7-difluoroquinazolin-4(3H)-one |
| 46 | 3-ethyl-2-(1-(4-ethyl-1,4-diazepan-1-yl)butyl)-6,7-difluoroquinazolin-4(3H)-one |
| 47 | 6-bromo-3-ethyl-2-(1-(4-ethyl-1,4-diazepan-1-yl)butyl)-5-methylquinazolin-4(3H)-one |
| 48 | 6-bromo-3-ethyl-2-(1-(4-ethyl-1,4-diazepan-1-yl)butyl)-7-methylquinazolin-4(3H)-one |
| 49 | 6-bromo-8-chloro-3-ethyl-2-(1-(4-methyl-1,4-diazepan-1-yl)butyl)quinazolin-4(3H)-one |
| 50 | 2-(1-(4-ethyl-1,4-diazepan-1-yl)butyl)-6-fluoro-3-isobutylquinazolin-4(3H)-one |
| 51 | 6-bromo-3-ethyl-5-fluoro-2-(1-(4-methyl-1,4-diazepan-1-yl)butyl)quinazolin-4(3H)-one |
| 52 | 6-bromo-3-ethyl-2-(1-(4-ethyl-1,4-diazepan-1-yl)butyl)-5-fluoroquinazolin-4(3H)-one |
| 53 | 5-bromo-3-ethyl-2-(1-(4-methyl-1,4-diazepan-1-yl)butyl)quinazolin-4(3H)one |
| 54 | 6-bromo-3-isobutyl-2-(1-(4-methyl-1,4-diazepan-1-yl)butyl)quinazolin-4(3H)-one |
| 55 | 2-(1-(1,4-diazepan-1-yl)butyl)-6-bromo-3-ethyl-8-fluoroquinazolin-4(3H)-one |
| 56 | 6-bromo-5-chloro-3-ethyl-2-(1-(4-methyl-1,4-diazepan-1-yl)butyl)quinazolin-4(3H)-one |
| 57 | 6-bromo-3-ethyl-2-(1-(4-ethyl-1,4-diazepan-1-yl)butyl)-8-fluoroquinazolin-4(3H)-one |
| 58 | 6-bromo-2-(1-(4-ethyl-1,4-diazepan-1-yl)butyl)3-isobutylquinazolin-4(3H)-one |
| 59 | 2-(1-(1,4-diazepan-1-yl)butyl)-6-bromo-3-ethyl-5-fluoroquinazolin-4(3H)-one |
| 60 | 6-bromo-3-ethyl-2-(1-(4-ethyl-1,4-diazepan-1-yl)butyl)-8-methylquinazolin-4(3H)-one |
| 61 | 6-bromo-2-(1-(4-ethyl-1,4-diazepan-1-yl)butyl)-7-fluoro-3-propylquinazolin-4(3H)-one |
| 62 | 7-bromo-2-(1-(4-ethyl-1,4-diazepan-1-yl)butyl)-6-fluoro-3-propylquinazolin-4(3H)-one |
| 63 | 7-bromo-3-ethyl-2-(1-(4-ethyl-1,4-diazepan-1-yl)butyl)-6-fluoroquinazolin-4(3H)-one |
| 64 | 8-chloro-3-ethyl-6-fluoro-2-(1-(4-methyl-1,4-diazepan-1-yl)butyl)quinazolin-4(3H)-one |
| 65 | 8-chloro-3-ethyl-2-(1-(4-ethyl-1,4-diazepan-1-yl)butyl)-6-fluoroquinazolin-4(3H)-one |
| 66 | (R)-2-(1-(1,4-diazabicyclo[3,2,2]nonan-4-yl)butyl)-6-bromo-3-ethylquinazolin-4(3H)-one |
| 67 | 6-bromo-2-((R)-1-((S)-6-methyl-1,4-diazepan-1-yl)butyl)-3-propylquinazolin-4(3H)-one |
| 68 | 6-bromo-2-((R)-1-((R)-6-methyl-1,4-diazepan-1-yl)butyl)-3-propylquinazolin-4(3H)-one |
| 69 | 6-bromo-2-((S)-1-((S)-6-methyl-1,4-diazepan-1-yl)butyl)-3-propylquinazolin-4(3H)-one |
| 70 | 6-bromo-2-((S)-1-((R)-6-methyl-1,4-diazepan-1-yl)butyl)-3-propylquinazolin-4(3H)-one |
| 71 | 2-(1-(1,4-diazepan-1-yl)butyl)-8-chloro-3-ethyl-6-fluoroquinazolin-4(3H)-one |
| 72 | 3-ethyl-5,6-difluoro-2-(1-(4-methyl-1,4-diazepan-1-yl)butyl)quinazolin-4(3H)-one |
| 73 | 6-chloro-2-((S)-1-((S)-4,6-dimethyl-1,4-diazepan-1-yl)butyl)-3-ethylquinazolin-4(3H)-one |
| 74 | 6-chloro-2-((S)-1-((R)-4,6-dimethyl-1,4-diazepan-1-yl)butyl)-3-ethylquinazolin-4(3H)-one |
| 75 | 6-chloro-2-((R)-1-((S)-4,6-dimethyl-1,4-diazepan-1-yl)butyl)-3-ethylquinazolin-4(3H)-one |
| 76 | 6-chloro-2-((R)-1-((R)-4,6-dimethyl-1,4-diazepan-1-yl)butyl)-3-ethylquinazolin-4(3H)-one |
| 77 | 6-bromo-7-fluoro-3-methyl-2-(1-(4-methyl-1,4-diazepan-1-yl)butyl)quinazolin-4(3H)-one |
| 78 | 3-ethyl-2-(1-(4-ethyl-1,4-diazepan-1-yl)butyl)-5,6-difluoroquinazolin-4(3H)-one |
| 79 | 6-chloro-2-(1-(4-ethyl-1,4-diazepan-1-yl)butyl)-3-propylquinazolin-4(3H)-one |

-continued

| EX | CHEMICAL NAME |
|---|---|
| 80 | 2-(1-(1,4-diazabicyclo[3,2,2]nonan-4-yl)butyl)-6-bromo-3-ethylquinazolin-4(3H)-one |
| 81 | 2-(1-(1,4-diazepan-1-yl)butyl)-3-ethyl-5,6-difluoroquinazolin-4(3H)-one |
| 82 | 2-(1-(1,4-diazepan-1-yl)butyl)-6-bromo-5-chloro-3-ethylquinazolin-4(3H)-one |
| 83 | 6-bromo-5-chloro-3-ethyl-2-(1-(4-ethyl-1,4-diazepan-1-yl)butyl)quinazolin-4(3H)-one |
| 84 | 6-bromo-3-methyl-2-(1-(4-methyl-1,4-diazepan-1-yl)butyl)quinazolin-4(3H)-one |
| 85 | 6-bromo-2-(1-(4-ethyl-1,4-diazepan-1-yl)butyl)-3-methylquinazolin-4(3H)-one |
| 86 | 3-ethyl-2-(1-(4-methyl-1,4-diazepan-1-yl)butyl)pyrido[3,2-d]pyrimidin-4(3H)-one |
| 87 | 6,7-dichloro-3-ethyl-2-(1-(4-methyl-1,4-diazepan-1-yl)butyl)quinazolin-4(3H)-one |
| 88 | 3-ethyl-2-(1-(4-ethyl-1,4-diazepan-1-yl)butyl)pyrido[3,2-d]pyrimidin-4(3H)-one |
| 89 | 6-chloro-3-ethyl-7-fluoro-2-(1-(4-methyl-1,4-diazepan-1-yl)butyl)quinazolin-4(3H)-one |
| 90 | 2-(1-(1,4-diazepan-1-yl)butyl)-6-chloro-3-ethyl-7-fluoroquinazolin-4(3H)-one |
| 91 | 2-(1-(1,4-diazepan-1-yl)butyl)-6,7-dichloro-3-ethylquinazolin-4(3H)-one |
| 92 | 6-bromo-3-ethyl-2-((R)-1-((R)-5-methyl-1,4-diazepan-1-yl)butyl)quinazolin-4(3H)-one |
| 93 | 6-bromo-3-ethyl-2-((R)-1-((S)-5-methyl-1,4-diazepan-1-yl)butyl)quinazolin-4(3H)-one |
| 94 | 6-bromo-3-ethyl-2-((S)-1-((R)-5-methyl-1,4-diazepan-1-yl)butyl)quinazolin-4(3H)-one |
| 95 | 6-bromo-3-ethyl-2-((S)-1-((S)-5-methyl-1,4-diazepan-1-yl)butyl)quinazolin-4(3H)-one |
| 96 | 6-bromo-3-ethyl-7-fluoro-2-((R)-1-((S)-6-methyl-1,4-diazepan-1-yl)butyl)quinazolin-4(3H)-one |
| 97 | 6-bromo-3-ethyl-7-fluoro-2-((R)-1-((R)-6-methyl-1,4-diazepan-1-yl)butyl)quinazolin-4(3H)-one |
| 98 | 6-bromo-3-ethyl-7-fluoro-2-((S)-1-((S)-6-methyl-1,4-diazepan-1-yl)butyl)quinazolin-4(3H)-one |
| 99 | 6-bromo-3-ethyl-7-fluoro-2-((S)-1-((R)-6-methyl-1,4-diazepan-1-yl)butyl)quinazolin-4(3H)-one |
| 100 | 2-(1-(1,4-diazepan-1-yl)butyl)-3-ethylpyrido[3,2-d]pyrimidin-4(3H)-one |
| 101 | 6-bromo-3-ethyl-2-((S)-1-((S)-6-ethyl-1,4-diazepan-1-yl)butyl)quinazolin-4(3H)-one |
| 102 | 6-bromo-3-ethyl-2-((S)-1-((R)-6-ethyl-1,4-diazepan-1-yl)butyl)quinazolin-4(3H)-one |
| 103 | 6-bromo-3-ethyl-2-((R)-1-((R)-6-ethyl-1,4-diazepan-1-yl)butyl)quinazolin-4(3H)-one |
| 104 | 6-bromo-3-ethyl-2-((R)-1-((S)-6-ethyl-1,4-diazepan-1-yl)butyl)quinazolin-4(3H)-one |
| 105 | 6-bromo-3-ethyl-2-((R)-1-((S)-6-(methoxymethyl)-4-methyl-1,4-diazepan-1-yl)butyl)quinazolin-4(3H)-one |
| 106 | 6-bromo-3-ethyl-2-((R)-1-((R)-6-(methoxymethyl)-4-methyl-1,4-diazepan-1-yl)butyl)quinazolin-4(3H)-one |
| 107 | 6-bromo-3-ethyl-2-((S)-1-((S)-6-(methoxymethyl)-4-methyl-1,4-diazepan-1-yl)butyl)quinazolin-4(3H)-one |
| 108 | 6-bromo-3-ethyl-2-((S)-1-((R)-6-(methoxymethyl)-4-methyl-1,4-diazepan-1-yl)butyl)quinazolin-4(3H)-one |
| 109 | 6,7-dichloro-3-ethyl-2-((R)-1-((S)-6-methyl-1,4-diazepan-1-yl)butyl)quinazolin-4(3H)-one |
| 110 | 6,7-dichloro-3-ethyl-2-((R)-1-((R)-6-methyl-1,4-diazepan-1-yl)butyl)quinazolin-4(3H)-one |
| 111 | 6,7-dichloro-3-ethyl-2-((S)-1-((S)-6-methyl-1,4-diazepan-1-yl)butyl)quinazolin-4(3H)-one |
| 112 | 6,7-dichloro-3-ethyl-2-((S)-1-((R)-6-methyl-1,4-diazepan-1-yl)butyl)quinazolin-4(3H)-one |
| 113 | 6-bromo-3-ethyl-2-((S)-1-((R)-6-hydroxy-1,4-diazepan-1-yl)butyl)quinazolin-4(3H)-one |
| 114 | 6-bromo-3-ethyl-2-((R)-1-((R)-6-hydroxy-1,4-diazepan-1-yl)butyl)quinazolin-4(3H)-one |
| 115 | 6-bromo-3-ethyl-2-((S)-1-((S)-6-hydroxy-1,4-diazepan-1-yl)butyl)quinazolin-4(3H)-one |
| 116 | 6-bromo-3-ethyl-2-((R)-1-((S)-6-hydroxy-1,4-diazepan-1-yl)butyl)quinazolin-4(3M)-one |
| 117 | 3-ethyl-8-fluoro-5-methoxy-2-(1-(4-methyl-1,4-diazepan-1-yl)butyl)quinazolin-4(3H)-one |
| 118 | 6-chloro-3-ethyl-7-fluoro-2-((R)-1-((S)-6-methyl-1,4-diazepan-1-yl)butyl)quinazolin-4(3H)-one |
| 119 | 6-chloro-3-ethyl-7-fluoro-2-((R)-1-((R)-6-methyl-1,4-diazepan-1-yl)butyl)quinazolin-4(3H)-one |
| 120 | 6-chloro-3-ethyl-7-fluoro-2-((S)-1-((S)-6-methyl-1,4-diazepan-1-yl)butyl)quinazolin-4(3H)-one |
| 121 | 6-chloro-3-ethyl-7-fluoro-2-((S)-1-((R)-6-methyl-1,4-diazepan-1-yl)butyl)quinazolin-4(3H)-one |
| 122 | 6-bromo-2-(1-(4-methyl-1,4-diazepan-1-yl)butyl)quinazolin-4(3H)-one |
| 123 | 6-bromo-3-ethyl-2-((R)-1-((S)-6-(hydroxymethyl)-4-methyl-1,4-diazepan-1-yl)butyl)quinazolin-4(3H)-one |
| 124 | 6-bromo-3-ethyl-2-((S)-1-((R)-6-(hydroxymethyl)-4-methyl-1,4-diazepan-1-yl)bulyl)quinazolin-4(3H)-one |
| 125 | 6-bromo-3-ethyl-2-((R)-1-((R)-6-(hydroxymethyl)-4-methyl-1,4-diazepan-1-yl)butyl)quinazolin-4(3H)-one |
| 126 | 6-bromo-3-ethyl-2-((S)-1-((S)-6-(hydroxymethyl)-4-methyl-1,4-diazepan-1-yl)butyl)quinazolin-4(3H)-one |
| 127 | 6-bromo-2-((R)-1-((S)-4,6-dimethyl-1,4-diazepan-1-yl)butyl)-3-ethyl-7-fluoroquinazolin-4(3H)-one |
| 128 | 6-bromo-2-((S)-1-((S)-4,6-dimethyl-1,4-diazepan-1-yl)butyl)-3-ethyl-7-fluoroquinazolin-4(3H)-one |
| 129 | 6-bromo-2-((S)-1-((R)-4,6-dimethyl-1,4-diazepan-1-yl)butyl)-3-ethyl-7-fluoroquinazolin-4(3H)-one |
| 130 | 6-bromo-2-((R)-1-((R)-4,6-dimethyl-1,4-diazepan-1-yl)butyl)-3-ethyl-7-fluoroquinazolin-4(3H)-one |
| 131 | 6,7-dichloro-2-((R)-1-((S)-4,6-dimethyl-1,4-diazepan-1-yl)butyl)-3-ethylquinazolin-4(3H)-one |
| 132 | 6,7-dichloro-2-((R)-1-((R)-4,6-dimethyl-1,4-diazepan-1-yl)butyl)-3-ethylquinazolin-4(3H)-one |
| 133 | 6,7-dichloro-2-((S)-1-((S)-4,6-dimethyl-1,4-diazepan-1-yl)butyl)-3-ethylquinazolin-4(3H)-one |
| 134 | 6,7-dichloro-2-((S)-1-((R)-4,6-dimethyl-1,4-diazepan-1-yl)butyl)-3-ethylquinazolin-4(3H)-one |
| 135 | 6-chloro-2-((R)-1-((S)-4,6-dimethyl-1,4-diazepan-1-yl)butyl)-3-ethyl-7-fluoroquinazolin-4(3H)-one |
| 136 | 6-chloro-2-((R)-1-((R)-4,6-dimethyl-1,4-diazepan-1-yl)butyl)-3-ethyl-7-fluoroquinazolin-4(3H)-one |
| 137 | 6-chloro-2-((S)-1-((S)-4,6-dimethyl-1,4-diazepan-1-yl)butyl)-3-ethyl-7-fluoroquinazolin-4(3H)-one |
| 138 | 6-chloro-2-((S)-1-((R)-4,6-dimethyl-1,4-diazepan-1-yl)butyl)-3-ethyl-7-fluoroqunazolin-4(3H)-one |
| 139 | 6-bromo-3-ethyl-2-((R)-1-((R)-3-methyl-1,4-diazepan-1-yl)butyl)quinazolin-4(3H)-one |
| 140 | 6-bromo-3-ethyl-2-((S)-1-((S)-3-methyl-1,4-diazepan-1-yl)butyl)quinazolin-4(3H)-one |
| 141 | 6-bromo-3-ethyl-2-((S)-1-((R)-3-methyl-1,4-diazepan-1-yl)butyl)quinazolin-4(3H)-one |
| 142 | 6-bromo-3-ethyl-2-((R)-1-((S)-3-methyl-1,4-diazepan-1-yl)butyl)quinazolin-4(3H)-one |
| 143 | 3-ethyl-6-fluoro-2-((R)-1-(R)-3-methyl-1,4-diazepan-1-yl)butyl)quinazolin-4(3H)-one |
| 144 | 3-ethyl-6-fluoro-2-((S)-1-((S)-3-methyl-1,4-diazepan-1-yl)butyl)quinazolin-4(3H)-one |
| 145 | 3-ethyl-6-fluoro-2-((R)-1-((S)-3-methyl-1,4-diazepan-1-yl)butyl)quinazolin-4(3H)-one |
| 146 | 3-ethyl-6-fluoro-2-((S)-1-((R)-3-methyl-1,4-diazepan-1-yl)butyl)quinazolin-4(3H)one |
| 147 | 6-chloro-3-methyl-2-((R)-1-((R)-3-methyl-1,4-diazepan-1-yl)butyl)quinazolin-4(3H)-one |
| 148 | 6-chloro-3-methyl-2-((R)-1-((S)-3-methyl-1,4-diazepan-1-yl)butyl)quinazolin-4(3H)-one |
| 149 | 6-chloro-3-methyl-2-((S)-1-((S)-3-methyl-1,4-diazepan-1-yl)butyl)quinazolin-4(3H)-one |
| 150 | 6-chloro-3-methyl-2-((S)-1-((R)-3-methyl-1,4-diazepan-1-yl)butyl)quinazolin-4(3H)-one |
| 151 | (R)-6-bromo-3-ethyl-2-(1-(4-methyl-1,4-diazepan-1-yl)butyl)quinazolin-4(3H)-one |
| 152 | (S)-6-bromo-3-ethyl-2-(1-(4-methyl-1,4-diazepan-1-yl)butyl)quinazolin-4(3H)-one |
| 153 | (R)-6-bromo-3-ethyl-2-(1-(4-ethyl-1,4-diazepan-1-yl)butyl)quinazolin-4(3H)-one |
| 154 | (S)-6-bromo-3-ethyl-2-(1-(4-ethyl-1,4-diazepan-1-yl)butyl)quinazolin-4(3H)-one |
| 155 | (R)-6-bromo-3-ethyl-7-fluoro-2-(1-(4-methyl-1,4-diazepan-1-yl)butyl)quinazolin-4(3H)-one |
| 156 | (S)-6-bromo-3-ethyl-7-fluoro-2-(1-(4-methyl-1,4-diazepan-1-yl)butyl)quinazolin-4(3H)-one |

-continued

| EX | CHEMICAL NAME |
|---|---|
| 157 | (R)-2-(1-(1,4-diazepan-1-yl)butyl)-6-bromo-3-ethyl-7-fluoroquinazolin-4(3H)-one |
| 158 | (S)-2-(1-(1,4-diazepan-1-yl)butyl)-6-bromo-3-ethyl-7-fluoroquinazolin-4(3H)-one |
| 159 | (R)-6-chloro-2-(1-(4-methyl-1,4-diazepan-1-yl)butyl)-3-propylquinazolin-4(3H)-one |
| 160 | (S)-6-chloro-2-(1-(4-methyl-1,4-diazepan-1-yl)butyl)-3-propylquinazolin-4(3H)-one |
| 161 | (R)-6-bromo-3-ethyl-8-fluoro-2-(1-(4-methyl-1,4-diazepan-1-yl)butyl)quinazolin-4(3H)-one |
| 162 | (S)-6-bromo-3-ethyl-8-fluoro-2-(1-(4-methyl-1,4-diazepan-1-yl)butyl)quinazolin-4(3H)-one |
| 163 | 3-ethyl-2-(1-(4-methyl-1,4-diazepan-1-yl)butyl)pyrido[4,3-d]pyrimidin-4(3H)-one |
| 164 | 3-ethyl-2-((R)-1-((S)-6-methyl-1,4-diazepan-1-yl)butyl)pyrido[4,3-d]pyrimidin-4(3H)-one |
| 165 | 3-ethyl-2-((R)-1-((R)-6-methyl-1,4-diazepan-1-yl)butyl)pyrido[4,3-d]pyrimidin-4(3H)-one |
| 166 | 3-ethyl-2-((S)-1-((S)-6-methyl-1,4-diazepan-1-yl)butyl)pyrido[4,3-d]pyrimidin-4(3H)-one |
| 167 | 3-ethyl-2-((S)-1-((R)-6-methyl-1,4-diazepan-1-yl)butyl)pyrido[4,3-d]pyrimidin-4(3H)-one |
| 168 | 2-((R)-1-((R)-4,6-dimethyl-1,4-diazepan-1-yl)butyl)-3-ethylpyrido[4,3-d]pyrimidin-4(3H)-one |
| 169 | 2-((R)-1-((S)-4,6-dimethyl-1,4-diazepan-1-yl)butyl)-3-ethylpyrido[4,3-d]pyrimidin-4(3H)-one |
| 170 | 2-((S)-1-((S)-4,6-dimethyl-1,4-diazepan-1-yl)butyl)-3-ethylpyrido[4,3-d]pyrimidin-4(3H)-one |
| 171 | 2-((S)-1-((R)-4,6-dimethyl-1,4-diazepan-1-yl)butyl)-3-ethylpyrido[4,3-d]pyrimidin-4(3H)-one |
| 172 | 2-(1-(1,4-diazepan-1-yl)butyl)-3-ethylpyrido[4,3-d]pyrimidin-4(3H)-one |
| 173 | (R)-3-ethyl-2-(1-(4-methyl-1,4-diazepan-1-yl)butyl)pyrido[4,3-d]pyrimidin-4(3H)-one |
| 174 | (S)-3-ethyl-2-(1-(4-methyl-1,4-diazepan-1-yl)butyl)pyrido[4,3-d]pyrimidin-4(3H)-one |
| 175 | 6-bromo-3-ethyl-2-(1-(4-methyl-1,4-diazepan-1-yl)butyl)pyrido[2,3-d]pyrimidin-4(3H)-one |
| 176 | 6-bromo-3-ethyl-2-(1-(4-ethyl-1,4-diazepan-1-yl)butyl)pyrido[2,3-d]pyrimidin-4(3H)-one |
| 177 | 2-(1-(1,4-diazepan-1-yl)butyl)-6-bromo-3-ethylpyrido[2,3-d]pyrimidin-4(3H)-one |
| 178 | 3-ethyl-2-(1-(4-ethyl-1,4-diazepan-1-yl)butyl)pyrido[2,3-d]pyrimidin-4(3H)-one |
| 179 | 2-(1-(1,4-diazepan-1-yl)butyl)-3-ethylpyrido[2,3-d]pyrimidin-4(3H)-one |
| 180 | 3-ethyl-2-(1-(4-methyl-1,4-diazepan-1-yl)butyl)pyrido[2,3-d]pyrimidin-4(3H)-one |
| 181 | 6-bromo-2-(1-(4-methyl-1,4-diazepan-1-yl)butyl)-3-propylpyrido[2,3-d]pyrimidin-4(3H)-one |
| 182 | 3-ethyl-6-fluoro-2-(1-(4-methyl-1,4-diazepan-1-yl)butyl)pyrido[2,3-d]pyrimidin-4(3H)-one |
| 183 | 6-bromo-3-(cyclopropylmethyl)-2-(1-(4-methyl-1,4-diazepan-1-yl)butyl)pyrido[2,3-d]pyrimidin-4(3H)-one |
| 184 | 3-(cyclopropylmethyl)-6-fluoro-2-(1-(4-methyl-1,4-diazepan-1-yl)butyl)pyrido[2,3-d]pyrimidin-4(3H)-one |
| 185 | 3-(cyclopropylmethyl)-2-(1-(4-ethyl-1,4-diazepan-1-yl)butyl)-6-fluoropyrido[2,3-d]pyrimidin-4(3H)-one |
| 186 | 6-bromo-2-((R)-1-((R)-4,6-dimethyl-1,4-diazepan-1-yl)butyl)-3-ethylpyrido[2,3-d]pyrimidin-4(3H)-one |
| 187 | 6-bromo-2-((R)-1-((S)-4,6-dimethyl-1,4-diazepan-1-yl)butyl)-3-ethylpyrido[2,3-d]pyrimidin-4(3H)-one |
| 188 | 6-bromo-2-((S)-1-((S)-4,6-dimethyl-1,4-diazepan-1-yl)butyl)-3-ethylpyrido[2,3-d]pyrimidin-4(3H)-one |
| 189 | 6-bromo-2-((S)-1-((R)-4,6-dimethyl-1,4-diazepan-1-yl)butyl)-3-ethylpyrido[2,3-d]pyrimidin-4(3H)-one |
| 190 | 3-ethyl-2-(1-(4-methyl-1,4-diazepan-1-yl)butyl)-7-(trifluoromethyl)pyrido[2,3-d]pyrimidin-4(3H)-one |
| 191 | 3-ethyl-6-methoxy-2-(1-(4-methyl-1,4-diazepan-1-yl)butyl)pyrido[3,4-d]pyrimidin-4(3H)-one |
| 192 | 3-ethyl-2-(1-(4-methyl-1,4-diazepan-1-yl)butyl)-6-(trifluoromethyl)pyrido[3,4-d]pyrimidin-4(3H)-one |
| 193 | 3-(cyclopropylmethyl)-6-fluoro-2-((S)-1-((R)-5-methyl-1,4-diazepan-1-yl)butyl)pyrido[2,3-d]pyrimidin-4(3H)-one |
| 194 | 3-(cyclopropylmethyl)-6-fluoro-2-((S)-1-((S)-5-methyl-1,4-diazepan-1-yl)butyl)pyrido[2,3-d]pyrimidin-4(3H)-one |
| 195 | 3-(cyclopropylmethyl)-6-fluoro-2-((R)-1-((S)-5-methyl-1,4-diazepan-1-yl)butyl)pyrido[2,3-d]pyrimidin-4(3H)-one |
| 196 | 3-(cyclopropylmethyl)-6-fluoro-2-((R)-1-((R)-5-methyl-1,4-diazepan-1-yl)butyl)pyrido[2,3-d]pyrimidin-4(3H)-one |
| 197 | 6-bromo-3-ethyl-2-((R)-1-((S)-6-methyl-1,4-diazepan-1-yl)butyl)pyrido[2,3-d]pyrimidin-4(3H)-one |
| 198 | 6-bromo-3-ethyl-2-((S)-1-((R)-6-methyl-1,4-diazepan-1-yl)butyl)pyrido[2,3-d]pyrimidin-4(3H)-one |
| 199 | 6-bromo-3-ethyl-2-((R)-1-((R)-6-methyl-1,4-diazepan-1-yl)butyl)pyrido[2,3-d]pyrimidin-4(3H)-one |
| 200 | 6-bromo-3-ethyl-2-((S)-1-((S)-6-methyl-1,4-diazepan-1-yl)butyl)pyrido[2,3-d]pyrimidin-4(3H)-one |
| 201 | (R)-3-ethyl-6-fluoro-2-(1-(4-methyl-1,4-diazepan-1-yl)butyl)pyrido[2,3-d]pyrimidin-4(3H)-one |
| 202 | (S)-3-ethyl-6-fluoro-2-(1-(4-methyl-1,4-diazepan-1-yl)butyl)pyrido[2,3-d]pyrimidin-4(3H)-one |
| 203 | 3-ethyl-6-hydroxy-2-(1-(4-methyl-1,4-diazepan-1-yl)butyl)quinazolin-4(3H)-one |
| 204 | 3-ethyl-2-(1-(4-methyl-1,4-diazepan-1-yl)butyl)-6-phenylquinazolin-4(3H)-one |
| 205 | 3,6-diethyl-2-(1-(4-methyl-1,4-diazepan-1-yl)butyl)quinazolin-4(3H)-one |
| 206 | 3-ethyl-2-(1-(4-methyl-1,4-diazepan-1-yl)butyl)-6-((1-methylpiperidin-4-yl)amino)quinazolin-4(3H)-one |
| 207 | 6-benzyl-3-ethyl-2-(1-(4-methyl-1,4-diazepan-1-yl)butyl)quinazolin-4(3H)-one |
| 208 | 2-(6-bromo-2-(1-(4-methyl-1,4-diazepan-1-yl)butyl)-4-oxoquinazolin-3(4H)-yl)acetic acid |
| 209 | (R)-3-ethyl-6-fluoro-2-(1-(4-methyl-1,4-diazepan-1-yl)butyl)quinazolin-4(3H)-one |
| 210 | (R)-3-ethyl-2-(1-(4-ethyl-1,4-diazepan-1-yl)butyl)-6-fluoroquinazolin-4(3H)-one |
| 211 | (R)-6-fluoro-2-(1-(4-methyl-1,4-diazepan-1-yl)butyl)-3-propylquinazolin-4(3H)-one |
| 212 | (R)-2-(1-(4-ethyl-1,4-diazepan-1-yl)butyl)-6-fluoro-3-propylquinazolin-4(3H)-one |
| 213 | (R)-3-ethyl-6-iodo-2-(1-(4-methyl-1,4-diazepan-1-yl)butyl)quinazolin-4(3H)-one |
| 214 | (R)-6-fluoro-3-isobutyl-2-(1-(4-methyl-1,4-diazepan-1-yl)butyl)quinazolin-4(3H)-one |
| 215 | (R)-2-(1-(4-ethyl-1,4-diazepan-1-yl)butyl)-6-fluoro-3-isobutylquinazolin-4(3H)-one |
| 216 | (R)-6-fluoro-3-methyl-2-(1-(4-methyl-1,4-diazepan-1-yl)butyl)quinazolin-4(3H)-one |
| 217 | (R)-2-(1-(4-ethyl-1,4-diazepan-1-yl)butyl)6-fluoro-3-methylquinazolin-4(3H)-one |
| 218 | (R)-3-(cyclopropylmethyl)-2-(1-(4-ethyl-1,4-diazepan-1-yl)butyl)-6-fluoroquinazolin-4(3H)-one |
| 219 | (R)-3-(cyclopropylmethyl)-6-fluoro-2-(1-(4-methyl-1,4-diazepan-1-yl)butyl)quinazolin-4(3H)-one |
| 220 | (R)-3-ethyl-7-fluoro-6-methoxy-2-(1-(4-methyl-1,4-diazepan-1-yl)butyl)quinazolin-4(3H)-one |
| 221 | (R)-2-(1-(4-ethyl-1,4-diazepan-1-yl)butyl)-6-fluoro-3-isopentylquinazolin-4(3H)-one |
| 222 | (R)-6-fluoro-3-isopropyl-2-(1-(4-methyl-1,4-diazepan-1-yl)butyl)quinazolin-4(3H)-one |
| 223 | (R)-2-(1-(4-ethyl-1,4-diazepan-1-yl)butyl)-6-fluoro-3-isopropylquinazolin-4(3H)-one |
| 224 | (R)-3-butyl-6-fluoro-2-(1-(4-methyl-1,4-diazepan-1-yl)butyl)quinazolin-4(3H)-one |
| 225 | (R)-3-butyl-2-(1-(4-ethyl-1,4-diazepan-1-yl)butyl)-6-fluoroquinazolin-4(3H)-one |
| 226 | (R)-6-fluoro-3-isopentyl-2-(1-(4-methyl-1,4-diazepan-1-yl)butyl)quinazolin-4(3H)one |
| 227 | ((R)-6-fluoro-3-(furan-3-ylmethyl)-2-(1-(4-methyl-1,4-diazepan-1-yl)butyl)quinazolin-4(3H)-one |
| 228 | (R)-2-(1-(4-ethyl-1,4-diazepan-1-yl)butyl)-6-fluoro-3-(furan-3-ylmethyl)quinazolin-4(3H)-one |
| 229 | (R)-2-(1-(4-ethyl-1,4-diazepan-1-yl)butyl)-6-fluoro-3-propylquinazolin-4(3H)-one |
| 230 | (R)-3-ethyl-6-fluoro-7-methoxy-2-(1-(4-methyl-1,4-diazepan-1-yl)butyl)quinazolin-4(3H)-one |
| 231 | (R)-3-ethyl-2-(1-(4-ethyl-1,4-diazepan-1-yl)butyl)-6-fluoro-7-methoxyquinazolin-4(3H)-one |
| 232 | (R)-3-ethyl-6,7-difluoro-2-(1-(4-methyl-1,4-diazepan-1-yl)butyl)quinazolin-4(3H)-one |
| 233 | (R)-3-ethyl-5,6-difluoro-2-(1-(4-methyl-1,4-diazepan-1-yl)butyl)quinazolin-4(3H)-one |

-continued

| EX | CHEMICAL NAME |
|---|---|
| 234 | (R)-6-chloro-3-ethyl-8-fluoro-2-(1-(4-methyl-1,4-diazepan-1-yl)butyl)quinazolin-4(3H)-one |
| 235 | 3-ethyl-6-fluoro-2-((R)-1-((R)-5-methyl-1,4-diazepan-1-yl)butyl)quinazolin-4(3H)-one |
| 236 | 3-ethyl 6-fluoro-2-((R)-1-((S)-5-methyl-1,4-diazepan-1-yl)butyl)quinazolin-4(3H)-one |
| 237 | 2-((R)-1-((R)-4,6-dimethyl-1,4-diazepan-1-yl)butyl)-3-ethyl-7-fluoro-6-methoxyquinazolin-4(3H)-one |
| 238 | 2-((R)-1-((S)-4,6-dimethyl-1,4-diazepan-1-yl)butyl)-3-ethyl-7-fluoro-6-methoxyquinazolin-4(3H)-one |
| 239 | 3-ethyl-5,6-difluoro-2-((R)-1-((R)-5-methyl-1,4-diazepan-1-yl)butyl)quinazolin-4(3H)-one |
| 240 | 3-ethyl-5,6-difluoro-2-((R)-1-((S)-5-methyl-1,4-diazepan-1-yl)butyl)quinazolin-4(3H)-one |
| 241 | 3-ethyl-6,7-difluoro-2-((R)-1-((R)-5-methyl-1,4-diazepan-1-yl)butyl)quinazolin-4(3H)-one |
| 242 | 3-ethyl-6,7-difluoro-2-((R)-1-((S)-5-methyl-1,4-diazepan-1-yl)butyl)quinazolin-4(3H)-one |
| 243 | 3-ethyl-7-fluoro-6-methoxy-2-((R)-1-((R)-6-methyl-1,4-diazepan-1-yl)butyl)quinazolin-4(3H)-one |
| 244 | 3-ethyl-7-fluoro-6-methoxy-2-((R)-1-((S)-6-methyl-1,4-diazepan-1-yl)butyl)quinazolin-4(3H)-one |
| 245 | 6-chloro-3-methyl-2-((R)-1-((R)-5-methyl-1,4-diazepan-1-yl)butyl)quinazolin-4(3H)-one |
| 246 | 6-chloro-3-methyl-2-((R)-1-((S)-5-methyl-1,4-diazepan-1-yl)butyl)quinazolin-4(3H)-one |
| 247 | (R)-3-ethyl-6,8-difluoro-2-(1-(4-methyl-1,4-diazepan-1-yl)butyl)quinazolin-4(3H)-one |
| 248 | (R)-3-ethyl-8-fluoro-2-(1-(4-methyl-1,4-diazepan-1-yl)butyl)quinazolin-4(3H)-one |
| 249 | (R)-3-ethyl-2-(1-(4-methyl-1,4-diazepan-1-yl)butyl)-6-(trifluoromethoxy)quinazolin-4(3H)-one |
| 250 | 3-ethyl-6,8-difluoro-2-((R)-1-((R)-5-methyl-1,4-diazepan-1-yl)butyl)quinazolin-4(3H)-one |
| 251 | 3-ethyl-6,8-difluoro-2-((R)-1-((S)-5-methyl-1,4-diazepan-1-yl)butyl)quinazolin-4(3H)-one |
| 252 | (R)-3-ethyl-2-(1-(4-methyl-1,4-diazepan-1-yl)butyl)-6-(trifluoromethyl)quinazolin-4(3H)-one |
| 253 | (R)-2-(1-(3,3-dimethyl-1,4-diazepan-1-yl)butyl)-3-ethyl-6-fluoroquinazolin-4(3H)-one |
| 254 | 6-chloro-2-((R)-1-((S)-4,5-dimethyl-1,4-diazepan-1-yl)butyl)-3-methylquinazolin-4(3H)-one |
| 255 | 6-fluoro-3-methyl-2-((R)-1-((R)-5-methyl-1,4-diazepan-1-yl)butyl)quinazolin-4(3H)-one |
| 256 | 6-fluoro-3-methyl-2-((R)-1-((S)-5-methyl-1,4-diazepan-1-yl)butyl)quinazolin-4(3H)-one |
| 257 | 6-chloro-2-((R)-1-((R)-4,5-dimethyl-1,4-diazepan-1-yl)butyl)-3-methylquinazolin-4(3H)-one |
| 258 | 3-ethyl-2-((R)-1-((R)-5-methyl-1,4-diazepan-1-yl)butyl)-6-(trifluoromethyl)quinazolin-4(3H)-one |
| 259 | 3-ethyl-2-((R)-1-((S)-5-methyl-1,4-diazepan-1-yl)butyl)-6-(trifluoromethyl)quinazolin-4(3H)-one |
| 260 | 3-ethyl-6,7-difluoro-2-((R)-1-((S)-3-methyl-1,4-diazepan-1-yl)butyl)quinazolin-4(3H)-one |
| 261 | 3-ethyl-6,7-difluoro-2-((R)-1-((R)-3-methyl-1,4-diazepan-1-yl)butyl)quinazolin-4(3H)-one |
| 262 | 6-bromo-2-((S)-1-((4S,7S)-1,7-dimethylazepan-4-yl)butyl)-3-ethylquinazolin-4(3H)-one |
| 263 | 6-bromo-2-((R)-1-((4R,7S)-1,7-dimethylazepan-4-yl)butyl)-3-ethylquinazolin-4(3H)-one |
| 264 | 6-bromo-2-((S)-1-((4S,7R)-1,7-dimethylazepan-4-yl)butyl)-3-ethylquinazolin-4(3H)-one |
| 265 | 6-bromo-2-((R)-1-((4R,7R)-1,7-dimethylazepan-4-yl)butyl)-3-ethylquinazolin-4(3H)-one |
| 266 | 2-(1-(Azepan-4-yl)butyl)-3-ethyl-6-fluoroquinazolin-4(3H)-one |
| 267 | 3-ethyl-6-fluoro-2-(1-(1-methylazepan-4-yl)butyl)quinazolin-4(3H)-one |
| 268 | 3-ethyl-2-(1-(1-ethylazepan-4-yl)butyl)-6-fluoroquinazolin-4(3H)-one |
| 269 | (6S,7R)-2-bromo-7-ethyl-6-(4-methyl-1,4-diazepan-1-yl)-8,9-dihydro-6H-pyrido[2,1-b]quinazolin-11(7H)-one |
| 270 | (6R,7S)-2-bromo-7-ethyl-6-(4-methyl-1,4-diazepan-1-yl)-8,9-dihydro-6H-pyrido[2,1-b]quinazolin-11(7H)-one |

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In the following the phrase "compound of the invention" is used. This is to be understood as any compound according to the invention as described above according to general Formulae (I'), ($I^{2'}$), ($I^{3'}$), ($I^{4'}$) or (Isl.

The compounds of the invention represented by the above described Formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

For the sake of clarity the expression "a compound according to Formula (I), wherein e.g. $R_1$, $R_2$, $R_3$, $R_4$, $R_5$, $R_5$', $R_5$", $R_5$''', $R_6$, $R_6$', $R_6$", $R_7$, $R_9$, $R_9$', $R_y$, $R_y$, $R_y$", $R_y$'''', W, $w_1$, $w_2$, $w_3$ and $w_4$ are as defined below in the detailed description" would (just like the expression "a compound of Formula (I) as defined in any one of claims e.g. 1 to 8" found in the claims) refer to "a compound according to Formula (I)", wherein the definitions of the respective substituents $R_1$ etc. (also from the cited claims) are applied. In addition, this would also mean, though (especially in regards to the claims) that also one or more disclaimers or provisos defined in the description (or used in any of the cited claims like e.g. claim 1) would be applicable to define the respective compound. Thus, a disclaimer or a proviso found in e.g. claim 1 would be also used to define the compound "of Formula (I) as defined in any one of the corresponding related claims e.g. 1 to 8".

In general the processes are described below in the experimental part. The starting materials are commercially available or can be prepared by conventional methods.

A preferred embodiment of the invention is a process for the production of a compound according to Formula (I), wherein, if not defined otherwise, $R_1$, $R_2$, $R_3$, $R_4$, $R_5$, $R_5$', $R_5$", $R_5$''', $R_6$, $R_6$', $R_6$''', $R_6$', $R_7$, $R_9$, $R_9$', $R_y$, $R_y$, $R_y$", $R_y$''', $R_y$'''', W, $w_1$, $w_2$, $w_3$ and $w_4$ have the meanings defined in the description. LG represents a leaving group (such as chloro, bromo, iodo, mesylate, tosylate, nosylate or triflate).

In a particular embodiment there is a process for the production of a compound according to Formula (I), wherein $R_1$, $R_2$, $R_3$, $R_4$, $R_5$, $R_5$', $R_5$", $R_5$''', $R_6$, $R_6$', $R_6$", $R_6$''', $R_7$, $R_9$, $R_9$', $R_y$, $R_y$', $R_y$", $R_y$''', $R_y$''', $w_1$, $w_2$, $w_3$ and we have the meanings as defined in the description, and W is nitrogen, said process comprises reacting a compound of formula VIII

VIII

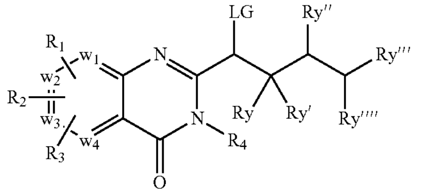

with a suitable amine of formula IX,

IX

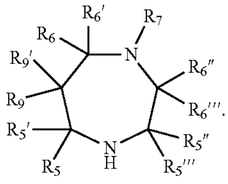

in a suitable solvent, such as acetonitrile or dimethylformamide, in the presence of a base such as triethylamine, $K_2CO_3$ or N,N-diisopropylethylamine, at a suitable temperature comprised between room temperature and the reflux temperature, preferably heating.

In another particular embodiment there is a process for the production of a compound according to Formula (I), wherein, $R_1$, $R_2$, $R_3$, $R_4$, $R_5$, $R_5'$, $R_5''$, $R_5'''$, $R_6$, $R_6'$, $R_6''$, $R_6'''$, $R_7$, $R_9$, $R_9'$, $R_y$, $R_y'$, $R_y$ ", $R_y''$, $R_y'$ ", $w_1$, $w_2$, $w_3$ and $w_4$ have the meanings as defined in the description, and Wis carbon, said process comprises the alkylation of a compound of formula XIV

XIV

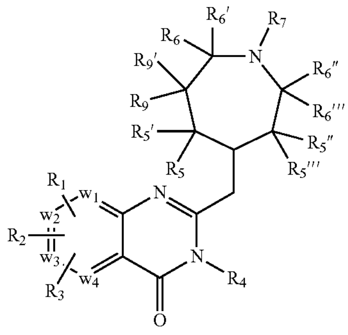

with a compound of formula XV,

XV

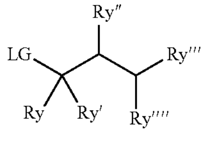

using a suitable base, such as lithium bis(trimethylsilyl) amide, in a suitable solvent, such as tetrahydrofuran at a suitable temperature, such as room temperature.

In a particular embodiment there is a process for the production of a compound according to Formula (I), wherein $R_1$, $R_2$, $R_3$, $R_4$, $R_5$, $R_5'$, $R_5''$, $R_5'''$, $R_6$, $R_6'$, $R_6''$, $R_7$, $R_9$, $R_9'$, $R_y$, $R_y$, $R_y''$, $R_y''''$, $w_1$, $w_2$, $w_3$ and $w_4$ have the meanings as defined in the description, said process comprises when W is nitrogen, reacting a compound of formula VIII

VIII

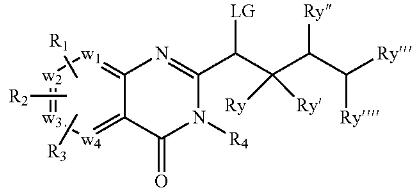

with a suitable amine of formula IX,

IX

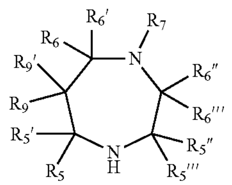

in a suitable solvent, such as acetonitrile or dimethylformamide, in the presence of a base such as triethylamine, $K_2CO_3$ or N,N-diisopropylethylamine, at a suitable temperature comprised between room temperature and the reflux temperature, preferably heating, or when W is carbon, said process comprises the alkylation of a compound of formula XIV

XIV

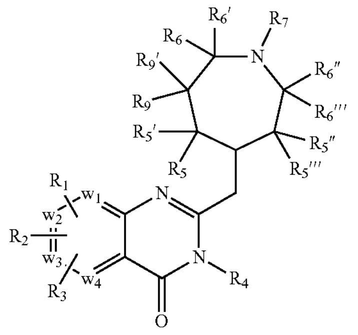

with a compound of formula XV,

XV

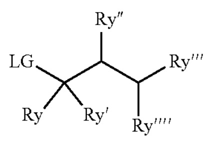

using a suitable base, such as lithium bis(trimethylsilyl) amide, in a suitable solvent, such as tetrahydrofuran at a suitable temperature, such as room temperature.

In a particular embodiment there is a process for the production of a compound according to Formula (I), by the reduction reaction of a carbonyl derivative with a suitable reductive reagent, preferably sodium borohydride, in an organic solvent, preferably MeOH, to afford a hydroxyl compound.

In a particular embodiment there is a process for the production of a compound according to Formula (I), by deprotection reaction of a compound of formula I that contains an amine protecting group such as a carbamate, preferably Cert-butoxy carbonyl, by any suitable method, such as treatment with an acid, preferably HCl or trifluoroacetic acid in an appropriate solvent such as 1,4-dioxane, DCM, ethyl acetate or a mixture of an organic solvent and water.

In a particular embodiment there is a process for the production of a compound according to Formula (I), by reductive amination reaction of a compound of formula I that contains an amino group with an aldehyde, preferably carried out with a reductive reagent, preferably sodium triacetoxyborohydride, in an organic solvent, preferably DCE, in the presence of an organic base, preferably DIPEA or TEA. Alternatively, the reaction can be carried out in the presence of an acid, preferably acetic acid.

In a particular embodiment there is a process for the production of a compound according to Formula (I), by reaction of a compound of formula I that contains an amino group with an alkylating reagent, in the presence of a base, preferably DIPEA or $K_2CO_3$, in an organic solvent, preferably acetonitrile, at suitable temperature, such as in the range of 0-120° C.

In a particular embodiment there is a process for the production of a compound according to Formula (I), by reaction of a compound of formula I that contains an amino group with a vinyl derivative, in an organic solvent, preferably 2-methoxyethanol, at suitable temperature, such as in the range of 20-140° C.

A particular embodiment of the invention refers to the use of a compound of Formula (IIa), IIa

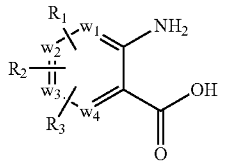

wherein $R_1$, $R_2$, $R_3$, $R_4$, $w_1$, $w_3$ and $w_4$ have the meaning as defined in the description, for the preparation of compounds of Formula (I).

A particular embodiment of the invention refers to the use of a compound of Formula (IIb), IIb

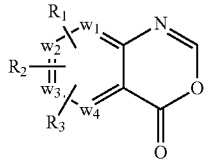

wherein $R_1$, $R_2$, $R_3$, $w_1$, $w_2$, $w_3$ and $w_4$ have the meaning as defined in the description, for the preparation of compounds of Formula (I).

A particular embodiment of the invention refers to the use of a compound of Formula (III),

III $H_2N—R_4$ wherein $R_4$ has the meaning as defined in the description, for the preparation of compounds of Formula (I).

A particular embodiment of the invention refers to the use of a propylmagnesium compound of Formula (IV),

IV

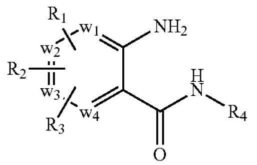

wherein $R_1$, $R_2$, $R_3$, $R_4$, $w_1$, $w_2$, $w_3$ and $w_4$ have the meaning as defined in the description, for the preparation of compounds of Formula (I).

A particular embodiment of the invention refers to the use of an allyl derivative of Formula (V),

V

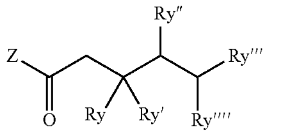

wherein $R_y$, $R_y'$, $R_y''$, $R_y'''$ and $R_y''''$ have the meaning as defined in the description, for the preparation of compounds of Formula (I).

A particular embodiment of the invention refers to the use of a compound of Formula (VI),

VI

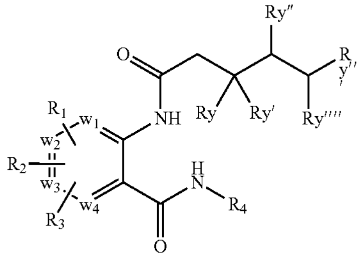

wherein $R_1$, $R_2$, $R_3$, $R_4$, $R_y$, $R_y'$, $R_y''$, $R_y'''$, $R_y''''$, W, $w_1$, $w_2$, $w_3$ and we have the meaning as defined in the description, for the preparation of compounds of Formula (I).

A particular embodiment of the invention refers to the use of a compound of Formula (VII),

VII

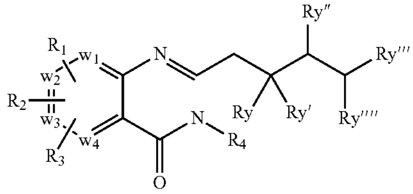

wherein $R_1$, $R_2$, $R_3$, $R_4$, $R_y$, $R_y'$, $R_y''$, $R_y'''$, $R_y''''$, $w_1$, $w_2$, $w_3$ and $w_4$ have the meaning as defined in the description, for the preparation of compounds of Formula (I).

A particular embodiment of the invention refers to the use of a compound of Formula (VIIa), VIIa

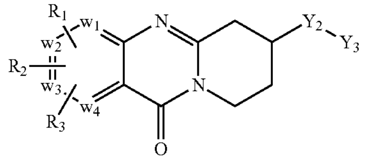

wherein $Y_2$-$Y_3$ means $-CHR_y''CHR_y'''R_y''''$, and $R_1$, $R_2$, $R_3$, $R_y$, $R_y'$, $R_y''$, $R_y'''$, $R_y''''$, $w_1$, $w_2$, $w_3$ and $w_4$ have the meaning as defined in the description, for the preparation of compounds of Formula (I).

A particular embodiment of the invention refers to the use of a compound of Formula (VIII),

VIII

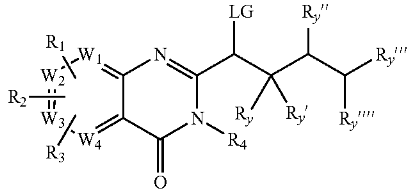

wherein $R_1$, $R_2$, $R_3$, $R_4$, $R_y$, $R_y'$, $R_y''$, $R_y'''$, $R_y''''$, $w_1$, $w_2$, $w_3$ and $w_4$ have the meaning as defined in the description, and LG represents a leaving group (such as chloro, bromo, iodo, mesylate, tosylate, nosylate or triflate) for the preparation of compounds of Formula (I).

A particular embodiment of the invention refers to the use of a butyl zinc compound of Formula (IX),

IX

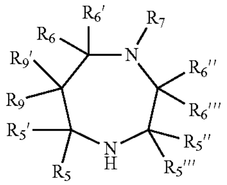

wherein $R_5$, $R_5'$, $R_5''$, $R_5'''$, $R_6$, $R_6'$, $R_6''$, $R_6'''$, $R_7$, $R_9$ and $R_9'$ have the meaning as defined in the description, for the preparation of compounds of Formula (I).

A particular embodiment of the invention refers to the use of a compound of Formula (XII),

XII

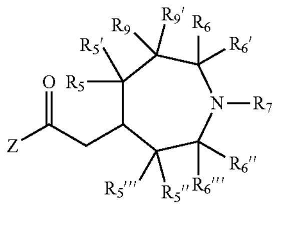

wherein $R_5$, $R_5'$, $R_5''$, $R_5'''$, $R_6$, $R_6'$, $R_6''$, $R_6'''$, $R_7$, $R_9$ and $R_9'$ have the meaning as defined in the description, and Z represents OH or a halogen atom for the preparation of compounds of Formula (I).

A particular embodiment of the invention refers to the use of a compound of Formula (XIII),

XIII

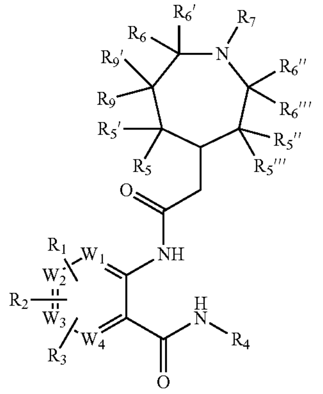

wherein $R_1$, $R_2$, $R_3$, $R_4$, $R_5$, $R_5'$, $R_5''$, $R_5'''$, $R_6$, $R_6'$, $R_6''$, $R_6'''$, $R_7$, $R_9$, $R_9'$, $w_1$, $w_2$, $w_3$ and $w_4$ have the meaning as defined in the description, for the preparation of compounds of Formula (I).

A particular embodiment of the invention refers to the use of a compound of Formula (XIV),

XIV

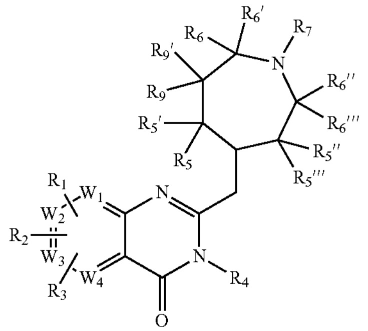

wherein $R_1$, $R_2$, $R_3$, $R_4$, $R_5$, $R_5'$, $R_5''$, $R_5'''$, $R_6$, $R_6'$, $R_6''$, $R_6'''$, $R_7$, $R_9$, $R_9'$, $w_1$, $w_2$, $w_3$ and $w_4$ have the meaning as defined in the description, for the preparation of compounds of Formula (I).

A particular embodiment of the invention refers to the use of a compound of Formula (XV),

XV

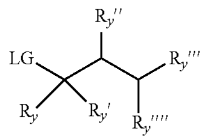

wherein $R_y$, $R_y'$, $R_y''$, $R_y'''$, $R_y''''$ have the meaning as defined in the description, and LG represents a leaving group (such as chloro, bromo, iodo, mesylate, tosylate, nosylate or triflate) for the preparation of compounds of Formula (I).

A particular embodiment of the invention refers to the use of a compound of Formula (XVI),

XVI

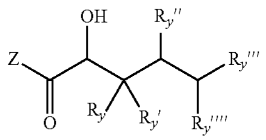

wherein $R_y$, $R_y'$, $R_y''$, $R_y'''$ and $R_y''''$ have the meaning as defined in the description, and Z represents OH or a halogen atom for the preparation of compounds of Formula (I).

A particular embodiment of the invention refers to the use of a compound of Formula (XVII),

XVII

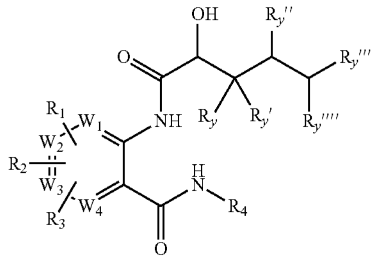

wherein $R_1$, $R_2$, $R_3$, $R_4$, $R_y$, $R_y'$, $R_y''$, $R_y'''$, $R_y'''$, $w_1$, $w_2$, $w_3$ and $w_4$ have the meaning as defined in the description, for the preparation of compounds of Formula (I).

A particular embodiment of the invention refers to the use of a compound of Formula (XVIII),

XVIII

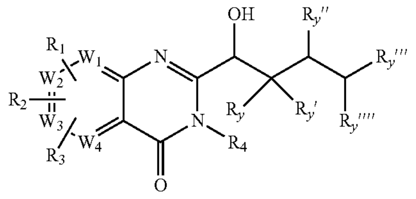

wherein $R_1$, $R_2$, $R_3$, $R_4$, $R_5$, $R_5'$, $R_5''$, $R_y$, $R_y'$, $R_y''$, $R_y'''$, $R_y''$, $w_1$, $w_2$, $w_3$ and $w_4$ have the meaning as defined in the description, for the preparation of compounds of Formula (I).

A particular embodiment of the invention refers to the use of a compound of Formula (XIX),

XIX

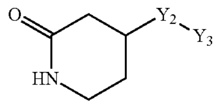

wherein $Y_2$-$Y_3$ means —$CHR_y''$ $CHR_y''R_y''$, and $R_y''$, $R_y''$ and $R_y''$ have the meaning as defined in the description, for the preparation of compounds of Formula (I).

A particular embodiment of the invention refers to the use of a compound of Formula IIa, IIb, III, IV, V, VI, VII, Vila, VIII, IX, XII, XIII, XIV, XV, XVI, XVII, XVIII or XIX, IIa

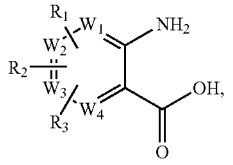

IIb

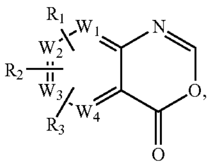

III $H_2N—R_4$,

IV

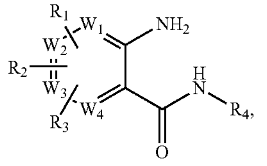

V

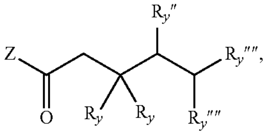

VI

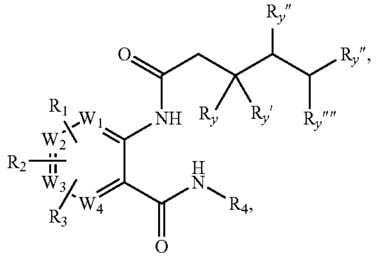

VII

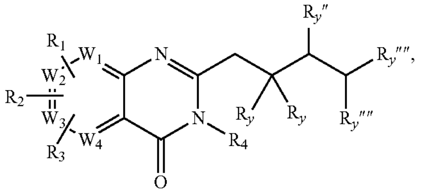

VIIa

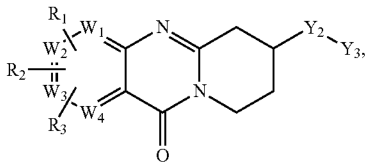

VIII

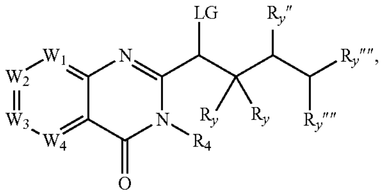

-continued

IX

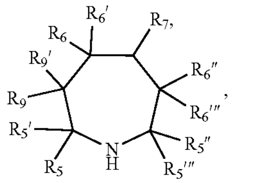

XII

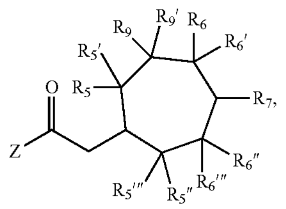

XIII

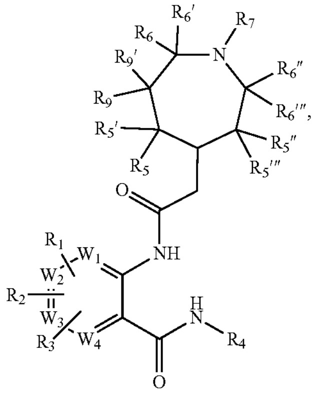

XIV

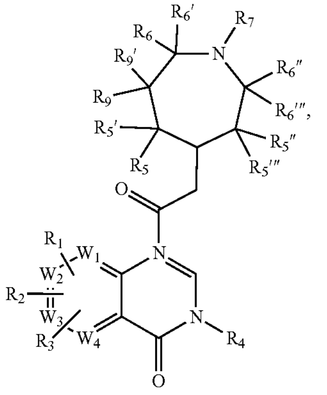

XV

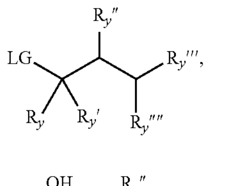

XVI

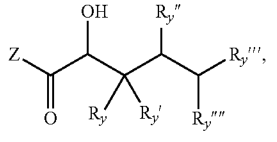

-continued

XVII

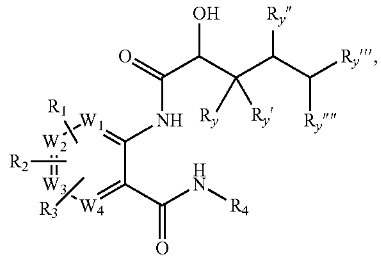

XVIII

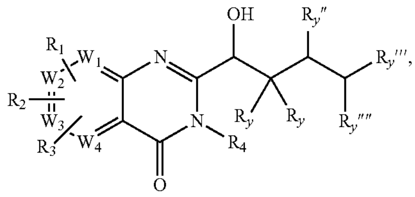

XIX

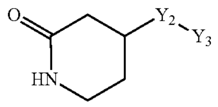

wherein $Y_2$-$Y_3$ means —$CHR_y$"$CHR_y$" $R_y$", and $R_1$, $R_2$, $R_3$, $R_4$, $R_5$, $R_5$', $R_5$", $R_5$"', $R_6$, $R_6$', $R_6$", $R_6$", $R_7$, $R_9$, $R_9$', $R_y$, $R_y$', $R_y$", $R_y$"', $R_y$", W, $w_1$, $w_2$, $w_3$ and $w_4$ have the meanings as defined in the description, LG represents a leaving group (such as chloro, bromo, iodo, mesylate, tosylate, nosylate or triflate) and Z represents OH or a halogen atom, for the preparation of compounds of Formula (I).

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or stereoisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration, Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general scope of the present invention.

GENERAL EXPERIMENTAL PART

Synthesis Description

The compounds of formula I may be prepared by a four to five step process as described in Scheme 1, Scheme 1
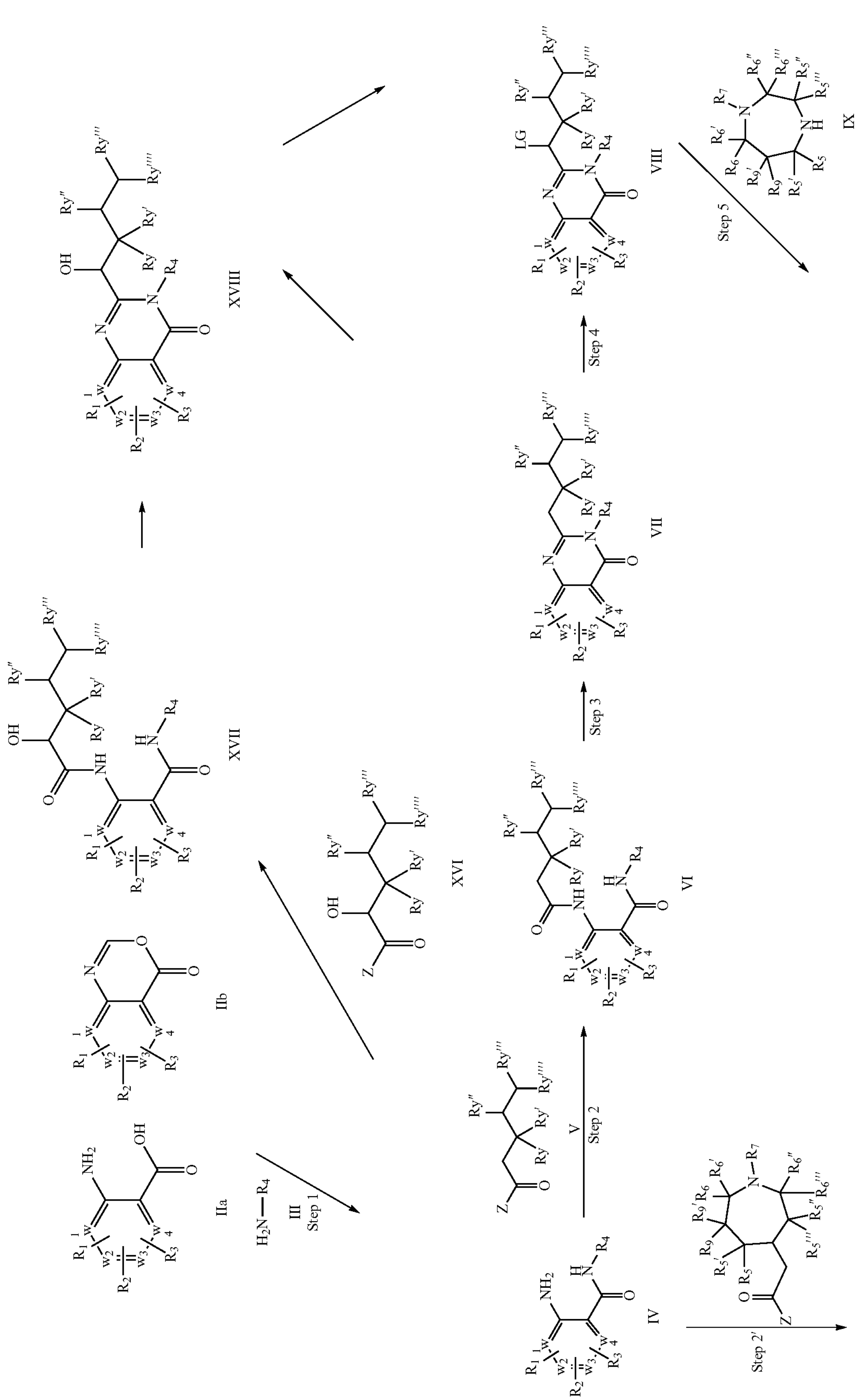

-continued
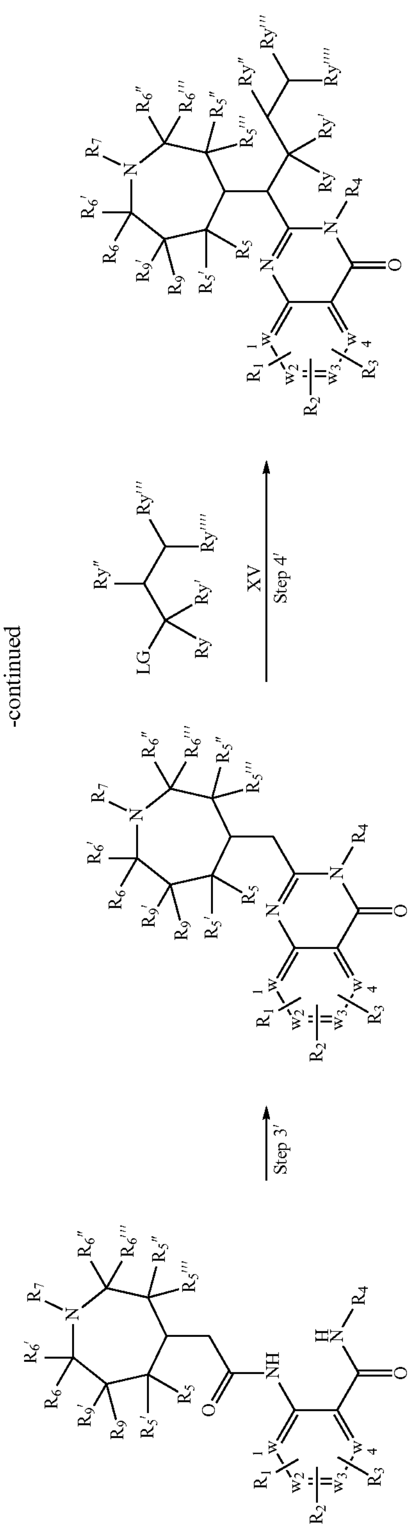
XIII XIV XV I wherein $R_1$, $R_2$, $R_3$, $R_4$, $R_{5\text{-}5''}$, $R_{6\text{-}6''}$, $R_{9\text{-}9''}$, $R_{y\text{-}y''}$, W, $w_1$, $w_2$, $w_3$, and we have the meanings as defined in claim 1, LG represents a leaving group (such as chloro, bromo, iodo, mesylate, tosylate, nosylate or triflate) and Z represents OH or a halogen atom.

The process can be carried out as described below:

Step 1: A compound of formula IV can be prepared by treating an acid of formula IIa with a suitable amine of formula III in the presence of a suitable coupling agent, such as 1-[bis(dimethylamino)methylene]-1H-1,2,3-triazolo[4,5-b]pyridinium 3-oxid hexafluorophosphate, in the presence of a base such as triethylamine, in a suitable solvent, such as dimethylformamide, at a suitable temperature, preferably at room temperature. Alternatively, an oxazine derivative of formula IIb may be used as starting material, in which case the reaction with the amine of formula III is performed in acetonitrile, at a suitable temperature, such as heating.

Step 2: A compound of formula VI can be prepared by treating a compound of formula IV with a suitable acid derivative of formula V. When Z is a halogen atom the reaction may be carried out in the presence of a base, such as triethylamine, in a suitable solvent, such as dichloromethane, at a suitable temperature, such as room temperature. When Z is OH the reaction can be carried out using similar conditions to those described in step 1.

Step 3: A compound of formula VII can be prepared by treating a compound of formula VI with a suitable halogen such as iodine, in the presence of a base, such as hexamethyldisilazane, in a suitable solvent, such as dichloromethane, at a suitable temperature, preferably room temperature. Alternatively, the reaction may be carried out using a strong base, such as lithium hydroxide in a suitable solvent, such as ethylene glycol, at a suitable temperature, such as heating.

Step 4: A compound of formula VIII, where LG represents a leaving group, such as a halogen atom, can be prepared by reacting a compound of formula VII with a suitable halogenating agent, such as bromine in the presence of a suitable base such as sodium acetate, in a suitable solvent, such as acetic acid, at a suitable temperature, preferably heating.

Alternatively, a compound of formula VIII can be prepared by converting the hydroxyl group of a compound of formula XVIII into a leaving group. For instance, it can be converted to a triflate group by using triflic anhydride in the presence of a suitable base, such as 2,6-lutidine, at a suitable temperature such as between −78° C. and room temperature. A compound of formula XVIII may be obtained from a compound of formula XVII using the conditions described in Step 3. In turn, XVII may be prepared by coupling a compound of formula IV with an acid derivative of formula XVI using the conditions described in Step 2. Alternatively a compound of formula XVIII may be obtained from a compound of formula VII using a hydroxylating reagent, such as (1R)-1-(((1,2-oxaziridin-2-yl)sulfonyl)methyl)-7,7-dimethylbicyclo[2.2.1]heptan-2-one in a suitable solvent, such as tetrahydrofuran, at a suitable temperature, such as cooling to −60° C.

Step 5: A compound of formula I, in which W is nitrogen, can be prepared by reacting a compound of formula VIII with a suitable amine of formula IX, in a suitable solvent, such as acetonitrile or dimethylformamide, in the presence of a base such as triethylamine, $K_2CO_3$ or N,N-diisopropylethylamine, at a suitable temperature comprised between room temperature and the reflux temperature, preferably heating. Alternatively, the reactions can be carried out under microwave heating and optionally using an activating agent such as sodium iodide or potassium iodide.

Alternatively, a compound of formula I, in which W is a carbon atom, may be prepared by reacting a compound of formula IV with a compound of formula XII under the conditions used in Step 2 (Step 2'), to give a compound of formula XIII. This may be followed by cyclization under the conditions used in Step 3 (Step 3') and final alkylation of a compound of formula XIV with a compound of formula XV, using a suitable base, such as lithium bis(trimethylsilyl) amide, in a suitable solvent, such as tetrahydrofuran at a suitable temperature, such as room temperature (Step 4').

In addition a compound of formula VIIa in which $Y_2$-$Y_3$ means —$CHR_y''CHR_y''R_y''$, and $R_1$, $R_2$, $R_3$, $R_y''$, $R_y'''$, $R_y''$, $w_1$, $w_2$, $w_3$ and $w_4$, may be prepared by reaction of a compound of formula IIa by treatment with thionyl chloride and subsequent addition of a piperidone compound of formula XIX, at a suitable temperature, such as room temperature.

Scheme 2

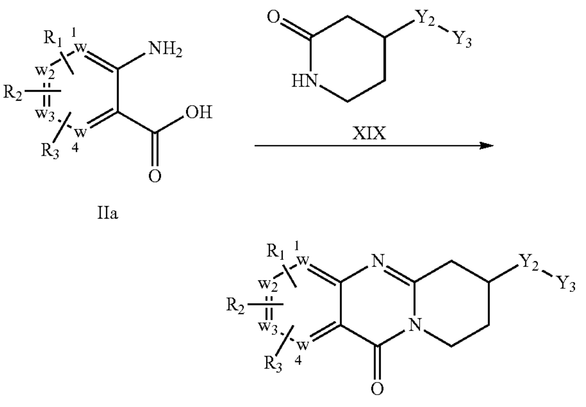

IIa

VIIa

In addition, certain compounds of the present invention can also be obtained by functional group interconversion over compounds of formula I or any of the intermediates shown in Scheme 1. The following conversions are examples of transformations that may be carried out:

An aromatic halogen atom, ie a bromine atom, may be converted to a hydroxyl group by conversion to a suitable boronic derivative, for example by reaction with bispinacol in the presence of a base, such as potassium acetate and a palladium catalyst, such as Pd(dppf)$FeCl_2$, in a suitable solvent, such as dioxane at a suitable temperature, such as heating, followed by reaction with sodium perborate, in a suitable solvent such as mixture of tetrahydrofuran and water, at a suitable temperature, such as room temperature.

An aromatic halogen atom, ie a bromine atom, may be converted to an aryl group by reaction with a suitable arylboronic acid derivative, in the presence of a Pd catalyst such as tetrakis(triphenylphosphine)palladium (O), in a suitable solvent, such as mixtures of dimethoxyethane-water, in the presence of a base, such as potassium carbonate, at a suitable temperature, such as heating.

An aromatic halogen atom, ie a bromine atom, may be converted to an amino derivative by reaction with a suitable amine under Buchwald-Hartwig conditions, using a Pd catalyst such as tris(dibenzylideneacetone) dipalladium(0) or palladium acetate, and a suitable ligand, preferably a phosphine ligand such as DavePhos. BINAP or XPhos, using a suitable base such as sodium tert-butoxide or cesium carbonate, in a suitable solvent such as tert-butanol, toluene or 1,4-dioxane, at a suitable temperature, preferably heating.

An aromatic halogen atom, ie a bromine atom, may be converted to an alkyl derivative by reaction with a suitable potassium trifluoroborate derivative, using a Pd catalyst, such as palladium acetate or bis(di-tert-butyl (4-dimethylaminophenyl)phosphine)dichloropalladium(II) and a suitable base, such as cesium carbonate, in a suitable solvent such as toluene-water mixtures, at a suitable temperature, preferably heating and optionally under microwave irradiation In some of the processes described above it may be necessary to protect the reactive or labile groups present with suitable protecting groups, such as for example Boc (tert-butoxycarbonyl), Teoc (2-(trimethylsilyl)ethoxycarbonyl) or benzyl for the protection of amino groups, and common silyl protecting groups for the protection of the hydroxyl group. The procedures for the introduction and removal of these protecting groups are well known in the art and can be found thoroughly described in the literature.

In addition, a compound of formula I can be obtained in enantiopure form by resolution of a racemic compound of formula I either by chiral preparative HPLC or by crystallization of a diastereomeric salt or co-crystal. Alternatively, the resolution step can be carried out at a previous stage, using any suitable intermediate.

The compounds of formula IIa, IIb, III, V, IX, XII, XV, XVI and XIX used in the methods disclosed above are commercially available or can be synthesized following common procedures described in the literature and exemplified in the synthesis of some intermediates.

EXAMPLES

The following abbreviations are used in the examples:

ACN: acetonitrile
AlBN: azobisisobutyronitrile
Aq: aqueous
Anh: anhydrous
Chx: Cyclohexane
DavePhos: 2-Dicyclohexylphosphino-2"-(N,N-dimethylamino)biphenyl
DCM: dichloromethane
DME: dimethoxyethane
DMF dimethylformamide
Eq: equivalent's
$Et_2O$: diethyl ether
EtOAc; ethyl acetate
EtOH: ethanol
h: hours
HATU: (1-[Bis(dimethylamino)methylene]-1H-1,2,3-triazolo[4,5-b]pyridinium 3-oxid hexafluorophosphate)
HMDS: hexamethyldisilazane
HPLC: high performance liquid chromatography
KOAc: Potassium acetate
LiHMDS: lithium bis(trimethylsilyl)amide
MeOH: methanol
MS: mass spectrometry
Min: minutes
NaOAc: sodium acetate
NaOtBu: sodium tert-butoxicle
NBS: N-Bromosuccinimide
$Pd_2dba_3$ Tris(dibenzylideneacetone)dipalladium(O)
$Pd(dppf)FeCl_2$:[1,1'-Bis(diphenylphosphino)ferrocene] dichloropalladium(II)
$Pd(PPh_3)_4$: (Tetrakis(triphenylphosphine)palladium(0)
Quant: quantitative
Rt.: retention time
r.t.: room temperature
Sat: saturated
Sol: solution
TBAF: Tetrabutylammonium fluoride
TEA: triethylamine
TFA: trifluoroacetic acid
THF: tetrahydrofuran
TMSCl: Trimethylsilyl chloride
XPhos: 2-Dicyclohexylphosphino-2',4',6'-triisopropylbiphenyl The following methods were used to determine the HPLC-MS spectra:

Method A

Column Acquity UPLC BEH C18 2.1×50 mm. 1.7 μm, flow rate 0.61 mL/min; A: $NH_4HCO_3$ 10 mM pH 10.6, B: ACN; gradient 0.3 min 98% A. 98% to 0% A in 2.7 min; isocratic 2 min 0% A.

Method B

Column Acquity UPLC BEH C18 2.1×50 mm, 1.7 μm, flow rate 0.61 mL/min; A: $NH_4CO_3$ 10 mM, B: ACN, C: MeOH+0.1% formic acid; gradient 0.3 min 98% A. 98% A to 0:95:5 A:B:C in 2.7 min; 0:95:5 A:B:C to 100% B in 0.1 min; isocratic 2 min 100% B.

Method C

Column Acquity UPLC BEH C18 2.1×50 mm, 1.7 μm, flow rate 0.61 mL/min; A: $NR_4HCO_{310}$ mM, ACN; gradient 0.3 min 98% A, 98% to 0% A in 2.7 min; isocratic 2 min 0% A.

Method D

Column Acquity UPLC BEH C18 2.1×50 mm, 1.7 μm, flow rate 0.60 mL/min; A: $NH_4HCO_3$ 10 mM, B: ACN: gradient 0.3 min 90% A, 90% A to 5% A in 2.7 min, 0.7 min isocratic 5% A.

Method E

Column Acquity UPLC BEH C18 2.1×50 mm. 1.7 μm, flow rate 0.60 mL/min: A: $NH_4HCO_3$ 10 Mm pH 10.6, B: ACN; gradient 0.3 min 90% A, 90% A to 5% A in 2.7 min, 0.7 min isocratic 5% A.

Method F

Column Acquity UPLC BEH C18 2.1×50 mm. 1.7 μm, flow rate 0.61 mL/min; A: $NH_4HCO_1$10 mM, B: ACN; gradient 0.3 min 98% A, 98% A to 100% B in 2.65 min; isocratic 2.05 min 100% B.

Method G

Column Acquity UPLC BEH C18 2.1×50 mm. 1.7 μm, flow rate 0.6 mL/min; A: Water+0.1% v/v TFA, B: ACN+0.1% v/v TFA; gradient 95% A to 5% A in 4 min, 5% A to 100 B in 0.02 min, isocratic 0.48 min 100% B.

SYNTHESIS OF EXAMPLES

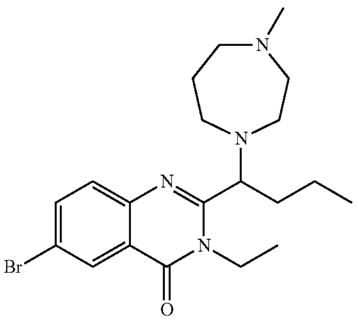 [SMILES: CCCC(c1nc2ccc(Br)cc2c(=O)n1CC)N1CCCN(C)CC1]

Example 1. 6-Bromo-3-ethyl-2-(1-(4-methyl-1,4-diazepan-1-yl)butyl)quinazolin-4(3H)-one Step a. 2-Amino-5-bromo-N-ethylbenzamide To a solution of 2-amino-5-bromobenzoic acid (6 g, 28 mmol) in anh DMF (75 mL) under argon atmosphere, TEA (8 mL, 57 mmol) and HATU (13.0 g, 33 mmol) were added and the reaction mixture was stirred at 0° C. for 10 min. Then, ethylamine (2 M in THF, 31 mL, 42 mmol) was added dropwise and the reaction mixture was allowed to reach r.t. and stirred overnight. The reaction crude was diluted with EtOAc:$Et_2O$ (1:1) and washed with aq $NaHCO_3$ sat sol. The organic layer was dried over anh $Na_2SO_4$, filtered and concentrated to dryness to give the title compound (7.0 g, Yield: 99%).

Step b. 5-Bromo-N-ethyl-2-pentanamidobenzamide

To a solution of the compound obtained in step a (7.0 g, 29 mmol) in anh DCM (120 mL) under argon atmosphere, TEA (6 mL, 43 mmol) was added dropwise and the mixture was stirred for 10 min. The solution was cooled at 0° C., pentanoyl chloride (4 mL, 33 mmol) was added dropwise and the reaction mixture was allowed to reach r.t. and stirred overnight. The resulting mixture was diluted with DCM and washed with aq. $NaHCO_3$ sat sol. The organic layer was dried over anh $Na_2SO_4$ and filtered and the solvent was removed under vacuum to give the title compound (10.0 g, Yield: 98%).

Step c. 6-Bromo-2-butyl-3-ethylquinazolin-4(3H)-one

To a solution of the compound obtained in step b (10.0 g. 30 mmol) in anh DCM (100 mL), iodine (15.0 g. 60 mmol) was added portionwise and the mixture was stirred until full solution was observed. The solution was cooled at 0° C. HMDS (25 mL, 120 mmol) was added dropwise and the reaction mixture was allowed to reach r.t. and stirred overnight. DCM was added and the reaction mixture was washed with a 5% $Na_2S_2O_3$ aq. sol. The organic layer was dried over anh $Na_2SO_4$, filtered and solvent was removed under vacuum to give the title compound (9.0 g, Yield: 99%).

Step d. 6-Bromo-2-(1-bromobutyl)-3-ethylquinazolin-4(3H)-one

To a solution of the compound obtained in step c (9.0 g, 28 mmol) in acetic acid (125 mL), NaOAc (2.8 g, 34 mmol) was slowly added and the reaction was stirred for 15 min at r.t. Bromine (2.2 mL, 42 mmol) was added dropwise and the reaction mixture was heated at 50° C. for 3 h. The mixture was concentrated under vacuum and the residue was dissolved in EtOAc and washed twice with 10% $NaHSO_3$ aq. sol and brine. The organic layer was dried over anh $Na_2SO_4$ and the solvent was removed under vacuum.

The crude product was purified by flash chromatography, silica gel, gradient Chx to Chx:EtOAc (9:1) to give the title compound (9.2 g, Yield: 84%).

Step e. Title Compound

To a solution of the compound obtained in step d (340 mg, 0,876 mmol) in anh ACN (20 mL), TEA (0.488 mL. 3.54 mmol) and KI (14.5 mg, 0.088 mmol) were added. The reaction was stirred for 20 min at r.t. and 1-methyl-1,4-diazepane (0.272 mL, 2.19 mmol) was added dropwise. The reaction mixture was heated at 90° C. and stirred overnight. The mixture was concentrated under reduced pressure, and the crude residue was dissolved in EtOAc and washed twice with sat. aq. $NaHCO_3$. The organic layer was dried over anh $Na_2SO_4$, filtered and evaporated to dryness. The crude product was purified by flash chromatography, silica gel, gradient DCM to DCM:MeOH (9:1) to give the title compound (140 mg, Yield: 38%).

HPLC-MS (A) Rt, 2.63 min; ESI+-MS m/z: 421.0 (M+1).

This method was used for the preparation of examples 2-150 using suitable starting materials:

| STRUCTURE | EX | CHEMICAL NAME | Rt (min) | MS (M + H) | HPLC Method |
|---|---|---|---|---|---|
| 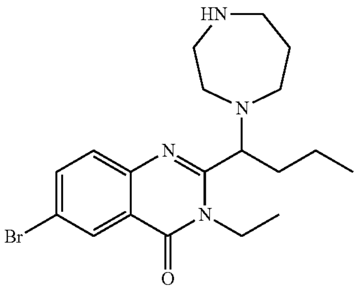 [SMILES: CCCC(c1nc2ccc(Br)cc2c(=O)n1CC)N1CCCNCC1] | 2 | 2-(1-(1,4-diazepan-1-yl) butyl)-6-bromo-3-ethylquinazolin-4(3H)-one | 1.93 | 407 | C |

-continued
| STRUCTURE | EX | CHEMICAL NAME | Rt (min) | MS (M + H) | HPLC Method |
|---|---|---|---|---|---|
| 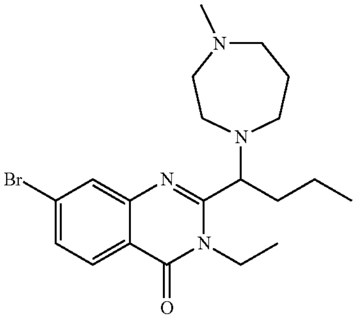 [SMILES: CCCC(c1nc2cc(Br)ccc2c(=O)n1CC)N1CCCN(C)CC1] | 3 | 7-bromo-3-ethyl-2-(1-(4-methyl-1,4-diazepan-1-yl)butyl)quinazolin-4(3H)-one | 2.31 | 421.1 | B |
| 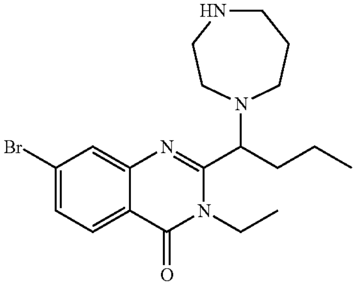 [SMILES: CCCC(c1nc2cc(Br)ccc2c(=O)n1CC)N1CCCNCC1] | 4 | 2-(1-(1,4-diazepan-1-yl)butyl)-7-bromo-3-ethylquinazolin-4(3H)-one | 2.87 | 407.5 | D |
| 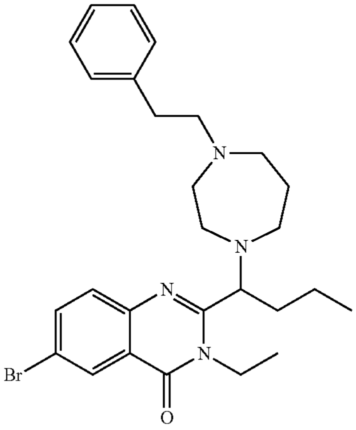 [SMILES: CCCC(c1nc2ccc(Br)cc2c(=O)n1CC)N1CCCN(CCc2ccccc2)CC1] | 5 | 6-bromo-3-ethyl-2-(1-(4-phenethyl-1,4-diazepan-1-yl)butyl)quinazolin-4(3H)-one | 3.75 | 511.2 | D |
| 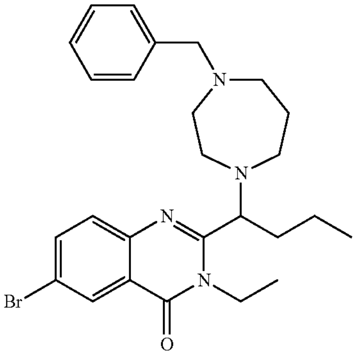 [SMILES: CCCC(c1nc2ccc(Br)cc2c(=O)n1CC)N1CCCN(Cc2ccccc2)CC1] | 6 | 2-(1-(4-benzyl-1,4-diazepan-1-yl)butyl)-6-bromo-3-ethylquinazolin-4(3H)-one | 3.21 | 497.4 | B |

-continued
| STRUCTURE | EX | CHEMICAL NAME | Rt (min) | MS (M + H) | HPLC Method |
|---|---|---|---|---|---|
| 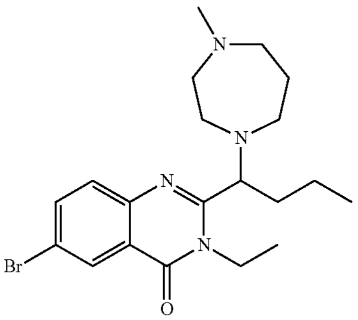 [SMILES: CCCC(c1nc2ccc(Br)cc2c(=O)n1CC)N1CCCN(C)CC1] | 7 | 6-bromo-3-ethyl-2-(1-(4-ethyl-1,4-diazepan-1-yl)butyl)quinazolin-4(3H)-one | 2.32 | 435.1 | B |
| 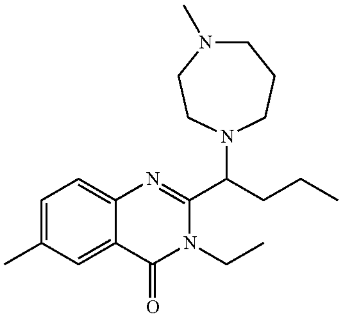 [SMILES: CCCC(c1nc2ccc(C)cc2c(=O)n1CC)N1CCCN(C)CC1] | 8 | 3-ethyl-6-methyl-2-(1-(4-methyl-1,4-diazepan-1-yl)butyl)quinazolin-4(3H)-one | 2.01 | 357 | B |
| 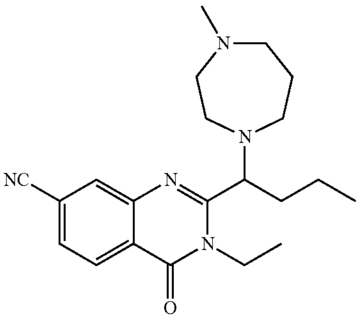 [SMILES: CCCC(c1nc2cc(C#N)ccc2c(=O)n1CC)N1CCCN(C)CC1] | 9 | 3-ethyl-2-(1-(4-methyl-1,4-diazepan-1-yl)butyl)-4-oxo-3,4-dihydroquinazoline-7-carbonitrile | 1.9 | 386.2 | B |
| 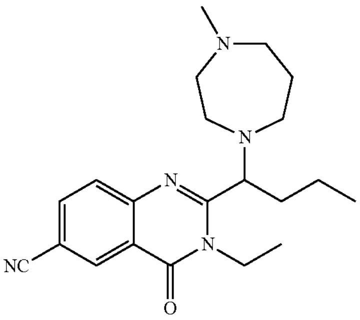 [SMILES: CCCC(c1nc2ccc(C#N)cc2c(=O)n1CC)N1CCCN(C)CC1] | 10 | 3-ethyl-2-(1-(4-methyl-1,4-diazepan-1-yl)butyl)-4-oxo-3,4-dihydroquinazoline-6-carbonitrile | 1.89 | 368.2 | B |

-continued
| STRUCTURE | EX | CHEMICAL NAME | Rt (min) | MS (M + H) | HPLC Method |
|---|---|---|---|---|---|
| 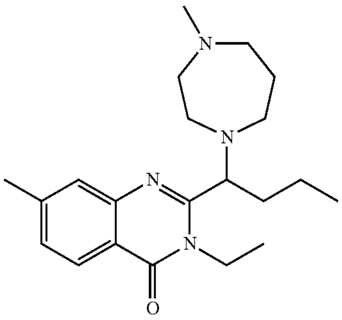 [SMILES: CCCC(c1nc2cc(C)ccc2c(=O)n1CC)N1CCCN(C)CC1] | 11 | 3-ethyl-7-methyl-2-(1-(4-methyl-1,4-diazepan-1-yl)butyl)quinazolin-4(3H)-one | 2.05 | 357.2 | B |
| 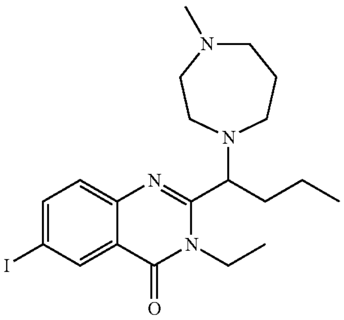 [SMILES: CCCC(c1nc2ccc(I)cc2c(=O)n1CC)N1CCCN(C)CC1] | 12 | 3-ethyl-6-iodo-2-(1-(4-methyl-1,4-diazepan-1-yl)butyl)quinazolin-4(3H)-one | 2.44 | 469.1 | B |
| 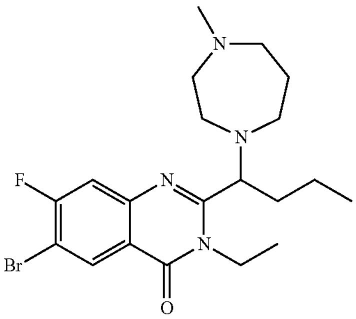 [SMILES: CCCC(c1nc2cc(F)c(Br)cc2c(=O)n1CC)N1CCCN(C)CC1] | 13 | 6-bromo-3-ethyl-7-fluoro-2-(1-(4-methyl-1,4-diazepan-1-yl)butyl)quinazolin-4(3H)-one | 2.41 | 539.1 | B |
| 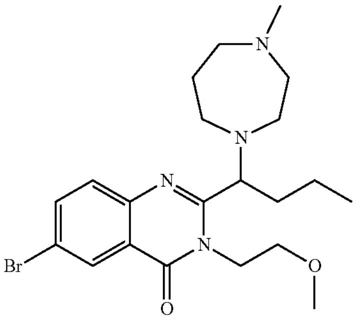 [SMILES: CCCC(c1nc2ccc(Br)cc2c(=O)n1CCOC)N1CCCN(C)CC1] | 14 | 6-bromo-3-(2-methoxyethyl)-2-(1-(4-methyl-1,4-diazepan-1-yl)butyl)quinazolin-4(3H)-one | 2.29 | 451.1 | B |

-continued
| STRUCTURE | EX | CHEMICAL NAME | Rt (min) | MS (M + H) | HPLC Method |
|---|---|---|---|---|---|
| 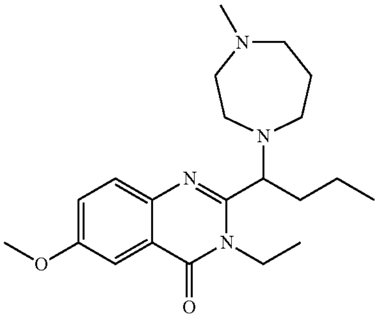 [SMILES: CCCC(c1nc2ccc(OC)cc2c(=O)n1CC)N1CCCN(C)CC1] | 15 | (R)-3-ethyl-6-methoxy-2-(1-(4-methyl-1,4-diazepan-1-yl)butyl)quinazolin-4(3H)-one | 1.92 | 373.2 | B |
| 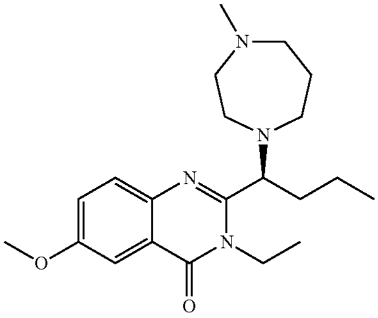 [SMILES: CCC[C@@H](c1nc2ccc(OC)cc2c(=O)n1CC)N1CCCN(C)CC1] | 16 | (S)-3-ethyl-6-methoxy-2-(1-(4-methyl-1,4-diazepan-1-yl)butyl)quinazolin-4(3H)-one | 1.93 | 373.2 | B |
| 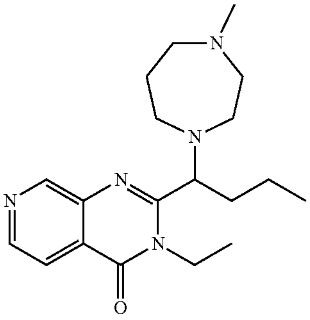 [SMILES: CCCC(c1nc2cnccc2c(=O)n1CC)N1CCCN(C)CC1] | 17 | 3-ethyl-2-(1-(4-methyl-1,4-diazepan-1-yl)butyl)pyrido[3,4-d]pyrimidin-4(3H)-one | 1.54 | 344.4 | B |
| 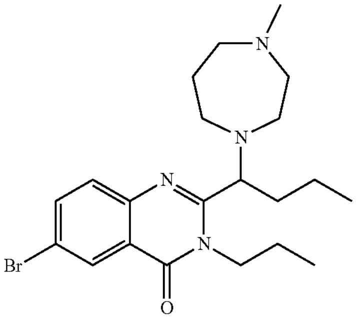 [SMILES: CCCC(c1nc2ccc(Br)cc2c(=O)n1CCC)N1CCCN(C)CC1] | 18 | 6-bromo-2-(1-(4-methyl-1,4-diazepan-1-yl)butyl)-3-propylquinazolin-4(3H)-one | 2.51 | 435.4 | B |

-continued
| STRUCTURE | EX | CHEMICAL NAME | Rt (min) | MS (M + H) | HPLC Method |
|---|---|---|---|---|---|
| 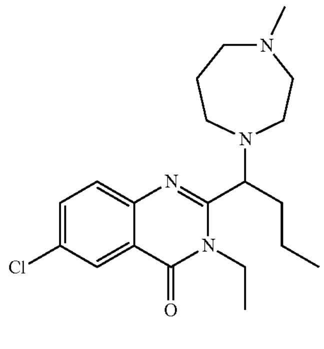 [SMILES: CCCC(c1nc2ccc(Cl)cc2c(=O)n1CC)N1CCCN(C)CC1] | 19 | 6-chloro-3-ethyl-2-(1-(4-methyl-1,4-diazepan-1-yl)butyl)quinazolin-4(3H)-one | 2.13 | 377.2 | B |
| 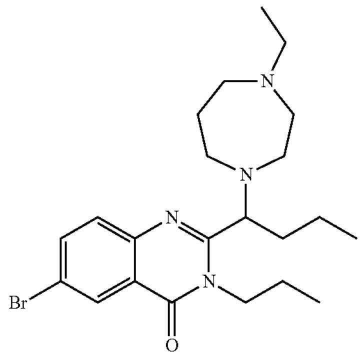 [SMILES: CCCC(c1nc2ccc(Br)cc2c(=O)n1CCC)N1CCCN(CC)CC1] | 20 | 6-bromo-2-(1-(4-ethyl-1,4-diazepan-1-yl)butyl)-3-propylquinazolin-4(3H)-one | 2.45 | 449.2 | B |
| 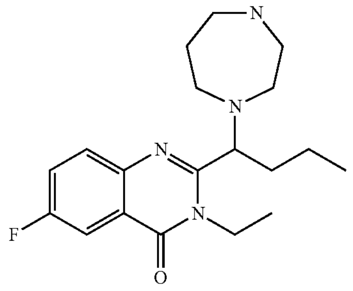 [SMILES: CCCC(c1nc2ccc(F)cc2c(=O)n1CC)N1CCCNCC1] | 21 | 3-ethyl-6-fluoro-2-(1-(4-methyl-1,4-diazepan-1-yl)butyl)quinazolin-4(3H)-one | 1.94 | 361.2 | B |
| 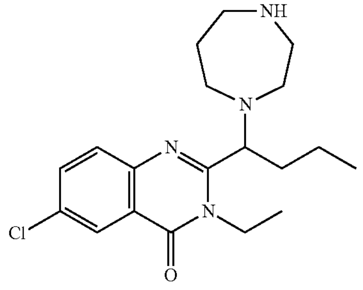 [SMILES: CCCC(c1nc2ccc(Cl)cc2c(=O)n1CC)N1CCCNCC1] | 22 | 2-(1-(1,4-diazepan-1-yl)butyl)-6-chloro-3-ethylquinazolin-4(3H)-one | 1.96 | 363.2 | B |

-continued
| STRUCTURE | EX | CHEMICAL NAME | Rt (min) | MS (M + H) | HPLC Method |
|---|---|---|---|---|---|
| 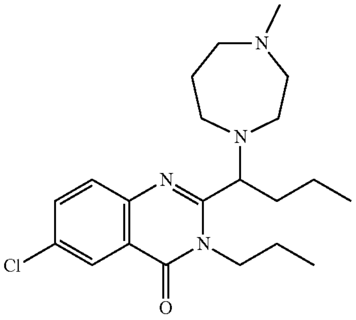 [SMILES: CCCC(c1nc2ccc(Cl)cc2c(=O)n1CCC)N1CCCN(C)CC1] | 23 | 6-chloro-2-(1-(4-methyl-1,4-diazepan-1-yl)butyl)-3-propylquinazolin-4(3H)-one | 2.38 | 391.2 | B |
| 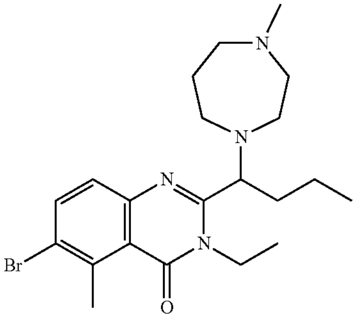 [SMILES: CCCC(c1nc2ccc(Br)c(C)c2c(=O)n1CC)N1CCCN(C)CC1] | 24 | 6-bromo-3-ethyl-5-methyl-2-(1-(4-methyl-1,4-diazepan-1-yl)butyl)quinazolin-4(3H)-one | 2.61 | 435.2 | B |
| 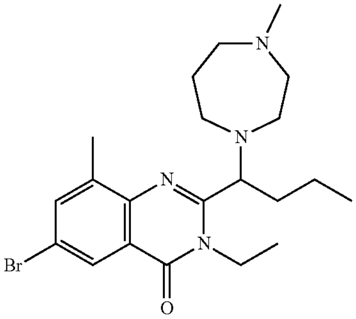 [SMILES: CCCC(c1nc2c(C)cc(Br)cc2c(=O)n1CC)N1CCCN(C)CC1] | 25 | 6-bromo-3-ethyl-8-methyl-2-(1-(4-methyl-1,4-diazepan-1-yl)butyl)quinazolin-4(3H)-one | 2.55 | 435.2 | B |
| 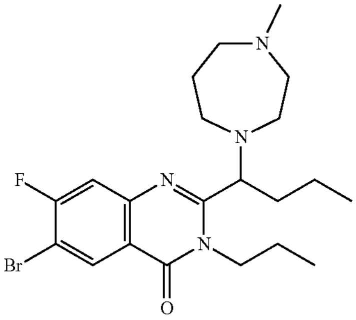 [SMILES: CCCC(c1nc2cc(F)c(Br)cc2c(=O)n1CCC)N1CCCN(C)CC1] | 26 | 6-bromo-7-fluoro-2-(1-(4-methyl-1,4-diazepan-1-yl)butyl)-3-propylquinazolin-4(3H)-one | 2.54 | 453.2 | B |

-continued
| STRUCTURE | EX | CHEMICAL NAME | Rt (min) | MS (M + H) | HPLC Method |
|---|---|---|---|---|---|
| 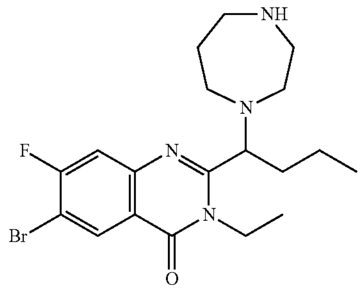 | 27 | 2-(1-(1,4-diazepan-1-yl)butyl)-6-bromo-3-ethyl-7-fluoroquinazolin-4(3H)-one | 2.09 | 425.2 | B |
| 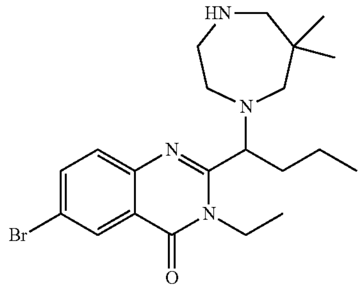 [SMILES: CCCC(c1nc2ccc(Br)cc2c(=O)n1CC)N1CCNCC(C)(C)C1] | 28 | 6-bromo-2-(1-(6,6-dimethyl-1,4-diazepan-1-yl)butyl)-3-ethylquinazolin-4(3H)-one | 2.47 | 435.2 | B |
| 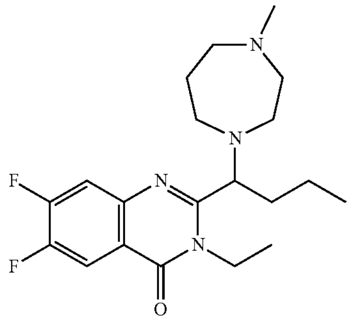 [SMILES: CCCC(c1nc2cc(F)c(F)cc2c(=O)n1CC)N1CCCN(C)CC1] | 29 | 3-ethyl-6,7-difluoro-2-(1-(4-methyl-1,4-diazepan-1-yl)butyl)quinazolin-4(3H)-one | 2.12 | 379.3 | B |
| 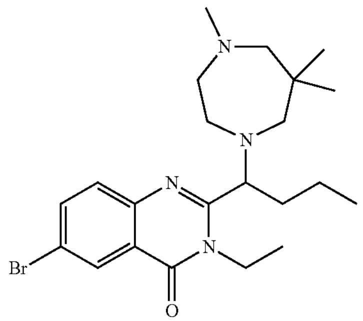 [SMILES: CCCC(c1nc2ccc(Br)cc2c(=O)n1CC)N1CCN(C)CC(C)(C)C1] | 30 | 6-bromo-3-ethyl-2-(1-(4-6,6-trimethyl-1,4-diazepan-1-yl)butyl)quinazolin-4(3H)-one | 2.98 | 449.3 | B |
| 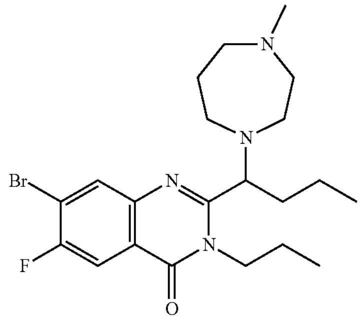 [SMILES: CCCC(c1nc2cc(Br)c(F)cc2c(=O)n1CCC)N1CCCN(C)CC1] | 31 | 7-bromo-6-fluoro-2-(1-(4-methyl-1,4-diazepan-1-yl)butyl)-3-propylquinazolin-4(3H)-one | 2.6 | 453.2 | B |

-continued
| STRUCTURE | EX | CHEMICAL NAME | Rt (min) | MS (M + H) | HPLC Method |
|---|---|---|---|---|---|
| 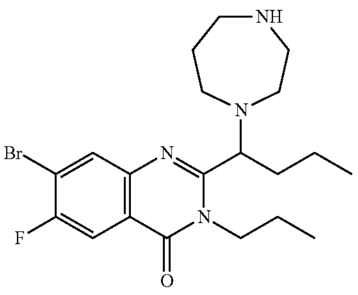 [SMILES: CCCC(c1nc2cc(Br)c(F)cc2c(=O)n1CCC)N1CCCNCC1] | 32 | 2-(1-(1,4-diazepan-1-yl)butyl)-7-bromo-3-ethyl-6-fluoroquinazolin-4(3H)-one | 2.12 | 423.2 | B |
| 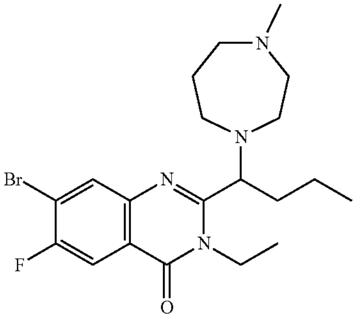 [SMILES: CCCC(c1nc2cc(Br)c(F)cc2c(=O)n1CC)N1CCCN(C)CC1] | 33 | 7-bromo-3-ethyl-6-fluoro-2-(1-(4-methyl-1,4-diazepan-1-yl)butyl)quinazolin-4(3H)-one | 2.35 | 439.2 | B |
| 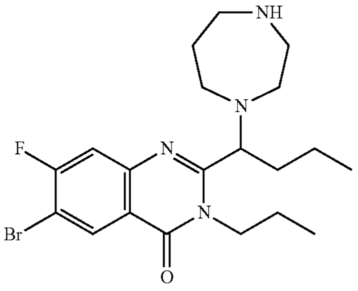 [SMILES: CCCC(c1nc2cc(F)c(Br)cc2c(=O)n1CCC)N1CCCNCC1] | 34 | 2-(1-(1,4-diazepan-1-yl)butyl)-6-bromo-7-fluoro-3-propylquinazolin-4(3H)-one | 2.27 | 439.1 | B |
| 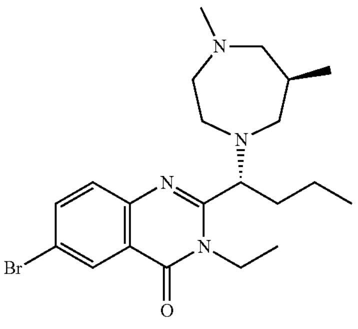 | 35 | 6-bromo-2-((R)-1-((R)-4,6-dimethyl-1,4-diazepan-1-yl)butyl)-3-ethylquinazolin-4(3H)-one | 2.27 | 439.2 | B |

-continued
| STRUCTURE | EX | CHEMICAL NAME | Rt (min) | MS (M + H) | HPLC Method |
|---|---|---|---|---|---|
| 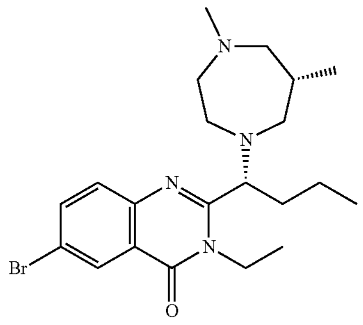 | 36 | 6-bromo-2-((R)-1-((S)-4,6-dimethyl-1,4-diazepan-1-yl)butyl)-3-ethylquinazolin-4(3H)-one | 2.5 | 435.2 | B |
| 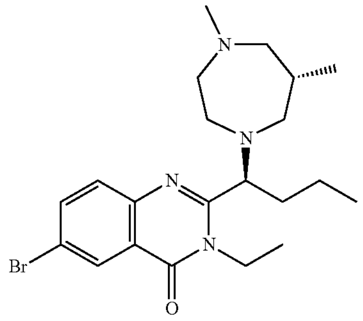 | 37 | 6-bromo-2-((S)-1-((S)-4,6-dimethyl-1,4-diazepan-1-yl)butyl)-3-ethylquinazolin-4(3H)-one | 2.5 | 435.2 | B |
| 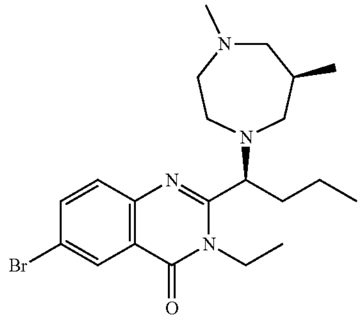 | 38 | 6-bromo-2-((S)-1-((R)-4,6-dimethyl-1,4-diazepan-1-yl)butyl)-3-ethylquinazolin-4(3H)-one | 2.5 | 435.2 | B |
| 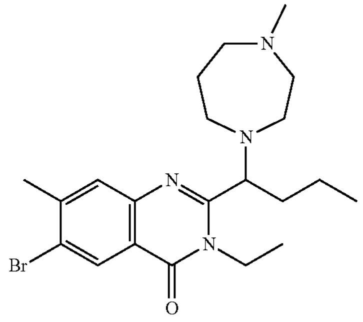 [SMILES: CCCC(c1nc2cc(C)c(Br)cc2c(=O)n1CC)N1CCCN(C)CC1] | 39 | 6-bromo-3-ethyl-7-methyl-2-(1-(4-methyl-1,4-diazepan-1-yl)butyl)quinazolin-4(3H)-one | 2.45 | 435.2 | B |

-continued
| STRUCTURE | EX | CHEMICAL NAME | Rt (min) | MS (M + H) | HPLC Method |
|---|---|---|---|---|---|
| 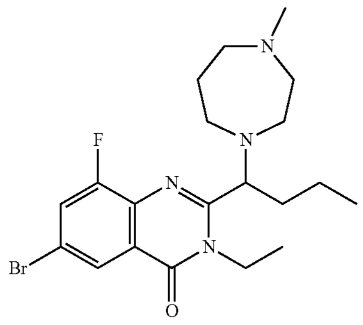 [SMILES: CCCC(c1nc2c(F)cc(Br)cc2c(=O)n1CC)N1CCCN(C)CC1] | 40 | 6-bromo-3-ethyl-8-fluoro-2-(1-(4-methyl-1,4-diazepan-1-yl)butyl)quinazolin-4(3H)-one | 2.31 | 439.2 | B |
| 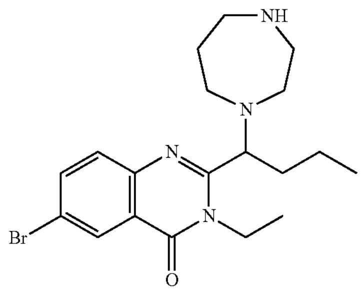 | 41 | 2-(1-(1,4-diazepan-1-yl)butyl)-6-bromo-3-ethyl-5-methylquinazolin-4(3H)-one | 2.25 | 421.2 | B |
| 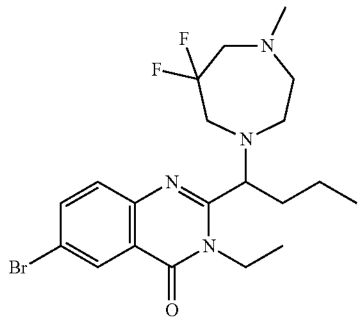 [SMILES: CCCC(c1nc2ccc(Br)cc2c(=O)n1CC)N1CCN(C)CC(F)(F)C1] | 42 | 6-bromo-2-(1-(6,6-difluoro-4-methyl-1,4-diazepan-1-yl)butyl)-3-ethylquinazolin-4(3H)-one | 2.77 | 457.2 | B |
| 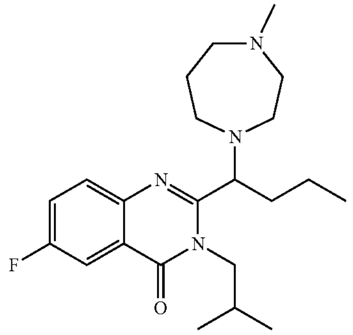 [SMILES: CCCC(c1nc2ccc(F)cc2c(=O)n1CC(C)C)N1CCCN(C)CC1] | 43 | 6-fluoro-3-isobutyl-2-(1-(4-methyl-1,4-diazepan-1-yl)butyl)quinazolin-4(3H)-one | 2.35 | 3.89.2 | B |

-continued
| STRUCTURE | EX | CHEMICAL NAME | Rt (min) | MS (M + H) | HPLC Method |
|---|---|---|---|---|---|
| 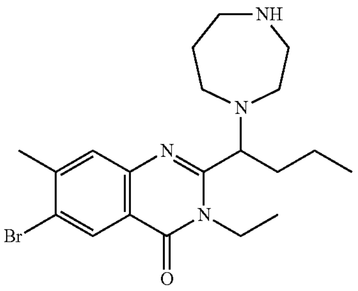 [SMILES: CCCC(c1nc2cc(C)c(Br)cc2c(=O)n1CC)N1CCCNCC1] | 44 | 2-(1-(1,4-diazepan-1-yl)butyl)-6-bromo-3-ethyl-7-methylquinazolin-4(3H)-one | 2.19 | 421.3 | B |
| 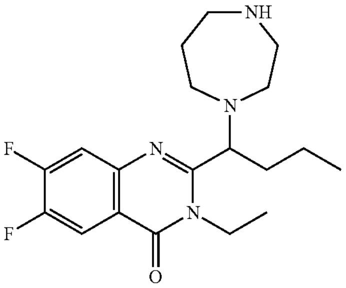 [SMILES: CCCC(c1nc2cc(F)c(F)cc2c(=O)n1CC)N1CCCNCC1] | 45 | 2-(1-(1,4-diazepan-1-yl)butyl)-3-ethyl-6,7-difluoroquinazolin-4(3H)-one | 1.93 | 365.2 | B |
| 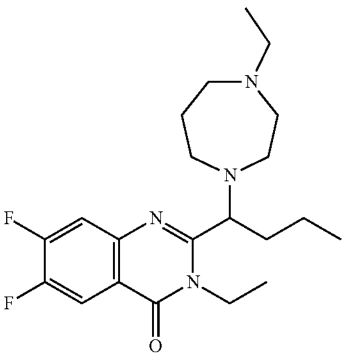 [SMILES: CCCC(c1nc2cc(F)c(F)cc2c(=O)n1CC)N1CCCN(CC)CC1] | 46 | 3-ethyl-2-(1-(4-ethyl-1,4-diazepan-1-yl)butyl)-6,7-difluoroquinazolin-4(3H)-one | 2.19 | 393.2 | B |
| 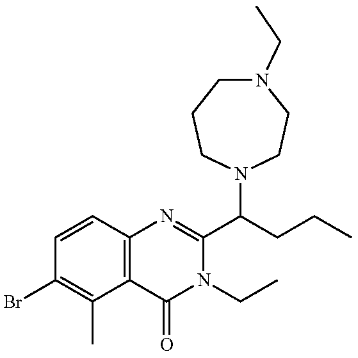 [SMILES: CCCC(c1nc2ccc(Br)c(C)c2c(=O)n1CC)N1CCCN(CC)CC1] | 47 | 6-bromo-3-ethyl-2-(1-(4-ethyl-1,4-diazepan-1-yl)butyl)-5-methylquinazolin-4(3H)-one | 2.74 | 449.2 | B |

-continued
| STRUCTURE | EX | CHEMICAL NAME | Rt (min) | MS (M + H) | HPLC Method |
|---|---|---|---|---|---|
| 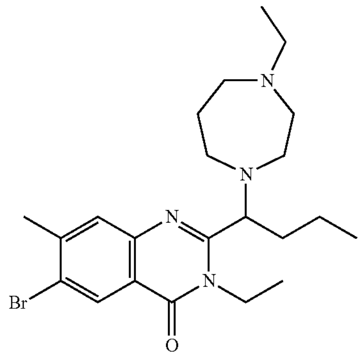 [SMILES: CCCC(c1nc2cc(C)c(Br)cc2c(=O)n1CC)N1CCCN(CC)CC1] | 48 | 6-bromo-3-ethyl-2-(1-(4-ethyl-1,4-diazepan-1-yl)butyl)-7-methylquinazolin-4(3H)-one | 2.51 | 449.2 | B |
| 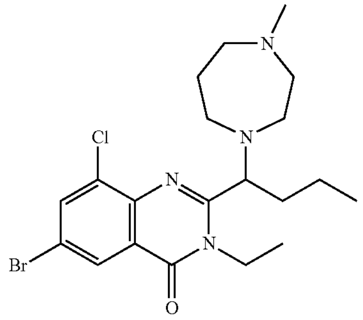 | 49 | 6-bromo-8-chloro-3-ethyl-2-(1-(4-methyl-1,4-diazepan-1-yl)butyl)quinazolin-4(3H)-one | 2.62 | 455.1 | B |
| 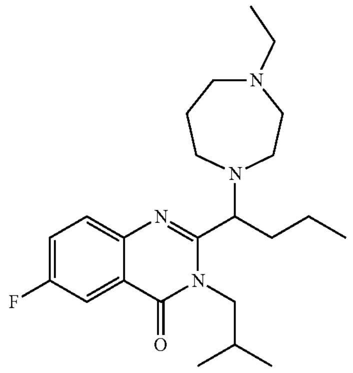 [SMILES: CCCC(c1nc2ccc(F)cc2c(=O)n1CC(C)C)N1CCCN(CC)CC1] | 50 | 2-(1-(4-ethyl-1,4-diazepan-1-yl)butyl)-6-fluoro-3-isobutylquinazolin-4(3H)-one | 2.43 | 403.3 | B |
| 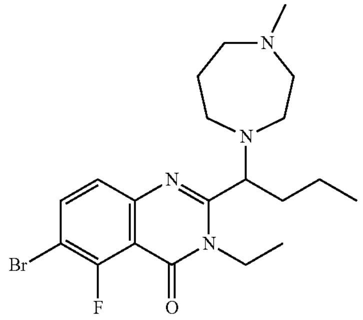 [SMILES: CCCC(c1nc2ccc(Br)c(F)c2c(=O)n1CC)N1CCCN(C)CC1] | 51 | 6-bromo-3-ethyl-5-fluoro-2-(1-(4-methyl-1,4-diazepan-1-yl)butyl)quinazolin-4(3H)-one | 2.24 | 439.2 | B |

-continued
| STRUCTURE | EX | CHEMICAL NAME | Rt (min) | MS (M + H) | HPLC Method |
|---|---|---|---|---|---|
| 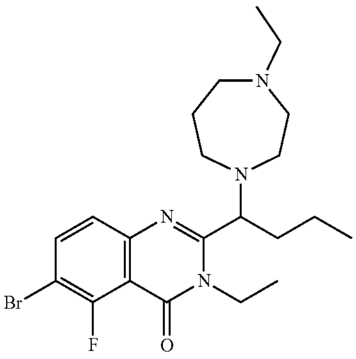 [SMILES: CCCC(c1nc2ccc(Br)c(F)c2c(=O)n1CC)N1CCCN(CC)CC1] | 52 | 6-bromo-3-ethyl-2-(1-(4-ethyl-1,4-diazepan-1-yl)butyl)-5-fluoroquinazolin-4(3H)-one | 2.29 | 453.2 | B |
| 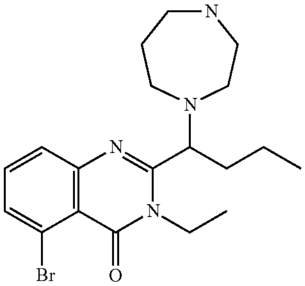 [SMILES: CCCC(c1nc2cccc(Br)c2c(=O)n1CC)N1CCCNCC1] | 53 | 5-bromo-3-ethyl-2-(1-(4-methyl-1,4-diazepan-1-yl)butyl)quinazolin-4(3H)-one | 2.16 | 421.2 | B |
| 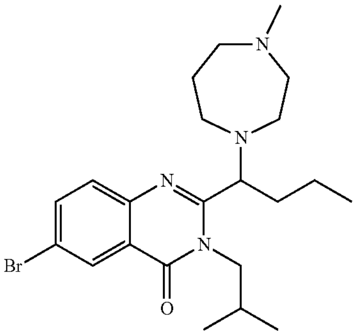 [SMILES: CCCC(c1nc2ccc(Br)cc2c(=O)n1CC(C)C)N1CCCN(C)CC1] | 54 | 6-bromo-3-isobutyl-2-(1-(4-methyl-1,4-diazepan-1-yl)butyl)quinazolin-4(3H)-one | 2.72 | 449.1 | B |
| 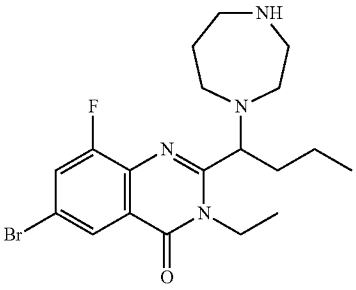 [SMILES: CCCC(c1nc2c(F)cc(Br)cc2c(=O)n1CC)N1CCCNCC1] | 55 | 2-(1-(1,4-diazepan-1-yl)butyl)-6-bromo-3-ethyl-8-fluoroquinazolin-4(3H)-one | 2.16 | 425.1 | B |

-continued
| STRUCTURE | EX | CHEMICAL NAME | Rt (min) | MS (M + H) | HPLC Method |
|---|---|---|---|---|---|
| 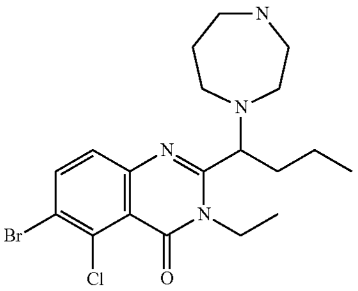 [SMILES: CCCC(c1nc2ccc(Br)c(Cl)c2c(=O)n1CC)N1CCCNCC1] | 56 | 6-bromo-5-chloro-3-ethyl-2-(1-(4-methyl-1,4-diazepan-1-yl)butyl)quinazolin-4(3H)-one | 2.44 | 455.1 | B |
| 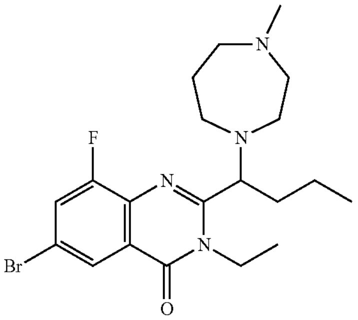 [SMILES: CCCC(c1nc2c(F)cc(Br)cc2c(=O)n1CC)N1CCCN(C)CC1] | 57 | 6-bromo-3-ethyl-2-(1-(4-ethyl-1,4-diazepan-1-yl)butyl)-8-fluoroquinazolin-4(3H)-one | 2.43 | 453.2 | B |
| 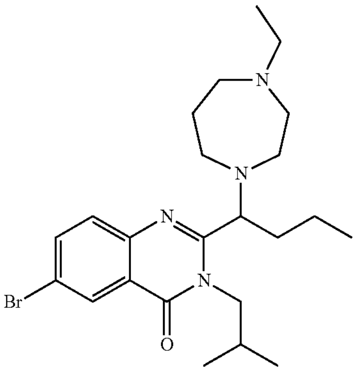 [SMILES: CCCC(c1nc2ccc(Br)cc2c(=O)n1CC(C)C)N1CCCN(CC)CC1] | 58 | 6-bromo-2-(1-(4-ethyl-1,4-diazepan-1-yl)butyl)-3-isobutylquinazolin-4(3H)-one | 2.75 | 463.2 | B |
| 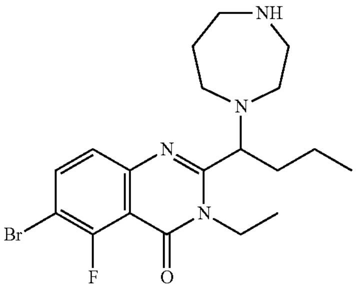 [SMILES: CCCC(c1nc2ccc(Br)c(F)c2c(=O)n1CC)N1CCCNCC1] | 59 | 2-(1-(1,4-diazepan-1-yl)butyl)-6-bromo-3-ethyl-5-fluoroquinazolin-4(3H)-one | 2.07 | 425.1 | B |

-continued
| STRUCTURE | EX | CHEMICAL NAME | Rt (min) | MS (M + H) | HPLC Method |
|---|---|---|---|---|---|
| 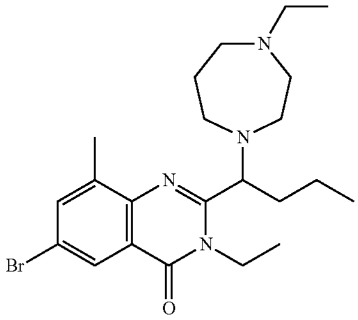 [SMILES: CCCC(c1nc2c(C)cc(Br)cc2c(=O)n1CC)N1CCCN(CC)CC1] | 60 | 6-bromo-3-ethyl-2-(1-(4-ethyl-1,4-diazepan-1-yl)butyl)-8-methylquinazolin-4(3H)-one | 2.66 | 449.1 | B |
| 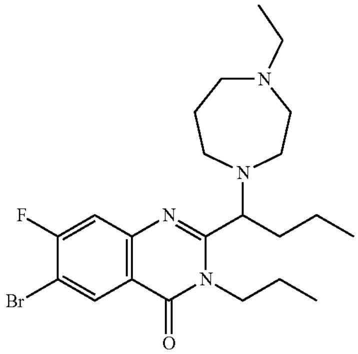 [SMILES: CCCC(c1nc2cc(F)c(Br)cc2c(=O)n1CCC)N1CCCN(CC)CC1] | 61 | 6-bromo-2-(1-(4-ethyl-1,4-diazepan-1-yl)butyl)-7-fluoro-3-propylquinazolin-4(3H)-one | 2.68 | 467.2 | B |
| 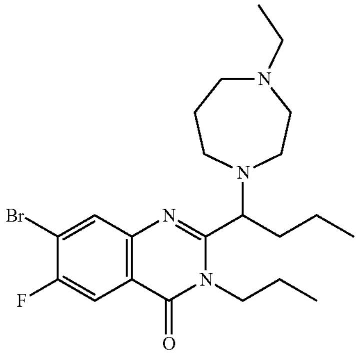 [SMILES: CCCC(c1nc2cc(Br)c(F)cc2c(=O)n1CCC)N1CCCN(CC)CC1] | 62 | 7-bromo-2-(1-(4-ethyl-1,4-diazepan-1-yl)butyl)-6-fluoro-3-propylquinazolin-4(3H)-one | 2.72 | 467.2 | B |
| 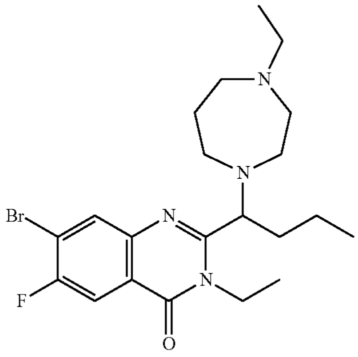 [SMILES: CCCC(c1nc2cc(Br)c(F)cc2c(=O)n1CC)N1CCCN(CC)CC1] | 63 | 7-bromo-3-ethyl-2-(1-(4-ethyl-1,4-diazepan-1-yl)butyl)-6-fluoroquinazolin-4(3H)-one | 2.5 | 453.2 | B |

-continued

| STRUCTURE | EX | CHEMICAL NAME | Rt (min) | MS (M + H) | HPLC Method |
|---|---|---|---|---|---|
| 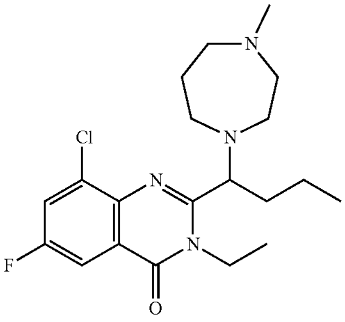 [SMILES: CCCC(c1nc2c(Cl)cc(F)cc2c(=O)n1CC)N1CCCN(C)CC1] | 64 | 8-chloro-3-ethyl-6-fluoro-2-(1-(4-methyl-1,4-diazepan-1-yl)butyl)quinazolin-4(3H)-one | 2.37 | 395.2 | B |
| 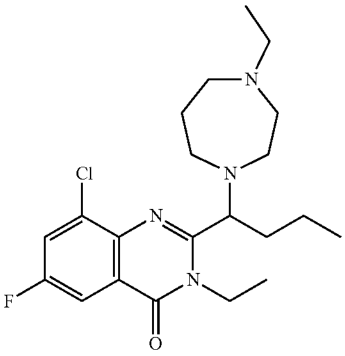 [SMILES: CCCC(c1nc2c(Cl)cc(F)cc2c(=O)n1CC)N1CCCN(CC)CC1] | 65 | 8-chloro-3-ethyl-2-(1-(4-ethyl-1,4-diazepan-1-yl)butyl)-6-fluoroquinazolin-4(3H)-one | 2.43 | 409.2 | B |
| 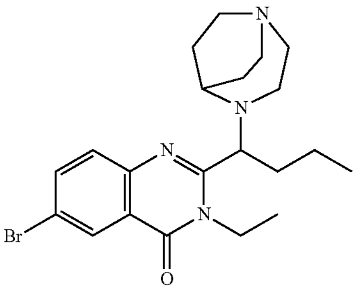 [SMILES: CCCC(c1nc2ccc(Br)cc2c(=O)n1CC)N1CCN2CCC1CC2] | 66 | (R)-2-(1-(1,4-diazabicyclo[3.2.2]nonan-4-yl)butyl)-6-bromo-3-ethylquinazolin-4(3H)-one | 2.33 | 433.2 | B |
| 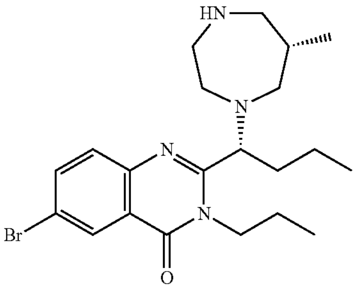 [SMILES: CCC[C@H](c1nc2ccc(Br)cc2c(=O)n1CCC)N1CCNC[C@H](C)C1] | 67 | 6-bromo-2-((R)-1-((S)-6-methyl-1,4-diazepan-1-yl)butyl)-3-propylquinazolin-4(3H)-one | 2.28 | 421.2 | B |
| 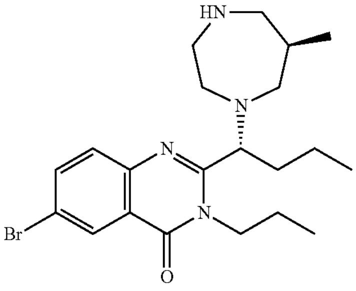 [SMILES: CCC[C@H](c1nc2ccc(Br)cc2c(=O)n1CCC)N1CCNC[C@@H](C)C1] | 68 | 6-bromo-2-((R)-1-((R)-6-methyl-1,4-diazepan-1-yl)butyl)-3-propylquinazolin-4(3H)-one | 2.28 | 421.2 | B |

-continued
| STRUCTURE | EX | CHEMICAL NAME | Rt (min) | MS (M + H) | HPLC Method |
|---|---|---|---|---|---|
| 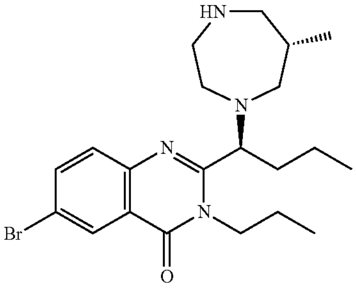 [SMILES: CCC[C@@H](c1nc2ccc(Br)cc2c(=O)n1CCC)N1CCNC[C@H](C)C1] | 69 | 6-bromo-2-((S)-1-((S)-6-methyl-1,4-diazepan-1-yl)butyl)-3-propylquinazolin-4(3H)-one | 2.27 | 421.3 | B |
| 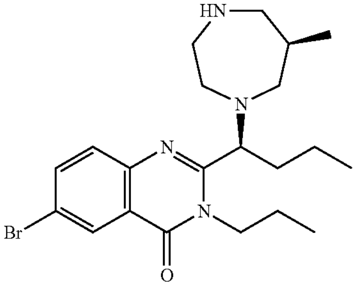 [SMILES: CCC[C@@H](c1nc2ccc(Br)cc2c(=O)n1CCC)N1CCNC[C@@H](C)C1] | 70 | 6-bromo-2-((S)-1-((R)-6-methyl-1,4-diazepan-1-yl)butyl)-3-propylquinazolin-4(3H)-one | 2.15 | 421.2 | B |
| 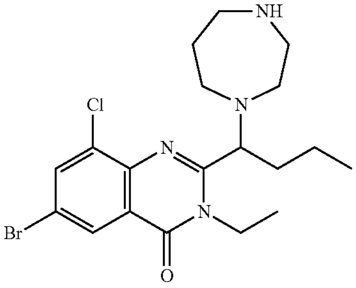 | 71 | 2-(1-(1,4-diazepan-1-yl)butyl)-8-chloro-3-ethyl-6-fluoroquinazolin-4(3H)-one | 2.05 | 381.2 | B |
| 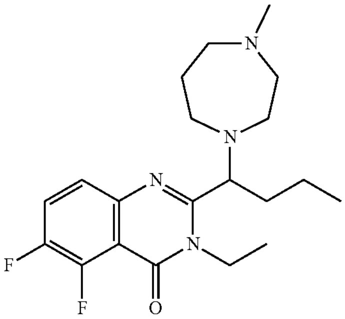 [SMILES: CCCC(c1nc2ccc(F)c(F)c2c(=O)n1CC)N1CCCN(C)CC1] | 72 | 3-ethyl-5,6-difluoro-2-(1-(4-methyl-1,4-diazepan-1-yl)butyl)quinazolin-4(3H)-one | 3.88 | 379.2 | B |
| 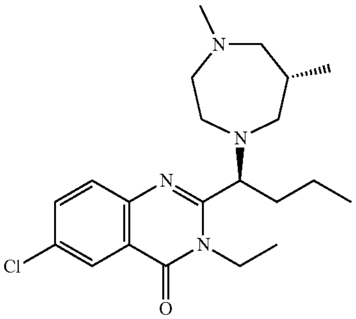 [SMILES: CCC[C@@H](c1nc2ccc(Cl)cc2c(=O)n1CC)N1CCN(C)C[C@H](C)C1] | 73 | 6-chloro-2-((S)-1-((S)-4,6-dimethyl-1,4-diazepan-1-yl)butyl)-3-ethylquinazolin-4(3H)-one | 2.4 | 391.2 | B |

-continued
| STRUCTURE | EX | CHEMICAL NAME | Rt (min) | MS (M + H) | HPLC Method |
|---|---|---|---|---|---|
| 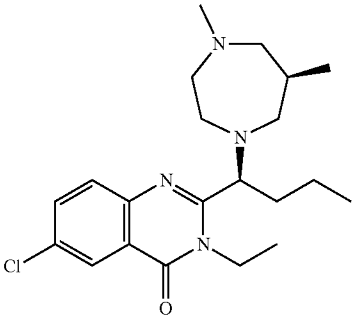 [SMILES: CCC[C@@H](c1nc2ccc(Cl)cc2c(=O)n1CC)N1CCN(C)C[C@@H](C)C1] | 74 | 6-chloro-2-((S)-1-((R)-4,6-dimethyl-1,4-diazepan-1-yl)butyl)-3-ethylquinazolin-4(3H)-one | 2.4 | 391.2 | B |
| 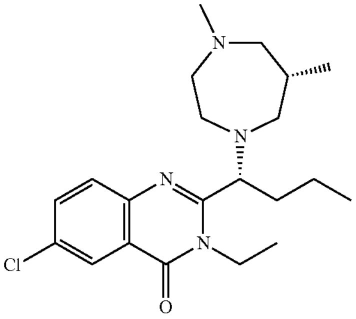 [SMILES: CCC[C@H](c1nc2ccc(Cl)cc2c(=O)n1CC)N1CCN(C)C[C@H](C)C1] | 75 | 6-chloro-2-((R)-1-((S)-4,6-dimethyl-1,4-diazepan-1-yl)butyl)-3-ethylquinazolin-4(3H)-one | 2.4 | 391.3 | B |
| 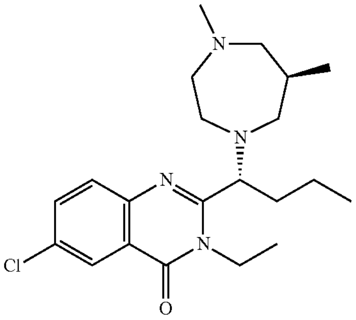 [SMILES: CCC[C@H](c1nc2ccc(Cl)cc2c(=O)n1CC)N1CCN(C)C[C@@H](C)C1] | 76 | 6-chloro-2-((R)-1-((R)-4,6-dimethyl-1,4-diazepan-1-yl)butyl)-3-ethylquinazolin-4(3H)-one | 2.4 | 391.2 | B |
| 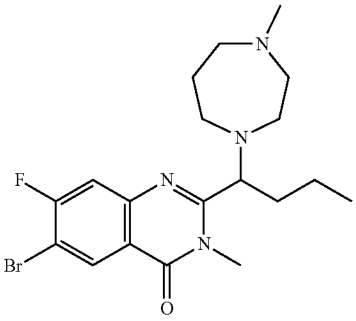 [SMILES: CCCC(c1nc2cc(F)c(Br)cc2c(=O)n1C)N1CCCN(C)CC1] | 77 | 6-bromo-7-fluoro-3-methyl-2-(1-(4-methyl-1,4-diazepan-1-yl)butyl)quinazolin-4(3H)-one | 2.13 | 425.1 | B |

-continued
| STRUCTURE | EX | CHEMICAL NAME | Rt (min) | MS (M + H) | HPLC Method |
|---|---|---|---|---|---|
| 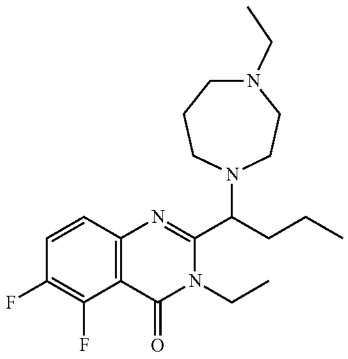 [SMILES: CCCC(c1nc2ccc(F)c(F)c2c(=O)n1CC)N1CCCN(CC)CC1] | 78 | 3-ethyl-2-(1-(4-ethyl-1,4-diazepan-1-yl)butyl)-5,6-difluoroquinazolin-4(3H)-one | 2.04 | 393.2 | F |
| 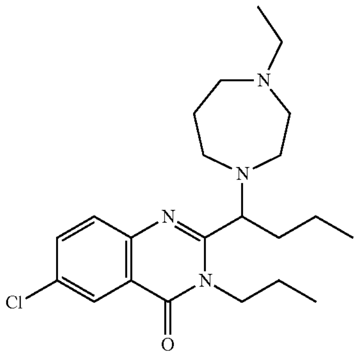 [SMILES: CCCC(c1nc2ccc(Cl)cc2c(=O)n1CCC)N1CCCN(CC)CC1] | 79 | 6-chloro-2-(1-(4-ethyl-1,4-diazepan-1-yl)butyl)-3-propylquinazolin-4(3H)-one | 2.45 | 405.3 | B |
| 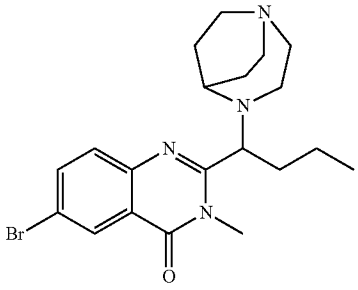 [SMILES: CCCC(c1nc2ccc(Br)cc2c(=O)n1C)N1CCN2CCC1CC2] | 80 | 2-(1-(1,4-diazabicyclo[3.2.2]nonan-4-yl)butyl)-6-bromo-3-ethylquinazolin-4(3H)-one | 2.21 | 433.2 | B |
| 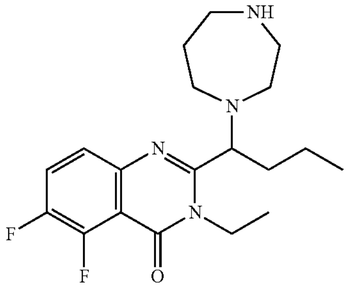 [SMILES: CCCC(c1nc2ccc(F)c(F)c2c(=O)n1CC)N1CCCNCC1] | 81 | 2-(1-(1,4-diazepan-1-yl)butyl)-3-ethyl-5,6-difluoroquinazolin-4(3H)-one | 1.83 | 365.2 | B |

-continued
| STRUCTURE | EX | CHEMICAL NAME | Rt (min) | MS (M + H) | HPLC Method |
|---|---|---|---|---|---|
| 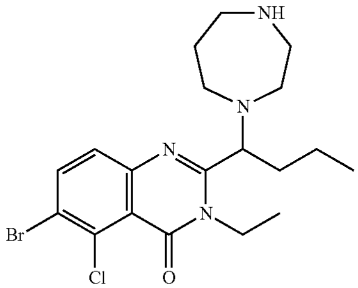 | 82 | 2-(1-(1,4-diazepan-1-yl)butyl)-6-bromo-5-chloro-3-ethylquinazolin-4(3H)-one | 2.14 | 441.1 | B |
| 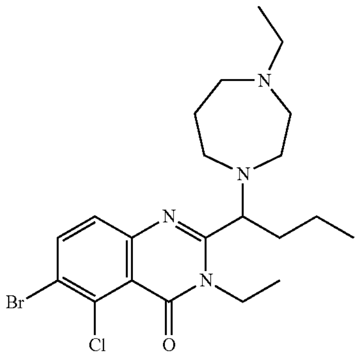 [SMILES: CCCC(c1nc2ccc(Br)c(Cl)c2c(=O)n1CC)N1CCCN(CC)CC1] | 83 | 6-bromo-5-chloro-3-ethyl-2-(1-(4-ethyl-1,4-diazepan-1-yl)butyl)quinazolin-4(3H)-one | 2.41 | 469.1 | B |
| 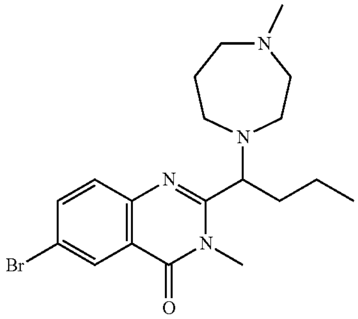 [SMILES: CCCC(c1nc2ccc(Br)cc2c(=O)n1C)N1CCCN(C)CC1] | 84 | 6-bromo-3-methyl-2-(1-(4-methyl-1,4-diazepan-1-yl)butyl)quinazolin-4(3H)-one | 2.08 | 407.1 | B |
| 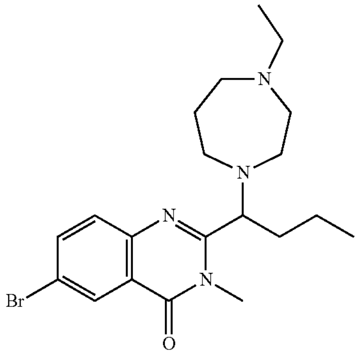 [SMILES: CCCC(c1nc2ccc(Br)cc2c(=O)n1C)N1CCCN(CC)CC1] | 85 | 6-bromo-2-(1-(4-ethyl-1,4-diazepan-1-yl)butyl)-3-methylquinazolin-4(3H)-one | 2.13 | 421.1 | B |

-continued
| STRUCTURE | EX | CHEMICAL NAME | Rt (min) | MS (M + H) | HPLC Method |
|---|---|---|---|---|---|
| 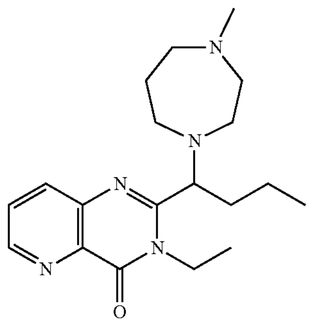 [SMILES: CCCC(c1nc2cccnc2c(=O)n1CC)N1CCCN(C)CC1] | 86 | 3-ethyl-2-(1-(4-methyl 1,4-diazepan-1-yl)butyl)pyrido[3,2-d]pyrimidin-4(3H)-one | 1.47 | 344.2 | B |
| 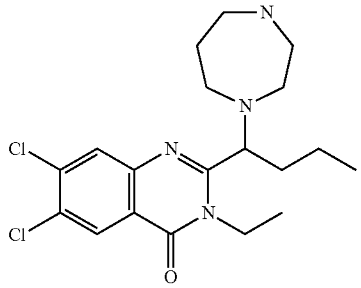 [SMILES: CCCC(c1nc2cc(Cl)c(Cl)cc2c(=O)n1CC)N1CCCNCC1] | 87 | 6,7-dichloro-3-ethyl-2-(1-(4-methyl-1,4-diazepan-1-yl)butyl)quinazolin-4(3H)-one | 2.59 | 411.2 | B |
| 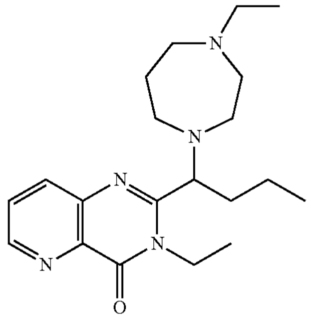 [SMILES: CCCC(c1nc2cccnc2c(=O)n1CC)N1CCCN(CC)CC1] | 88 | 3-ethyl-2-(1-(4-ethyl-1,4-diazepan-1-yl)butyl)pyrido[3,2-d]pyrimidin-4(3H)-one | 1.54 | 358.2 | B |
| 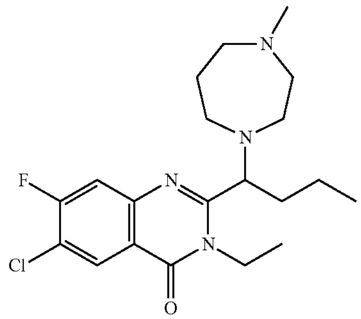 [SMILES: CCCC(c1nc2cc(F)c(Cl)cc2c(=O)n1CC)N1CCCN(C)CC1] | 89 | 6-chloro-3-ethyl-7-fluoro-2-(1-(4-methyl-1,4-diazepan-1-yl)butyl)quinazolin-4(3H)-one | 2.36 | 395.2 | B |
| 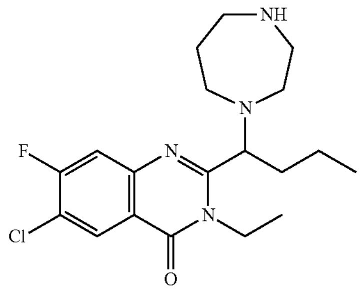 [SMILES: CCCC(c1nc2cc(F)c(Cl)cc2c(=O)n1CC)N1CCCNCC1] | 90 | 2-(1-(1,4-diazepan-1-yl)butyl)-6-chloro-3-ethyl-7-fluoroquinazolin-4(3H)-one | 2.08 | 381.1 | B |

-continued
| STRUCTURE | EX | CHEMICAL NAME | Rt (min) | MS (M + H) | HPLC Method |
|---|---|---|---|---|---|
| 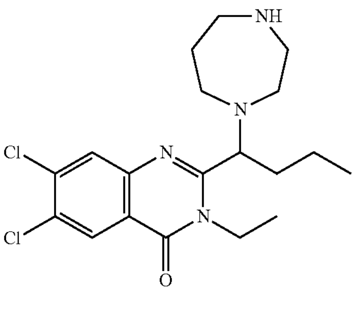 [SMILES: CCCC(c1nc2cc(Cl)c(Cl)cc2c(=O)n1CC)N1CCCNCC1] | 91 | 2-(1-(1,4-diazepan-1-yl)butyl)-6,7-dichloro-3-ethylquinazolin-4(3H)-one | 2.25 | 397.1 | B |
| 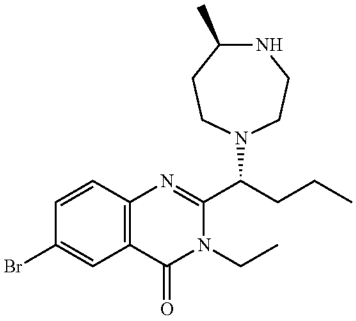 [SMILES: CCC[C@H](c1nc2ccc(Br)cc2c(=O)n1CC)N1CCN[C@H](C)CC1] | 92 | 6-bromo-3-ethyl-2-((R)-1-((R)-5-methyl-1,4-diazepan-1-yl)butyl)quinazolin-4(3H)-one | 2.08 | 421.2 | B |
| 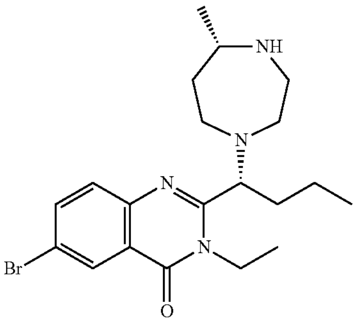 [SMILES: CCC[C@H](c1nc2ccc(Br)cc2c(=O)n1CC)N1CCN[C@@H](C)CC1] | 93 | 6-bromo-3-ethyl-2-((R)-1-((S)-5-methyl-1,4-diazepan-1-yl)butyl)quinazolin-4(3H)-one | 2.06 | 421.2 | B |
| 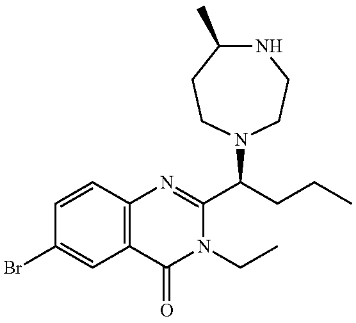 [SMILES: CCC[C@@H](c1nc2ccc(Br)cc2c(=O)n1CC)N1CCN[C@H](C)CC1] | 94 | 6-bromo-3-ethyl-2-((S)-1-((R)-5-methyl-1,4-diazepan-1-yl)butyl)quinazolin-4(3H)-one | 2.05 | 421.2 | B |

-continued

| STRUCTURE | EX | CHEMICAL NAME | Rt (min) | MS (M + H) | HPLC Method |
|---|---|---|---|---|---|
| 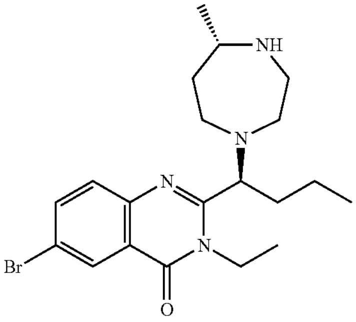 [SMILES: CCC[C@@H](c1nc2ccc(Br)cc2c(=O)n1CC)N1CCN[C@@H](C)CC1] | 95 | 6-bromo-3-ethyl-2-((S)-1-((S)-5-methyl-1,4-diazepan-1-yl)butyl)quinazolin-4(3H)-one | 2.07 | 421.2 | B |
| 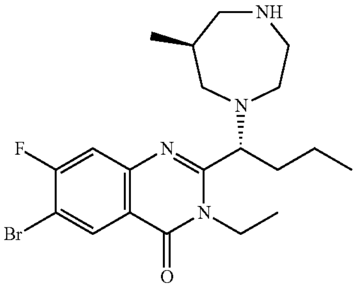 | 96 | 6-bromo-3-ethyl-7-fluoro-2-((R)-1-((S)-6-methyl-1,4-diazepan-1-yl)butyl)quinazolin-4(3H)-one | 2.22 | 439.2 | B |
| 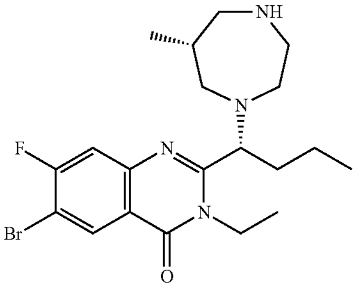 | 97 | 6-bromo-3-ethyl-7-fluoro-2-((R)-1-((R)-6-methyl-1,4-diazepan-1-yl)butyl)quinazolin-4(3H)-one | 2.21 | 439.2 | B |
| 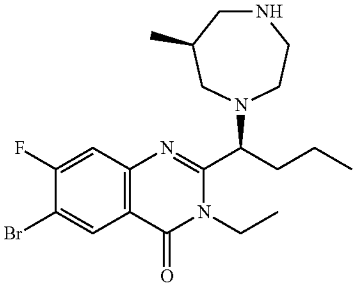 | 98 | 6-bromo-3-ethyl-7-fluoro-2-((S)-1-((S)-6-methyl-1,4-diazepan-1-yl)butyl)quinazolin-4(3H)-one | 2.23 | 439.2 | B |
| 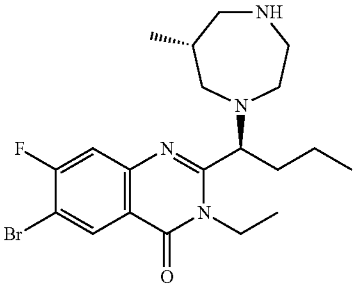 | 99 | 6-bromo-3-ethyl-7-fluoro-2-((S)-1-((R)-6-methyl-1,4-diazepan-1-yl)butyl)quinazolin-4(3H)-one | 2.24 | 439.2 | B |

-continued
| STRUCTURE | EX | CHEMICAL NAME | Rt (min) | MS (M + H) | HPLC Method |
|---|---|---|---|---|---|
| 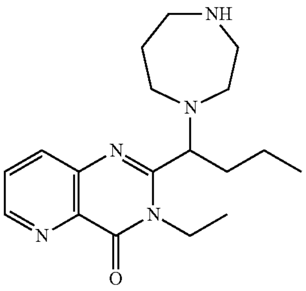 [SMILES: CCCC(c1nc2cccnc2c(=O)n1CC)N1CCCNCC1] | 100 | 2-(1-(1,4-diazepan-1-yl)butyl)-3-ethylpyrido[3,2-d]pyrimidin-4(3H)-one | 1.32 | 358.3 | B |
| 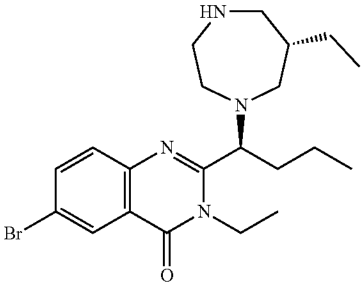 [SMILES: CCC[C@@H](c1nc2ccc(Br)cc2c(=O)n1CC)N1CCNC[C@H](CC)C1] | 101 | 6-bromo-3-ethyl-2-((S)-1-((S)-6-ethyl-1,4-diazepan-1-yl)butyl)quinazolin-4(3H)-one | 2.63 | 449.2 | B |
| 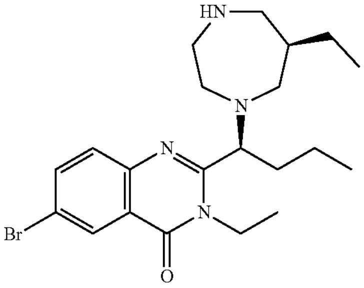 [SMILES: CCC[C@@H](c1nc2ccc(Br)cc2c(=O)n1CC)N1CCNC[C@@H](CC)C1] | 102 | 6-bromo-3-ethyl-2-((S)-1-((R)-6-ethyl-1,4-diazepan-1-yl)butyl)quinazolin-4(3H)-one | 2.65 | 449.2 | B |
| 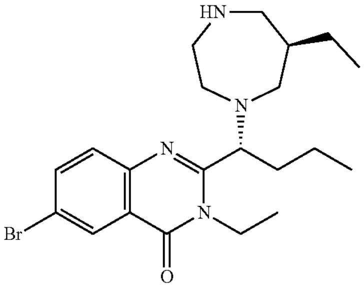 [SMILES: CCC[C@H](c1nc2ccc(Br)cc2c(=O)n1CC)N1CCNC[C@@H](CC)C1] | 103 | 6-bromo-3-ethyl-2-((R)-1-((R)-6-ethyl-1,4-diazepan-1-yl)butyl)quinazolin-4(3H)-one | 2.69 | 449.2 | B |
| 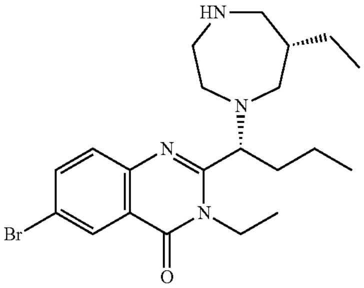 [SMILES: CCC[C@H](c1nc2ccc(Br)cc2c(=O)n1CC)N1CCNC[C@H](CC)C1] | 104 | 6-bromo-3-ethyl-2-((R)-1-((S)-6-ethyl-1,4-diazepan-1-yl)butyl)quinazolin-4(3H)-one | 2.69 | 449.2 | B |

-continued
| STRUCTURE | EX | CHEMICAL NAME | Rt (min) | MS (M + H) | HPLC Method |
|---|---|---|---|---|---|
| 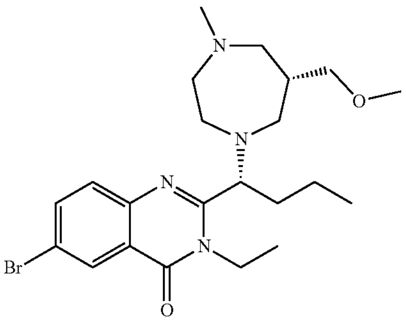 [SMILES: CCC[C@H](c1nc2ccc(Br)cc2c(=O)n1CC)N1CCN(C)C[C@H](COC)C1] | 105 | 6-bromo-3-ethyl-2-((R)-1-((S)-6-(methoxymethyl)-4-methyl-1,4-diazepan-1-yl)butyl)quinazolin-4(3H)-one | 2.51 | 465.2 | B |
| 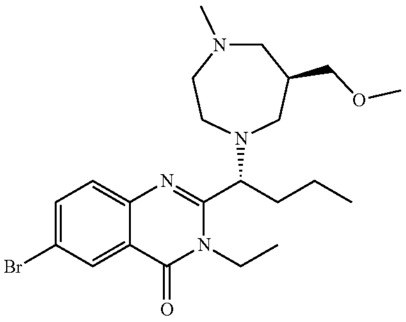 [SMILES: CCC[C@H](c1nc2ccc(Br)cc2c(=O)n1CC)N1CCN(C)C[C@@H](COC)C1] | 106 | 6-bromo-3-ethyl-2-((R)-1-((R)-6-(methoxymethyl)-4-methyl-1,4-diazepan-1-yl)butyl)quinazolin-4(3H)-one | 2.5 | 465.2 | B |
| 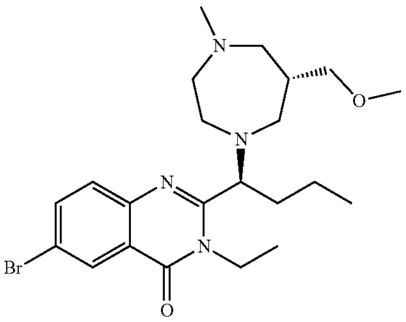 [SMILES: CCC[C@@H](c1nc2ccc(Br)cc2c(=O)n1CC)N1CCN(C)C[C@H](COC)C1] | 107 | 6-bromo-3-ethyl-2-((S)-1-((S)-6-(methoxymethyl)-4-methyl-1,4-diazepan-1-yl)butyl)quinazolin-4(3H)-one | 2.5 | 465.2 | B |
| 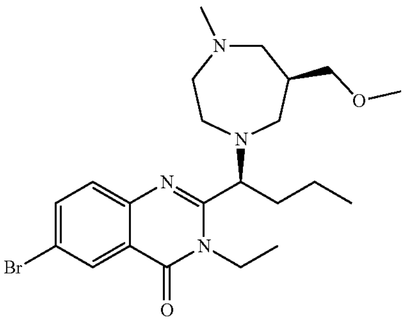 [SMILES: CCC[C@@H](c1nc2ccc(Br)cc2c(=O)n1CC)N1CCN(C)C[C@@H](COC)C1] | 108 | 6-bromo-3-ethyl-2-((S)-1-((R)-6-(methoxymethyl)-4-methyl-1,4-diazepan-1-yl)butyl)quinazolin-4(3H)-one | 2.51 | 465.2 | B |

-continued

| STRUCTURE | EX | CHEMICAL NAME | Rt (min) | MS (M + H) | HPLC Method |
|---|---|---|---|---|---|
| 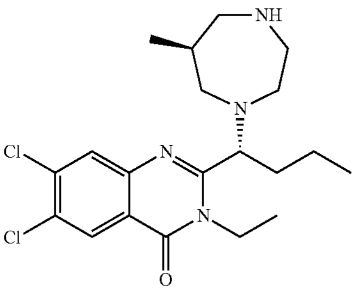 [SMILES: CCC[C@H](c1nc2cc(Cl)c(Cl)cc2c(=O)n1CC)N1CCNC[C@H](C)C1] | 109 | 6,7-dichloro-3-ethyl-2-((R)-1-((S)-6-methyl-1,4-diazepan-1-yl)butyl)quinazolin-4(3H)-one | 2.41 | 411.2 | B |
| 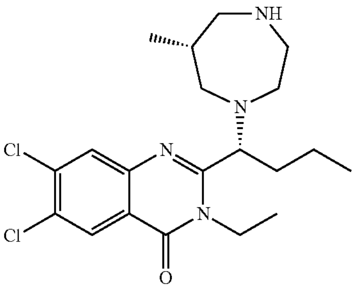 [SMILES: CCC[C@H](c1nc2cc(Cl)c(Cl)cc2c(=O)n1CC)N1CCNC[C@@H](C)C1] | 110 | 6,7-dichloro-3-ethyl-2-((R)-1-((R)-6-methyl-1,4-diazepan-1-yl)butyl)quinazolin-4(3H)-one | 2.41 | 411.2 | B |
| 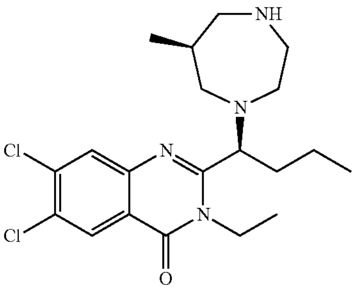 [SMILES: CCC[C@@H](c1nc2cc(Cl)c(Cl)cc2c(=O)n1CC)N1CCNC[C@H](C)C1] | 111 | 6,7-dichloro-3-ethyl-2-((S)-1-((S)-6-methyl-1,4-diazepan-1-yl)butyl)quinazolin-4(3H)-one | 2.41 | 411.2 | B |
| 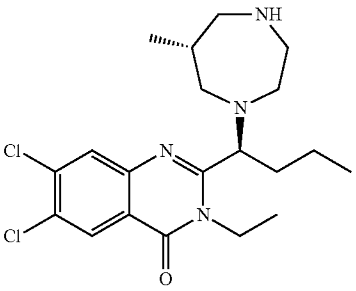 [SMILES: CCC[C@@H](c1nc2cc(Cl)c(Cl)cc2c(=O)n1CC)N1CCNC[C@@H](C)C1] | 112 | 6,7-dichloro-3-ethyl-2-((S)-1-((R)-6-methyl-1,4-diazepan-1-yl)butyl)quinazolin-4(3H)-one | 2.41 | 411.2 | B |
| 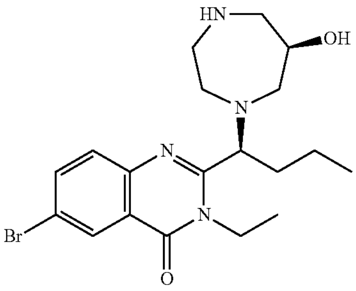 [SMILES: CCC[C@@H](c1nc2ccc(Br)cc2c(=O)n1CC)N1CCNC[C@@H](O)C1] | 113 | 6-bromo-3-ethyl-2-((S)-1-((R)-6-hydroxy-1,4-diazepan-1-yl)butyl)quinazolin-4(3H)-one | 1.96 | 423.2 | B |

-continued

| STRUCTURE | EX | CHEMICAL NAME | Rt (min) | MS (M + H) | HPLC Method |
|---|---|---|---|---|---|
| 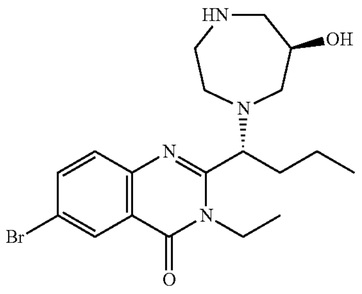 [SMILES: CCC[C@H](c1nc2ccc(Br)cc2c(=O)n1CC)N1CCNC[C@@H](O)C1] | 114 | 6-bromo-3-ethyl-2-((R)-1-((R)-6-hydroxy-1,4-diazepan-1-yl)butyl)quinazolin-4(3H)-one | 1.95 | 423.2 | B |
| 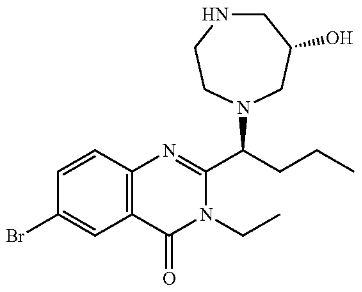 [SMILES: CCC[C@@H](c1nc2ccc(Br)cc2c(=O)n1CC)N1CCNC[C@H](O)C1] | 115 | 6-bromo-3-ethyl-2-((S)-1-((S)-6-hydroxy-1,4-diazepan-1-yl)butyl)quinazolin-4(3H)-one | 1.94 | 423.2 | B |
| 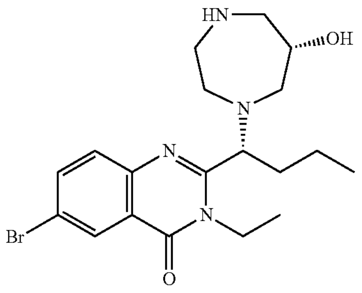 [SMILES: CCC[C@H](c1nc2ccc(Br)cc2c(=O)n1CC)N1CCNC[C@H](O)C1] | 116 | 6-bromo-3-ethyl-2-((R)-1-((S)-6-hydroxy-1,4-diazepan-1-yl)butyl)quinazolin-4(3H)-one | 1.96 | 423.2 | B |
| 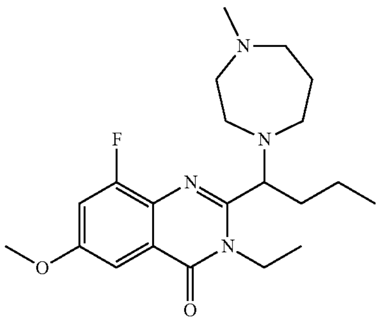 [SMILES: CCCC(c1nc2c(F)cc(OC)cc2c(=O)n1CC)N1CCCN(C)CC1] | 117 | 3-ethyl-8-fluoro-6-methoxy-2-(1-(4-methyl-1,4-diazepan-1-yl)butyl)quinazolin-4(3H)-one | 2.01 | 391.3 | B |
| 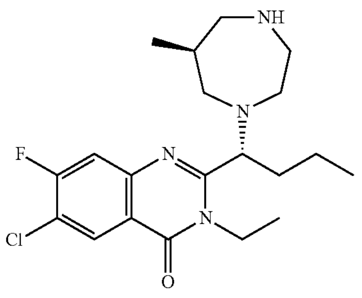 [SMILES: CCC[C@H](c1nc2cc(F)c(Cl)cc2c(=O)n1CC)N1CCNC[C@H](C)C1] | 118 | 6-chloro-3-ethyl-7-fluoro-2-((R)-1-((S)-6-methyl-1,4-diazepan-1-yl)butyl)quinazolin-4(3H)-one | 2.24 | 395.2 | B |

-continued

| STRUCTURE | EX | CHEMICAL NAME | Rt (min) | MS (M + H) | HPLC Method |
|---|---|---|---|---|---|
| 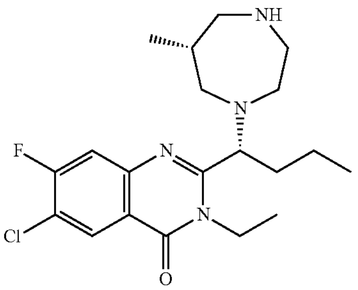 [SMILES: CCC[C@H](c1nc2cc(F)c(Cl)cc2c(=O)n1CC)N1CCNC[C@@H](C)C1] | 119 | 6-chloro-3-ethyl-7-fluoro-2-((R)-1-((R)-6-methyl-1,4-diazepan-1-yl)butyl)quinazolin-4(3H)-one | 2.24 | 395.2 | B |
| 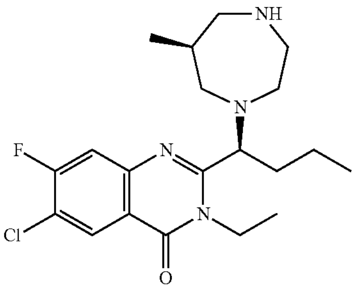 [SMILES: CCC[C@@H](c1nc2cc(F)c(Cl)cc2c(=O)n1CC)N1CCNC[C@H](C)C1] | 120 | 6-chloro-3-ethyl-7-fluoro-2-((S)-1-((S)-6-methyl-1,4-diazepan-1-yl)butyl)quinazolin-4(3H)-one | 2.23 | 395.2 | B |
| 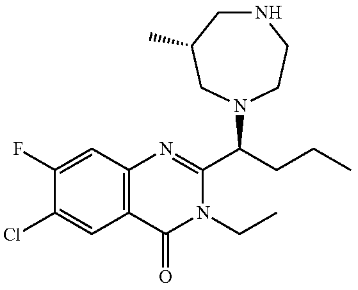 [SMILES: CCC[C@@H](c1nc2cc(F)c(Cl)cc2c(=O)n1CC)N1CCNC[C@@H](C)C1] | 121 | 6-chloro-3-ethyl-7-fluoro-2-((S)-1-((R)-6-methyl-1,4-diazepan-1-yl)butyl)quinazolin-4(3H)-one | 2.24 | 395.2 | B |
| 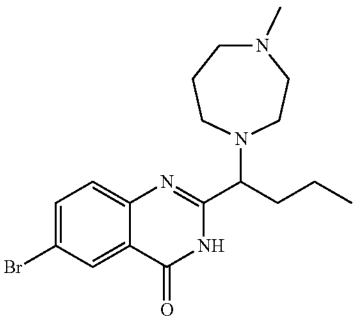 [SMILES: CCCC(c1nc2ccc(Br)cc2c(=O)[nH]1)N1CCCN(C)CC1] | 122 | 6-bromo-2-(1-(4-methyl-1,4-diazepan-1-yl)butyl)quinazolin-4(3H)-one | 1.79 | 393.2 | B |
| 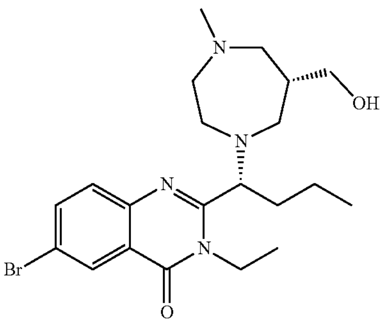 [SMILES: CCC[C@H](c1nc2ccc(Br)cc2c(=O)n1CC)N1CCN(C)C[C@H](CO)C1] | 123 | 6-bromo-3-ethyl-2-((R)-1-((S)-6-(hydroxymethyl)-4-methyl-1,4-diazepan-1-yl)butyl)quinazolin-4(3H)-one | 2.08 | 451.2 | B |

-continued
| STRUCTURE | EX | CHEMICAL NAME | Rt (min) | MS (M + H) | HPLC Method |
|---|---|---|---|---|---|
| 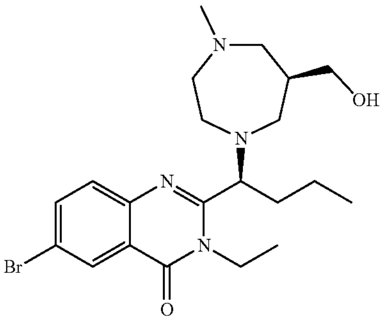 [SMILES: CCC[C@@H](c1nc2ccc(Br)cc2c(=O)n1CC)N1CCN(C)C[C@@H](CO)C1] | 124 | 6-bromo-3-ethyl-2-((S)-1-((R)-6-(hydroxymethyl)-4-methyl-1,4-diazepan-1-yl)butyl)quinazolin-4(3H)-one | 2.08 | 451.2 | B |
| 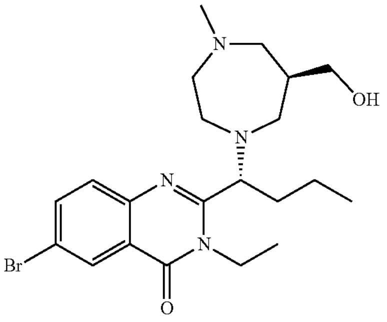 [SMILES: CCC[C@H](c1nc2ccc(Br)cc2c(=O)n1CC)N1CCN(C)C[C@@H](CO)C1] | 125 | 6-bromo-3-ethyl-2-((R)-1-((R)-6-(hydroxymethyl)-4-methyl-1,4-diazepan-1-yl)butyl)quinazolin-4(3H)-one | 2.07 | 451.2 | B |
| 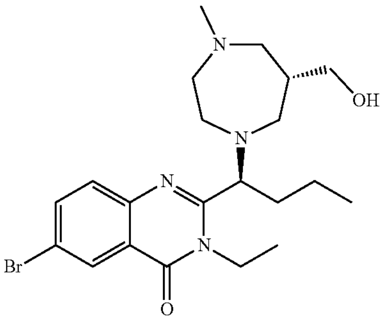 [SMILES: CCC[C@@H](c1nc2ccc(Br)cc2c(=O)n1CC)N1CCN(C)C[C@H](CO)C1] | 126 | 6-bromo-3-ethyl-2-((S)-1-((S)-6-(hydroxymethyl)-4-methyl-1,4-diazepan-1-yl)butyl)quinazolin-4(3H)-one | 2.07 | 451.2 | B |
| 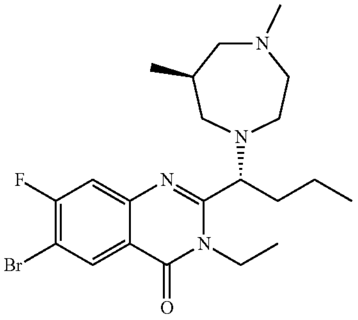 | 127 | 6-bromo-2-((R)-1-((S)-4,6-dimethyl-1,4-diazepan-1-yl)butyl)-3-ethyl-7-fluoroquinazolin-4(3H)-one | 2.64 | 453.2 | B |

-continued
| STRUCTURE | EX | CHEMICAL NAME | Rt (min) | MS (M + H) | HPLC Method |
|---|---|---|---|---|---|
| 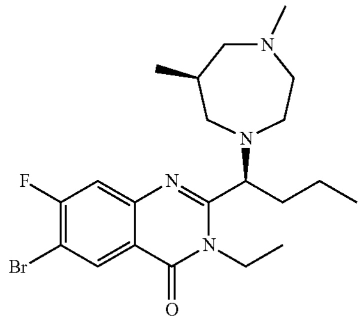 | 128 | 6-bromo-2-((S)-1-((S)-4,6-dimethyl-1,4-diazepan-1-yl)butyl)-3-ethyl-7-fluoroquinazolin-4(3H)-one | 2.63 | 453.3 | B |
| 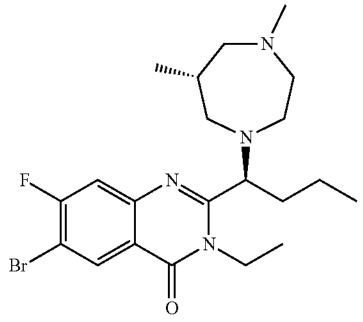 | 129 | 6-bromo-2-((S)-1-((R)-4,6-dimethyl-1,4-diazepan-1-yl)butyl)-3-ethyl-7-fluoroquinazolin-4(3H)-one | 2.63 | 453.2 | B |
| 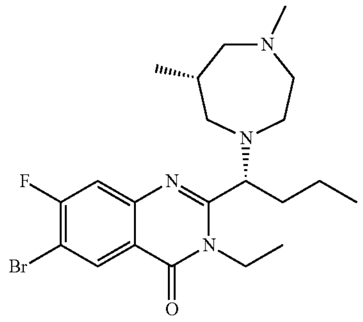 | 130 | 6-bromo-2-((R)-1-((R)-4,6-dimethyl-1,4-diazepan-1-yl)butyl)-3-ethyl-7-fluoroquinazolin-4(3H)-one | 2.63 | 453.2 | B |
| 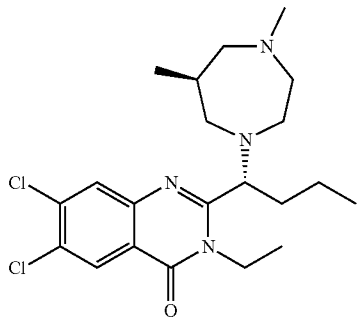 [SMILES: CCC[C@H](c1nc2cc(Cl)c(Cl)cc2c(=O)n1CC)N1CCN(C)C[C@H](C)C1] | 131 | 6,7-dichloro-2-((R)-1-((S)-4,6-dimethyl-1,4-diazepan-1-yl)butyl)-3-ethylquinazolin-4(3H)-one | 2.91 | 425.3 | B |

-continued
| STRUCTURE | EX | CHEMICAL NAME | Rt (min) | MS (M + H) | HPLC Method |
|---|---|---|---|---|---|
| 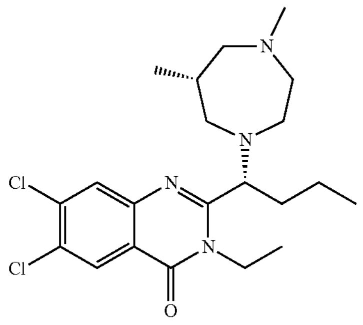 [SMILES: CCC[C@H](c1nc2cc(Cl)c(Cl)cc2c(=O)n1CC)N1CCN(C)C[C@@H](C)C1] | 132 | 6,7-dichloro-2-((R)-1-((R)-4,6-dimethyl-1,4-diazepan-1-yl)butyl)-3-ethylquinazolin-4(3H)-one | 2.9 | 425.3 | B |
| 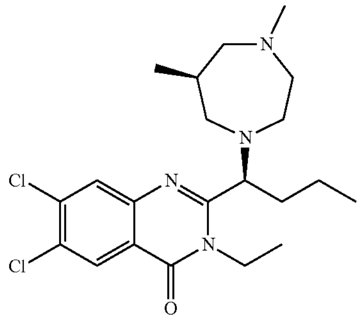 [SMILES: CCC[C@@H](c1nc2cc(Cl)c(Cl)cc2c(=O)n1CC)N1CCN(C)C[C@H](C)C1] | 133 | 6,7-dichloro-2-((S)-1-((S)-4,6-dimethyl-1,4-diazepan-1-yl)butyl)-3-ethylquinazolin-4(3H)-one | 2.91 | 425.3 | B |
| 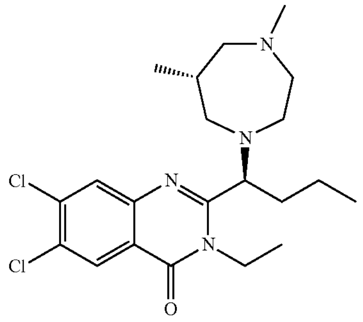 [SMILES: CCC[C@@H](c1nc2cc(Cl)c(Cl)cc2c(=O)n1CC)N1CCN(C)C[C@@H](C)C1] | 134 | 6,7-dichloro-2-((S)-1-((R)-4,6-dimethyl-1,4-diazepan-1-yl)butyl)-3-ethylquinazolin-4(3H)-one | 2.6 | 425.3 | B |
| 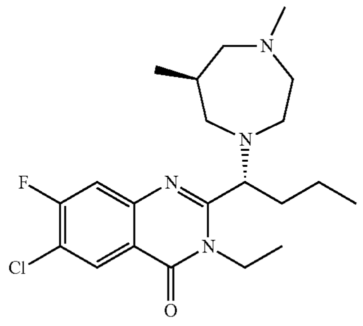 [SMILES: CCC[C@H](c1nc2cc(F)c(Cl)cc2c(=O)n1CC)N1CCN(C)C[C@H](C)C1] | 135 | 6-chloro-2-((R)-1-((S)-4,6-dimethyl-1,4-diazepan-1-yl)butyl)-3-ethyl-7-fluoroquinazolin-4(3H)-one | 2.6 | 409.3 | B |

-continued

| STRUCTURE | EX | CHEMICAL NAME | Rt (min) | MS (M + H) | HPLC Method |
|---|---|---|---|---|---|
| 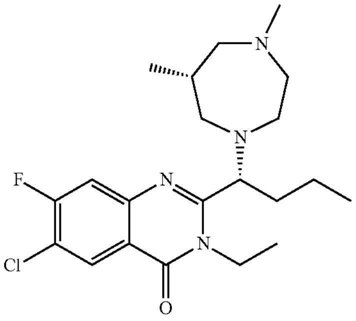 [SMILES: CCC[C@H](c1nc2cc(F)c(Cl)cc2c(=O)n1CC)N1CCN(C)C[C@@H](C)C1] | 136 | 6-chloro-2-((R)-1-((R)-4,6-dimethyl-1,4-diazepan-1-yl)butyl)-3-ethyl-7-fluoroquinazolin-4(3H)-one | 2.6 | 409.3 | B |
| 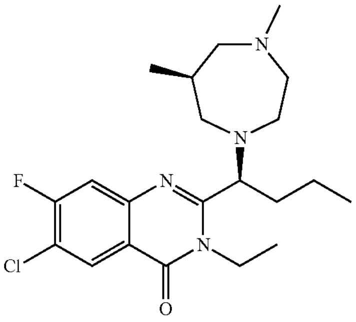 [SMILES: CCC[C@@H](c1nc2cc(F)c(Cl)cc2c(=O)n1CC)N1CCN(C)C[C@H](C)C1] | 137 | 6-chloro-2-((S)-1-((S)-4,6-dimethyl-1,4-diazepan-1-yl)butyl)-3-ethyl-7-fluoroquinazolin-4(3H)-one | 2.59 | 409.2 | B |
| 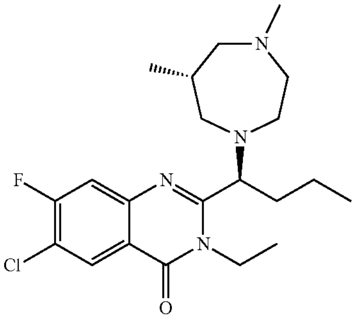 [SMILES: CCC[C@@H](c1nc2cc(F)c(Cl)cc2c(=O)n1CC)N1CCN(C)C[C@@H](C)C1] | 138 | 6-chloro-2-((S)-1-((R)-4,6-dimethyl-1,4-diazepan-1-yl)butyl)-3-ethyl-7-fluoroquinazolin-4(3H)-one | 2.6 | 409.3 | B |
| 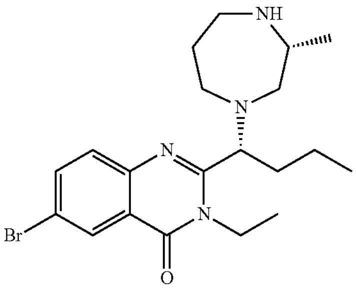 [SMILES: CCC[C@H](c1nc2ccc(Br)cc2c(=O)n1CC)N1CCCN[C@H](C)C1] | 139 | 6-bromo-3-ethyl-2-((R)-1-((R)-3-methyl-1,4-diazepan-1-yl)butyl)quinazolin-4(3H)-one | 2.01 | 421.2 | F |
| 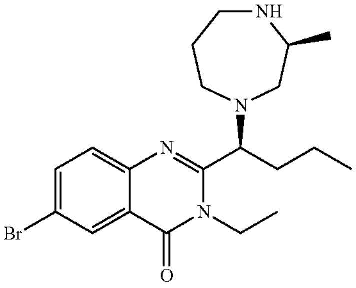 [SMILES: CCC[C@@H](c1nc2ccc(Br)cc2c(=O)n1CC)N1CCCN[C@@H](C)C1] | 140 | 6-bromo-3-ethyl-2-((S)-1-((S)-3-methyl-1,4-diazepan-1-yl)butyl)quinazolin-4(3H)-one | 2.01 | 421.2 | F |

-continued
| STRUCTURE | EX | CHEMICAL NAME | Rt (min) | MS (M + H) | HPLC Method |
|---|---|---|---|---|---|
| 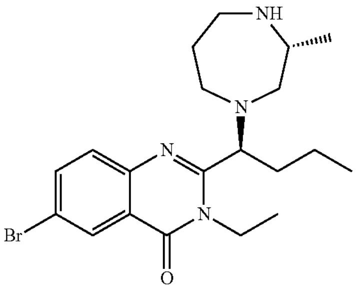 [SMILES: CCC[C@@H](c1nc2ccc(Br)cc2c(=O)n1CC)N1CCCN[C@H](C)C1] | 141 | 6-bromo-3-ethyl-2-((S)-1-((R)-3-methyl-1,4-diazepan-1-yl)butyl)quinazolin-4(3H)-one | 2.04 | 421.2 | F |
| 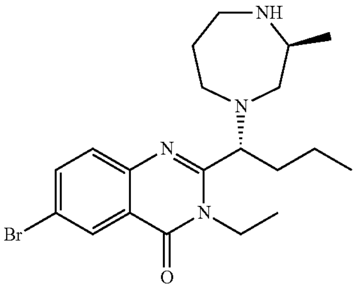 [SMILES: CCC[C@H](c1nc2ccc(Br)cc2c(=O)n1CC)N1CCCN[C@@H](C)C1] | 142 | 6-bromo-3-ethyl-2-((R)-1-((S)-3-methyl-1,4-diazepan-1-yl)butyl)quinazolin-4(3H)-one | 2.08 | 421 | B |
| 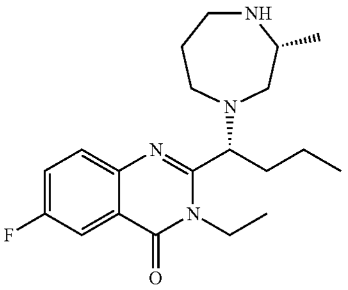 [SMILES: CCC[C@H](c1nc2ccc(F)cc2c(=O)n1CC)N1CCCN[C@H](C)C1] | 143 | 3-ethyl-6-fluoro-2-((R)-1-((R)-3-methyl-1,4-diazepan-1-yl)butyl)quinazolin-4(3H)-one | 1.9 | 361.2 | F |
| 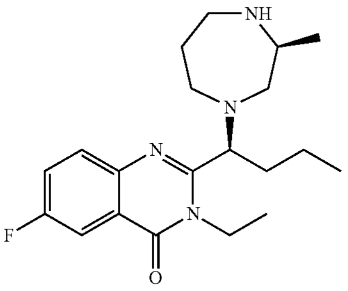 [SMILES: CCC[C@@H](c1nc2ccc(F)cc2c(=O)n1CC)N1CCCN[C@@H](C)C1] | 144 | 3-ethyl-6-fluoro-2-((S)-1-((S)-3-methyl-1,4-diazepan-1-yl)butyl)quinazolin-4(3H)-one | 1.9 | 361.2 | F |
| 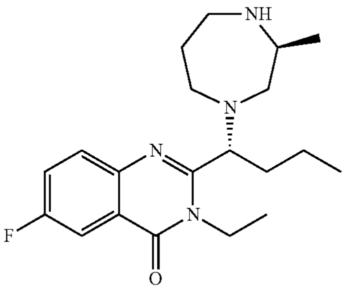 [SMILES: CCC[C@H](c1nc2ccc(F)cc2c(=O)n1CC)N1CCCN[C@@H](C)C1] | 145 | 3-ethyl-6-fluoro-2-((R)-1-((S)-3-methyl-1,4-diazepan-1-yl)butyl)quinazolin-4(3H)-one | 1.92 | 361.2 | F |

-continued

| STRUCTURE | EX | CHEMICAL NAME | Rt (min) | MS (M + H) | HPLC Method |
|---|---|---|---|---|---|
| 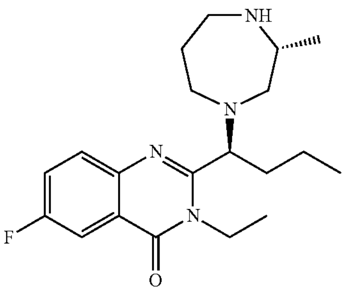 [SMILES: CCC[C@@H](c1nc2ccc(F)cc2c(=O)n1CC)N1CCCN[C@H](C)C1] | 146 | 3-ethyl-6-fluoro-2-((S)-1-((R)-3-methyl-1,4-diazepan-1-yl)butyl)quinazolin-4(3H)-one | 1.92 | 361.2 | F |
| 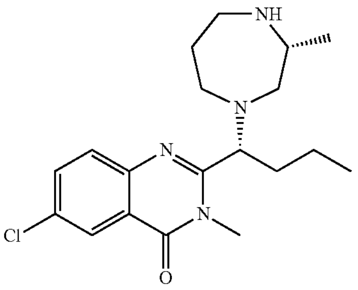 [SMILES: CCC[C@H](c1nc2ccc(Cl)cc2c(=O)n1C)N1CCCN[C@H](C)C1] | 147 | 6-chloro-3-methyl-2-((R)-1-((R)-3-methyl-1,4-diazepan-1-yl)butyl)quinazolin-4(3H)-one | 1.98 | 363 | F |
| 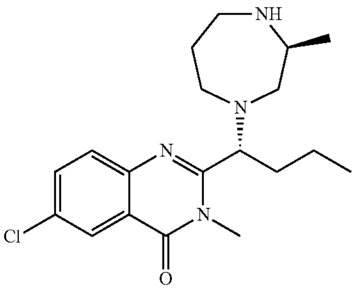 [SMILES: CCC[C@H](c1nc2ccc(Cl)cc2c(=O)n1C)N1CCCN[C@@H](C)C1] | 148 | 6-chloro-3-methyl-2-((R)-1-((S)-3-methyl-1,4-diazepan-1-yl)butyl)quinazolin-4(3H)-one | 1.99 | 363 | F |
| 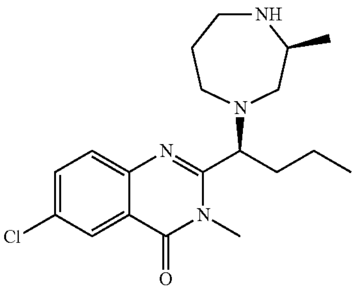 [SMILES: CCC[C@@H](c1nc2ccc(Cl)cc2c(=O)n1C)N1CCCN[C@@H](C)C1] | 149 | 6-chloro-3-methyl-2-((S)-1-((S)-3-methyl-1,4-diazepan-1-yl)butyl)quinazolin-4(3H)-one | 1.99 | 363 | F |
| 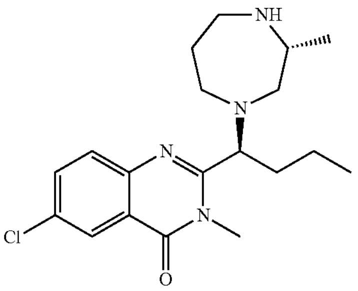 [SMILES: CCC[C@@H](c1nc2ccc(Cl)cc2c(=O)n1C)N1CCCN[C@H](C)C1] | 150 | 6-chloro-3-methyl-2-((S)-1-((R)-3-methyl-1,4-diazepan-1-yl)butyl)quinazolin-4(3H)-one | 1.99 | 363 | F |

Examples 15 and 16. (R)-3-Ethyl-6-methoxy-2-(1-(4-methyl-1,4-diazepan-1-yl)butyl)quinazolin-4(3H)-one and (S)-3-ethyl-6-methoxy-2-(1-(4-methyl-1,4-diazepan-1-yl)butyl)quinazolin-4(3H)-one Examples 15 and 16 were directly separated using preparative HPLC: column: SunFire C18, 10 μm. 19×150 mm; temperature: 30° C.: flow rate: 14 mL/min; A: $CH_3CN$; B: 10 mM ammonium bicarbonate buffer pH 7, gradient: 8 min in 5:95+from 5:95 to 80:20 in 15 min+7 min in 80:20.

Examples 35, 36, 37 and 38. 6-Bromo-2-((R)-1-((R)-4,6-dimethyl-1,4-diazepan-1-yl)butyl)-3-ethylquinazolin-4(3H)-one, 6-bromo-2-((R)-1-((S)-4,6-dimethyl-1,4-diazepan-1-yl)butyl)-3-ethylquinazolin-4(3H)-one, 6-bromo-2-((S)-1-((S)-4,6-dimethyl-1,4-diazepan-1-yl)butyl)-3-ethylquinazolin-4(3H)-one and 6-bromo-2-((S)-1-((R)-4,6-dimethyl-1,4-diazepan-1-yl)butyl)-3-ethylquinazolin-4(3H)-one Examples 35, 36, 37 and 38 were directly separated using preparative HPLC: column: SunFire C18. 10 ppm, 19×150 mm; temperature: 30° C.; flow rate: 14 mL/min; A: $CH_3CN$; B: 10 mM ammonium bicarbonate buffer pH 7: gradient: 8 min in 5:95+from 5:95 to 80:20 in 15 min+7 min in 80:20.

Example 66. (R)-2-(1-(1,4-Diazabicyclo[3.2.2]nonan-4-yl)butyl)-6-bromo-3-ethylquinazolin-4(3H)-one.

Starting from the compound obtained in Example 80 a chiral preparative HPLC separation (Column LUX C4 21.2×250 mm. 5 μm; temperature: r.t.; eluent: MeOH (0.2% v/v $NH_3$); flow rate 21 mL/min; Rt1: 4.7 min) was carried out to give the title compound.

Examples 67, 68, 69 and 70. 6-Bromo-3-ethyl-2-((R)-1-((S)-6-methyl-1,4-diazepan-1-yl)butyl)quinazolin-4(3H)-one, 6-bromo-3-ethyl-2-((R)-1-((R)-6-methyl-1,4-diazepan-1-yl)butyl)quinazolin-4(3H)-one, 6-bromo-3-ethyl-2-((S)-1-((S)-6-methyl-1,4-diazepan-1-yl)butyl)quinazolin-4(3H)-one and 6-bromo-3-ethyl-2-((S)-1-((R)-6-methyl-1,4-diazepan-1-yl)butyl)quinazolin-4(3H)-one Examples 67, 68, 69 and 70 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 73, 74, 75 and 76. 6-Chloro-2-((S)-1-((S)-4,6-dimethyl-1,4-diazepan-1-yl)butyl)-3-ethylquinazolin-4(3H)-one, 6-chloro-2-((S)-1-((R)-4,6-dimethyl-1,4-diazepan-1-yl)butyl)-3-ethylquinazolin-4(3H)-one, 6-chloro-2-((R)-1-((S)-4,6-dimethyl-1,4-diazepan-1-yl)butyl)-3-ethylquinazolin-4(3H)-one and 6-chloro-2-((R)-1-((R)-4,6-dimethyl-1,4-diazepan-1-yl)butyl)-3-ethylquinazolin-4(3H)-one.

Examples 73, 74, 75 and 76 were directly separated using preparative HPLC: column: SunFire C18, 10 μm, 19×150 mm; temperature: 30° C.: flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 92, 93, 94 and 95. 6-Bromo-3-ethyl-2-((R)-1-((R)-5-methyl-1,4-diazepan-1-yl)butyl)quinazolin-4(3H)-one, 6-bromo-3-ethyl-2-((R)-1-((S)-5-methyl-1,4-diazepan-1-yl)butyl)quinazolin-4(3H)-one, 6-bromo-3-ethyl-2-((S)-1-((R)-5-methyl-1,4-diazepan-1-yl)butyl)quinazolin-4(3H)-one, and 6-bromo-3-ethyl-2-((S)-1-((S)-5-methyl-1,4-diazepan-1-yl)butyl)quinazolin-4(3H)-one.

Examples 92, 93, 94 and 95 were directly separated using preparative HPLC: column: SunFire C18, 10 μm, 19×150 mm; temperature: 30° C.: flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 96, 97, 98 and 99. 6-Bromo-3-ethyl-7-fluoro-2-((R)-1-((S)-6-methyl-1,4-diazepan-1-yl)butyl)quinazolin-4(3H)-one, 6-bromo-3-ethyl-7-fluoro-2-((R)-1-((R)-6-methyl-1,4-diazepan-1-yl)butyl)quinazolin-4(3H)-one, 6-bromo-3-ethyl-7-fluoro-2-((S)-1-((S)-6-methyl-1,4-diazepan-1-yl)butyl)quinazolin-4(3M-one and 6-bromo-3-ethyl-7-fluoro-2-((S)-1-((R)-6-meth yl-1,4-d]azepan-1-yl)butyl)quinazolin-4 (3H)-one.

Examples 96, 97, 98 and 991 were directly separated using preparative HPLC: column: SunFire C18, 10 μm, 19×150 mm; temperature: 30° C.; flow rate: 14 mL/min; A: $CH_3CN$: B: 10 mM ammonium bicarbonate buffer pH 7; gradient: 8 min in 5:95+from 5:95 to 80:20 in 15 min+7 min in 80:20.

Examples 101, 102, 103 and 104. 6-Bromo-3-ethyl-2-((S)-1-((S)-6-ethyl-4-methyl-1,4-diazepan-1-yl)butyl)quinazolin-4(3H)-one, 6-bromo-3-ethyl-2-((S)-1-((R)-6-ethyl-4-methyl-1,4-diazepan-1-yl)butyl)quinazolin-4 (3H)-one, 6-bromo-3-ethyl-2-((R)-1-((R)-6-ethyl-4-methyl-1,4-diazepan-1-yl)butyl)quinazolin-4(3H)-one and 6-bromo-3-ethyl-2-((R)-1-((S)-6-ethyl-4-methyl-1,4-diazepan-1-yl)butyl)quinazolin-4(3H)-one.

Examples 101, 102, 103 and 104 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 105, 106, 107 and 108. 6-Bromo-3-ethyl-2-((R)-1-((S)-6-(methoxymethyl)-4-methyl-1,4-diazepan-1-yl)butyl)quin-4 (3H)-one, 6-bromo-3-ethyl-2-((R)-1-((R)-6-(methoxymethyl)-4-methyl-1,4-diazepan-1-yl)butyl)quinazolin-4(3H)-one, 6-bromo-3-ethyl-2-((S)-1-((S)-6-(methoxymethyl)-4-methyl-1,4-diazepan-1-yl)butyl)quinazolin-4(31-)-one and 6-bromo-3-ethyl-2-((S)-1-((R)-6-(methoxymethyl)-4-methyl-1,4-diazepan-1-yl)butyl)quinazolin-4(3/1)-one.

Examples 105, 106, 107 and 108 were directly separated using preparative HPLC: column: SunFire C18, 10 μm. 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 109, 110, 111 and 112. 6,7-Dichloro-3-ethyl-2-((R)-1-((S)-6-methyl-1,4-diazepan-1-yl)butyl)quinazolin-4(3H)-one, 6,7-dichloro-3-ethyl-2-((R)-1-((R)-6-methyl-1,4-diazepan-1-yl)butyl)quinazolin-4(3H)-one, 6,7-dichloro-3-ethyl-2-((S)-1-((S)-6-methyl-1,4-diazepan-1-yl)butyl)quinazolin-4(3H)-one and 6,7-dichloro-3-ethyl-2-((S)-1-((R)-6-methyl-1,4-diazepan-1-yl)butyl)quinazolin-4 (3H)-one Examples 109, 110, 111 and 112 were directly separated using preparative HPLC: column: SunFire C18, 10 μm, 19×150 mm; temperature: 30° C.: flow rate: 14 mL/min: A: $CH_3CN$; B: 10 mM ammonium bicarbonate buffer pH 7; gradient: 8 min in 5:95+from 5:95 to 80:20 in 15 min+7 min in 80:20.

Examples 113, 114, 115 and 116. 6-Bromo-3-ethyl-2-((S)-1-((R)-6-hydroxy-1,4-diazepan-1-yl)butyl)quinazolin-4(3H)-one, 6-bromo-3-ethyl-2-((R)-1-((R)-6-hydroxy-1,4-diazepan-1-yl)butyl)quinazolin-4(3H)-one, 6-bromo-3-ethyl-2-((S)-1-((S)-6-hydroxy-1,4-diazepan-1-yl)butyl)

quinazolin-4(3H)-one and 6-bromo-3-ethyl-2-((R)-1-((S)-6-hydroxy-1,4-diazepan-1-yl)butyl)quinazolin-4(3H)-one Examples 113, 114, 115 and 116 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 118, 119, 120 and 121, 6-Chloro-3-ethyl-7-fluoro-2-((R)-1-((S)-6-methyl-1,4-diazepan-1-yl)butyl)quinazolin-4(3H)-one, 6-chloro-3-ethyl-7-fluoro-2-((R)-1-((R)-6-methyl-1,4-diazepan-1-yl)butyl)quinazolin-4(3H)-one, 6-chloro-3-ethyl-7-fluoro-2-((S)-1-((S)-6-methyl-1,4-diazepan-1-yl)butyl)quinazolin-4(3H)-one and 6-chloro-3-ethyl-7-fluoro-2-((S)-1-((R)-6-methyl-1,4-diazepan-1-yl)butyl)quinazolin-4 (3H)-one.

Examples 118, 119, 120 and 121 were directly separated using preparative HPLC: column: SunFire C18, 10 μm. 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 123, 124, 125 and 126. 6-Bromo-3-ethyl-2-((R)-1-((S)-6-(hydroxymethyl)-4-methyl-1,4-diazepan-1-yl)butyl)quinazolin-4(3H)-one, 6-bromo-3-ethyl-2-((S)-1-((R)-6-(hydroxymethyl)-4-methyl-1,4-diazepan-1-yl)butyl)quinazolin-4(3H)-one, 6-bromo-3-ethyl-2-((R)-1-((R)-6-(hydroxymethyl)-4-methyl-1,4-diazepan-1-yl)butyl)quinazolin-4(3H)-one and 6-bromo-3-ethyl-2-((S)-1-((S)-6-(hydroxymethyl)-4-methyl-1,4-diazepan-1-yl)butyl)quinazolin-4(3H)-one.

Examples 123, 124, 125 and 126 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7: gradient: 8 min in 5:95+from 5:95 to 80:20 in 15 min+7 min in 80:20.

Examples 127, 128, 129 and 130. 6-Bromo-2-((R)-1-((S)-4,6-dimethyl-1,4-diazepan-1-yl)butyl)-3-ethyl-7-fluoroquinazolin-4(3H)-one, 6-bromo-2-((S)-1-((S)-4,6-dimethyl-1,4-diazepan-1-yl)butyl)-3-ethyl-7-fluoroquinazolin-4(3H)-one, 6-bromo-2-((S)-1-((R)-4,6-dimethyl-1,4-diazepan-1-yl)butyl)-3-ethyl-7-fluoroquinazolin-4(3H)-one and 6-bromo-2-((R)-1-((R)-4,6-dimethyl-1,4-diazepan-1-yl)butyl)-3-ethyl-7-fluoroquinazolin-4 (3H)-one.

Examples 127, 128, 129 and 130 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 131, 132, 133 and 134. 6,7-Dichloro-2-((R)-1-((S)-4,6-dimethyl-1,4-diazepan-1-yl)butyl)-3-ethylquinazolin-4(3H)-one, 6,7-dichloro-2-((R)-1-((R)-4,6-dimethyl-1,4-diazepan-1-yl)butyl)-3-ethylquinazolin-4(3H)-one, 6,7-dichloro-2-((S)-1-((S)-4,6-dimethyl-1,4-diazepan-1-yl)butyl)-3-ethylquinazolin-4(3H)-one and 6,7-dichloro-2-((S)-1-((R)-4,6-dimethyl-1,4-diazepan-1-yl)butyl)-3-ethylquinazolin-4(3H)-one.

Examples 131, 132, 133 and 134 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 135, 136, 137 and 138. 6-Chloro-2-((R)-1-((S)-4,6-dimethyl-1,4-diazepan-1-yl)butyl)-3-ethyl-7-fluoroquinazolin-4(3H)-one, 6-chloro-2-((R)-1-((R)-4,6-dimethyl-1,4-diazepan-1-yl)butyl)-3-ethyl-7-fluoroquinazolin-4(3H)-one, 6-chloro-2-((S)-1-((S)-4,6-dimethyl-1,4-diazepan-1-yl)butyl)-3-ethyl-7-fluoroquinazolin-4(3H)-one and 6-chloro-2-((S)-1-((R)-4,6-dimethyl-1,4-diazepan-1-yl)butyl)-3-ethyl-7-fluoroquinazolin-4 (3H)-one.

Examples 135, 136, 137 and 138 were directly separated using preparative HPLC: column: SunFire C18, 10 μm, 19×150 mm; temperature: 30° C.; flow rate: 14 mL/min: A: $CH_3CN$; B: 10 mM ammonium bicarbonate buffet pH 7; gradient: 8 min in 5:95+from 5:95 to 80:20 in 15 min+7 min in 80:20.

Examples 139, 140, 141 and 142. 6-Bromo-3-ethyl-2-((R)-1-((R)-3-methyl-1,4-diazepan-1-yl)butyl)quinazolin-4 (3H)-one, 6-bromo-3-ethyl-2-((S)-1-((S)-3-methyl-1,4-diazepan-1-yl)butyl)quinazolin-4(3H)-one, 6-bromo-3-ethyl-2-((S)-1-((R)-3-methyl-1,4-diazepan-1-yl)butyl)quinazolin-4(3H)-one and 6-bromo-3-ethyl-2-((R)-1-((S)-3-methyl-1,4-diazepan-1-yl)butyl)quinazolin-4(3H)-one.

Examples 139, 140, 141 and 142 were directly separated using preparative HPLC: column: SunFire C18, 10 μm, 19×150 mm; temperature: 30° C.; flow rate: 14 mL/min; A: $CH_3CN$; 8: 10 mM ammonium bicarbonate buffer pH 7; gradient: 8 min in 5:95+from 5:95 to 80:20 in 15 min+7 min in 80:20.

Examples, 143, 144, 145 and 146. 3-Ethyl-6-fluoro-2-((R)-1-((R)-3-methyl-1,4-diazepan-1-yl)butyl)quinazolin-4 (3H)-one, 3-ethyl-6-fluoro-2-((S)-1-((S)-3-methyl-1,4-diazepan-1-yl)butyl)quinazolin-4(3H)-one, 3-ethyl-6-fluoro-2-((R)-1-((S)-3-methyl-1,4-diazepan-1-yl)butyl)quinazolin-4 (3H)-one, 3-ethyl-6-fluoro-24(5)-1-((R)-3-methyl-1,4-diazepan-1-yl)butyl)quinazolin-4(3H)-one.

Examples 143, 144, 145 and 146 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 147, 148, 149 and 150. 6-Chloro-3-methyl-2-((R)-1-((R)-3-methyl-1,4-diazepan-1-yl)butyl)quinazolin-4 (3H)-one, 6-chloro-3-methyl-2-((R)-1-((S)-3-methyl-1,4-diazepan-1-yl)butyl)quinazolin-4(3H)-one, 6-chloro-3-methyl-2-((S)-1-((S)-3-methyl-1,4-diazepan-1-yl)butyl)quinazolin-4(3H)-one and 6-chloro-3-methyl-2-((S)-1-((R)-3-methyl-1,4-diazepan-1-yl)butyl)quinazolin-4(3H)-one.

Examples 147, 148, 149 and 150 were directly separated using preparative HPLC: column: SunFire C18, 10 μm, 19×150 mm; temperature: 30° C.; flow rate: 14 mL/min; A: $CH_3CN$: B: 10 mM ammonium bicarbonate buffer pH 7; gradient: 8 min in 5:95+from 5:95 to 80:20 in 15 min+7 min in 80:20.

Examples 151 and 152. (R)-6-Bromo-3-ethyl-2-(1-(4-methyl-1,4-diazepan-1-yl)butyl)quinazolin-4(3H)-one and (S)-6-bromo-3-ethyl-2-(1-(4-methyl-1,4-diazepan-1-yl)butyl)quinazolin-4(3H)-one Starting from the compound obtained in Example 1 a chiral preparative HPLC separation (column: Chiralpak AD-H, 20×250 mm, 5 μm; temperature: r.t.: eluent: n-Heptane/EtOH/$Et_2NH$ 80/20/0.06 v/v/v; flow rate 11 mL/min; Rt1: 6.9 min, Rt2: 10.3 min) was carried out to give the title compounds.

Examples 153 and 154. (R)-6-Bromo-3-ethyl-2-(1-(4-ethyl-1,4-diazepan-1-yl)butyl)quinazolin-4(3H)-one and (S)-6-bromo-3-ethyl-2-(1-(4-ethyl-1,4-diazepan-1-yl)butyl)quinazolin-4(3H)-one Starting from the compound obtained in Example 7 a chiral preparative HPLC separation (column: Chiralpak AD-H, 20×250 mm, 5 μm; temperature: r.t.; eluent: n-Heptane/EtOH/$Et_2NH$ 95/5/0.015 v/v/v; flow rate 14 mL/min; Rt1: 6.6 min, Rt2: 7.8 min) was carried out to give the title compounds.

Examples 155 and 156. (R)-6-Bromo-3-ethyl-7-fluoro-2-(1-(4-methyl-1,4-diazepan-1-yl)butyl)quinazolin-4(3H)-one and (S)-6-bromo-3-ethyl-7-fluoro-2-(1-(4-methyl-1,4-diazepan-1-yl)butyl)quinazolin-4(3H)-one Starting from the compound obtained in Example 13 a chiral preparative HPLC separation (column: Chiralpak AD-H, 20×250 mm, 5 μm; temperature: r.t.: eluent: n-Heptane/EtOH/$Et_2NH$ 80/20/0.06 v/v/v; flow rate 13 mL/min; Rt1: 5.5 min, Rt2: 6.6 min) was carried out to give the title compounds.

Examples 157 and 158, (R)-2-(1-(1,4-Diazepan-1-yl) butyl)-6-bromo-3-ethyl-7-fluoroquinazolin-4(3H)-one and (S)-2-(1-(1,4-diazepan-1-yl)butyl)-6-bromo-3-ethyl-7-fluoroquinazolin-4(3H)-one Starting from the compound obtained in Example 27 a chiral preparative SFC separation (column: Amy C, 20×250 mm, 5 μm; temperature: 40 C.; eluent: 40/60 EtOH/$CO_2$ (0.2% v/v $NH_3$); flow rate 50 mL/min; Rt1: 1.5 min, Rt2: 3.0 min) was carried out to give the title compounds.

Examples 159 and 160. (R)-6-Chloro-2-(1-(4-methyl-1,4-diazepan-1-yl)butyl)-3-propylquinazolin-4(3H)-one and (S)-6-chloro-2-(1-(4-methyl-1,4-diazepan-1-yl)butyl)-3-propylquinazolin-4(3H)-one Starting from the compound obtained in Example 23 a chiral preparative SFC separation (column: Chiralpak IG, 20×250 mm. 5 μm, temperature: 40 C.; eluent; 30/70 EtOH/CO: (0.5% v/v $NH_3$); flow rate 50 mL/min: Rt1: 2.4 min, Rt2: 2.9 min) was carried out to give the title compounds.

Examples 161 and 162. (R)-6-Bromo-3-ethyl-8-fluoro-2-(1-(4-methyl-1,4-diazepan-1-yl)butyl)quinazolin-4(3H)-one and (S)-6-bromo-3-ethyl-8-fluoro-2-(1-(4-methyl-1,4-diazepan-1-yl)butyl)quinazolin-4(3H)-one Starting from the compound obtained in Example 40 a chiral preparative HPLC separation (column: Chiralpak AD-H. 20×250 mm, 5 μm; temperature: r.t.: eluent: n-Heptane/EtOH/$Et_2NH$ 97/3/0.01 May: flow rate 12 mL/min; Rt1: 9.3 min, Rt2: 12.6 min) was carried out to give the title compounds.

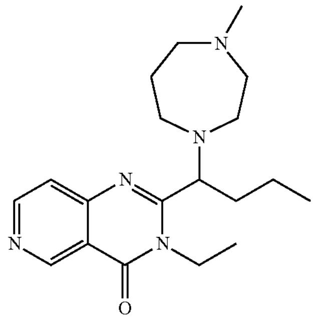 [SMILES: CCCC(c1nc2ccncc2c(=O)n1CC)N1CCCN(C)CC1]

Example 163. 3-Ethyl-2-(1-(4-methyl-1,4-diazepan-1-yl)butyl)pyrido[4,3-d]pyrimidin-4(3H)-one Step a. 4-Aminonicotinoyl chloride To a solution of 4-aminonicotinic acid (4.02 g, 29 mmol) in toluene (19 mL) under argon atmosphere, DMF (0.1 mL) and thionyl chloride (21 mL g, 291 mmol) were added and the reaction mixture was heated at 95° C. for 16 h. The reaction crude was cooled down to r.t. and the solvent was removed under vacuum and stripped down twice with toluene to give the title compound (4.6 g, Yield: quant).

Step b. 4-Amino-N-ethylnicotinamide

To a solution of the compound obtained in step a (4.6 g. 29 mmol) in anh ACN (30 mL), ethylamine (2M in THF, 29 mL, 58 mmol) and TEA (8 mL, 58 mmol) were added dropwise and the reaction mixture was stirred at r.t. for 16 h. The solvent was removed under vacuum and the crude product was dissolved in EtOAc and washed twice with sat. aq. $NaHCO_3$ The aq layer was extracted with EtOAc, the combined organic layers were dried over anh $Na_2SO_4$ and the solvent was removed under vacuum to give the title compound (2.13 g, Yield: 44%).

Step c. N-Ethyl-4-pentanamidonicotinamide

Starting from the product obtained in step b (2.13 g, 13 mmol) and following the experimental procedure described in step b of Example 1, the title compound was obtained (3.45 g, Yield: 99%).

Step d. 2-Butyl-3-ethylpyrido[4,3-d]pyrimidin-4(3H)-one

To a solution of the compound obtained in step c (3.45 g 12.9 mmol) in anh THF, TEA (10.8 mL, 77 mmol) and TMSCl (4.08 mL, 32 mmol) were added dropwise. The reaction mixture was heated at 85° C. for 16 h and it was quenched by the addition of $NH_4Cl$ sat. solution. The product was extracted with EtOAc and the combined organic layers were washed with brine, dried over anh $Na_2SO_4$ and filtered. The solvent was removed under vacuum and the crude product was purified by flash chromatography, silica gel, gradient Chx to Chx:EtOAc (4:6) to give the title compound (1.97 g, Yield: 66%).

Step e. 2-(1-Bromobutyl)-3-ethylpyrido[4,3-d]pyrimidin-4(3H)one

To a solution of the compound obtained in step d (1.09 g, 4.7 mmol) in anh ACN, NBS (1.048 g. 5.88 mmol) and AIBN (77 mg. 0.47 mmol) were added portion wise and the reaction was heated at 95° C. for 2.5 h. The mixture was allowed to cool to r.t. and dissolved in EtOAc. The organic layer was washed with $Na_2CO_3$ sat. solution and brine and dried over anh $Na_2SO_4$ After filtration, the solvent was removed under vacuum to give the title compound, which was used in next step without further purification (1.4 g, Yield: 66%).

Step f. 3-Ethyl-2-(1-(4-methyl-1,4-diazepan-1-yl butyl)pyrido[4,3-d]pyrimidin-4(3H)-one To a solution of the compound obtained in step e (75 mg, 0.24 mmol) in anh ACN. 1-methyl-1,4-diazepane (0.09 mL, 0.73 mmol) was added and the reaction was heated at 50° C. for 16 h. The mixture was allowed to cool to r.t. and dissolved in EtOAc. The organic layer was washed with $NaHCO_3$ sat. solution and brine. The organic layer was dried over anh $Na_2SO_4$ filtered and the solvent removed under vacuum to give the title compound. (56 mg, Yield: 59%), HPLC-MS (8) Rt, 1.49 min: ESI+-MS m/z: 344.2 (M+1).

This method was used for the preparation of examples 164-172 using suitable starting materials:

| STRUCTURE | EX | CHEMICAL NAME | Rt (min) | MS (M + H) | HPLC Method |
|---|---|---|---|---|---|
| 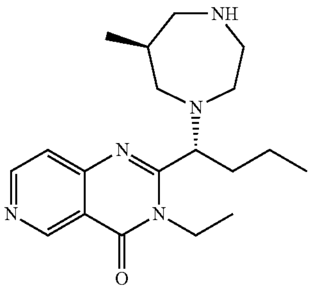 [SMILES: CCC[C@H](c1nc2ccncc2c(=O)n1CC)N1CCNC[C@H](C)C1] | 164 | 3-ethyl-2-((R)-1-((S)-6-methyl-1,4-diazepan-1-yl)butyl)pyrido[4,3-d]pyrimidin-4(3H)-one | 2.08 | 344.2 | G |
| 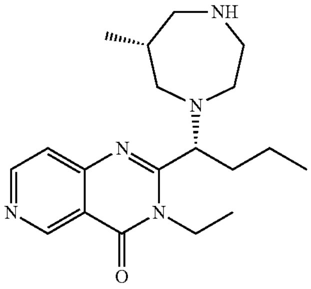 [SMILES: CCC[C@H](c1nc2ccncc2c(=O)n1CC)N1CCNC[C@@H](C)C1] | 165 | 3-ethyl-2-((R)-1-((R)-6-methyl-1,4-diazepan-1-yl)butyl)pyrido[4,3-d]pyrimidin-4(3H)-one | 2.1 | 344.3 | G |
| 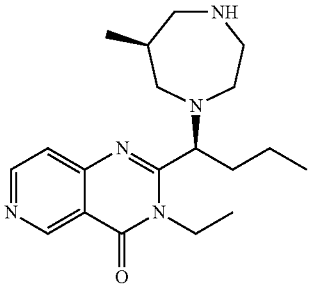 [SMILES: CCC[C@@H](c1nc2ccncc2c(=O)n1CC)N1CCNC[C@H](C)C1] | 166 | 3-ethyl-2-((S)-1-((S)-6-methyl-1,4-diazepan-1-yl)butyl)pyrido[4,3-d]pyrimidin-4(3H)-one | 2.1 | 344.3 | G |
| 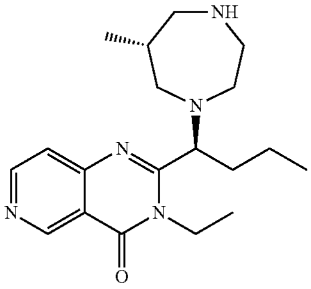 [SMILES: CCC[C@@H](c1nc2ccncc2c(=O)n1CC)N1CCNC[C@@H](C)C1] | 167 | 3-ethyl-2-((S)-1-((R)-6-methyl-1,4-diazepan-1-yl)butyl)pyrido[4,3-d]pyrimidin-4(3H)-one | 2.07 | 344.3 | G |

-continued
| STRUCTURE | EX | CHEMICAL NAME | Rt (min) | MS (M + H) | HPLC Method |
|---|---|---|---|---|---|
| 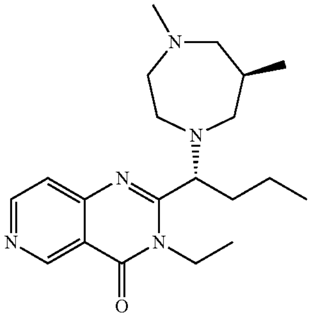 [SMILES: CCC[C@H](c1nc2ccncc2c(=O)n1CC)N1CCN(C)C[C@@H](C)C1] | 168 | 2-((R)-1-((R)-4,6-dimethyl-1,4-diazepan-1-yl)butyl)-3-ethylpyrido[4,3-d]pyrimidin-4(3H)-one | 1.67 | 358.3 | B |
| 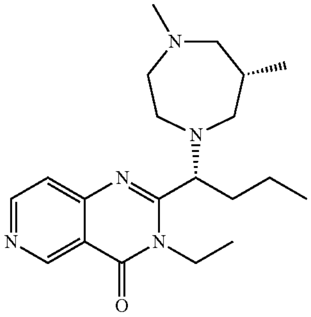 [SMILES: CCC[C@H](c1nc2ccncc2c(=O)n1CC)N1CCN(C)C[C@H](C)C1] | 169 | 2-((R)-1-((S)-4,6-dimethyl-1,4-diazepan-1-yl)butyl)-3-ethylpyrido[4,3-d]pyrimidin-4(3H)-one | 1.67 | 358.3 | B |
| 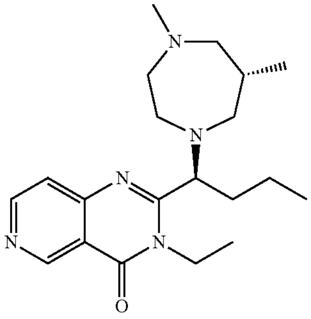 [SMILES: CCC[C@@H](c1nc2ccncc2c(=O)n1CC)N1CCN(C)C[C@H](C)C1] | 170 | 2-((S)-1-((S)-4,6-dimethyl-1,4-diazepan-1-yl)butyl)-3-ethylpyrido[4,3-d]pyrimidin-4(3H)-one | 1.67 | 358.3 | B |
| 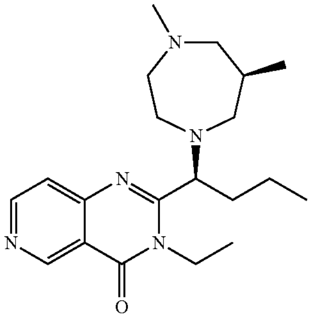 [SMILES: CCC[C@@H](c1nc2ccncc2c(=O)n1CC)N1CCN(C)C[C@@H](C)C1] | 171 | 2-((S)-1-((R)-4,6-dimethyl-1,4-diazepan-1-yl)butyl)-3-ethylpyrido[4,3-d]pyrimidin-4(3H)-one | 1.67 | 358.3 | B |

-continued

| STRUCTURE | EX | CHEMICAL NAME | Rt (min) | MS (M + H) | HPLC Method |
|---|---|---|---|---|---|
| 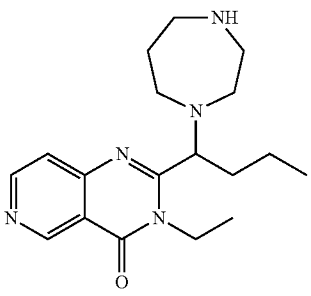 [SMILES: CCCC(c1nc2ccncc2c(=O)n1CC)N1CCCNCC1] | 172 | 2-(1-(1,4-diazepan-1-yl)butyl)-3-ethylpyrido[4,3-d]pyrimidin-4(3H)-one | 1.41 | 330.2 | B |

Examples 164, 165, 166 and 167. 3-Ethyl-2-((R)-1-((S)-6-methyl-1,4-diazepan-1-yl)butyl)pyrido[4,3-d]pyrimidin-4(3H)-one, 3-ethyl-2-((R)-1-((R)-6-methyl-1,4-diazepan-1-yl)butyl)pyrido[4,3-d]pyrimidin-4(3H)-one, 3-ethyl-2-((S)-1-((S)-6-methyl-1-yl-diazepan-1-yl)butyl)pyrido[4,3-d]pyrimidin-4(3H)-one and 3-ethyl-2-((S)-1-((R)-6-methyl-1,4-diazepan-1-yl)butyl)pyrido[4,3-d]pyrimidin-4(3H)-one Examples 164, 165, 166 and 167 were directly separated using preparative HPLC: column: SunFire C18, 10 μm, 19×150 mm: temperature: 30° C.: flow rate: 14 mL/min: A: $CH_3CN$: B: 10 mM ammonium bicarbonate buffer pH 7; gradient: 8 min in 5:95+from 5:95 to 80:20 in 15 min+7 min in 80:20.

Examples 168, 169, 170 and 171. 2—((R)-1-((R)-4,6-Dimethyl-1,4-diazepan-1-yl)butyl)-3-ethylpyrido[4,3-d]pyrimidin-4(3H)-one, 2-((R)-1-((S)-4,6-dimethyl-1,4-diazepan-1-yl)butyl)-3-ethylpyrido[4,3-d]pyrimidin-4(3H)-one, 2-((S)-1-((S)-4,6-dimethyl-1,4-diazepan-1-yl)butyl)-3-ethylpyrido[4,3-d]pyrimidin-4(3H)-one and 2-((S)-1-((R)-4,6-dimethyl-1,4-diazepan-1-yl)butyl)-3-ethylpyrido[4,3-d]pyrimidin-4(3H)-one Examples 168, 169, 170 and 171 were directly separated using preparative HPLC: column: SunFire C18, 10 μm, 19×150 mm: temperature: 30° C.; flow rate: 14 mL/min; A: $CH_3CN$: B: 10 mM ammonium bicarbonate buffer pH 7; gradient: 8 min in 5:95+from 5:95 to 80:20 in 15 min+7 min in 80:20.

Examples 173 and 174. (R)-3-Ethyl-2-(1-(4-methyl-1,4-diazepan-1-yl)butyl)pyrido[4,3-d]pyrimidin-4(3H)-one and (S)-3-ethyl-2-(1-(4-methyl-1,4-diazepan-1-yl)butyl)pyrido[4,3-d]pyrimidin-4(3H)-one Starting from the compound obtained in Example 163 a chiral preparative HPLC separation (column: Chiralpak AD-H, 20×250 mm, 5 μm; temperature: r.t.; eluent: n-Heptane/EtOH/$Et_2NH$ 90/10/0.03 v/v/v; flow rate 12 mL/min: Rt1: 10.5 min, Rt2: 13.9 min) was carried out to give the title compound.

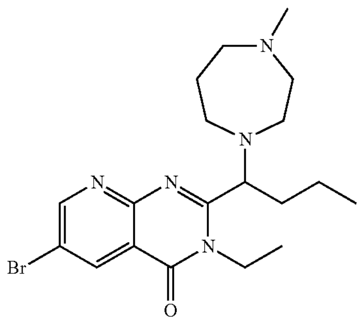 [SMILES: CCCC(c1nc2ncc(Br)cc2c(=O)n1CC)N1CCCN(C)CC1]

Example 175. 6-Bromo-3-ethyl-2-(1-(4-methyl-1,4-diazepan-1-yl)butyl)pyrido[2,3-d]pyrimidin-4(3H)-one Step a. 2-Amino-5-bromo-N-ethylnicotinamide Starting from 2-amino-5-bromonicotinic acid (2 g, 9.21 mmol) and following the experimental procedure described in step a of Example 1, the title compound was obtained (2.4 g, Yield: quant).

Step b. 6-Bromo-2-butyl-3-ethylpyrido(2,3-yl)pyrimidin-4(3H)-one

To a solution of compound obtained in step a (2.4 g, 9.8 mmol) in PPA (12 g), pentanoic acid (1.28 mL, 11.8 mmol) was added dropwise and the reaction was heated at 100° C. for 5 h. The reaction was allowed to cool to r.t. and EtOAc and 10% NaOH aq solution was added and the crude mixture was stirred at r.t. overnight. The solution was extracted with EtOAc and the combined organic layers were dried over anh $Na_2SO_4$, filtered and evaporated under vacuum to give the title compound (3.1 g, Yield: 75%).

Step c. 6-Bromo-2-(1-bromobutyl)-3-ethylpyrido[2,3-d]pyrimidin-4(3H)-one

Starting from the compound obtained in step b (3.1 g, 7.49 mmol) and following the experimental procedure described in step d of Example 1, the title compound was obtained (1.85 g, Yield: 63%).

Step d. Title Compound

Starting from the compound obtained in step c (80 mg, 0.21 mmol) and following the experimental procedure described in step e of Example 1, the title compound was obtained (15 mg, Yield: 17%).

HPLC-MS (B) Rt, 1.8 min; ESI+-MS m/z: 422.1 (M+1).

This method was used for the preparation of examples 176-200 using suitable starting materials:

| STRUCTURE | EX | CHEMICAL NAME | Rt (min) | MS (M + H) | HPLC Method |
|---|---|---|---|---|---|
| 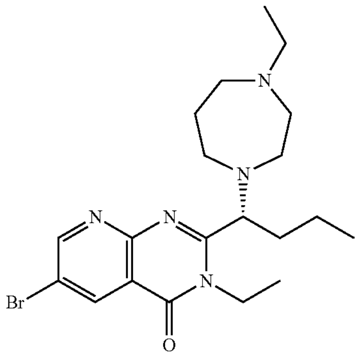 [SMILES: CCC[C@H](c1nc2ncc(Br)cc2c(=O)n1CC)N1CCCN(CC)CC1] | 176 | 6-bromo-3-ethyl-2-(1-(4-ethyl-1,4-diazepan-1-yl)butyl)pyrido[2,3-d]pyrimidin-4(3H)-one | 1.83 | 436.2 | B |
| 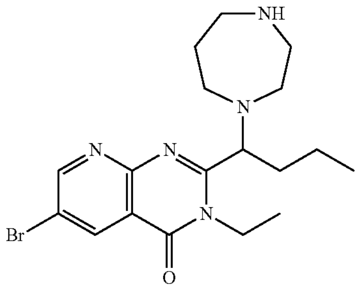 [SMILES: CCCC(c1nc2ncc(Br)cc2c(=O)n1CC)N1CCCNCC1] | 177 | 2-(1-(1,4-diazepan-1-yl)butyl)-6-bromo-3-ethylpyrido[2,3-d]pyrimidin-4(3H)-one | 1.67 | 408.1 | B |
| 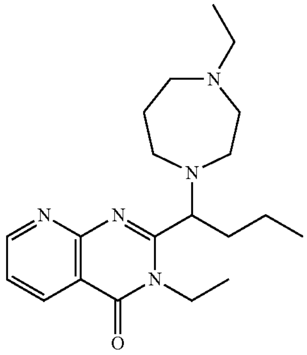 [SMILES: CCCC(c1nc2ncccc2c(=O)n1CC)N1CCCN(CC)CC1] | 178 | 3-ethyl-2-(1-(4-ethyl-1,4-diazepan-1-yl)butyl)pyrido[2,3-d]pyrimidin-4(3H)-one | 1.41 | 358.3 | B |
| 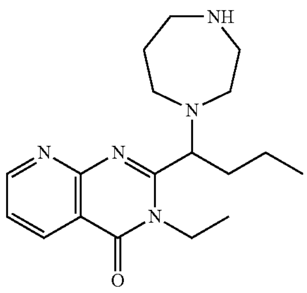 [SMILES: CCCC(c1nc2ncccc2c(=O)n1CC)N1CCCNCC1] | 179 | 2-(1-(1,4-diazepan-1-yl)butyl)-3-ethylpyrido[2,3-d]pyrimidin-4(3H)-one | 1.31 | 330.2 | B |

-continued
| STRUCTURE | EX | CHEMICAL NAME | Rt (min) | MS (M + H) | HPLC Method |
|---|---|---|---|---|---|
| 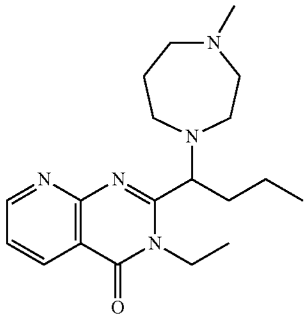 [SMILES: CCCC(c1nc2ncccc2c(=O)n1CC)N1CCCN(C)CC1] | 180 | 3-ethyl-2-(1-(4-methyl-1,4-diazepan-1-yl)butyl)pyrido[2,3-d]pyrimidin-4(3H)-one | 1.38 | 344.2 | B |
| 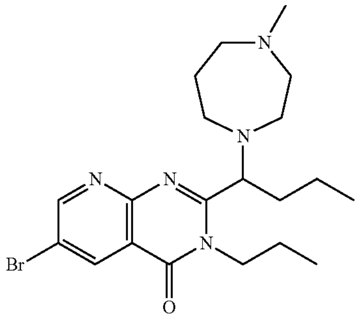 [SMILES: CCCC(c1nc2ncc(Br)cc2c(=O)n1CCC)N1CCCN(C)CC1] | 181 | 6-bromo-2-(1-(4-methyl-1,4-diazepan-1-yl)butyl)-3-propylpyrido[2,3-d]pyrimidin-4(3H)-one | 1.92 | 436.5 | B |
| 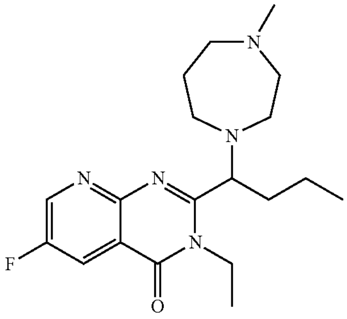 [SMILES: CCCC(c1nc2ncc(F)cc2c(=O)n1CC)N1CCCN(C)CC1] | 182 | 3-ethyl-6-fluoro-2-(1-(4-methyl-1,4-diazepan-1-yl)butyl)pyrido[2,3-d]pyridin-4(3H)-one | 1.53 | 362.2 | B |
| 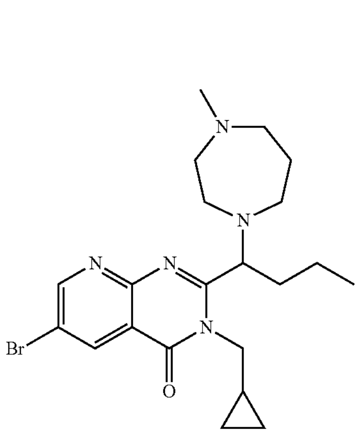 [SMILES: CCCC(c1nc2ncc(Br)cc2c(=O)n1CC1CC1)N1CCCN(C)CC1] | 183 | 6-bromo-3-(cyclopropylmethyl)-2-(1-(4-methyl-1,4-diazepan-1-yl)butyl)pyrido[2,3-d]pyrimidin-4(3H)-one | 2.02 | 448.2 | B |

-continued
| STRUCTURE | EX | CHEMICAL NAME | Rt (min) | MS (M + H) | HPLC Method |
|---|---|---|---|---|---|
| 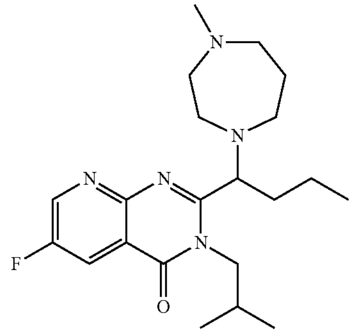 [SMILES: CCCC(c1nc2ncc(F)cc2c(=O)n1CC(C)C)N1CCCN(C)CC1] | 184 | 3-(cyclopropylmethyl)-6-fluoro-2-(1-(4-methyl-1,4-diazepan-1-yl)butyl)pyrido[2,3-d]pyrimidin-4(3H)-one | 1.75 | 388.3 | B |
| 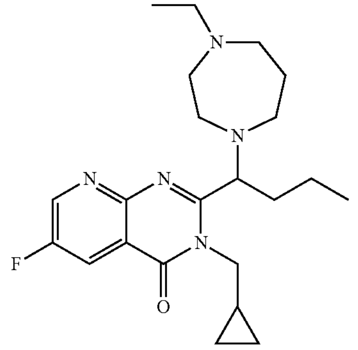 [SMILES: CCCC(c1nc2ncc(F)cc2c(=O)n1CC1CC1)N1CCCN(CC)CC1] | 185 | 3-(cyclopropylmethyl)-2-(1-(4-ethyl-1,4-diazepan-1-yl)butyl)-6-fluoropyrido[2,3-d]pyrimidin-4(3H)-one | 1.86 | 402.3 | B |
| 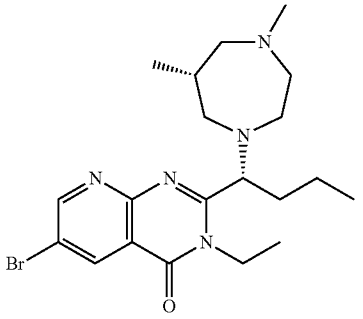 [SMILES: CCC[C@H](c1nc2ncc(Br)cc2c(=O)n1CC)N1CCN(C)C[C@@H](C)C1] | 186 | 6-bromo-2-((R)-1-((R)-4,6-dimethyl-1,4-diazepan-1-yl)butyl)-3-ethylpyrido[2,3-d]pyrimidin-4(3H)-one | 1.96 | 436.3 | B |
| 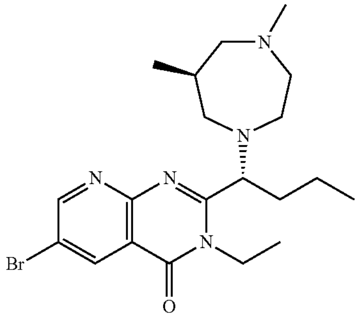 [SMILES: CCC[C@H](c1nc2ncc(Br)cc2c(=O)n1CC)N1CCN(C)C[C@H](C)C1] | 187 | 6-bromo-2-((R)-1-((S)-4,6-dimethyl-1,4-diazepan-1-yl)butyl)-3-ethylpyrido[2,3-d]pyrimidin-4(3H)-one | 1.96 | 436.2 | B |

-continued
| STRUCTURE | EX | CHEMICAL NAME | Rt (min) | MS (M + H) | HPLC Method |
|---|---|---|---|---|---|
| 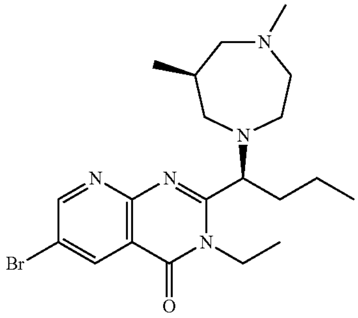 [SMILES: CCC[C@@H](c1nc2ncc(Br)cc2c(=O)n1CC)N1CCN(C)C[C@H](C)C1] | 188 | 6-bromo-2-((S)-1-((S)-4,6-dimethyl-1,4-diazepan-1-yl)butyl)-3-ethylpyrido[2,3-d]pyrimidin-4(3H)-one | 1.97 | 436.2 | B |
| 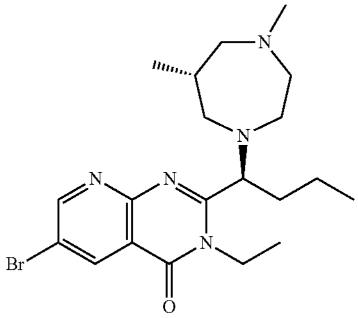 [SMILES: CCC[C@@H](c1nc2ncc(Br)cc2c(=O)n1CC)N1CCN(C)C[C@@H](C)C1] | 189 | 6-bromo-2-((S)-1-((R)-4,6-dimethyl-1,4-diazepan-1-yl)butyl)-3-ethylpyrido[2,3-d]pyrimidin-4(3H)-one | 1.97 | 436.2 | B |
| 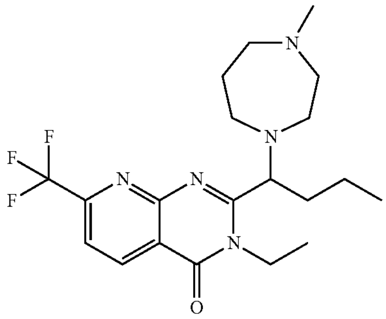 [SMILES: CCCC(c1nc2nc(C(F)(F)F)ccc2c(=O)n1CC)N1CCCN(C)CC1] | 190 | 3-ethyl-2-(1-(4-methyl-1,4-diazepan-1-yl)butyl)-7-(trifluoromethyl)pyrido[2,3-d]pyrimidin-4(3H)-one | 1.89 | 412.1 | B |
| 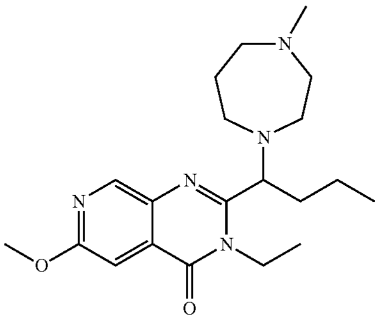 [SMILES: CCCC(c1nc2cnc(OC)cc2c(=O)n1CC)N1CCCN(C)CC1] | 191 | 3-ethyl-6-methoxy-2-(1-(4-methyl-1,4-diazepan-1-yl)butyl)pyrido[3,4-d]pyrimidin-4(3H)-one | 1.81 | 374.1 | B |

-continued

| STRUCTURE | EX | CHEMICAL NAME | Rt (min) | MS (M + H) | HPLC Method |
|---|---|---|---|---|---|
| 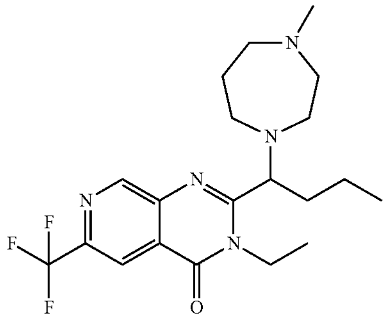 [SMILES: CCCC(c1nc2cnc(C(F)(F)F)cc2c(=O)n1CC)N1CCCN(C)CC1] | 192 | 3-ethyl-2-(1-(4-methyl-1,4-diazepan-1-yl)butyl)-6-(trifluoromethyl)pyrido[3,4-d]pyrimidin-4(3H)-one | 2.09 | 412.1 | B |
| 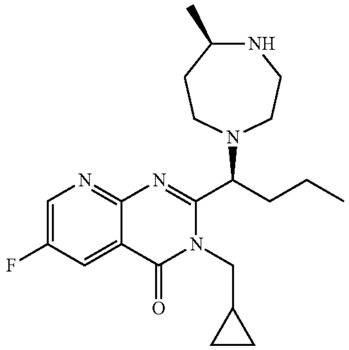 [SMILES: CCC[C@@H](c1nc2ncc(F)cc2c(=O)n1CC1CC1)N1CCN[C@H](C)CC1] | 193 | 3-(cyclopropylmethyl)-6-fluoro-2-((S)-1-((R)-5-methyl-1,4-diazepan-1-yl)butyl)pyrido[2,3-d]pyrimidin-4(3H)-one | 1.7 | 388.1 | B |
| 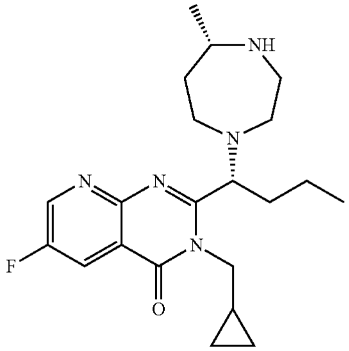 [SMILES: CCC[C@H](c1nc2ncc(F)cc2c(=O)n1CC1CC1)N1CCN[C@@H](C)CC1] | 194 | 3-(cyclopropylmethyl)-6-fluoro-2-((S)-1-((S)-5-methyl-1,4-diazepan-1-yl)butyl)pyrido[2,3-d]pyrimidin-4(3H)-one | 1.69 | 388.1 | B |
| 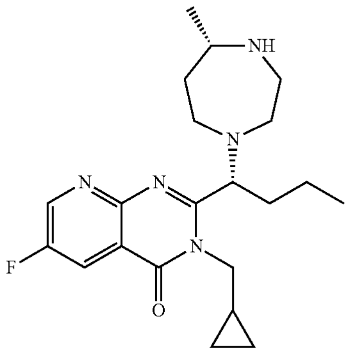 [SMILES: CCC[C@H](c1nc2ncc(F)cc2c(=O)n1CC1CC1)N1CCN[C@@H](C)CC1] | 195 | 3-(cyclopropylmethyl)-6-fluoro-2-((R)-1-((S)-5-methyl-1,4-diazepan-1-yl)butyl)pyrido[2,3-d]pyrimidin-4(3H)-one | 1.69 | 388.1 | B |

-continued

| STRUCTURE | EX | CHEMICAL NAME | Rt (min) | MS (M + H) | HPLC Method |
|---|---|---|---|---|---|
| 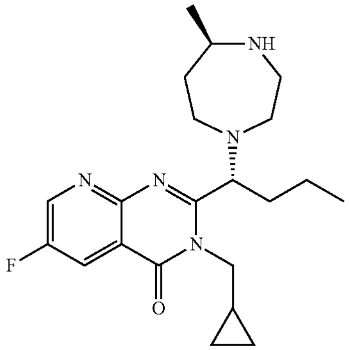 [SMILES: CCC[C@H](c1nc2ncc(F)cc2c(=O)n1CC1CC1)N1CCN[C@H](C)CC1] | 196 | 3-(cyclopropylmethyl)-6-fluoro-2-((R)-1-((R)-5-methyl-1,4-diazepan-1-yl)butyl)pyrido[2,3-d]pyrimidin-4(3H)-one | 1.68 | 388.1 | B |
| 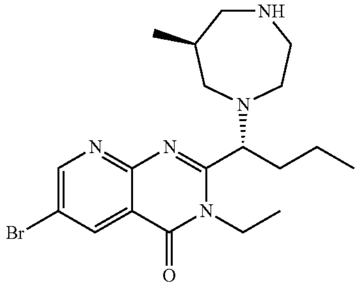 [SMILES: CCC[C@H](c1nc2ncc(Br)cc2c(=O)n1CC)N1CCNC[C@H](C)C1] | 197 | 6-bormo-3-ethyl-2-((R)-1-((S)-6-methyl-1,4-diazepan-1-yl)butyl)pyrido[2,3-d]pyrimidin-4(3H)-one | 1.72 | 422 | B |
| 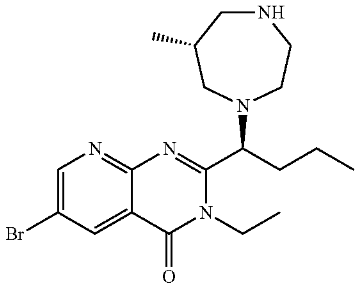 [SMILES: CCC[C@@H](c1nc2ncc(Br)cc2c(=O)n1CC)N1CCNC[C@@H](C)C1] | 198 | 6-bromo-3-ethyl-2-((S)-1-((R)-6-methyl-1,4-diazepan-1-yl)butyl)pyrido[2,3-d]pyrimidin-4(3H)-one | 1.74 | 422 | B |
| 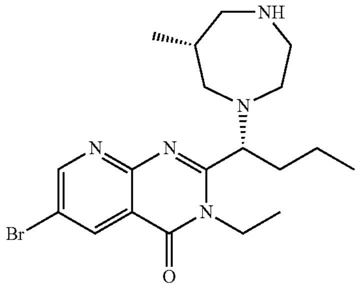 [SMILES: CCC[C@H](c1nc2ncc(Br)cc2c(=O)n1CC)N1CCNC[C@@H](C)C1] | 199 | 6-bromo-3-ethyl-2-((R)-1-((R)-6-methyl-1,4-diazepan-1-yl)butyl)pyrido[2,3-d]pyrimidin-4(3H)-one | 1.73 | 422 | B |
| 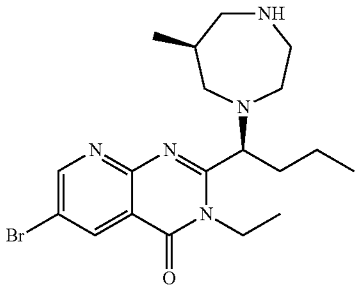 [SMILES: CCC[C@@H](c1nc2ncc(Br)cc2c(=O)n1CC)N1CCNC[C@H](C)C1] | 200 | 6-bromo-3-ethyl-2-((S)-1-((S)-6-methyl-1,4-diazepan-1-yl)butyl)pyrido[2,3-d]pyrimidin-4(3H)-one | 1.73 | 422 | B |

Examples 186, 187, 188 and 189. 6-Bromo-2-((R)-1-((R)-4,6-dimethyl-1,4-diazepan-1-yl)butyl)-3-ethylpyrido[2,3-d]pyrimidin-4(3H)-one, 6-bromo-2-((R)-1-((S)-4,6-dimethyl-1,4-diazepan-1-yl)butyl)-3-ethylpyrido[2,3-d]pyrimidin-4(3H)-one, 6-bromo-2-((S)-1-((S)-4,6-dimethyl-1,4-diazepan-1-yl)butyl)-3-ethylpyrido[2,3-d]pyrimidin-4(3H)-one and 6-bromo-2-((S)-1-((R)-4,6-dimethyl-1,4-diazepan-1-yl)butyl)-3-ethylpyrido[2,3-d]pyrimidin-4(3H)-one Examples 186, 187, 188 and 189 were directly separated using preparative HPLC: column: SunFire C18. 10 µm. 19×150 mm: temperature: 30° C.: flow rate: 14 mL/min; A: $CH_3CN$. B: 10 mM ammonium bicarbonate buffer pH 7: gradient: 8 min in 5:95+from 5:95 to 80:20 in 15 min+7 min in 80:20.

Examples 193, 194, 195 and 196. 3-(Cyclopropylmethyl)-6-fluoro-2-((S)-1-((R)-5-methyl-1,4-diazepan-1-yl)butyl) pyrido[2,3-d]pyrimidin-4(3H)-one, 3-(cyclopropylmethyl)-6-fluoro-2-((S)-1-((S)-5-methyl-1,4-diazepan-1-yl)butyl) pyrido[2,3-d]pyrimidin-4(3H)-one, 3-(cyclopropylmethyl)-6-fluoro-2-((R)-1-((S)-5-methyl-1,4-diazepan-1-yl)butyl) pyrido[2,3-d]pyrimidin-4(3H)-one and 3-(cyclopropylmethyl)-6-fluoro-2-((R)-1-((R)-5-methyl-1,4-diazepan-1-yl)butyl)pyrido[2,3-d]pyrimidin-4(3H)-one Examples 193, 194, 195 and 196 were directly separated using preparative HPLC: column; SunFire C18, 10 µm, 19×150 mm: temperature: 30° C. flow rate: 14 mL/min; A: $CH_3CN$: B: 10 mM ammonium bicarbonate buffer pH 7: gradient: 8 min in 5:95+from 5:95 to 80:20 in 15 min+7 min in 80:20.

Examples 197, 198, 199 and 200. 6-Bromo-3-ethyl-2-((R)-1-((S)-6-methyl-1,4-diazepan-1-yl)butyl) pyrido[2,3-d]pyrimidin-4(3H)-one, 6-bromo-3-ethyl-2-((S)-1-((R)-6-methyl-1,4-diazepan-111)butyl) pyrido[2,3-d]pyrimidin-4(3H)-one, 6-bromo-3-ethyl-2-((R)-1-((R)-6-methyl-1,4-diazepan-1-yl)butyl) pyrido[2,3-d]pyrimidin-4(3H)-one and 6-bromo-3-ethyl-2-((S)-1-((S)-6-methyl-1,4-diazepan-1-yl) butyl)pyrido[2,3-d]pyrimidin-4(3H)-one Examples 197, 198, 199 and 200 were directly separated using preparative HPLC: column: SunFire C18, 10 µm, 19×150 mm, temperature. 30° C. flow rate. 14 mL/min; A: $CH_3CN$: B: 10 mM ammonium bicarbonate buffer pH 7: gradient: 8 min in 5:95+from 5:95 to 80:20 in 15 min+7 min in 80:20.

Examples 201 and 202. (R)-3-Ethyl-6-fluoro-2-(1-(4-methyl-1,4-d azepan-1-yl)butyl)pyrido[2,3-d] pyrimidin-4(3H)-one and (S)-3-ethyl-6-fluoro-2-(1-(4-methyl-1,4-diazepan-1-yl)butyl)pyrido[2,3-d] pyrimidin-4(3H)-one Starting from the compound obtained in Example 182 a chiral preparative HPLC separation (column: Chiralpak AD-H, 20×250 mm, 5 µm; temperature: r.t.; eluent: n-Heptane/EtOH/$Et_2NH$ 95/510.015 v/v/v; flow rate 13 mL/min: Rt1: 11.8 min, Rt2: 14.2 min) was carried out to give the title compounds.

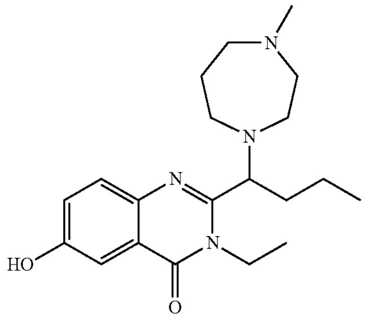 [SMILES: CCCC(c1nc2ccc(O)cc2c(=O)n1CC)N1CCCN(C)CC1]

Example 203. 3-Ethyl-6-hydroxy-2-(1-(4-methyl-1,4-diazepan-1-yl)butyl)quinazolin-4(3H)-one Step a. (3-Ethyl-2-(1-(4-methyl-1,4-diazepan-1-yl) butyl)-4-oxo-3,4-dihydroquinazolin-6-yl)boronic acid A Schlenk flask was charged with the compound obtained in Example 1 (221 mg, 0.52 mmol), bispinacol (199 mg, 0.78 mmol), KOAc (154 mg, 1.57 mmol), Pd(dppf)$FeCl_2$ (23 mg. 0.031 mmol), and it was purged and backfilled three times with argon. Dioxane (5 mL) was added under argon atmosphere and the reaction mixture was heated at 90° C. for 2 h. The reaction was allowed to cool to r.t. filtered through celite, washed with EtOAc and the solvent was removed under vacuum to give the title compound (189 mg. Yield: 27%).

Step b. Title Compound

To a solution of the compound obtained in step a (36 mg, 0.09 mmol) in THF:$H_2O$ (1 mL: 0.5 mL), sodium perborate (26 mg, 0.032 mmol) was added and the reaction was stirred at r.t. overnight. The mixture was diluted with EtOAc and extracted twice with EtOAc. The combined organic layer was washed with brine, dried over anh $Na_2SO_4$, filtered and the solvent was removed under vacuum. The crude product was purified by flash chromatography, silica gel, gradient DCM to DCM:MeOH (9:1) to give the title compound (4 mg, Yield: 10%).

HPLC-MS (B) Rt, 1.57 min; ESI+-MS m/z: 359.4 (M+1).

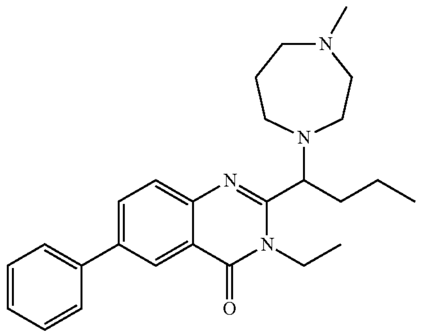 [SMILES: CCCC(c1nc2ccc(-c3ccccc3)cc2c(=O)n1CC)N1CCCN(C)CC1]

Example 204. 3-Ethyl-2-(1-(4-methyl-1,4-diazepan-1-yl)butyl)-6-phenylquinazolin-4(3H)-one To a microwave vial charged with the compound obtained in Example 1 (64 mg, 0.15 mmol), phenylboronic acid (30 mg, 0.25 mmol), $K_2CO_3$ (35 mg, 0.25 mmol), $Pd(PPh_3)_4$ (8 mg, 0.07 mmol) and a mixture of DME:$H_2O$ (3 mL. 1:1) were added and the reaction mixture was heated under MW irradiation (150 W) at 130° C. for 20 min. $NaHCO_3$ was added and the product was extracted with EtOAc. The combined organic layers were dried over anh $Na_2SO_4$, filtered and concentrated to dryness. The crude product was purified by flash chromatography, silica gel, gradient DCM to DCM:MeOH (90:10) to give the title compound (13 mg, Yield: 17%).

HPLC-MS (B) Rt. 2.23 mini ESI+-MS m/z: 419.3 (M+1).

This method was used for the preparation of example 205 using suitable starting materials:

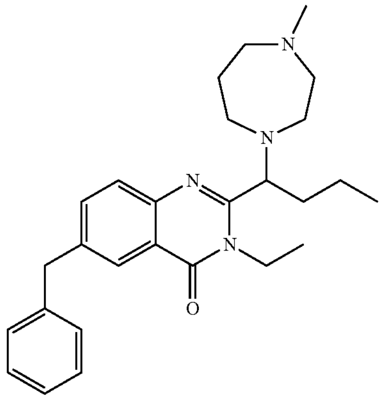

| STRUCTURE | EX | CHEMICAL NAME | Rt (min) | MS (M + H) | HPLC Method |
|---|---|---|---|---|---|
| 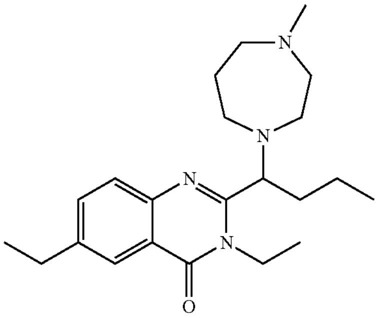 [SMILES: CCCC(c1nc2ccc(CC)cc2c(=O)n1CC)N1CCCN(C)CC1] | 205 | 3,6-diethyl-2-(1-(4-methyl-1,4-diazepan-1-yl)butyl)quinazolin-4(3H)-one | 2.23 | 371.2 | B |

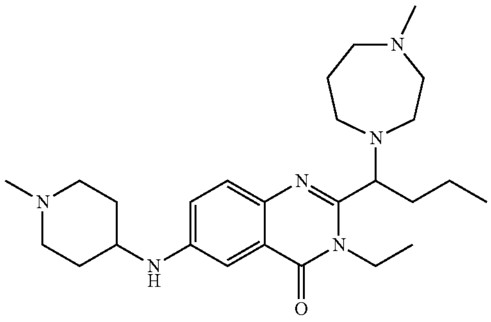 [SMILES: CCCC(c1nc2ccc(NC3CCN(C)CC3)cc2c(=O)n1CC)N1CCCN(C)CC1]

Example 206. 3-Ethyl-2-(1-(4-methyl-1,4-diazepan-1-yl)butyl)-6-((1-methylpiperidin-4-yl)amino)quinazolin-4(3H)-one A Schlenk flask was charged with the product obtained in Example 1 (75 mg, 0.2 mmol). DavePhos (10 mg, 0.3 mmol), $Pd_2dba_{si}$ (16 mg, 0.02 mmol) and NaO$^t$Bu (68 mg, 0.7 mmol) were added and the mixture was evacuated and backfilled with argon. Dioxane (2 mL), degassed by means of bubbling argon to the solution for 5 min, and 1-methylpiperidin-4-amine (44 µL, 0.3 mmol) were added and the reaction mixture was heated at 100° C. overnight. The suspension was filtered through celite, washed with EtOAc and the solvent was removed under vacuum. The crude product was purified by flash chromatography, silica gel, gradient DCM to MeOH (100%) to give the title compound (22 mg, Yield: 25%).

HPLC-MS (B) Rt, 1.58 min; ESI+-MS m/z: 455.4 (M+1).

Example 207. 6-Benzyl-3-ethyl-2-(1-(4-methyl-1,4-diazepan-1-yl)butyl)quinazolin-4(3H)-one A Schlenk flask was charged with the product obtained in Example 1 (50 mg, 0.1 mmol). CsF (36 mg, 0.2 mmol). $K_2CO_3$ (50, 0.4 mmol), Pd(ddppf)$Cl_2$ (19 mg, 0.02 mmol) were added and the mixture was evacuated and backfilled with argon. Dioxane (2 mL), degassed by means of bubbling argon to the solution for 5 min, and 2-benzyl-4,4,5,5-tetramethyl-1,3,2-dioxaborolane (31 mg, 14 mmol) were added and the reaction mixture was heated at 80° C. overnight. Water was added and the product was extracted with EtOAc. The combined organic layers were dried over anh $Na_2SO_4$, filtered and concentrated to dryness. The crude product was purified by flash chromatography. $Al_2O_3$, gradient Chx to Chx:EtOAc (4:1) to give the title compound (14 mg, Yield: 28%). HPLC-MS (B) Rt. 2.5 min: ESI+-MS m/z: 433.3 (M+1).

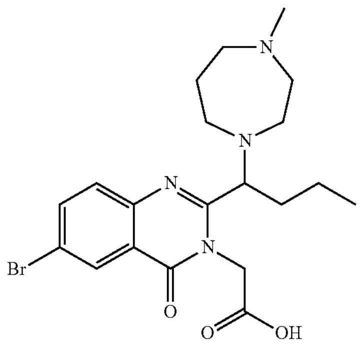 [SMILES: CCCC(c1nc2ccc(Br)cc2c(=O)n1CC(=O)O)N1CCCN(C)CC1]

Example 208. 2-(6-Bromo-2-(1-(4-methyl-1,4-diazepan-1-yl)butyl)-4-oxoquinazolin-3(4H)-yl)acetic acid To a solution of ethyl 2-(6-bromo-2-(1-(4-methyl-1,4-diazepan-1-yl)butyl)-4-oxoquinazolin-3(4H)-yl)acetate (obtained following the procedure described in example 1, 127 mg, 0.273 mmol) in MeOH (5 mL). 1.1011 (20 mg. 0.819 mmol) was added at 0° C. The reaction was allowed to reach r.t. and was stirred at this temperature overnight. The solvent was removed under vacuum and the title compound was obtained by eluting it through an SCX column using 2 N $NH_3$ in MeOH to give the title compound (42 mg, Yield: 34%).

HPLC-MS (8) Rt, 1.58 min; ESI+-MS m/z: 451.2 (M+1).

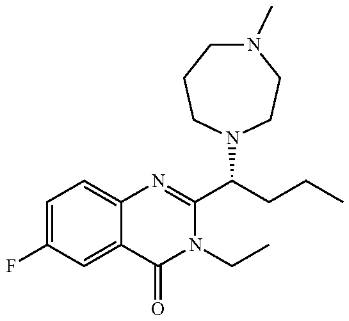 [SMILES: CCC[C@H](c1nc2ccc(F)cc2c(=O)n1CC)N1CCCN(C)CC1]

Example 209. (R)-3-Ethyl-6-fluoro-2-(1-(4-methyl-1,4-diazepan-1-yl)butyl)quinazolin-4(3H)-one Step a. 2-Amino-N-ethyl-5-fluorobenzamide Starting from 2-amino-5-fluorobenzoic acid (4 g, 26.3 mmol) and following the procedure described in step a of example 1 the title compound was obtained (4.9 g. Yield: 99%).

Step b. (S)—N-Ethyl-5-fluoro-2-(2-hydroxypentanamido)benzamide

Starting from compound obtained in step a (4.9 g, 26.3 mmol) and following the procedure described in step b of example 1 the title compound was obtained (7.77 g. Yield: 99%), Step c. (S)-3-Ethyl-6-fluoro-2-(1-((trimethylsilyl)oxy)butyl)quinazolin-4(3H)-one To a solution of the compound obtained in step b (7.77 g. 27.3 mmol) in anh DCM (70 mL), iodine (13.8 g, 54 mmol) was added portion wise and the mixture was stirred until complete dissolution of iodine. HMDS (22 mL, 109 mmol) was then added and the reaction mixture was stirred at r.t. overnight. The mixture was diluted with DCM, washed with sat sot $Na_2S_2O_3$ and brine. The organic layer was dried over anh $Na_2SO_4$, filtered and concentrated under reduced vacuum to give the title compound (7 g, Yield: 89%).

Step d. (S)-6-Chloro-2-(1-hydroxybutyl)-3-methylquinazolin-4(3H)-one

To a solution of the compound obtained in step c (7.7 g. 22.8 mmol) in anh THF (125 mL), TBAF (1 M in THF, 25 mL, 25 mmol) was added and the reaction mixture was stirred for 30 min at 0° C. The mixture was diluted with EtOAc and washed with $H_2O$ and sat NaCl sol. The organic layer was dried over anh $Na_2SO_4$, filtered and concentrated under vacuum. The crude product was purified by flash chromatography, silica gel, gradient Chx to EtOAc to give the title compound (3.1 g, Yield: 52%).

Step e. Title Compound

To a solution of the compound obtained in step d (50 mg, 0.2 mmol) in anh DCM (3 mL) at −78° C., 2,6-lutidine (87 μL, 0.7 mmol) and triflate anhydride (1 M in DCM, 0.24 mL, 0.24 mmol) were added and the mixture was stirred at −78° C. for 2 h. A solution of 1-methyl-1,4-diazepane (86 mg. 0.75 mmol) in DMF:DCM (1:1, 0.6 mL) was added and the mixture was allowed to reach r.t. during 4 h. $NaHCO_3$ was added and the product was extracted with EtOAc. The combined organic layers were washed with brine, dried over anh $Na_2SO_4$, filtered and concentrated under reduced vacuum. The crude product was purified by flash chromatography, silica gel, gradient DCM to MeOH to give the title compound (27 mg, Yield: 70%).

HPLC-MS (B) Rt. 1.96 min; ESI+-MS m/z: 361.3 (M+1).

This method was used for the preparation of examples 210-265 using suitable starting materials:

| STRUCTURE | EX | CHEMICAL NAME | Rt (min) | MS (M + H) | HPLC Method |
|---|---|---|---|---|---|
| 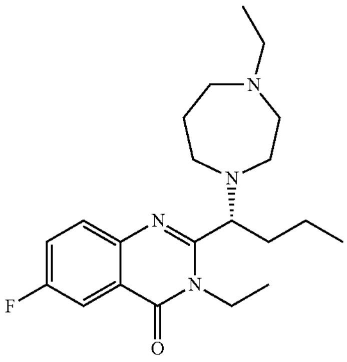 [SMILES: CCC[C@H](c1nc2ccc(F)cc2c(=O)n1CC)N1CCCN(CC)CC1] | 210 | (R)-3-ethyl-2-(1-(4-ethyl-1,4-diazepan-1-yl)butyl)-6-fluoroquinazolin-4(3H)-one | 2.03 | 375.2 | B |

-continued
| STRUCTURE | EX | CHEMICAL NAME | Rt (min) | MS (M + H) | HPLC Method |
|---|---|---|---|---|---|
| 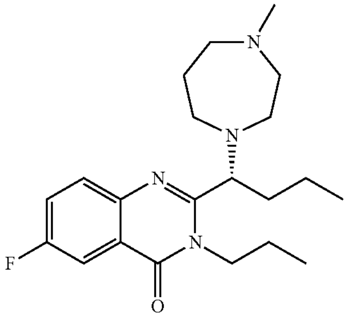 [SMILES: CCC[C@H](c1nc2ccc(F)cc2c(=O)n1CCC)N1CCCN(C)CC1] | 211 | (R)-6-fluoro-2-(1-(4-methyl-1,4-diazepan-1-yl)butyl)-3-propylquinazolin-4(3H)-one | 2.21 | 375.2 | B |
| 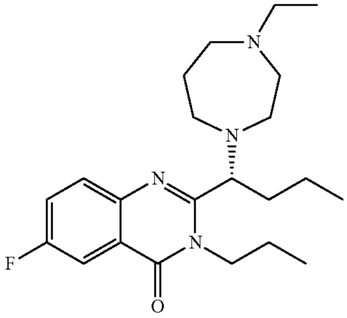 [SMILES: CCC[C@H](c1nc2ccc(F)cc2c(=O)n1CCC)N1CCCN(CC)CC1] | 212 | (R)-2-(1-(4-ethyl-1,4-diazepan-1-yl)butyl)-6-fluoro-3-propylquinazolin-4(3H)-one | 2.27 | 389.3 | B |
| 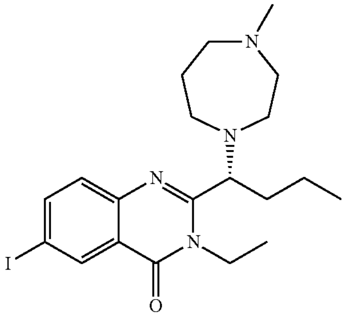 [SMILES: CCC[C@H](c1nc2ccc(I)cc2c(=O)n1CC)N1CCCN(C)CC1] | 213 | (R)-3-ethyl-6-iodo-2-(1-(4-methyl-1,4-diazepan-1-yl)butyl)quinazolin-4(3H)-one | 2.4 | 469.2 | B |
| 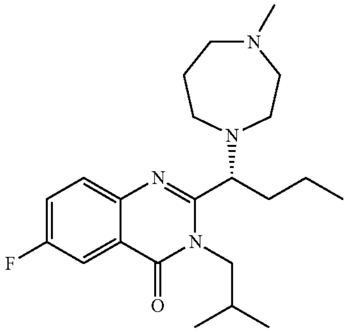 [SMILES: CCC[C@H](c1nc2ccc(F)cc2c(=O)n1CC(C)C)N1CCCN(C)CC1] | 214 | (R)-6-fluoro-3-isobutyl-2-(1-(4-methyl-1,4-diazepan-1-yl)butyl)quinazolin-4(3H)-one | 2.41 | 389.2 | B |

-continued
| STRUCTURE | EX | CHEMICAL NAME | Rt (min) | MS (M + H) | HPLC Method |
|---|---|---|---|---|---|
| 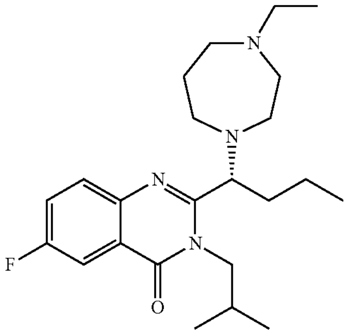 [SMILES: CCC[C@H](c1nc2ccc(F)cc2c(=O)n1CC(C)C)N1CCCN(CC)CC1] | 215 | (R)-2-(1-(4-ethyl-1,4-diazepan-1-yl)butyl)-6-fluoro-3-isobutylquinazolin-4(3H)-one | 2.49 | 403.3 | B |
| 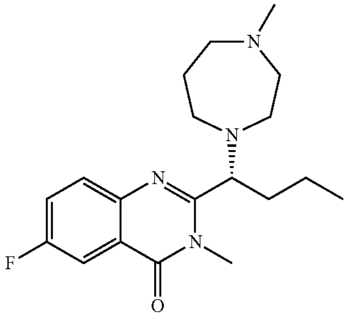 [SMILES: CCC[C@H](c1nc2ccc(F)cc2c(=O)n1C)N1CCCN(C)CC1] | 216 | (R)-6-fluoro-3-methyl-2-(1-(4-methyl-1,4-diazepan-1-yl)butyl)quinazolin-4(3H)-one | 1.91 | 347.1 | B |
| 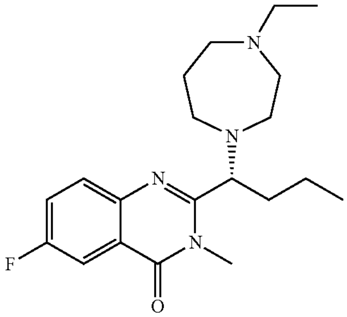 [SMILES: CCC[C@H](c1nc2ccc(F)cc2c(=O)n1C)N1CCCN(CC)CC1] | 217 | (R)-2-(1-(4-ethyl-1,4-diazepan-1-yl)butyl)-6-fluoro-3-methylquinazolin-4(3H)-one | 1.96 | 361.2 | B |
| 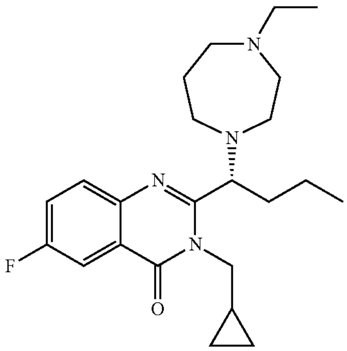 [SMILES: CCC[C@H](c1nc2ccc(F)cc2c(=O)n1CC1CC1)N1CCCN(CC)CC1] | 218 | (R)-3-(cyclopropylmethyl)-2-(1-(4-ethyl-1,4-diazepan-1-yl)butyl)-6-fluoroquinazolin-4(3H)-one | 2.05 | 381.2 | B |

-continued
| STRUCTURE | EX | CHEMICAL NAME | Rt (min) | MS (M + H) | HPLC Method |
|---|---|---|---|---|---|
| 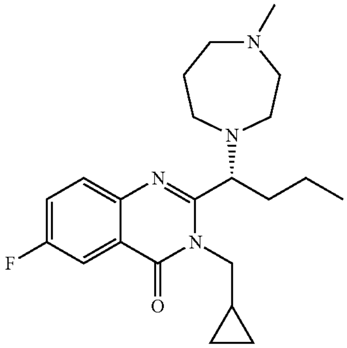 [SMILES: CCC[C@H](c1nc2ccc(F)cc2c(=O)n1CC1CC1)N1CCCN(C)CC1] | 219 | (R)-3-(cyclopropylmethyl)-6-fluoro-2-(1-(4-methyl-1,4-diazepan-1-yl)butyl)quinazolin-4(3H)-one | 2.2 | 387.2 | B |
| 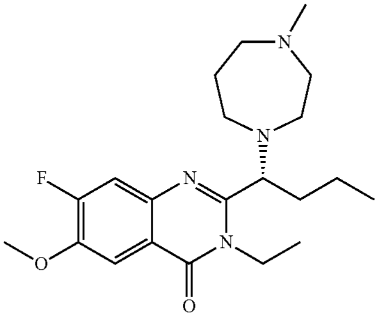 [SMILES: CCC[C@H](c1nc2cc(F)c(OC)cc2c(=O)n1CC)N1CCCN(C)CC1] | 220 | (R)-3-ethyl-7-fluoro-6-methoxy-2-(1-(4-methyl-1,4-diazepan-1-yl)butyl)quinazolin-4(3H)-one | 1.90 | 391.2 | B |
| 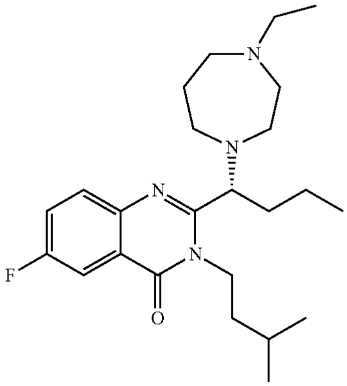 [SMILES: CCC[C@H](c1nc2ccc(F)cc2c(=O)n1CCC(C)C)N1CCCN(CC)CC1] | 221 | (R)-2-(1-(4-ethyl-1,4-diazepan-1-yl)butyl)-6-fluoro-3-isopentylquinazolin-4(3H)-one | 2.59 | 417.3 | B |
| 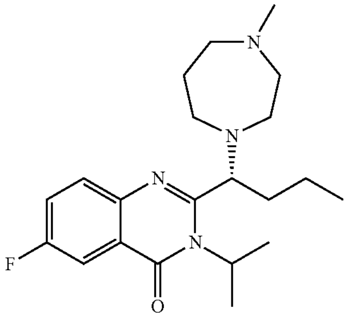 [SMILES: CCC[C@H](c1nc2ccc(F)cc2c(=O)n1C(C)C)N1CCCN(C)CC1] | 222 | (R)-6-fluoro-3-isopropyl-2-(1-(4-methyl-1,4-diazepan-1-yl)butyl)quinazolin-4(3H)-one | 2.27 | 375.2 | B |

-continued
| STRUCTURE | EX | CHEMICAL NAME | Rt (min) | MS (M + H) | HPLC Method |
|---|---|---|---|---|---|
| 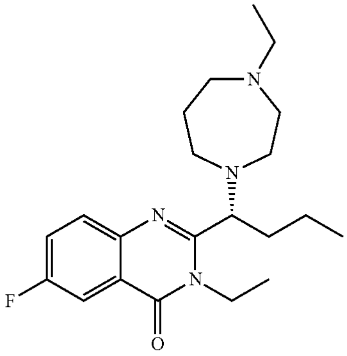 [SMILES: CCC[C@H](c1nc2ccc(F)cc2c(=O)n1CC)N1CCCN(CC)CC1] | 223 | (R)-2-(1-(4-ethyl-1,4-diazepan-1-yl)butyl)-6-fluoro-3-isopropylquinazolin-4(3H)-one | 2.31 | 389.3 | B |
| 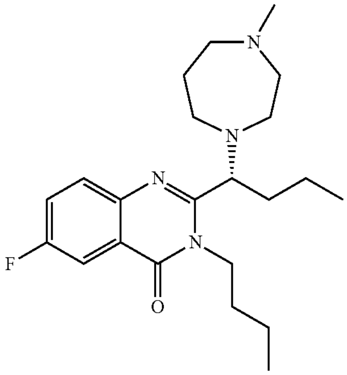 [SMILES: CCCCn1c([C@@H](CCC)N2CCCN(C)CC2)nc2ccc(F)cc2c1=O] | 224 | (R)-3-butyl-6-fluoro-2-(1-(4-methyl-1,4-diazepan-1-yl)butyl)quinazolin-4(3H)-one | 2.39 | 389.3 | B |
| 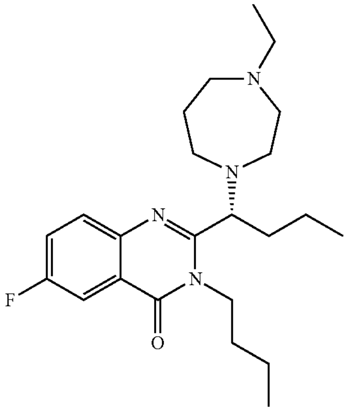 [SMILES: CCCCn1c([C@@H](CCC)N2CCCN(CC)CC2)nc2ccc(F)cc2c1=O] | 225 | (R)-3-butyl-2-(1-(4-ethyl-1,4-diazepan-1-yl)butyl)-6-fluoroquinazolin-4(3H)-one | 2.41 | 403.3 | B |
| 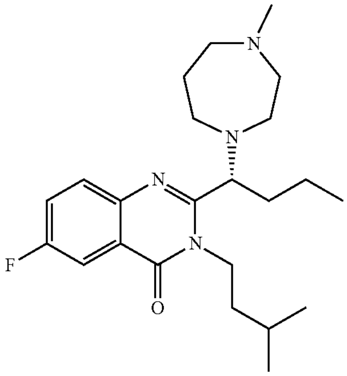 [SMILES: CCC[C@H](c1nc2ccc(F)cc2c(=O)n1CCC(C)C)N1CCCN(C)CC1] | 226 | (R)-6-fluoro-3-isopentyl-2-(1-(4-methyl-1,4-diazepan-1-yl)butyl)quinazolin-4(3H)-one | 2.51 | 403.3 | B |

-continued
| STRUCTURE | EX | CHEMICAL NAME | Rt (min) | MS (M + H) | HPLC Method |
|---|---|---|---|---|---|
| 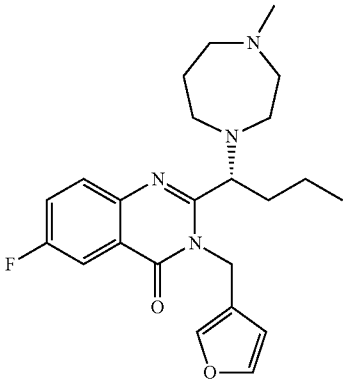 [SMILES: CCC[C@H](c1nc2ccc(F)cc2c(=O)n1Cc1ccoc1)N1CCCN(C)CC1] | 227 | ((R)-6-fluoro-3-(furan-3-ylmethyl)-2-(1-(4-methyl-1,4-diazepan-1-yl)butyl)quinazolin-4(3H)-one | 2.17 | 413.2 | B |
| 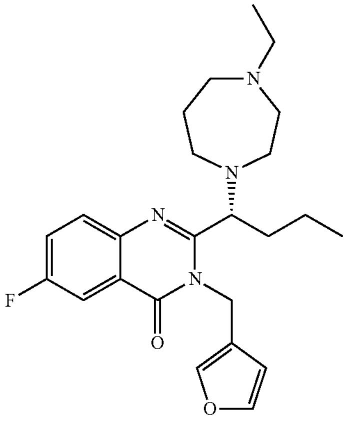 [SMILES: CCC[C@H](c1nc2ccc(F)cc2c(=O)n1Cc1ccoc1)N1CCCN(CC)CC1] | 228 | (R)-2-(1-(4-ethyl-1,4-diazepan-1-yl)butyl)-6-fluoro-3-(furan-3-ylmethyl)quinazolin-4(3H)-one | 2.2 | 427.3 | B |
| 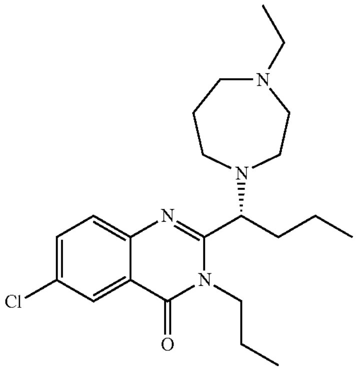 [SMILES: CCC[C@H](c1nc2ccc(Cl)cc2c(=O)n1CCC)N1CCCN(CC)CC1] | 229 | (R)-2-(1-(4-ethyl-1,4-diazepan-1-yl)butyl)-6-fluoro-3-propylquinazolin-4(3H)-one | 2.41 | 405.3 | B |
| 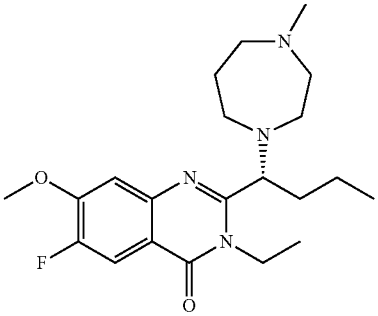 [SMILES: CCC[C@H](c1nc2cc(OC)c(F)cc2c(=O)n1CC)N1CCCN(C)CC1] | 230 | (R)-3-ethyl-6-fluoro-7-methoxy-2-(1-(4-methyl-1,4-diazepan-1-yl)butyl)quinazolin-4(3H)-one | 1.91 | 391.3 | B |

-continued
| STRUCTURE | EX | CHEMICAL NAME | Rt (min) | MS (M + H) | HPLC Method |
|---|---|---|---|---|---|
| 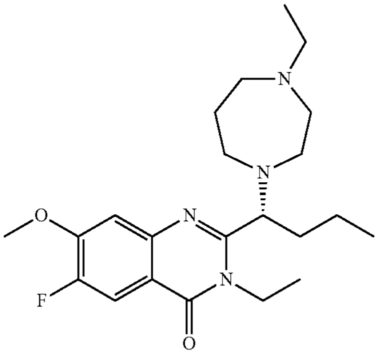 [SMILES: CCC[C@H](c1nc2cc(OC)c(F)cc2c(=O)n1CC)N1CCCN(CC)CC1] | 231 | (R)-3-ethyl-2-(1-(4-ethyl-1,4-diazepan-1-yl)butyl)-6-fluoro-7-methoxyquinazolin-4(3H)-one | 1.94 | 405.3 | B |
| 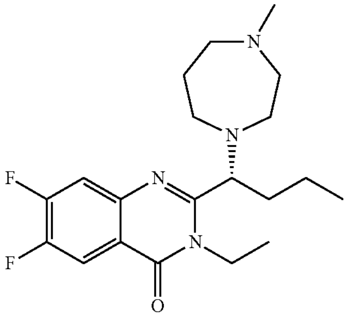 [SMILES: CCC[C@H](c1nc2cc(F)c(F)cc2c(=O)n1CC)N1CCCN(C)CC1] | 232 | (R)-3-ethyl-6,7-difluoro-2-(1-(4-methyl-1,4-diazepan-1-yl)butyl)quinazolin-4(3H)-one | 2.14 | 379.2 | B |
| 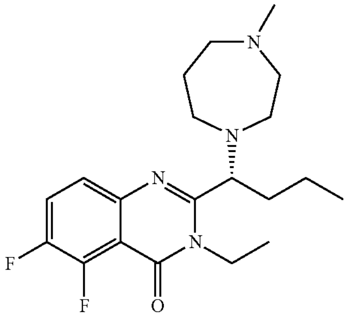 [SMILES: CCC[C@H](c1nc2ccc(F)c(F)c2c(=O)n1CC)N1CCCN(C)CC1] | 233 | (R)-3-ethyl-5,6-difluoro-2-(1-(4-methyl-1,4-diazepan-1-yl)butyl)quinazolin-4(3H)-one | 1.99 | 379.2 | B |
| 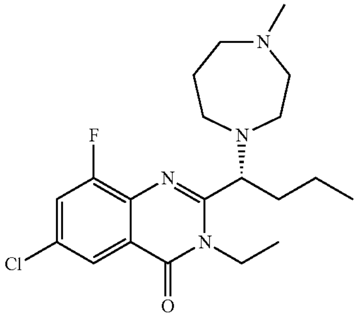 [SMILES: CCC[C@H](c1nc2c(F)cc(Cl)cc2c(=O)n1CC)N1CCCN(C)CC1] | 234 | (R)-6-chloro-3-ethyl-8-fluoro-2-(1-(4-methyl-1,4-diazepan-1-yl)butyl)quinazolin-4(3H)-one | 2.27 | 395.2 | B |

-continued
| STRUCTURE | EX | CHEMICAL NAME | Rt (min) | MS (M + H) | HPLC Method |
|---|---|---|---|---|---|
| 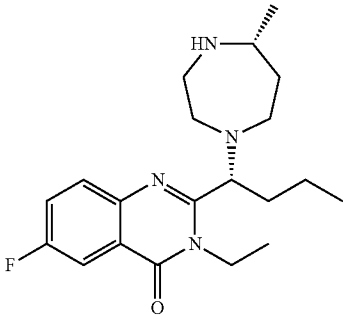 [SMILES: CCC[C@H](c1nc2ccc(F)cc2c(=O)n1CC)N1CCN[C@H](C)CC1] | 235 | 3-ethyl-6-fluoro-2-((R)-1-((R)-5-methyl-1,4-diazepan-1-yl)butyl)quinazolin-4(3H)-one | 1.9 | 361.2 | F |
| 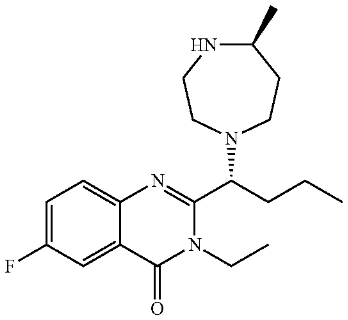 [SMILES: CCC[C@H](c1nc2ccc(F)cc2c(=O)n1CC)N1CCN[C@@H](C)CC1] | 236 | 3-ethyl-6-fluoro-2-((R)-1-((S)-5-methyl-1,4-diazepan-1-yl)butyl)quinazolin-4(3H)-one | 1.87 | 361.2 | F |
| 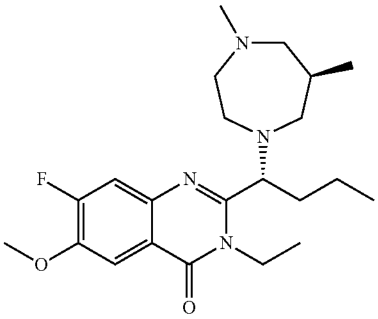 [SMILES: CCC[C@H](c1nc2cc(F)c(OC)cc2c(=O)n1CC)N1CCN(C)C[C@@H](C)C1] | 237 | 2-((R)-1-((R)-4,6-dimethyl-1,4-diazepan-1-yl)butyl)-3-ethyl-7-fluoro-6-methoxyquinazolin-4(3H)-one | 2.2 | 405.2 | F |
| 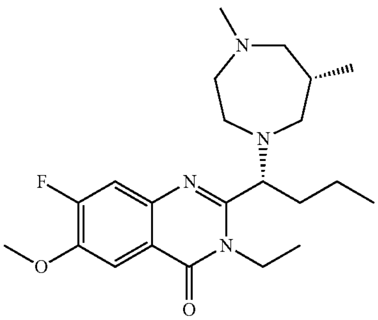 [SMILES: CCC[C@H](c1nc2cc(F)c(OC)cc2c(=O)n1CC)N1CCN(C)C[C@H](C)C1] | 238 | 2-((R)-1-((S)-4,6-dimethyl-1,4-diazepan-1-yl)butyl)-3-ethyl-7-fluoro-6-methoxyquinazolin-4(3H)-one | 2.21 | 405.4 | F |

-continued
| STRUCTURE | EX | CHEMICAL NAME | Rt (min) | MS (M + H) | HPLC Method |
|---|---|---|---|---|---|
| 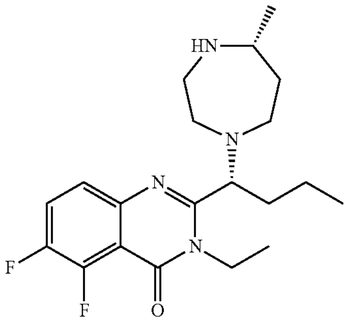 [SMILES: CCC[C@H](c1nc2ccc(F)c(F)c2c(=O)n1CC)N1CCN[C@H](C)CC1] | 239 | 3-ethyl-5,6-difluoro-2-((R)-1-((R)-5-methyl-1,4-diazepan-1-yl)butyl)quinazolin-4(3H)-one | 1.95 | 379.3 | B |
| 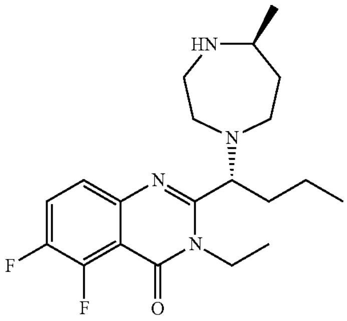 [SMILES: CCC[C@H](c1nc2ccc(F)c(F)c2c(=O)n1CC)N1CCN[C@@H](C)CC1] | 240 | 3-ethyl-5,6-difluoro-2-((R)-1-((S)-5-methyl-1,4-diazepan-1-yl)butyl)quinazolin-4(3H)-one | 1.92 | 379.2 | B |
| 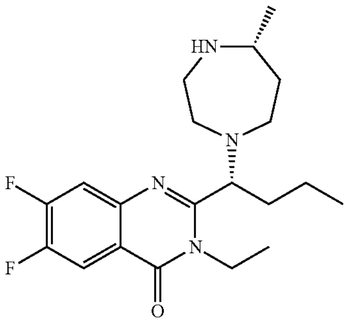 [SMILES: CCC[C@H](c1nc2cc(F)c(F)cc2c(=O)n1CC)N1CCN[C@H](C)CC1] | 241 | 3-ethyl-6,7-difluoro-2-((R)-1-((R)-5-methyl-1,4-diazepan-1-yl)butyl)quinazolin-4(3H)-one | 2.08 | 379.3 | B |
| 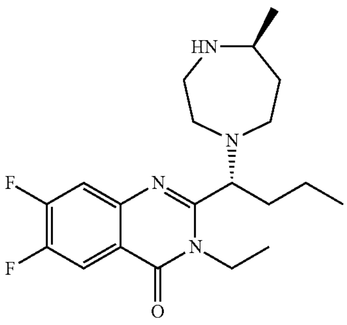 [SMILES: CCC[C@H](c1nc2cc(F)c(F)cc2c(=O)n1CC)N1CCN[C@@H](C)CC1] | 242 | 3-ethyl-6,7-difluoro-2-((R)-1-((S)-5-methyl-1,4-diazepan-1-yl)butyl)quinazolin-4(3H)-one | 2.05 | 379.3 | B |

-continued

| STRUCTURE | EX | CHEMICAL NAME | Rt (min) | MS (M + H) | HPLC Method |
|---|---|---|---|---|---|
| 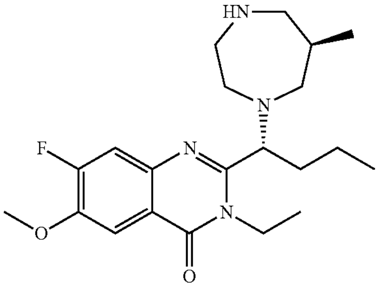 [SMILES: CCC[C@H](c1nc2cc(F)c(OC)cc2c(=O)n1CC)N1CCNC[C@@H](C)C1] | 243 | 3-ethyl-7-fluroo-6-methoxy-2-((R)-1-((R)-6-methyl-1,4-diazepan-1-yl)butyl)quinazolin-4(3H)-one | 2.0 | 391.2 | F |
| 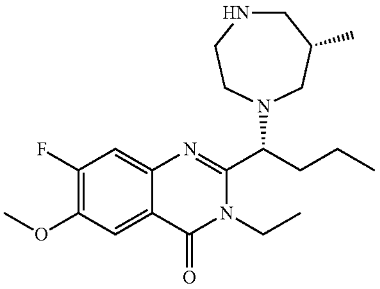 [SMILES: CCC[C@H](c1nc2cc(F)c(OC)cc2c(=O)n1CC)N1CCNC[C@H](C)C1] | 244 | 3-ethyl-7-fluoro-6-methoxy-2-((R)-1-((S)-6-methyl-1,4-diazepan-1-yl)butyl)quinazolin-4(3H)-one | 2.0 | 391.2 | F |
| 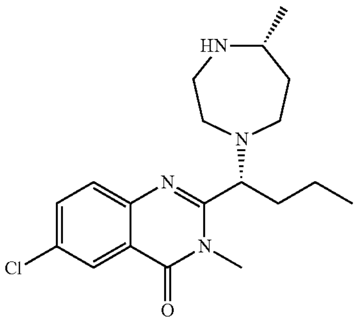 [SMILES: CCC[C@H](c1nc2ccc(Cl)cc2c(=O)n1C)N1CCN[C@H](C)CC1] | 245 | 6-chloro-3-methyl-2-((R)-1-((R)-5-methyl-1,4-diazepan-1-yl)butyl)quinazolin-4(3H)-one | 1.9 | 363 | B |
| 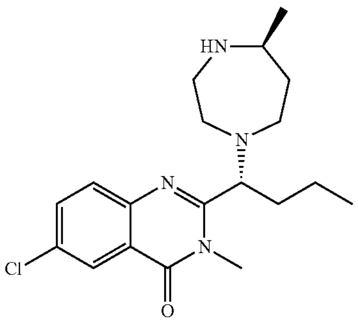 [SMILES: CCC[C@H](c1nc2ccc(Cl)cc2c(=O)n1C)N1CCN[C@@H](C)CC1] | 246 | 6-chloro-3-methyl-2-((R)-1-((S)-5-methyl-1,4-diazepan-1-yl)butyl)quinazolin-4(3H)-one | 1.87 | 363 | B |
| 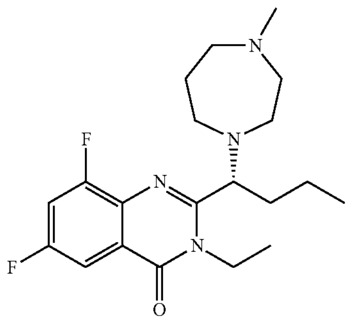 [SMILES: CCC[C@H](c1nc2c(F)cc(F)cc2c(=O)n1CC)N1CCCN(C)CC1] | 247 | (R)-3-ethyl-6,8-difluoro-2-(1-(4-methyl-1,4-diazepan-1-yl)butyl)quinazolin-4(3H)-one | 2.12 | 379.1 | B |

-continued
| STRUCTURE | EX | CHEMICAL NAME | Rt (min) | MS (M + H) | HPLC Method |
|---|---|---|---|---|---|
| 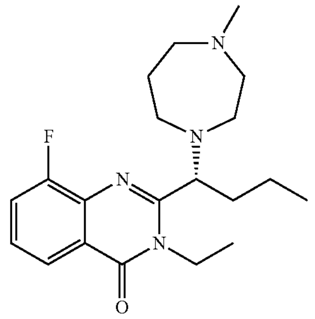 [SMILES: CCC[C@H](c1nc2c(F)cccc2c(=O)n1CC)N1CCCN(C)CC1] | 248 | (R)-3-ethyl-8-fluoro-2-(1-(4-methyl-1,4-diazepan-1-yl)butyl)quinazolin-4(3H)-one | 1.92 | 361.1 | B |
| 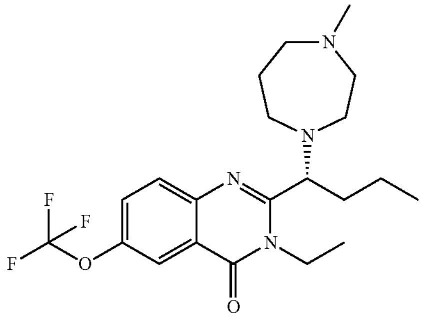 [SMILES: CCC[C@H](c1nc2ccc(OC(F)(F)F)cc2c(=O)n1CC)N1CCCN(C)CC1] | 249 | (R)-3-ethyl-2-(1-(4-methyl-1,4-diazepan-1-yl)butyl)-6-(trifluoromethoxy)quinazolin-4(3H)-one | 2.37 | 427.1 | B |
| 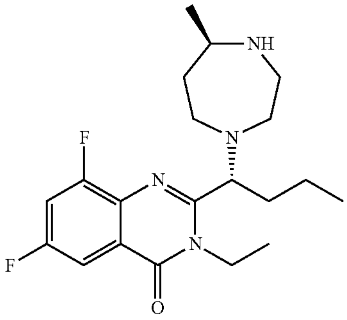 [SMILES: CCC[C@H](c1nc2c(F)cc(F)cc2c(=O)n1CC)N1CCN[C@H](C)CC1] | 250 | 3-ethyl-6,8-difluoro-2-((R)-1-((R)-5-methyl-1,4-diazepan-1-yl)butyl)quinazolin-4(3H)-one | 1.9 | 379.1 | B |
| 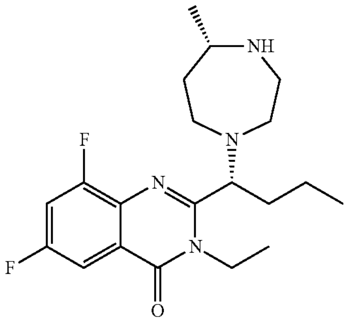 [SMILES: CCC[C@H](c1nc2c(F)cc(F)cc2c(=O)n1CC)N1CCN[C@@H](C)CC1] | 251 | 3-ethyl-6,8-difluoro-2-((R)-1-((S)-5-methyl-1,4-diazepan-1-yl)butyl)quinazolin-4(3H)-one | 1.88 | 379.1 | B |

-continued

| STRUCTURE | EX | CHEMICAL NAME | Rt (min) | MS (M + H) | HPLC Method |
|---|---|---|---|---|---|
| 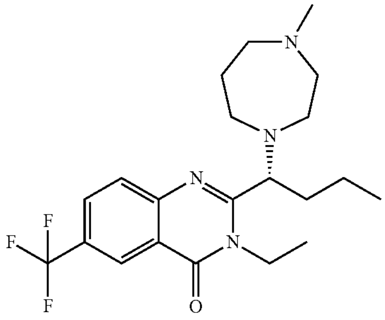 [SMILES: CCC[C@H](c1nc2ccc(C(F)(F)F)cc2c(=O)n1CC)N1CCCN(C)CC1] | 252 | (R)-3-ethyl-2-(1-(4-methyl-1,4-diazepan-1-yl)butyl)-6-(trifluoromethyl)quinazolin-4(3H)-one | 2.34 | 411.2 | F |
| 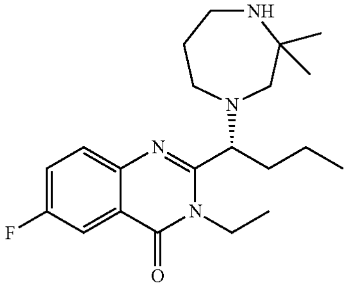 [SMILES: CCC[C@H](c1nc2ccc(F)cc2c(=O)n1CC)N1CCCNC(C)(C)C1] | 253 | (R)-2-(1-(3,3-dimethyl-1,4-diazepan-1-yl)butyl)-3-ethyl-6-fluoroquinolin-4(3H)-one | 2.05 | 375.2 | F |
| 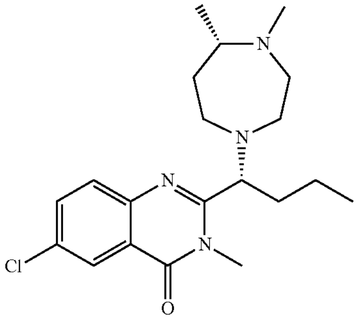 [SMILES: CCC[C@H](c1nc2ccc(Cl)cc2c(=O)n1C)N1CC[C@H](C)N(C)CC1] | 254 | 6-chloro-2-((R)-1-((S)-4,5-dimethyl-1,4-diazepan-1-yl)butyl)-3-methylquinazolin-4(3H)-one | 2.04 | 377.2 | F |
| 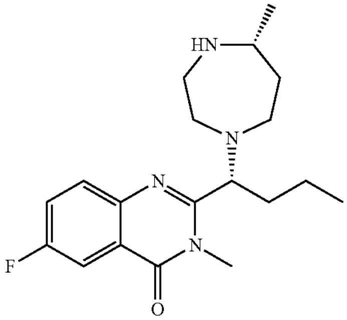 [SMILES: CCC[C@H](c1nc2ccc(F)cc2c(=O)n1C)N1CCN[C@H](C)CC1] | 255 | 6-fluoro-3-methyl-2-((R)-1-((R)-5-methyl-1,4-diazepan-1-yl)butyl)quinazolin-4(3H)-one | 1.72 | 347.2 | F |
| 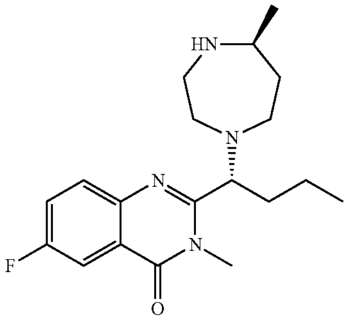 [SMILES: CCC[C@H](c1nc2ccc(F)cc2c(=O)n1C)N1CCN[C@@H](C)CC1] | 256 | 6-fluoro-3-methyl-2-((R)-1-((S)-5-methyl-1,4-diazepan-1-yl)butyl)quinazolin-4(3H)-one | 1.7 | 347.2 | F |

-continued

| STRUCTURE | EX | CHEMICAL NAME | Rt (min) | MS (M + H) | HPLC Method |
|---|---|---|---|---|---|
| 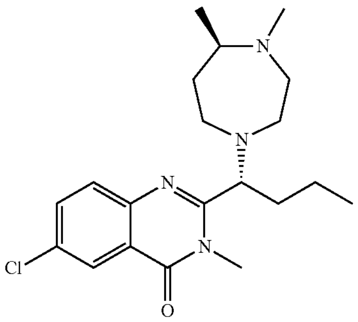 [SMILES: CCC[C@H](c1nc2ccc(Cl)cc2c(=O)n1C)N1CC[C@@H](C)N(C)CC1] | 257 | 6-chloro-2-((R)-1-((R)-4,5-dimethyl-1,4-diazepan-1-yl)butyl)-3-mehtylquinazolin-4(3H)-one | 2.05 | 377 | B |
| 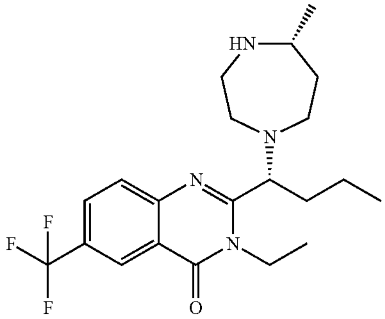 [SMILES: CCC[C@H](c1nc2ccc(C(F)(F)F)cc2c(=O)n1CC)N1CCN[C@H](C)CC1] | 258 | 3-ethyl-2-((R)-1-((R)-5-methyl-1,4-diazepan-1-yl)butyl)-6-(trifluoromethyl)quinazolin-4(3H)-one | 2.1 | 411.3 | B |
| 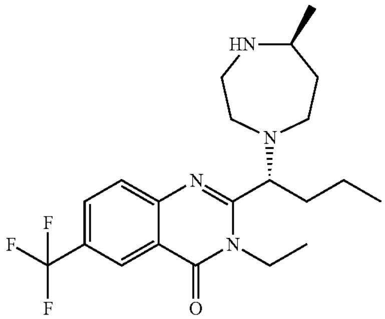 [SMILES: CCC[C@H](c1nc2ccc(C(F)(F)F)cc2c(=O)n1CC)N1CCN[C@@H](C)CC1] | 259 | 3-ethyl-2-((R)-1-((S)-5-methyl-1,4-diazepan-1-yl)butyl)-6-(trifluoromethyl)quinazolin-4(3H)-one | 2.13 | 411.2 | B |
| 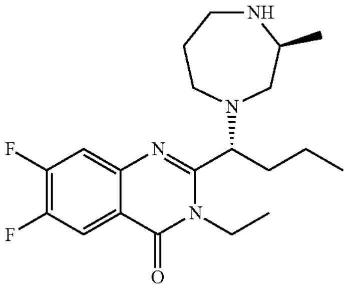 [SMILES: CCC[C@H](c1nc2cc(F)c(F)cc2c(=O)n1CC)N1CCCN[C@@H](C)C1] | 260 | 3-ethyl-6,7-difluoro-2-((R)-1-((S)-3-methyl-1,4-diazepan-1-yl)butyl)quinazolin-4(3H)-one | 2.08 | 379.2 | F |
| 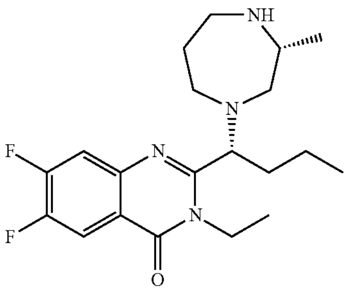 [SMILES: CCC[C@H](c1nc2cc(F)c(F)cc2c(=O)n1CC)N1CCCN[C@H](C)C1] | 261 | 3-ethyl-6,7-difluoro-2-((R)-1-((R)-3-methyl-1,4-diazepan-1-yl)butyl)quinazolin-4(3H)-one | 2.09 | 379.2 | F |

-continued
| STRUCTURE | EX | CHEMICAL NAME | Rt (min) | MS (M + H) | HPLC Method |
|---|---|---|---|---|---|
| 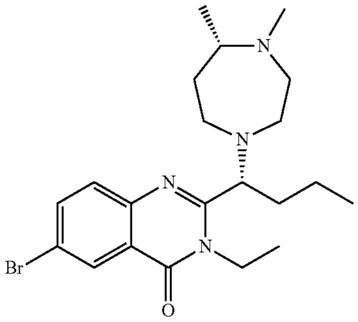 [SMILES: CCC[C@H](c1nc2ccc(Br)cc2c(=O)n1CC)N1CC[C@H](C)N(C)CC1] | 262 | 6-bromo-2-((S)-1-((4S,7S)-1,7-dimethylazepan-4-yl)butyl)-3-ethylquinazolin-4(3H)-one | 2.3 | 435.2 | B |
| 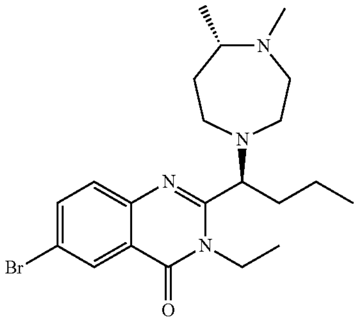 [SMILES: CCC[C@@H](c1nc2ccc(Br)cc2c(=O)n1CC)N1CC[C@H](C)N(C)CC1] | 263 | 6-bromo-2-((R)-1-((4R,7S)-1,7-dimethylazepan-4-yl)butyl)-3-ethylquinazolin-4(3H)-one | 2.3 | 435.2 | B |
| 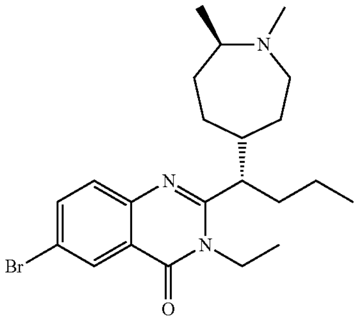 [SMILES: CCC[C@H](c1nc2ccc(Br)cc2c(=O)n1CC)C1CC[C@@H](C)N(C)CC1] | 264 | 6-bromo-2-((S)-1-((4S,7R)-1,7-dimethylazepan-4-yl)butyl)-3-ethylquinazolin-4(3H)-one | 2.3 | 435.2 | B |
| 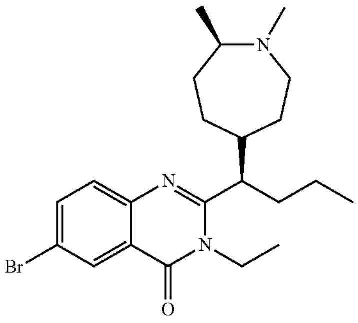 [SMILES: CCC[C@@H](c1nc2ccc(Br)cc2c(=O)n1CC)C1CC[C@@H](C)N(C)CC1] | 265 | 6-bromo-2-((R)-1-((4R,7R)-1,7-dimethylazepan-4-yl)butyl)-3-ethylquinazolin-4(3H)-one | 2.3 | 435.2 | B |

Examples 235 and 236. 3-Ethyl-6-fluoro-2-((R)-1-((R)-5-methyl-1,4-diazepan-1-yl)butyl)quinazolin-4(3H)-one and 3-ethyl-6-fluoro-2-((R)-1-((S)-5-methyl-1,4-diazepan-1-yl)butyl)quinazolin-4(3H)-one Examples 235 and 236 were directly separated using preparative HPLC: column: SunFire C18, 10 μm, 19×150 mm; temperature: 30° C.; flow rate: 14 mL/min; A: $CH_3CN$: B: 10 mM ammonium bicarbonate buffer pH 7; gradient: 8 min in 5:95+from 5:95 to 80:20 in 15 min+7 min in 80:20.

Examples 237 and 238. 2—((R)-1-((R)-4,6-Dimethyl-1,4-diazepan-1-yl)butyl)-3-ethyl-7-fluoro-6-methoxyquinazolin-4(3H)-one and 2-((R)-1-((S)-4,6-dimethyl-1,4-diazepan-1-yl)butyl)-3-ethyl-7-fluoro-6-methoxyquinazolin-4(3H)-one Examples 237 and 238 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 239 and 240. 3-Ethyl-5,6-difluoro-2-((R)-1-((R)-5-methyl-1,4-diazepan-1-yl)butyl)quinazolin-4(3H)-one and 3-ethyl-5,6-difluoro-2-((R)-1-((S)-5-methyl-1,4-diazepan-1-yl)butyl)quinazolin-4(3H)-one Examples 239 and 240 were directly separated using preparative HPLC: column: SunFire C18, 10 μm. 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 241 and 242. 3-Ethyl-6,7-difluoro-2-((R)-1-((R)-5-methyl-1,4-diazepan-1-yl)butyl)quinazolin-4(3H)-one and 3-ethyl-6,7-difluoro-2-((R)-1-((S)-5-methyl-1,4-diazepan-1-yl)butyl)quinazolin-4(3H)-one Examples 241 and 242 were directly separated using preparative HPLC: column: SunFire C18, 10 μm. 19×150 mm; temperature: 30° C.: flow rate: 14 mL/min; A: $CH_3CN$: B: 10 mM ammonium bicarbonate buffer pH 7; gradient: 8 min in 5:95+from 5:95 to 80:20 in 15 min+7 min in 80:20.

Examples 243 and 244. 3-Ethyl-7-fluoro-6-methoxy-2-((R)-1-((R)-6-methyl-1,4-diazepan-1-yl)butyl)quinazolin-4(3H)-one and 3-ethyl-7-fluoro-6-methoxy-2-((R)-1-((S)-6-methyl-1,4-diazepan-1-yl)butyl)quinazolin-4(3H)-one Examples 243 and 244 were directly separated using preparative HPLC: column: SunFire C18, 10 μm. 19×150 mm; temperature: 30° C.; flow rate: 14 mL/min; A: $CH_3CN$: B: 10 mM ammonium bicarbonate buffer pH 7; gradient: 8 min in 5:95+from 5:95 to 80:20 in 15 min+7 min in 80:20.

Examples 245 and 246. 6-Chloro-3-methyl-2-((R)-1-((R)-5-methyl-1,4-diazepan-1-yl)butyl)quinazolin-4(3H)-one and 6-chloro-3-methyl-2-((R)-1-((S)-5-methyl-1,4-diazepan-1-yl)butyl)quinazolin-4(3H)-one Examples 245 and 246 were directly separated using preparative HPLC: column: SunFire C18, 10 μm. 19×150 mm; temperature: 30° C.; flow rate: 14 mL/min; A: $CH_3CN$: B: 10 mM ammonium bicarbonate buffer pH 7; gradient: 8 min in 5:95+from 5:95 to 80:20 in 15 min+7 min in 80:20.

Examples 250 and 251. 3-Ethyl-6,8-difluoro-2-((R)-1-((R)-5-methyl-1,4-diazepan-1-yl)butyl)quinazolin-4(3H)-one and 3-ethyl-6,8-difluoro-2-((R)-1-((S)-5-methyl-1,4-diazepan-1-yl)butyl)quinazolin-4 (3H)-one Examples 250 and 251 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 254 and 257. 6-Chloro-2-((R)-1-((S)-4,5-dimethyl-1,4-diazepan-1-yl)butyl)-3-methylquinazolin-4(3H)-one and 6-Chloro-2-((R)-1-((R)-4,5-dimethyl-1,4-diazepan-1-yl)butyl)-3-methylquinazolin-4(3H)-one Examples 254 and 257 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7: gradient: 8 min in 5:95+from 5:95 to 80:20 in 15 min+7 min in 80:20.

Examples 255 and 256, 6-Fluoro-3-methyl-2-((R)-1-((R)-5-methyl-1,4-diazepan-1-yl)butyl)quinazolin-4(3H)-one and 6-fluoro-3-methyl-2-((R)-1-((S)-5-methyl-1,4-diazepan-1-yl)butyl)quinazolin-4(3H)-one Examples 255 and 256 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 258 and 259. 3-Ethyl-2-((R)-1-((R)-5-methyl-1,4-diazepan-1-yl)butyl)-6-(trifluoromethyl)quinazolin-4(3H)-one and 3-ethyl-2-((R)-1-((R)-5-methyl-1,4-diazepan-1-yl)butyl)-6-(trifluoromethyl)quinazolin-4(3H)-one Examples 258 and 259 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 260 and 261, 3-Ethyl-6,7-difluoro-2-((R)-1-((S)-3-methyl-1,4-diazepan-1-yl)butyl)quinazolin-4(3H)-one and 3-ethyl-6,7-difluoro-2-((R)-1-((R)-3-methyl-1,4-diazepan-1-yl)butyl)quinazolin-4(3H)-one Examples 260 and 261 were directly separated using preparative HPLC: column: SunFire C18, 10 μM, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

Examples 262, 263, 264 and 265, 6-Bromo-2-((R)-1-((S)-4,5-dimethyl-1,4-diazepan-1-yl)butyl)-3-ethylquinazolin-4(3H)-one, 6-bromo-2-((S)-1-((S)-4,5-dimethyl-1,4-diazepan-1-yl)butyl)-3-ethylquinazolin-4(3H)-one, 6-bromo-2-((R)-1-((R)-4,5-dimethyl-1,4-diazepan-1-yl)butyl)-3-ethylquinazolin-4(3H)-one and 6-bromo-2-((S)-1-((R)-4,5-dimethyl-1,4-diazepan-1-yl)butyl)-3-ethylquinazolin-4(3H)-one Examples 262, 263, 264 and 265 were directly separated using preparative HPLC: column: SunFire C18, 10 μm, 19×150 mm; temperature: 30° C.; flow rate: 14 mL/min; A: $CH_3CN$; B: 10 mM ammonium bicarbonate buffer pH 7; gradient: 8 min in 5:95+from 5:95 to 80:20 in 15 min+7 min in 80:20.

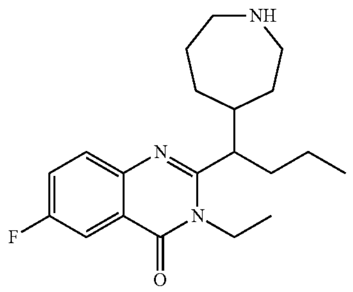 [SMILES: CCCC(c1nc2ccc(F)cc2c(=O)n1CC)C1CCCNCC1]

Example 266. 2-(1-(Azepan-4-yl)butyl)-3-ethyl-6-fluoroquinazolin-4(3H)-one

Step a. Cert-Butyl 4-(2-((2-(ethylcarbamoyl)-4-fluorophenyl)amino)-2-oxoethyl)azepane-1-carboxylate To a solution of 2-(1-(tert-butoxycarbonyl)azepan-4-yl) acetic acid (0.6 g. 3.29 mmol) in anh DMF (5 mL) under argon atmosphere, TEA (1.14 mL, 8.2 mmol), HATU (1.6 g, 3.9 mmol) and 2-amino-5-bromo-N-ethylbenzamide (0.847 g, 3.29 mmol) were added and the mixture was stirred at r.t. overnight. The reaction mixture was diluted with DCM, washed with $NaHCO_3$, and brine. The combined organic layers were dried over $Na_2SO_4$, filtered and the solvent was removed under vacuum. The crude product was purified by flash chromatography, silica gel, gradient Chx (100%) to EtOAc (100%) to give the title compound (1.23 g, Yield: 89%).

Step b. 2-(Azepan-4-ylmethyl)-3-ethyl-6-fluoroquinazolin-4(3H)-one

To a solution of the compound obtained in step a (1.23 g, 2.9 mmol) and iodine (1.48 g, 5.8 mmol) in DCM (50 mL), HMDS (2.44 mL, 11.7 mmol) was added dropwise and the reaction mixture was stirred at r.t. overnight. The reaction mixture was diluted with DCM, washed with 5% $Na_2S_2O_3$ aq sol, water and brine. The organic layer was dried over $Na_2SO_4$ and the solvent was removed under vacuum. The crude product was purified by flash chromatography, silica gel, gradient DCM (100%) to MeOH (100%) to give the title compound (0.809 g, Yield: 91%).

Step c. tert-Butyl 44(3-ethyl-6-fluoro-4-oxo-3,4-dihydroquinazolin-2-yl)methyl)azepane-1-carboxylate To a solution of the compound obtained in step b (0.809 g, 0.226 mmol) in DCM (10 mL), TEA (0.743 mL, 5.33 mmol) and di-tert-butyl dicarbonate (0.873 g, 4 mmol) were added and the reaction mixture was stirred at rt overnight. The mixture was washed with $NaHCO_3$ and brine and the organic layer was dried over $Na_2SO_4$ and filtered. The solvent was removed under vacuum to give the title compound (0.96 g, Yield: 89%).

Step d. tert-Butyl 4-(1-(3-ethyl-6-fluoro-4-oxo-3,4-dihydroquinazolin-2-yl)butyl)azepane-1-carboxylate To a solution of the compound obtained in step c (0.96 g, 0.23 mmol) in THF (50 mL) under argon atmosphere, LiHMDS (5.9 mL, 5.9 mmol) was added and the mixture was stirred for 45 min at −78° C. 1-Iodopropane (2.32 mL, 23.8 mmol) was added and the reaction mixture was stirred at −78° C. for 1 h and stirred overnight at r.t. The reaction mixture was diluted with EtOAc and $NH_4Cl$, and the organic layer was washed with water, $Na_2SO_3$ and brine. The organic layer was dried over anh $Na_2SO_4$ and the solvent was removed under vacuum. The crude product was purified by flash chromatography, silica gel, gradient Chx (100%) to EtOAc (100%) to give the title compound (0.685 g, Yield: 65%).

Step e. Title Compound

To a solution of the compound obtained in step d (0.685 g, 1.53 mmol) in anh. DCM (70 mL), TFA (2.3 mL) was added dropwise at 0° C. and the reaction mixture was stirred overnight at r.t. The mixture was neutralised by the addition of 20% aqueous NaOH, diluted with DCM and washed with sat aqueous $NaHCO_3$. The organic layer was dried over anhydrous $Na_2SO_4$, filtered and evaporated to dryness to give the title compound (451 mg, Yield: 85%).

HPLC-MS (B) Rt, 1.75 min: ESI+-MS m/z: 346.2 (M+1).

This method was used for the preparation of examples 267-268 using suitable starting materials:

| STRUCTURE | EX | CHEMICAL NAME | Rt (min) | MS (M + H) | HPLC Method |
|---|---|---|---|---|---|
| 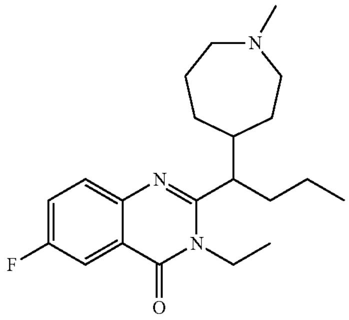 [SMILES: CCCC(c1nc2ccc(F)cc2c(=O)n1CC)C1CCCN(C)CC1] | 267 | 3-ethyl-6-fluoro-2-(1-(1-methylazepan-4-yl)butyl)quinazolin-4(3H)-one | 1.88 | 360.2 | B |

-continued

| STRUCTURE | EX | CHEMICAL NAME | Rt (min) | MS (M + H) | HPLC Method |
|---|---|---|---|---|---|
| 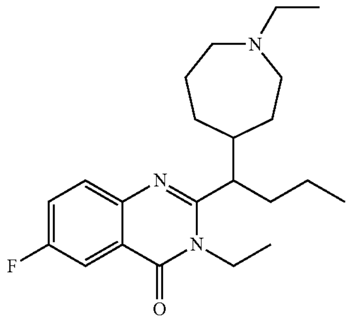 [SMILES: CCCC(c1nc2ccc(F)cc2c(=O)n1CC)C1CCCN(CC)CC1] | 268 | 3-ethyl-2-(1-(1-ethylazepan-4-yl)butyl)-6-fluoroquinazolin-4(3H)-one | 1.99 | 374.2 | B |

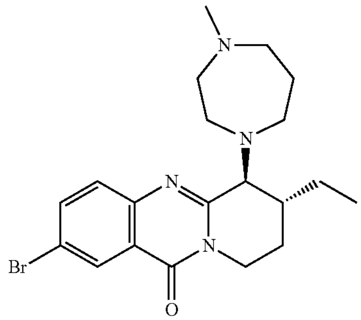

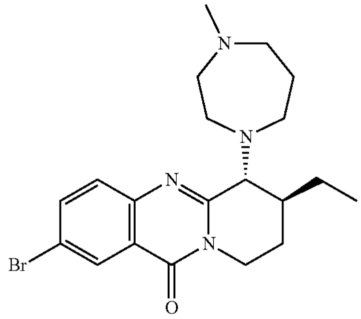

Examples 269 and 270, (6S,7R)-2-Bromo-7-ethyl-6-(4-methyl-1,4-diazepan-1-yl)-8,9-dihydro-6H-pyrido[2,1-b]quinazolin-11(7H)-one and (6R,7S)-2-bromo-7-ethyl-6-(4-methyl-1,4-diazepan-1-yl)-8,9-dihydro-6H-pyrido[2,1-b]quinazolin-11(7H)-one Step a. 2-Bromo-7-ethyl-8,9-dihydro-6H-pyrido[2,1-b]quinazolin-11(7H)-one To a solution of 2-amino-5-bromobenzoic acid (1.7 g, 1.87 mmol) in anh toluene (30 mL), thionyl chloride (5 mL. 39 mmol) was added at rt and the reaction mixture was heated at 80° C. for 2 h. The crude mixture was evaporated under vacuum and 4-ethylpiperidin-2-one (1.0 g, 1.87 mmol) was added and the reaction mixture was stirred at rt for 16 h. The crude mixture was evaporated to dryness, dissolved in EtOAc and washed with sat $NaHCO_3$, The aq phase was extracted with EtOAc and the organic layer was dried over anh $Na_2SO_4$, filtered and evaporated to dryness. The crude product was purified by flash chromatography, silica gel, gradient Chx to Chx:EtOAc (8:2), to give the title compound (1.81 g, Yield: 75%).

Step b. 2-Bromo-7-ethyl-6-hydroxy-8,9-dihydro-6H-pyrido[2,1-b]quinazolin-11(7H)-one To a solution of the compound obtained in step a (1.81 g, 5.89 mmol) in anh THF (20 mL) under Ar. LiHMDS (1M in THF, 6.48 mL. 6.48 mmol) was added dropwise at −78° C. and the reaction mixture was stirred for 3 h at −78° C. (1R)-1-(((1,2-oxaziridin-2-yl)sulfonyl)methyl)-7,7-dimethylbicyclo[2.2.1]heptan-2-one (1.98 g, 7.66 mmol) dissolved in anh THF (15 mL) was added dropwise and the reaction mixture was stirred at −60° C. for 16 h. Then sat $NH_4Cl$ solution was added and THF was removed under vacuum. The crude mixture was dissolved in EtOAc, washed with water and the organic layer was dried over anh $Na_2SO_4$, filtered and evaporated to dryness. The crude product was purified by flash chromatography, silica gel, gradient DCM to DCM:MeOH (85:15) to give the title compound (1.08 g, Yield: 56%)

Step c. Title Compounds

Starting from compound obtained in step b (300 mg, 0.93 mmol) and following the experimental procedure described in step e of example 209, 2-bromo-7-ethyl-6-(4-methyl-1,4-diazepan-1-yl)-8,9-dihydro-6H-pyrido[2,1-b]quinazolin-11(7H)-one (140 mg, Yield: 35%) was obtained.

Examples 269 and 270 were separated using preparative HPLC: column: Chiralpak IG, 5 μm, 20×250 mm; temperature: r.t; eluent: n-Heptane/EtOH/$Et_2NH$ 90/10/0.3 v/v/v; flow rate: 16 mL/min; Rt1; 21.6 min, Rt2: 24.2 min.

Biological Activity

Pharmacological Study

Human $\alpha_2\delta$-1 Subunit of $Ca_v2.2$ Calcium Channel Assay

Human $\alpha_2\delta$-1 enriched membranes (2.5 μg) were incubated with 15 nM of radiolabeled [$^3$H]-Gabapentin in assay buffer containing Hepes-KOH 10 mM. pH 7.4. NSB (non specific binding) was measured by adding 10 μM pregabalin. The binding of the test compound was measured at either one concentration (% inhibition at 1 or 10 μM) or five different concentrations to determine affinity values (Ki). After 60 min incubation at 27° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, pH 7.4. Filter plates were dried at 60° C. for 1 h and 30 μL of scintillation cocktail were added to each well before radioactivity reading. Readings were performed in a Trilux 1450 Microbeta radioactive counter (Perkin Elmer).

Human $\sigma_1$ Receptor Radioligand Assay

Transfected HEK-293 membranes (7 μg) were incubated with 5 nM of [$^3$H](+)-pentazocine in assay buffer containing Tris-HCl 50 mM at pH 8. NBS (non-specific binding) was measured by adding 10 μM haloperidol. The binding of the test compound was measured at either one concentration (% inhibition at 1 or 10 μM) or five different concentrations to determine affinity values (Ki). Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\alpha_2\delta$ subunit of voltage-gated calcium channels and the $\sigma_1$ receptor it is a very preferred embodiment in which the compounds are selected which act as dual ligands of the $\alpha_2\delta$ subunit of voltage-gated calcium channels and the $\sigma_1$-receptor and especially compounds which have a binding expressed as $K_i$ responding to the following scales:

$K_i(\sigma_1)$ is preferably <1000 nM, more preferably <500 nM, even more preferably <100 nM.

$K_s(\alpha_2\delta\text{-}1)$ is preferably <10000 nM, more preferably <5000 nM, or even more preferably <500 nM.

The following scale has been adopted for representing the binding to σ1-receptor expressed as $K_i$:

+$K_i$ ($\sigma_1$)>1000 nM

++500 nM<=$K_i(\sigma_1)$<=1000 nM

+++$K_i(\sigma_1)$<500 nM

Preferably, when $K_i$ ($\sigma_1$)>1000 nM, the following scale has been adopted for representing the binding to the σ1-receptor:

+$K_i$ ($\sigma_1$)>1000 nM or inhibition ranges between 1% and 50%,

The following scale has been adopted for representing the binding to the $\alpha_2\delta$-1 subunit of voltage-gated calcium channels expressed as K:

+K($\alpha_2\delta$-1)>5000 nM

++500 nM<=K($\alpha_2\delta$-1)<=5000 nM

+++$K_i$($\alpha_2\delta$-1)<500 nM

Preferably, when K(($\alpha_2\delta$-1)>5000 nM, the following scale has been adopted for representing the binding to the $\alpha_2\delta$-1 subunit of voltage-gated calcium channels:

+K($\alpha_2\delta$-1)>5000 nM or inhibition ranges between 1% and 50%

All compounds prepared in the present application exhibit binding to the $\alpha_2\delta$-1 subunit of voltage-gated calcium channels and to the CFI receptor, in particular the following binding results are shown:

Table of Examples with Binding to the $\sigma_1$ Receptor and the $\alpha_1\delta$-1 Subunit of the Voltage-Gated Calcium Channel:

| Example | α2δ − 1 binding | σ1 binding |
|---|---|---|
| 1 | +++ | +++ |
| 2 | +++ | + |
| 3 | +++ | + |
| 4 | +++ | + |
| 5 | ++ | +++ |
| 6 | + | +++ |
| 7 | +++ | +++ |
| 8 | +++ | + |
| 9 | +++ | + |
| 10 | +++ | + |
| 11 | +++ | + |
| 12 | +++ | +++ |
| 13 | +++ | +++ |
| 14 | ++ | + |
| 15 | +++ | + |
| 16 | + | + |
| 17 | +++ | + |
| 18 | +++ | +++ |
| 19 | +++ | ++ |
| 20 | +++ | +++ |
| 21 | +++ | +++ |
| 22 | +++ | + |
| 23 | +++ | ++ |
| 24 | ++ | +++ |
| 25 | + | ++ |
| 26 | +++ | +++ |
| 27 | +++ | + |
| 28 | ++ | ++ |
| 29 | +++ | ++ |
| 30 | + | + |
| 31 | +++ | ++ |
| 32 | +++ | + |
| 33 | +++ | +++ |
| 34 | +++ | + |
| 35 | +++ | + |
| 36 | +++ | ++ |
| 37 | + | + |
| 38 | + | + |
| 39 | +++ | ++ |
| 40 | +++ | ++ |
| 41 | + | + |
| 42 | + | + |
| 43 | +++ | +++ |
| 44 | +++ | + |
| 45 | +++ | + |
| 46 | +++ | +++ |
| 47 | ++ | +++ |
| 48 | +++ | +++ |
| 49 | + | ++ |
| 50 | +++ | +++ |
| 51 | ++ + | +++ |
| 52 | ++ | +++ |
| 53 | ++ | +++ |
| 54 | +++ | ++ |
| 55 | ++ | + |
| 56 | ++ | +++ |
| 57 | ++ | ++ |
| 58 | +++ | +++ |
| 59 | +++ | + |
| 60 | + | +++ |
| 61 | +++ | +++ |
| 62 | +++ | +++ |
| 63 | +++ | +++ |
| 64 | + | + |
| 65 | + | + |
| 66 | + | + |
| 67 | +++ | + |
| 68 | +++ | + |
| 69 | ++ | + |
| 70 | + | + |
| 71 | + | + |
| 72 | +++ | +++ |
| 73 | + | + |
| 74 | + | + |
| 75 | +++ | ++ |
| 76 | +++ | ++ |
| 77 | ++ | +++ |
| 78 | ++ | +++ |
| 79 | +++ | +++ |
| 80 | + | + |
| 81 | +++ | ++ |
| 82 | ++ | ++ |
| 83 | + | +++ |
| 84 | ++ | +++ |
| 85 | + | +++ |
| 86 | + | + |
| 87 | +++ | +++ |
| 88 | + | + |

-continued

| Example | α2δ − 1 binding | σ1 binding |
|---|---|---|
| 89 | +++ | +++ |
| 90 | +++ | + |
| 91 | +++ | ++ |
| 92 | ++ | + |
| 93 | +++ | ++ |
| 94 | ++ | + |
| 95 | + | + |
| 96 | +++ | ++ |
| 97 | +++ | ++ |
| 98 | ++ | + |
| 99 | ++ | + |
| 100 | + | + |
| 101 | + | ++ |
| 102 | + | + |
| 103 | +++ | +++ |
| 104 | +++ | + |
| 105 | ++ | + |
| 106 | +++ | + |
| 107 | ++ | ++ |
| 108 | + | ++ |
| 109 | +++ | + |
| 110 | +++ | + |
| 111 | ++ | + |
| 112 | + | + |
| 113 | + | + |
| 114 | +++ | + |
| 115 | + | + |
| 116 | +++ | + |
| 117 | ++ | ++ |
| 118 | +++ | ++ |
| 119 | +++ | ++ |
| 120 | + | + |
| 121 | + | + |
| 122 | + | ++ |
| 123 | +++ | ++ |
| 124 | ++ | + |
| 125 | ++ | ++ |
| 126 | ++ | ++ |
| 127 | +++ | ++ |
| 128 | + | + |
| 129 | ++ | + |
| 130 | +++ | ++ |
| 131 | +++ | +++ |
| 132 | +++ | +++ |
| 133 | + | + |
| 134 | + | ++ |
| 135 | +++ | +++ |
| 136 | +++ | ++ |
| 137 | + | ++ |
| 138 | + | ++ |
| 139 | +++ | ++ |
| 140 | + | + |
| 141 | + | ++ |
| 142 | +++ | + |
| 143 | +++ | +++ |
| 144 | + | + |
| 145 | +++ | + |
| 146 | + | + |
| 147 | +++ | +++ |
| 148 | +++ | + |
| 149 | + | +++ |
| 150 | + | ++ |
| 151 | +++ | +++ |
| 152 | + | ++ |
| 153 | +++ | +++ |
| 154 | + | +++ |
| 155 | + | + |
| 156 | + | ++ |
| 157 | +++ | + |
| 158 | + | + |
| 159 | +++ | +++ |
| 160 | + | + |
| 161 | +++ | ++ |
| 162 | + | ++ |
| 163 | +++ | + |
| 164 | +++ | + |
| 165 | +++ | + |
| 166 | + | + |
| 167 | ++ | + |
| 168 | +++ | + |
| 169 | +++ | + |
| 170 | ++ | + |
| 171 | + | + |
| 172 | +++ | + |
| 173 | +++ | + |
| 174 | + | + |
| 175 | +++ | + |
| 176 | + | + |
| 177 | +++ | + |
| 178 | +++ | + |
| 179 | ++ | + |
| 180 | +++ | + |
| 181 | +++ | + |
| 182 | +++ | + |
| 183 | +++ | + |
| 184 | +++ | + |
| 185 | +++ | + |
| 186 | +++ | + |
| 187 | +++ | + |
| 188 | + | + |
| 189 | + | + |
| 190 | ++ | + |
| 191 | +++ | + |
| 192 | +++ | + |
| 193 | + | + |
| 194 | + | + |
| 195 | +++ | + |
| 196 | +++ | + |
| 197 | +++ | + |
| 198 | + | + |
| 199 | +++ | + |
| 200 | + | + |
| 201 | +++ | + |
| 202 | + | + |
| 203 | +++ | + |
| 204 | +++ | + |
| 205 | +++ | + |
| 206 | +++ | + |
| 207 | +++ | ++ |
| 208 | + | + |
| 209 | +++ | +++ |
| 210 | +++ | +++ |
| 211 | +++ | +++ |
| 212 | +++ | +++ |
| 213 | +++ | ++ |
| 214 | +++ | +++ |
| 215 | +++ | +++ |
| 216 | ++ | +++ |
| 217 | + | +++ |
| 218 | +++ | +++ |
| 219 | +++ | +++ |
| 220 | +++ | + |
| 221 | + | +++ |
| 222 | + | ++ |
| 223 | + | +++ |
| 224 | +++ | +++ |
| 225 | +++ | +++ |
| 226 | + | +++ |
| 227 | +++ | +++ |
| 228 | ++ | +++ |
| 229 | +++ | +++ |
| 230 | +++ | ++ |
| 231 | +++ | ++ |
| 232 | +++ | +++ |
| 233 | +++ | +++ |
| 234 | +++ | ++ |
| 235 | +++ | + |
| 236 | +++ | +++ |
| 237 | +++ | + |
| 238 | +++ | ++ |
| 239 | + | + |
| 240 | +++ | +++ |

-continued

| Example | α2δ − 1 binding | σ1 binding |
|---|---|---|
| 241 | +++ | ++ |
| 242 | +++ | +++ |
| 243 | +++ | + |
| 244 | ++ | + |
| 245 | + | ++ |
| 246 | ++ | +++ |
| 247 | +++ | ++ |
| 248 | +++ | + |
| 249 | +++ | ++ |
| 250 | + | + |
| 251 | ++ | +++ |
| 252 | +++ | +++ |
| 253 | + | ++ |
| 254 | + | +++ |
| 255 | + | + |
| 256 | ++ | +++ |
| 257 | + | +++ |
| 258 | ++ | +++ |
| 259 | +++ | +++ |
| 260 | +++ | + |
| 261 | +++ | + |
| 262 | +++ | ++ |
| 263 | + | + |
| 264 | +++ | ++ |
| 265 | + | + |
| 266 | +++ | + |
| 267 | +++ | ++ |
| 268 | ++ | +++ |
| 269 | + | ++ |
| 270 | + | ++ |

The invention claimed is:

1. A compound of general formula (I)

(I)

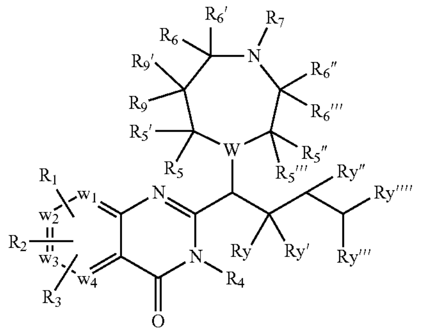

wherein $R_y$ and $R_y'$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

or $R_y$ and $R_y'$, together with the carbon atom to which they are attached, form a substituted or unsubstituted cycloalkyl;

$R_y$" is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_y$''' and $R_y$'''' are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

or $R_y$''' and $R_y$'''', together with the carbon atom to which they are attached, form a substituted or unsubstituted cycloalkyl;

W is nitrogen or —$CR_w$—; wherein $R_w$ is hydrogen or halogen;

or $R_w$ and one of $R_5$, $R_5$' $R_5$" or $R_5$''' form a double bond;

w1, w2, w3 and w4 independently represent nitrogen or carbon, wherein w1, w2, w3 and w4 are all carbon, or wherein one or two of w1, w2, w3 and w4 are nitrogen while the others are carbon;

$R_1$ is selected from the group consisting of hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_8$, —$NR_8R_8$', —$NR_8C(O)R_8$', —$NR_8C(O)OR_8$', —$C(O)NR_8R_8$, —$C(O)OR_8$, —$OCHR_8R_8$', haloalkyl, haloalkoxy, —CN, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

wherein $R_8$ and $R_8$' are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

$R_2$ is selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_{21}$, —$NO_2$, —$NR_{21}R_{21}$', —$NR_{21}C(O)R_{21}$', —$NR_{21}S(O)_2R_{21}$', —$S(O)_2NR_{21}R_{21}$', —$NR_{21}C(O)NR_{21}$'$R_{21}$", —$SR_{21}$, —$S(O)R_{21}$, —$S(O)_2R_{21}$, —CN, haloalkyl, haloalkoxy, —$C(O)OR_{21}$, —$C(O)NR_{21}R_{21}$', —$NR_{21}S(O)_2NR_{21}$'$R_{21}$" and —$C(CH_3)_2OR_{21}$, wherein $R_{21}$, $R_{21}$' and $R_{21}$" are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_3$ is selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, —$OR_{31}$, —$NO_3$, —$NR_{31}R_{31}$', —$NR_{31}C(O)R_{31}$', —$NR_{31}S(O)_3R_{31}$', —$S(O)_3NR_{31}R_{31}$', —$NR_{31}C(O)NR_{31}$'$R_{31}$", —$SR_{31}$, —$S(O)R_{31}$, —$S(O)_3R_{31}$, —CN, haloalkyl, haloalkoxy, —$C(O)OR_{31}$, —$C(O)NR_{31}R_{31}$', —$NR_{31}S(O)_3NR_{31}$'$R_{31}$" and —$C(CH_3)_3OR_{31}$, wherein $R_{31}$, $R_{31}$' and $R_{31}$" are independently selected from hydrogen, substituted or unsubstituted $C_{1-6}$ alkyl, substituted or unsubstituted $C_{3-6}$ alkenyl and substituted or unsubstituted $C_{3-6}$ alkynyl;

$R_4$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylheterocyclyl, substituted or unsubstituted alkylaryl and substituted or unsubstituted alkylcycloalkyl;

or $R_4$ and $R_y$, together with the nitrogen and carbon atoms to which they are attached, respectively, form a five or six membered substituted or unsubstituted heterocyclyl;

or $R_4$ and $R_y$''', together with the nitrogen and carbon atoms to which they are attached, respectively, form a six membered substituted or unsubstituted heterocyclyl;

$R_5$, $R_5'$, $R_5''$ and $R_5'''$ are independently selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;

or $R_5$ and $R_5'$ and/or $R_5''$ and $R_5'''$, together with the carbon atom to which they are attached, form a carbonyl group;

$R_6$, $R_6'$, $R_6''$ and $R_6'''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_7$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

or one of $R_5$ and $R_5'$ is taken together with $R_7$ to form a —$[CH_2]_n$— bridge; or one of $R_5''$ and $R_5'''$ is taken together with $R_7$ to form a —$[CH_2]_n$— bridge; or one of $R_5$ and $R_5'$ is taken together with one of $R_5''$ and $R_5'''$ to form a —$[CH_2]_n$— bridge; or one of $R_5$ and $R_5'$ is taken together with one of $R_6''$ and $R_6'''$ to form a —$[CH_2]_n$— bridge; or one of $R_6$ and $R_6'$, taken together with one of $R_6''$ and $R_6'''$ to form a —$[CH_2]_n$— bridge; or one of $R_6$ and $R_6'$ is taken together with one of $R_5''$ and $R_5'''$ to form a —$[CH_2]_n$— bridge; or one of $R_9$ and $R_9'$ is taken together with $R_7$ to form a —$[CH_2]_n$— bridge; or one of $R_9$ and $R_9'$ is taken together with one of $R_6''$ and $R_6'''$ to form a —$[CH_2]_n$— bridge; or one of $R_9$ and $R_9'$ is taken together with one of $R_5''$ and $R_5'''$ to form a —$[CH_2]_n$— bridge;

wherein n is 1, 2 or 3;

$R_9$ and $R_9'$ are independently selected from the group consisting of hydrogen, halogen, —$OR_{91}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted aryl, substituted or unsubstituted alkylcycloalkyl, substituted or unsubstituted alkylheterocyclyl and substituted or unsubstituted alkylaryl;

optionally as a stereoisomer, including enantiomers or diastereomers, a racemate or in form of a mixture of at least two stereoisomers, including enantiomers and/or diastereomers, in any mixing ratio, or a corresponding salt thereof, or a corresponding solvate thereof.

2. The compound according to claim 1, wherein the compound of Formula (I) is a compound of Formula (I')

(I')

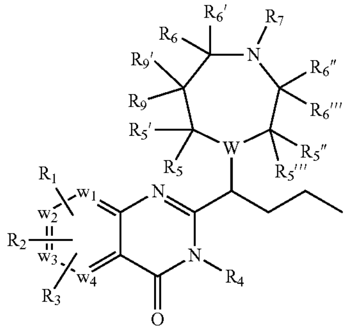

wherein $R_1$, $R_2$, $R_3$, $R_4$, $R_5$, $R_5'$, $R_5''$, $R_5'''$, $R_6$, $R_6'$, $R_6''$, $R_6'''$, $R_7$, $R_9$, $R_9'$, W, $w_1$, $w_2$, $w_3$ and $w_4$ are as defined in claim 1.

3. The compound according to claim 1, wherein the compound of Formula (I) is a compound of Formula ($I^{2'}$)

($I^{2'}$)

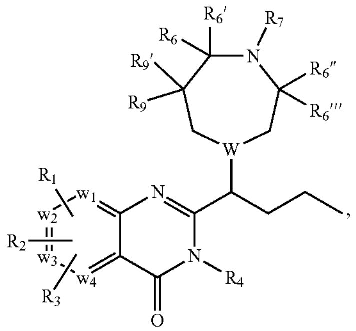

wherein $R_1$, $R_2$, $R_3$, $R_4$, $R_6$, $R_6'$, $R_6''$, $R_6'''$, $R_7$, $R_9$, $R_9'$, W, $w_1$, $w_2$, $w_3$ and $w_4$ are as defined in claim 1.

4. The compound according to claim 1, wherein the compound of Formula (I) is a compound of Formula ($I^3$), ($I^4$) or ($I^5$)

($I^{3'}$)

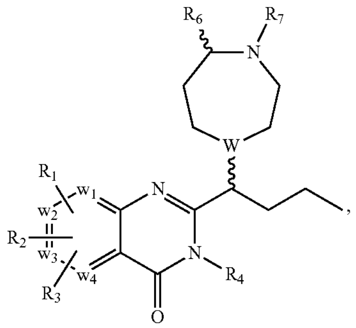

-continued $(I^{4'})$

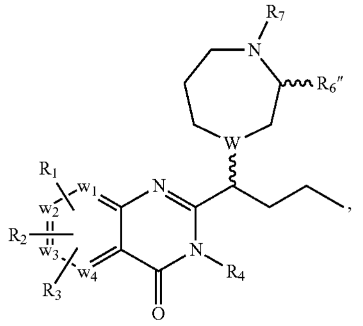

$(I^{5'})$

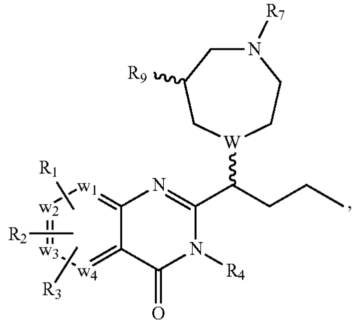

wherein $R_1$, $R_2$, $R_3$, $R_4$, $R_6$, $R_6''$, $R_7$, $R_9$, W, $w_1$, $w_2$, $w_3$ and $w_4$ are as defined in claim 1.

5. The compound according to claim 4, wherein $R_7$ is hydrogen while $R_6$, $R_6''$ and $R_9$ are substituted or unsubstituted $C_{1-6}$ alkyl.

6. The compound according to claim 4, wherein $R_7$ is substituted or unsubstituted $C_{1-6}$ alkyl while $R_6$, $R_6''$ and $R_9$ are hydrogen.

7. The compound according to claim 4, wherein $R_7$ is substituted or unsubstituted $C_{1-6}$ alkyl while $R_6$, $R_6''$ and $R_9$ are substituted or unsubstituted $C_{1-6}$ alkyl.

8. The compound according to claim 1, wherein $R_7$ is selected from hydrogen and substituted or unsubstituted $C_{1-6}$alkyl.

9. The compound according to claim 1, wherein the compound of Formula (I) is a compound of Formula $(I^6)$ or $(I^7)$ $(I^{6'})$

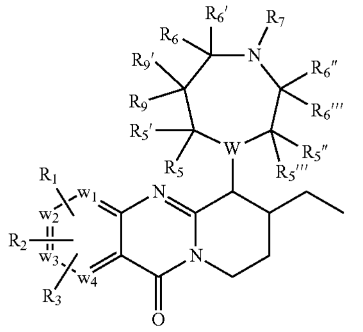

-continued $(I^{7'})$

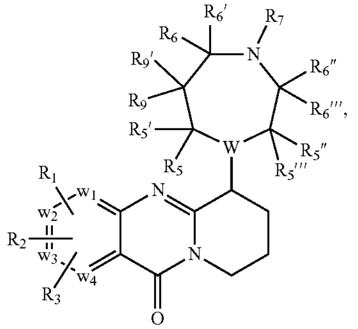

wherein $R_1$, $R_2$, $R_3$, $R_5$, $R_5'$, $R_5''$, $R_5'''$, $R_6$, $R_6'$, $R_6''$, $R_6'''$, $R_7$, $R_9$, $R_9'$, W, $w_1$, $w_2$, $w_3$ and $w_4$ are as defined in claim 1.

10. The compound according to claim 1, wherein the compound of Formula (I) is selected from:

6-bromo-3-ethyl-2-(1-(4-methyl-1,4-diazepan-1-yl)butyl)quinazolin-4(3H)-one, 2-(1-(1,4-diazepan-1-yl)butyl)-6-bromo-3-ethylquinazolin-4(3H)-one, 7-bromo-3-ethyl-2-(1-(4-methyl-1,4-diazepan-1-yl)butyl)quinazolin-4(3H)-one, 2-(1-(1,4-diazepan-1-yl)butyl)-7-bromo-3-ethylquinazolin-4(3H)-one, 6-bromo-3-ethyl-2-(1-(4-phenethyl-1,4-diazepan-1-yl)butyl)quinazolin-4(3H)-one, 2-(1-(4-benzyl-1,4-diazepan-1-yl)butyl)-6-bromo-3-ethylquinazolin-4(3H)-one, 6-bromo-3-ethyl-2-(1-(4-ethyl-1,4-diazepan-1-yl)butyl)quinazolin-4(3H)-one, 3-ethyl-6-methyl-2-(1-(4-methyl-1,4-diazepan-1-yl)butyl)quinazolin-4(3H)-one, 3-ethyl-2-(1-(4-methyl-1,4-diazepan-1-yl)butyl)-4-oxo-3,4-dihydroquinazoline-7-carbonitrile, 3-ethyl-2-(1-(4-methyl-1,4-diazepan-1-yl)butyl)-4-oxo-3,4-dihydroquinazoline-6-carbonitrile, 3-ethyl-7-methyl-2-(1-(4-methyl-1,4-diazepan-1-yl)butyl)quinazolin-4(3H)-one, 3-ethyl-6-iodo-2-(1-(4-methyl-1,4-diazepan-1-yl)butyl)quinazolin-4(3H)-one, 6-bromo-3-ethyl-7-fluoro-2-(1-(4-methyl-1,4-diazepan-1-yl)butyl)quinazolin-4(3H)-one, 6-bromo-3-(2-methoxyethyl)-2-(1-(4-methyl-1,4-diazepan-1-yl)butyl)quinazolin-4(3H)-one, (R)-3-ethyl-6-methoxy-2-(1-(4-methyl-1,4-diazepan-1-yl)butyl)quinazolin-4(3H)-one, (S)-3-ethyl-6-methoxy-2-(1-(4-methyl-1,4-diazepan-1-yl)butyl)quinazolin-4(3H)-one, 3-ethyl-2-(1-(4-methyl-1,4-diazepan-1-yl)butyl)pyrido[3,4-d]pyrimidin-4(3H)-one, 6-bromo-2-(1-(4-methyl-1,4-diazepan-1-yl)butyl)-3-propylquinazolin-4(3H)-one, 6-chloro-3-ethyl-2-(1-(4-methyl-1,4-diazepan-1-yl)butyl)quinazolin-4(3H)-one, 6-bromo-2-(1-(4-ethyl-1,4-diazepan-1-yl)butyl)-3-propylquinazolin-4(3H)-one, 3-ethyl-6-fluoro-2-(1-(4-methyl-1,4-diazepan-1-yl)butyl)quinazolin-4(3H)-one, 2-(1-(1,4-diazepan-1-yl)butyl)-6-chloro-3-ethylquinazolin-4(3H)-one, 6-chloro-2-(1-(4-methyl-1,4-diazepan-1-yl)butyl)-3-propylquinazolin-4(3H)-one, 6-bromo-3-ethyl-5-methyl-2-(1-(4-methyl-1,4-diazepan-1-yl)butyl)quinazolin-4(3H)-one, 6-bromo-3-ethyl-8-methyl-2-(1-(4-methyl-1,4-diazepan-1-yl)butyl)quinazolin-4(3H)-one,
6-bromo-7-fluoro-2-(1-(4-methyl-1,4-diazepan-1-yl)butyl)-3-propylquinazolin-4(3H)-one,
2-(1-(1,4-diazepan-1-yl)butyl)-6-bromo-3-ethyl-7-fluoroquinazolin-4(3H)-one,
6-bromo-2-(1-(6,6-dimethyl-1,4-diazepan-1-yl)butyl)-3-ethylquinazolin-4(3H)-one,
3-ethyl-6,7-difluoro-2-(1-(4-methyl-1,4-diazepan-1-yl)butyl)quinazolin-4(3H)-one,
6-bromo-3-ethyl-2-(1-(4,6,6-trimethyl-1,4-diazepan-1-yl)butyl)quinazolin-4(3H)-one,
7-bromo-6-fluoro-2-(1-(4-methyl-1,4-diazepan-1-yl)butyl)-3-propylquinazolin-4(3H)-one,
2-(1-(1,4-diazepan-1-yl)butyl)-7-bromo-3-ethyl-6-fluoroquinazolin-4(3H)-one,
7-bromo-3-ethyl-6-fluoro-2-(1-(4-methyl-1,4-diazepan-1-yl)butyl)quinazolin-4(3H)-one,
2-(1-(1,4-diazepan-1-yl)butyl)-6-bromo-7-fluoro-3-propylquinazolin-4(3H)-one,
6-bromo-2-((R)-1-((R)-4,6-dimethyl-1,4-diazepan-1-yl)butyl)-3-ethylquinazolin-4(3H)-one,
6-bromo-2-((R)-1-((S)-4,6-dimethyl-1,4-diazepan-1-yl)butyl)-3-ethylquinazolin-4(3H)-one,
6-bromo-2-((S)-1-((S)-4,6-dimethyl-1,4-diazepan-1-yl)butyl)-3-ethylquinazolin-4(3H)-one,
6-bromo-2-((S)-1-((R)-4,6-dimethyl-1,4-diazepan-1-yl)butyl)-3-ethylquinazolin-4(3H)-one,
6-bromo-3-ethyl-7-methyl-2-(1-(4-methyl-1,4-diazepan-1-yl)butyl)quinazolin-4(3H)-one,
6-bromo-3-ethyl-8-fluoro-2-(1-(4-methyl-1,4-diazepan-1-yl)butyl)quinazolin-4(3H)-one,
2-(1-(1,4-diazepan-1-yl)butyl)-6-bromo-3-ethyl-5-methylquinazolin-4(3H)-one,
6-bromo-2-(1-(6,6-difluoro-4-methyl-1,4-diazepan-1-yl)butyl)-3-ethylquinazolin-4(3H)-one,
6-fluoro-3-isobutyl-2-(1-(4-methyl-1,4-diazepan-1-yl)butyl)quinazolin-4(3H)-one,
2-(1-(1,4-diazepan-1-yl)butyl)-6-bromo-3-ethyl-7-methylquinazolin-4(3H)-one,
2-(1-(1,4-diazepan-1-yl)butyl)-3-ethyl-6,7-difluoroquinazolin-4(3H)-one,
3-ethyl-2-(1-(4-ethyl-1,4-diazepan-1-yl)butyl)-6,7-difluoroquinazolin-4(3H)-one,
6-bromo-3-ethyl-2-(1-(4-ethyl-1,4-diazepan-1-yl)butyl)-5-methylquinazolin-4(3H)-one,
6-bromo-3-ethyl-2-(1-(4-ethyl-1,4-diazepan-1-yl)butyl)-7-methylquinazolin-4(3H)-one,
6-bromo-8-chloro-3-ethyl-2-(1-(4-methyl-1,4-diazepan-1-yl)butyl)quinazolin-4(3H)-one,
2-(1-(4-ethyl-1,4-diazepan-1-yl)butyl)-6-fluoro-3-isobutylquinazolin-4(3H)-one,
6-bromo-3-ethyl-5-fluoro-2-(1-(4-methyl-1,4-diazepan-1-yl)butyl)quinazolin-4(3H)-one,
6-bromo-3-ethyl-2-(1-(4-ethyl-1,4-diazepan-1-yl)butyl)-5-fluoroquinazolin-4(3H)-one,
5-bromo-3-ethyl-2-(1-(4-methyl-1,4-diazepan-1-yl)butyl)quinazolin-4(3H)-one,
6-bromo-3-isobutyl-2-(1-(4-methyl-1,4-diazepan-1-yl)butyl)quinazolin-4(3H)-one,
2-(1-(1,4-diazepan-1-yl)butyl)-6-bromo-3-ethyl-8-fluoroquinazolin-4(3H)-one,
6-bromo-5-chloro-3-ethyl-2-(1-(4-methyl-1,4-diazepan-1-yl)butyl)quinazolin-4(3H)-one,
6-bromo-3-ethyl-2-(1-(4-ethyl-1,4-diazepan-1-yl)butyl)-8-fluoroquinazolin-4(3H)-one,
6-bromo-2-(1-(4-ethyl-1,4-diazepan-1-yl)butyl)-3-isobutylquinazolin-4(3H)-one,
2-(1-(1,4-diazepan-1-yl)butyl)-6-bromo-3-ethyl-5-fluoroquinazolin-4(3H)-one,
6-bromo-3-ethyl-2-(1-(4-ethyl-1,4-diazepan-1-yl)butyl)-8-methylquinazolin-4(3H)-one,
6-bromo-2-(1-(4-ethyl-1,4-diazepan-1-yl)butyl)-7-fluoro-3-propylquinazolin-4(3H)-one,
7-bromo-2-(1-(4-ethyl-1,4-diazepan-1-yl)butyl)-6-fluoro-3-propylquinazolin-4(3H)-one,
7-bromo-3-ethyl-2-(1-(4-ethyl-1,4-diazepan-1-yl)butyl)-6-fluoroquinazolin-4(3H)-one,
8-chloro-3-ethyl-6-fluoro-2-(1-(4-methyl-1,4-diazepan-1-yl)butyl)quinazolin-4(3H)-one,
8-chloro-3-ethyl-2-(1-(4-ethyl-1,4-diazepan-1-yl)butyl)-6-fluoroquinazolin-4(3H)-one,
(R)-2-(1-(1,4-diazabicyclo[3.2.2]nonan-4-yl)butyl)-6-bromo-3-ethylquinazolin-4(3H)-one,
6-bromo-2-((R)-1-((S)-6-methyl-1,4-diazepan-1-yl)butyl)-3-propylquinazolin-4(3H)-one,
6-bromo-2-((R)-1-((R)-6-methyl-1,4-diazepan-1-yl)butyl)-3-propylquinazolin-4(3H)-one,
6-bromo-2-((S)-1-((S)-6-methyl-1,4-diazepan-1-yl)butyl)-3-propylquinazolin-4(3H)-one,
6-bromo-2-((S)-1-((R)-6-methyl-1,4-diazepan-1-yl)butyl)-3-propylquinazolin-4(3H)-one,
2-(1-(1,4-diazepan-1-yl)butyl)-8-chloro-3-ethyl-6-fluoroquinazolin-4(3H)-one,
3-ethyl-5,6-difluoro-2-(1-(4-methyl-1,4-diazepan-1-yl)butyl)quinazolin-4(3H)-one,
6-chloro-2-((S)-1-((S)-4,6-dimethyl-1,4-diazepan-1-yl)butyl)-3-ethylquinazolin-4(3H)-one,
6-chloro-2-((S)-1-((R)-4,6-dimethyl-1,4-diazepan-1-yl)butyl)-3-ethylquinazolin-4(3H)-one,
6-chloro-2-((R)-1-((S)-4,6-dimethyl-1,4-diazepan-1-yl)butyl)-3-ethylquinazolin-4(3H)-one,
6-chloro-2-((R)-1-((R)-4,6-dimethyl-1, 4-diazepan-1-yl)butyl)-3-ethylquinazolin-4(3H)-one,
6-bromo-7-fluoro-3-methyl-2-(1-(4-methyl-1,4-diazepan-1-yl)butyl)quinazolin-4(3H)-one,
3-ethyl-2-(1-(4-ethyl-1,4-diazepan-1-yl)butyl)-5,6-difluoroquinazolin-4(3H)-one,
6-chloro-2-(1-(4-ethyl-1,4-diazepan-1-yl)butyl)-3-propylquinazolin-4(3H)-one,
2-(1-(1,4-diazabicyclo[3.2.2]nonan-4-yl)butyl)-6-bromo-3-ethylquinazolin-4(3H)-one,
2-(1-(1,4-diazepan-1-yl)butyl)-3-ethyl-5,6-difluoroquinazolin-4(3H)-one,
2-(1-(1,4-diazepan-1-yl)butyl)-6-bromo-5-chloro-3-ethylquinazolin-4(3H)-one,
6-bromo-5-chloro-3-ethyl-2-(1-(4-ethyl-1,4-diazepan-1-yl)butyl)quinazolin-4(3H)-one,
6-bromo-3-methyl-2-(1-(4-methyl-1,4-diazepan-1-yl)butyl)quinazolin-4(3H)-one,
6-bromo-2-(1-(4-ethyl-1,4-diazepan-1-yl)butyl)-3-methylquinazolin-4(3H)-one,
3-ethyl-2-(1-(4-methyl-1,4-diazepan-1-yl)butyl)pyrido[3,2-d]pyrimidin-4(3H)-one,
6,7-dichloro-3-ethyl-2-(1-(4-methyl-1,4-diazepan-1-yl)butyl)quinazolin-4(3H)-one,
3-ethyl-2-(1-(4-ethyl-1,4-diazepan-1-yl)butyl)pyrido[3,2-d]pyrimidin-4(3H)-one,
6-chloro-3-ethyl-7-fluoro-2-(1-(4-methyl-1,4-diazepan-1-yl)butyl)quinazolin-4(3H)-one,
2-(1-(1,4-diazepan-1-yl)butyl)-6-chloro-3-ethyl-7-fluoroquinazolin-4(3H)-one,
2-(1-(1,4-diazepan-1-yl)butyl)-6,7-dichloro-3-ethylquinazolin-4(3H)-one,
6-bromo-3-ethyl-2-((R)-1-((R)-5-methyl-1,4-diazepan-1-yl)butyl)quinazolin-4(3H)-one,
6-bromo-3-ethyl-2-((R)-1-((S)-5-methyl-1,4-diazepan-1-yl)butyl)quinazolin-4(3H)-one,
6-bromo-3-ethyl-2-((S)-1-((R)-5-methyl-1,4-diazepan-1-yl)butyl)quinazolin-4(3H)-one, 6-bromo-3-ethyl-2-((S)-R-((S)-5-methyl-1,4-diazepan-1-yl)butyl)quinazolin-4(3H)-one, 6-bromo-3-ethyl-7-fluoro-2-((R)-1-((S)-6-methyl-1,4-diazepan-1-yl)butyl)quinazolin-4(3H)-one, 6-bromo-3-ethyl-7-fluoro-2-((R)-1-((R)-6-methyl-1, 4-diazepan-1-yl)butyl)quinazolin-4(3H)-one, 6-bromo-3-ethyl-7-fluoro-2-((S)-1-((S)-6-methyl-1,4-diazepan-1-yl)butyl)quinazolin-4(3H)-one, 6-bromo-3-ethyl-7-fluoro-2-((S)-1-((R)-6-methyl-1,4-diazepan-1-yl)butyl)quinazolin-4(3H)-one, 2-(1-(1,4-diazepan-1-yl)butyl)-3-ethylpyrido[3,2-d]pyrimidin-4(3H)-one, 6-bromo-3-ethyl-2-((S)-1-((S)-6-ethyl-1,4-diazepan-1-yl)butyl)quinazolin-4(3H)-one, 6-bromo-3-ethyl-2-((S)-1-((R)-6-ethyl-1,4-diazepan-1-yl)butyl)quinazolin-4(3H)-one, 6-bromo-3-ethyl-2-((R)-1-((R)-6-ethyl-1,4-diazepan-1-yl)butyl)quinazolin-4(3H)-one, 6-bromo-3-ethyl-2-((R)-1-((S)-6-ethyl-1,4-diazepan-1-yl)butyl)quinazolin-4(3H)-one, 6-bromo-3-ethyl-2-((R)-1-((S)-6-(methoxymethyl)-4-methyl-1,4-diazepan-1-yl)butyl)quinazolin-4(3H)-one, 6-bromo-3-ethyl-2-((R)-1-((R)-6-(methoxymethyl)-4-methyl-1,4-diazepan-1-yl)butyl)quinazolin-4(3H)-one, 6-bromo-3-ethyl-2-((S)-1-((S)-6-(methoxymethyl)-4-methyl-1,4-diazepan-1-yl)butyl)quinazolin-4(3H)-one, 6-bromo-3-ethyl-2-((S)-1-((R)-6-(methoxymethyl)-4-methyl-1,4-diazepan-1-yl)butyl)quinazolin-4(3H)-one, 6,7-dichloro-3-ethyl-2-((R)-1-((S)-6-methyl-1,4-diazepan-1-yl)butyl)quinazolin-4(3H)-one, 6,7-dichloro-3-ethyl-2-((R)-1-((R)-6-methyl-1,4-diazepan-1-yl)butyl)quinazolin-4(3H)-one, 6,7-dichloro-3-ethyl-2-((S)-1-((S)-6-methyl-1,4-diazepan-1-yl)butyl)quinazolin-4(3H)-one, 6,7-dichloro-3-ethyl-2-((S)-1-((R)-6-methyl-1,4-diazepan-1-yl)butyl)quinazolin-4(3H)-one, 6-bromo-3-ethyl-2-((S)-1-((R)-6-hydroxy-1,4-diazepan-1-yl)butyl)quinazolin-4(3H)-one, 6-bromo-3-ethyl-2-((R)-1-((R)-6-hydroxy-1,4-diazepan-1-yl)butyl)quinazolin-4(3H)-one, 6-bromo-3-ethyl-2-((S)-1-((S)-6-hydroxy-1,4-diazepan-1-yl)butyl)quinazolin-4(3H)-one, 6-bromo-3-ethyl-2-((R)-1-((S)-6-hydroxy-1,4-diazepan-1-yl)butyl)quinazolin-4(3H)-one, 3-ethyl-8-fluoro-6-methoxy-2-(1-(4-methyl-1,4-diazepan-1-yl)butyl)quinazolin-4(3H)-one, 6-chloro-3-ethyl-7-fluoro-2-((R)-1-((S)-6-methyl-1,4-diazepan-1-yl)butyl)quinazolin-4(3H)-one, 6-chloro-3-ethyl-7-fluoro-2-((R)-1-((R)-6-methyl-1,4-diazepan-1-yl)butyl)quinazolin-4(3H)-one, 6-chloro-3-ethyl-7-fluoro-2-((S)-1-((S)-6-methyl-1,4-diazepan-1-yl)butyl)quinazolin-4(3H)-one, 6-chloro-3-ethyl-7-fluoro-2-((S)-1-((R)-6-methyl-1,4-diazepan-1-yl)butyl)quinazolin-4(3H)-one, 6-bromo-2-(1-(4-methyl-1,4-diazepan-1-yl)butyl)quinazolin-4(3H)-one, 6-bromo-3-ethyl-2-((R)-1-((S)-6-(hydroxymethyl)-4-methyl-1, 4-diazepan-1-yl)butyl)quinazolin-4(3H)-one, 6-bromo-3-ethyl-2-((S)-1-((R)-6-(hydroxymethyl)-4-methyl-1,4-diazepan-1-yl)butyl)quinazolin-4(3H)-one, 6-bromo-3-ethyl-2-((R)-1-((R)-6-(hydroxymethyl)-4-methyl-1,4-diazepan-1-yl)butyl)quinazolin-4(3H)-one, 6-bromo-3-ethyl-2-((S)-1-((S)-6-(hydroxymethyl)-4-methyl-1,4-diazepan-1-yl)butyl)quinazolin-4(3H)-one, 6-bromo-2-((R)-1-((S)-4,6-dimethyl-1,4-diazepan-1-yl)butyl)-3-ethyl-7-fluoroquinazolin-4(3H)-one, 6-bromo-2-((S)-1-((S)-4,6-dimethyl-1,4-diazepan-1-yl)butyl)-3-ethyl-7-fluoroquinazolin-4(3H)-one, 6-bromo-2-((S)-1-((R)-4,6-dimethyl-1,4-diazepan-1-yl)butyl)-3-ethyl-7-fluoroquinazolin-4(3H)-one, 6-bromo-2-((R)-1-((R)-4,6-dimethyl-1,4-diazepan-1-yl)butyl)-3-ethyl-7-fluoroquinazolin-4(3H)-one, 6,7-dichloro-2-((R)-1-((S)-4,6-dimethyl-1,4-diazepan-1-yl)butyl)-3-ethylquinazolin-4(3H)-one, 6,7-dichloro-2-((R)-1-((R)-4,6-dimethyl-1,4-diazepan-1-yl)butyl)-3-ethylquinazolin-4(3H)-one, 6,7-dichloro-2-((S)-1-((S)-4,6-dimethyl-1,4-diazepan-1-yl)butyl)-3-ethylquinazolin-4(3H)-one, 6,7-dichloro-2-((S)-1-((R)-4,6-dimethyl-1,4-diazepan-1-yl)butyl)-3-ethylquinazolin-4(3H)-one, 6-chloro-2-((R)-1-((S)-4,6-dimethyl-1,4-diazepan-1-yl)butyl)-3-ethyl-7-fluoroquinazolin-4(3H)-one, 6-chloro-2-((R)-1-((R)-4,6-dimethyl-1,4-diazepan-1-yl)butyl)-3-ethyl-7-fluoroquinazolin-4(3H)-one, 6-chloro-2-((S)-1-((S)-4,6-dimethyl-1,4-diazepan-1-yl)butyl)-3-ethyl-7-fluoroquinazolin-4(3H)-one, 6-chloro-2-((S)-1-((R)-4,6-dimethyl-1,4-diazepan-1-yl)butyl)-3-ethyl-7-fluoroquinazolin-4(3H)-one, 6-bromo-3-ethyl-2-((R)-1-((R)-3-methyl-1,4-diazepan-1-yl)butyl)quinazolin-4(3H)-one, 6-bromo-3-ethyl-2-((S)-1-((S)-3-methyl-1,4-diazepan-1-yl)butyl)quinazolin-4(3H)-one, 6-bromo-3-ethyl-2-((S)-1-((R)-3-methyl-1,4-diazepan-1-yl)butyl)quinazolin-4(3H)-one, 6-bromo-3-ethyl-2-((R)-1-((S)-3-methyl-1,4-diazepan-1-yl)butyl)quinazolin-4(3H)-one, 3-ethyl-6-fluoro-2-((R)-1-((R)-3-methyl-1,4-diazepan-1-yl)butyl)quinazolin-4(3H)-one, 3-ethyl-6-fluoro-2-((S)-1-((S)-3-methyl-1,4-diazepan-1-yl)butyl)quinazolin-4(3H)-one, 3-ethyl-6-fluoro-2-((R)-1-((S)-3-methyl-1,4-diazepan-1-yl)butyl)quinazolin-4(3H)-one, 3-ethyl-6-fluoro-2-((S)-1-((R)-3-methyl-1,4-diazepan-1-yl)butyl)quinazolin-4(3H)-one, 6-chloro-3-methyl-2-((R)-1-((R)-3-methyl-1,4-diazepan-1-yl)butyl)quinazolin-4(3H)-one, 6-chloro-3-methyl-2-((R)-1-((S)-3-methyl-1,4-diazepan-1-yl)butyl)quinazolin-4(3H)-one, 6-chloro-3-methyl-2-((S)-1-((S)-3-methyl-1,4-diazepan-1-yl)butyl)quinazolin-4(3H)-one, 6-chloro-3-methyl-2-((S)-1-((R)-3-methyl-1,4-diazepan-1-yl)butyl)quinazolin-4(3H)-one, (R)-6-bromo-3-ethyl-2-(1-(4-methyl-1,4-diazepan-1-yl)butyl)quinazolin-4(3H)-one, (S)-6-bromo-3-ethyl-2-(1-(4-methyl-1,4-diazepan-1-yl)butyl)quinazolin-4(3H)-one, (R)-6-Bromo-3-ethyl-2-(1-(4-ethyl-1,4-diazepan-1-yl)butyl)quinazolin-4(3H)-one, (S)-6-bromo-3-ethyl-2-(1-(4-ethyl-1,4-diazepan-1-yl)butyl)quinazolin-4(3H)-one, (R)-6-bromo-3-ethyl-7-fluoro-2-(1-(4-methyl-1,4-diazepan-1-yl)butyl)quinazolin-4(3H)-one, (S)-6-bromo-3-ethyl-7-fluoro-2-(1-(4-methyl-1,4-diazepan-1-yl)butyl)quinazolin-4(3H)-one, (R)-2-(1-(1, 4-Diazepan-1-yl)butyl)-6-bromo-3-ethyl-7-fluoroquinazolin-4(3H)-one, (S)-2-(1-(1,4-diazepan-1-yl)butyl)-6-bromo-3-ethyl-7-fluoroquinazolin-4(3H)-one, (R)-6-chloro-2-(1-(4-methyl-1,4-diazepan-1-yl)butyl)-3-propylquinazolin-4(3H)-one, (S)-6-chloro-2-(1-(4-methyl-1,4-diazepan-1-yl)butyl)-3-propylquinazolin-4(3H)-one, (R)-6-bromo-3-ethyl-8-fluoro-2-(1-(4-methyl-1,4-diazepan-1-yl)butyl)quinazolin-4(3H)-one, (S)-6-bromo-3-ethyl-8-fluoro-2-(1-(4-methyl-1,4-diazepan-1-yl)butyl)quinazolin-4(3H)-one, 3-ethyl-2-(1-(4-methyl-1,4-diazepan-1-yl)butyl)pyrido[4,3-d]pyrimidin-4(3H)-one, 3-ethyl-2-((R)-1-((S)-6-methyl-1,4-diazepan-1-yl)butyl)pyrido[4,3-d]pyrimidin-4(3H)-one, 3-ethyl-2-((R)-1-((R)-6-methyl-1,4-diazepan-1-yl)butyl) pyrido[4,3-d]pyrimidin-4(3H)-one,
3-ethyl-2-((S)-1-((S)-6-methyl-1,4-diazepan-1-yl)butyl) pyrido[4,3-d]pyrimidin-4(3H)-one,
3-ethyl-2-((S)-1-((R)-6-methyl-1,4-diazepan-1-yl)butyl) pyrido[4,3-d]pyrimidin-4(3H)-one,
2-((R)-1-((R)-4,6-dimethyl-1,4-diazepan-1-yl)butyl)-3-ethylpyrido[4,3-d]pyrimidin-4(3H)-one,
2-((R)-1-((S)-4,6-dimethyl-1,4-diazepan-1-yl)butyl)-3-ethylpyrido[4,3-d]pyrimidin-4(3H)-one,
2-((S)-1-((S)-4,6-dimethyl-1,4-diazepan-1-yl)butyl)-3-ethylpyrido[4,3-d]pyrimidin-4(3H)-one,
2-((S)-1-((R)-4,6-dimethyl-1,4-diazepan-1-yl)butyl)-3-ethylpyrido[4,3-d]pyrimidin-4(3H)-one,
2-(1-(1-1,4-diazepan-1-yl)butyl)-3-ethylpyrido[4,3-d]pyrimidin-4(3H)-one,
(R)-3-ethyl-2-(1-(4-methyl-1,4-diazepan-1-yl)butyl) pyrido[4,3-d]pyrimidin-4(3H)-one,
(S)-3-ethyl-2-(1-(4-methyl-1,4-diazepan-1-yl)butyl) pyrido[4,3-d]pyrimidin-4(3H)-one,
6-bromo-3-ethyl-2-(1-(4-methyl-1,4-diazepan-1-yl) butyl)pyrido[2,3-d]pyrimidin-4(3H)-one,
6-bromo-3-ethyl-2-(1-(4-ethyl-1,4-diazepan-1-yl)butyl) pyrido[2,3-d]pyrimidin-4(3H)-one,
2-(1-((1,4-diazepan-1-yl)butyl)-6-bromo-3-ethylpyrido [2,3-d]pyrimidin-4(3H)-one,
3-ethyl-2-(1-(4-ethyl-(1,4-diazepan-1-yl)butyl)pyrido[2, 3-d]pyrimidin-4(3H)-one,
2-(1-(1,4-diazepan-1-yl)butyl)-3-ethylpyrido[2,3-d]pyrimidin-4(3H)-one,
3-ethyl-2-(1-(4-methyl-1,4-diazepan-1-yl)butyl)pyrido[2, 3-d]pyrimidin-4(3H)-one,
6-bromo-2-(1-(4-methyl-1,4-diazepan-1-yl)butyl)-3-propylpyrido[2,3-d]pyrimidin-4(3H)-one,
3-ethyl-6-fluoro-2-(1-(4-methyl-1,4-diazepan-1-yl)butyl) pyrido[2, 3-d]pyrimidin-4(3H)-one,
6-bromo-3-(cyclopropylmethyl)-2-(1-(4-methyl-1,4-diazepan-1-yl)butyl)pyrido[2,3-d]pyrimidin-4(3H)-one,
3-(cyclopropylmethyl)-6-fluoro-2-(1-(4-methyl-1,4-diazepan-1-yl)butyl)pyrido[2,3-d]pyrimidin-4(3H)-one,
3-(cyclopropylmethyl)-2-(1-(4-ethyl-1,4-diazepan-1-yl) butyl)-6-fluoropyrido[2,3-d]pyrimidin-4(3H)-one,
6-bromo-2-((R)-1-((R)-4,6-dimethyl-1,4-diazepan-1-yl) butyl)-3-ethylpyrido[2,3-d]pyrimidin-4(3H)-one,
6-bromo-2-((R)-1-((S)-4,6-dimethyl-1,4-diazepan-1-yl) butyl)-3-ethylpyrido[2,3-d]pyrimidin-4(3H)-one,
6-bromo-2-((S)-1-((S)-4,6-dimethyl-1,4-diazepan-1-yl) butyl)-3-ethylpyrido[2,3-d]pyrimidin-4(3H)-one,
6-bromo-2-((S)-1-((R)-4,6-dimethyl-1,4-diazepan-1-yl) butyl)-3-ethylpyrido[2,3-d]pyrimidin-4(3H)-one,
3-ethyl-2-(1-(4-methyl-1,4-diazepan-1-yl)buty)-trifluoromethyl)pyrido[2,3-d]pyrimidin-4(3H)-one,
3-ethyl-6-methoxy-2-(1-(4-methyl-1,4-diazepan-1-yl) butyl)pyrido[3,4-d]pyrimidin-4(3H)-one,
3-ethyl-2-(1-(4-methyl-1,4-diazepan-1-yl)butyl)-6-(trifluoromethyl)pyrido[3,4-d]pyrimidin-4(3H)-one,
3-(cyclopropylmethyl)-6-fluoro-2-((S)-1-((R)-5-methyl-1,4-diazepan-1-yl)butyl)pyrido[2,3-d]pyrimidin-4 (3H)-one,
3-(cyclopropylmethyl)-6-fluoro-2-((S)-1-((S)-5-methyl-1,4-diazepan-1-yl)butyl)pyrido[2,3-d]pyrimidin-4 (3H)-one,
3-(cyclopropylmethyl)-6-fluoro-2-((R)-1-((S)-5-methyl-1,4-diazepan-1-yl)butyl)pyrido[2,3-d]pyrimidin-4 (3H)-one,
3-(cyclopropylmethyl)-6-fluoro-2-((R)-1-((R)-5-methyl-1,4-diazepan-1-yl)butyl)pyrido[2,3-d]pyrimidin-4 (3H)-one,
6-bromo-3-ethyl-2-((R)-1-((S)-6-methyl-1,4-diazepan-1-yl)butyl)pyrido[2,3-d]pyrimidin-4(3H)-one,
6-bromo-3-ethyl-2-((S)-1-((R)-6-methyl-1,4-diazepan-1-yl)butyl)pyrido[2,3-d]pyrimidin-4(3H)-one,
6-bromo-3-ethyl-2-((R)-1-((R)-6-methyl-1,4-diazepan-1-yl)butyl)pyrido[2,3-d]pyrimidin-4(3H)-one,
6-bromo-3-ethyl-2-((S)-1-((S)-6-methyl-1,4-diazepan-1-yl)butyl)pyrido[2,3-d]pyrimidin-4(3H)-one,
(R)-3-ethyl-6-fluoro-2-(1-(4-methyl-1,4-diazepan-1-yl) butyl)pyrido[2,3-d]pyrimidin-4(3H)-one,
(S)-3-ethyl-6-fluoro-2-(1-(4-methyl-1,4-diazepan-1-yl) butyl)pyrido[2,3-d]pyrimidin-4(3H)-one,
3-ethyl-6-hydroxy-2-(1-(4-methyl-1,4-diazepan-1-yl) butyl)quinazolin-4(3H)-one,
3-ethyl-2-(1-(4-methyl-1,4-diazepan-1-yl)butyl)-6-phenylquinazolin-4(3H)-one,
3,6-diethyl-2-(1-(4-methyl-1,4-diazepan-1-yl)butyl)quinazolin-4(3H)-one,
3-ethyl-2-(1-(4-methyl-1,4-diazepan-1-yl)butyl)-6-((1-methylpiperidin-4-yl)amino)quinazolin-4(3H)-one,
6-benzyl-3-ethyl-2-(1-(4-methyl-1,4-diazepan-1-yl) butyl)quinazolin-4(3H)-one,
2-(6-bromo-2-(1-(4-methyl-1,4-diazepan-1-yl)butyl)-4-oxoquinazolin-3(4H)-yl)acetic acid,
(R)-3-ethyl-6-fluoro-2-(1-(4-methyl-1,4-diazepan-1-yl) butyl)quinazolin-4(3H)-one,
(R)-3-ethyl-2-(1-(4-ethyl-1,4-diazepan-1-yl)butyl)-6-fluoroquinazolin-4(3H)-one,
(R)-6-fluoro-2-(1-(4-methyl-1,4-diazepan-1-yl)butyl)-3-propylquinazolin-4(3H)-one,
(R)-2-(1-(4-ethyl-1,4-diazepan-1-yl)butyl)-6-fluoro-3-propylquinazolin-4(3H)-one,
(R)-3-ethyl-6-iodo-2-(1-(4-methyl-1,4-diazepan-1-yl) butyl)quinazolin-4(3H)-one,
(R)-6-fluoro-3-isobutyl-2-(1-(4-methyl-1,4-diazepan-1-yl)butyl)quinazolin-4(3H)-one,
(R)-2-(1-(4-ethyl-1,4-diazepan-1-yl)butyl)-6-fluoro-3-isobutylquinazolin-4(3H)-one,
(R)-6-fluoro-3-methyl-2-(1-(4-methyl-1,4-diazepan-1-yl) butyl)quinazolin-4(3H)-one,
(R)-2-(1-(4-ethyl-1,4-diazepan-1-yl)butyl)-6-fluoro-3-methylquinazolin-4(3H)-one,
(R)-3-(cyclopropylmethyl)-1-2-(1-(4-ethyl-1,4-diazepan-1-yl)butyl)-6-fluoroquinazolin-4(3H)-one,
(R)-3-(cyclopropylmethyl)-6-fluoro-2-(1-(4-methyl-1,4-diazepan-1-yl)butyl)quinazolin-4(3H)-one,
(R)-3-ethyl-7-fluoro-6-methoxy-2-(1-(4-methyl-1,4-diazepan-1-yl)butyl)quinazolin-4(3H)-one,
(R)-2-(1-(4-ethyl-1,4-diazepan-1-yl)butyl)-6-fluoro-3-isopentylquinazolin-4(3H)-one,
(R)-6-fluoro-3-isopropyl-2-(1-(4-methyl-1,4-diazepan-1-yl)butyl)quinazolin-4(3H)-one,
(R)-2-(1-(4-ethyl-1,4-diazepan-1-yl)butyl)-6-fluoro-3-isopropylquinazolin-4(3H)-one,
(R)-3-butyl-6-fluoro-2-(1-(4-methyl-1,4-diazepan-1-yl) butyl)quinazolin-4(3H)-one,
(R)-3-butyl-2-(1-(4-ethyl-1,4-diazepan-1-yl)butyl)-6-fluoroquinazolin-4(3H)-one,
(R)-6-fluoro-3-isopentyl-2-(1-(4-methyl-1,4-diazepan-1-yl)butyl)quinazolin-4(3H)-one,
((R)-6-fluoro-3-(furan-3-ylmethyl)-2-(1-(4-methyl-1,4-diazepan-1-yl)butyl)quinazolin-4(3H)-one,
(R)-2-(1-(4-ethyl-1,4-diazepan-1-yl)butyl)-6-fluoro-3-(furan-3-ylmethyl)quinazolin-4(3H)-one,
(R)-2-(1-(4-ethyl-1,4-diazepan-1-yl)butyl)-6-fluoro-3-propylquinazolin-4(3H)-one,
(R)-3-ethyl-6-fluoro-7-methoxy-2-(1-(4-methyl-1,4-diazepan-1-yl)butyl)quinazolin-4(3H)-one,
(R)-3-ethyl-2-(1-(4-ethyl-1,4-diazepan-1-yl)butyl)-6-fluoro-7-methoxyquinazolin-4(3H)-one,
(R)-3-ethyl-6,7-difluoro-2-(1-(4-methyl-1,4-diazepan-1-yl)butyl)quinazolin-4(3H)-one, (R)-3-ethyl-5,6-difluoro-2-(1-(4-methyl-1,4-diazepan-1-yl)butyl)quinazolin-4(3H)-one, (R)-6-chloro-3-ethyl-8-fluoro-2-(1-(4-methyl-1,4-diazepan-1-yl)butyl)quinazolin-4(3H)-one, 3-ethyl-6-fluoro-2-((R)-1-((R)-5-methyl-1,4-diazepan-1-yl)butyl)quinazolin-4(3H)-one, 3-ethyl-6-fluoro-2-((R)-1-((S)-5-methyl-1,4-diazepan-1-yl)butyl)quinazolin-4(3H)-one, 2-((R)-1-((R)-4,6-dimethyl-1,4-diazepan-1-yl)butyl)-3-ethyl-7-fluoro-6-methoxyquinazolin-4(3H)-one, 2-((R)-1-((S)-4,6-dimethyl-1,4-diazepan-1-yl)butyl)-3-ethyl-7-fluoro-6-methoxyquinazolin-4(3H)-one, 3-ethyl-5,6-difluoro-2-((R)-1-((R)-5-methyl-1,4-diazepan-1-yl)butyl)quinazolin-4(3H)-one, 3-ethyl-5,6-difluoro-2-((R)-1-((S)-5-methyl-1,4-diazepan-1-yl)butyl)quinazolin-4(3H)-one, 3-ethyl-6,7-difluoro-2-((R)-1-((R)-5-methyl-1,4-diazepan-1-yl)butyl)quinazolin-4(3H)-one, 3-ethyl-6,7-difluoro-2-((R)-1-((S)-5-methyl-1,4-diazepan-1-yl)butyl)quinazolin-4(3H)-one, 3-ethyl-7-fluoro-6-methoxy-2-((R)-1-((R)-6-methyl-1,4-diazepan-1-yl)butyl)quinazolin-4(3H)-one, 3-ethyl-7-fluoro-6-methoxy-2-((R)-1-((S)-6-methyl-1,4-diazepan-1-yl)butyl)quinazolin-4(3H)-one, 6-chloro-3-methyl-2-((R)-1-((R)-5-methyl-1,4-diazepan-1-yl)butyl)quinazolin-4(3H)-one, 6-chloro-3-methyl-2-((R)-1-((S)-5-methyl-1,4-diazepan-1-yl)butyl)quinazolin-4(3H)-one, (R)-3-ethyl-6,8-difluoro-2-(1-(4-methyl-1,4-diazepan-1-yl)butyl)quinazolin-4(3H)-one, (R)-3-ethyl-8-fluoro-2-(1-(4-methyl-1,4-diazepan-1-yl)butyl)quinazolin-4(3H)-one, (R)-3-ethyl-2-(1-(4-methyl-1,4-diazepan-1-yl)butyl)-6-(trifluoromethoxy)quinazolin-4(3H)-one, 3-ethyl-6,8-difluoro-2-((R)-1-((R)-5-methyl-1,4-diazepan-1-yl)butyl)quinazolin-4(3H)-one, 3-ethyl-6,8-difluoro-2-((R)-1-((S)-5-methyl-1,4-diazepan-1-yl)butyl)quinazolin-4(3H)-one, (R)-3-ethyl-2-(1-(4-methyl-1,4-diazepan-1-yl)butyl)-6-(trifluoromethyl)quinazolin-4(3H)-one, (R)-2-(1-(3,3-dimethyl-1,4-diazepan-1-yl)butyl)-3-ethyl-6-fluoroquinazolin-4(3H)-one, 6-chloro-2-((R)-1-((S)-4,5-dimethyl-1,4-diazepan-1-yl)butyl)-3-methylquinazolin-4(3H)-one, 6-fluoro-3-methyl-2-((R)-1-((R)-5-methyl-1, 4-diazepan-1-yl)butyl)quinazolin-4(3H)-one, 6-fluoro-3-methyl-2-((R)-1-((S)-5-methyl-1,4-diazepan-1-yl)butyl)quinazolin-4(3H)-one, 6-chloro-2-((R)-1-((R)-4,5-dimethyl-1,4-diazepan-1-yl)butyl)-3-methylquinazolin-4(3H)-one, 3-ethyl-2-((R)-1-((R)-5-methyl-1,4-diazepan-1-yl)butyl)-6-(trifluoromethyl)quinazolin-4(3H)-one, 3-ethyl-2-((R)-1-((S)-5-methyl-1,4-diazepan-1-yl)butyl)-6-(trifluoromethyl)quinazolin-4(3H)-one, 3-ethyl-6,7-difluoro-2-((R)-1-((S)-3-methyl-1,4-diazepan-1-yl)butyl)quinazolin-4(3H)-one, 3-ethyl-6,7-difluoro-2-((R)-1-((R)-3-methyl-1,4-diazepan-1-yl)butyl)quinazolin-4(3H)-one, 6-bromo-2-((S)-1-((4S,7S)-1,7-dimethylazepan-4-yl)butyl)-3-ethylquinazolin-4(3H)-one, 6-bromo-2-((R)-1-((4R,7S)-1,7-dimethylazepan-4-yl)butyl)-3-ethylquinazolin-4(3H)-one, 6-bromo-2-((S)-1-((4S,7R)-1, 7-dimethylazepan-4-yl)butyl)-3-ethylquinazolin-4(3H)-one, 6-bromo-2-((R)-1-((4R,7R)-1,7-dimethylazepan-4-yl)butyl)-3-ethylquinazolin-4(3H)-one, 2-(1-(azepan-4-yl)butyl)-3-ethyl-6-fluoroquinazolin-4(3H)-one, 3-ethyl-6-fluoro-2-(1-(1-methylazepan-4-yl)butyl)quinazolin-4(3H)-one, 3-ethyl-2-(1-(1-ethylazepan-4-yl)butyl)-6-fluoroquinazolin-4(3H)-one, (6S,7R)-2-bromo-7-ethyl-6-(4-methyl-1,4-diazepan-1-yl)-8,9-dihydro-6H-pyrido[2,1-b]quinazolin-11(7H)-one and (6R,7S)-2-bromo-7-ethyl-6-(4-methyl-1,4-diazepan-1-yl)-8,9-dihydro-6H-pyrido[2,1-b]quinazolin-11(7H)-one.

11. A pharmaceutical composition comprising the compound according to claim 1, or a pharmaceutically acceptable salt thereof, and a pharmaceutically acceptable carrier, adjuvant or vehicle.

12. A process for the preparation of the compound of Formula (I) according to claim 1, wherein when W is nitrogen, the process comprises reacting a compound of formula VIII

VIII

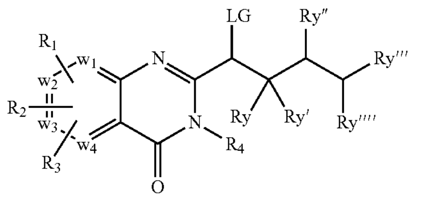

with a suitable amine of formula IX,

IX

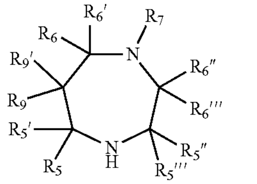

in a suitable solvent in the presence of a base at a suitable temperature comprised between room temperature and reflux temperature, or when W is carbon, the process comprises alkylation of a compound of formula XIV

XIV

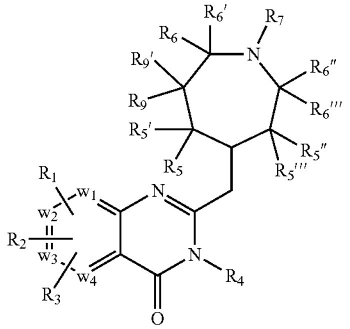

with a compound of formula XV,

XV

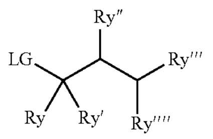

using a suitable base in a suitable solvent at a suitable temperature, wherein $R_1$, $R_2$, $R_3$, $R_4$, $R_5$, $R_5'$, $R_5''$, $R_5'''$, $R_6$, $R_6'$, $R_6''$, $R_6'''$, $R_7$, $R_9$, $R_9'$, $R_y$, $R_y'$, $R_y''$, $R_y'''$, $R_y''''$, $w_1$, $w_2$, $w_3$ and $w_4$ are as defined in claim 1, and LG represents a leaving group.

13. A process for the preparation of the compound of Formula (I) according to claim 1 employing a compound of Formula IIa, IIb, III, IV, V, VI, VII, VIIa, VIII, IX, XII, XIII, XIV, XV, XVI, XVII, XVIII or XIX, IIa

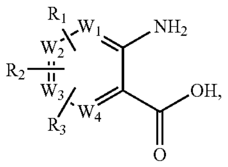

IIb

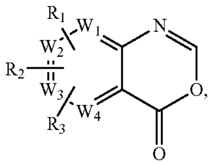

III $H_2N—R_4$,

IV

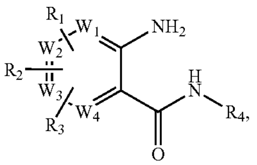

V

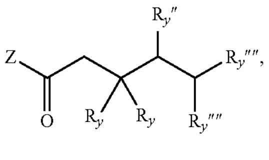

VI

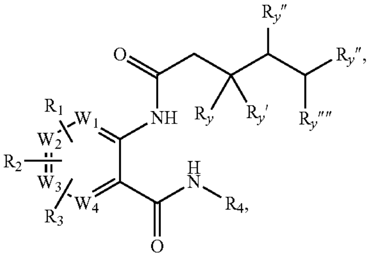

-continued

VII

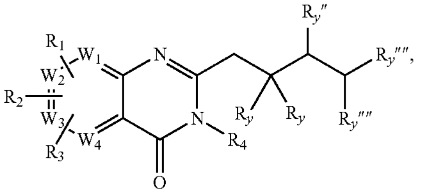

VIIa

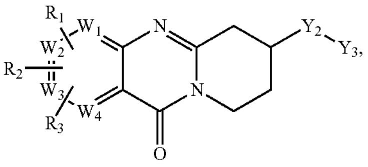

VIII

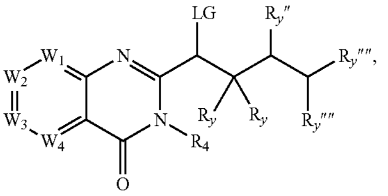

IX

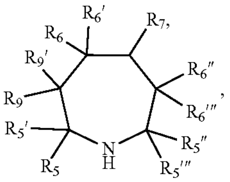

XII

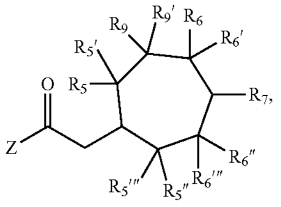

XIII

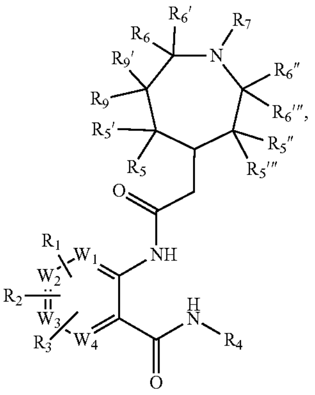

-continued

XIV

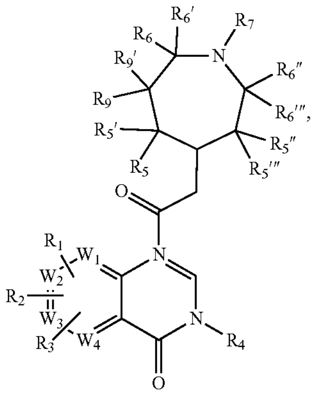

XV

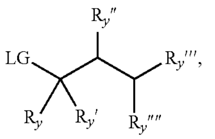

XVI

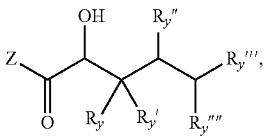

XVII

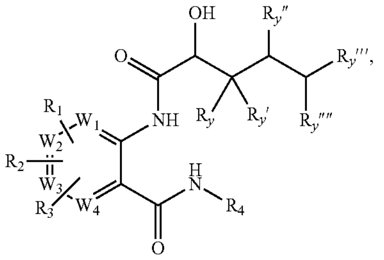

-continued

XVIII

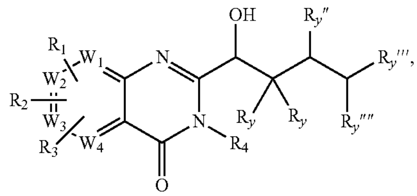

XIX

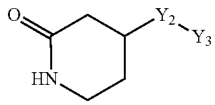

wherein $R_1$, $R_2$, $R_3$, $R_4$, $R_5$, $R_5'$, $R_5''$, $R_5'''$, $R_6$, $R_6'$, $R_6''$, $R_6'''$, $R_7$, $R_9$, $R_9'$, $R_y$, $R_y'$, $R_y''$, $R_y'''$, $R_y''''$, W, $w_1$, $w_2$, $w_3$ and $w_4$ are as defined in claim 1; Y2-Y3 represents —$CHR_y''CHR_y'''$ $R_y''''$; and LG represents a leaving group.

14. A method of treating pain in a subject in need thereof, comprising administration of an effective amount of the compound according to claim 1.

15. The method according to claim 14, wherein the pain is medium to severe pain, visceral pain, chronic pain, cancer pain, migraine, inflammatory pain, acute pain or neuropathic pain, allodynia or hyperalgesia.

16. The process according to claim 12, wherein the reaction of the compound of formula VIII with the amine of formula IX is carried out in a suitable solvent selected from acetonitrile and dimethylformamide in the presence of a base selected from triethylamine, $K_2CO_3$ and N,N-diisopropylethylamine.

17. The process according to claim 12, wherein the reaction of the compound of formula XIV with the compound of XV is carried out using lithium bis(trimethylsilyl) amide in tetrahydrofuran at room temperature.

18. The process according to claim 12, wherein LG represents a leaving group selected from chloro, bromo, iodo, mesylate, tosylate, nosylate and triflate.

19. The process according to claim 13, wherein LG represents a leaving group selected from chloro, bromo, iodo, mesylate, tosylate, nosylate and triflate.

* * * * *